(12) United States Patent
Gray et al.

(10) Patent No.: US 10,112,957 B2
(45) Date of Patent: Oct. 30, 2018

(54) THIAZOLYL-CONTAINING COMPOUNDS FOR TREATING PROLIFERATIVE DISEASES

(71) Applicant: Dana-Farber Cancer Institute, Inc., Boston, MA (US)

(72) Inventors: Nathanael S. Gray, Boston, MA (US); Sara Jean Buhrlage, Somerville, MA (US); Steven P. Treon, Jamaica Plain, MA (US); Hwan Geun Choi, Chestnut Hill, MA (US); Yuan Xiong, Brookline, MA (US); Guang Yang, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/518,541

(22) PCT Filed: Oct. 22, 2015

(86) PCT No.: PCT/US2015/056899
§ 371 (c)(1),
(2) Date: Apr. 12, 2017

(87) PCT Pub. No.: WO2016/065138
PCT Pub. Date: Apr. 28, 2016

(65) Prior Publication Data
US 2017/0233411 A1    Aug. 17, 2017

Related U.S. Application Data

(60) Provisional application No. 62/067,178, filed on Oct. 22, 2014.

(51) Int. Cl.
| C07D 277/20 | (2006.01) |
| C07D 277/56 | (2006.01) |
| C07D 417/12 | (2006.01) |
| C07D 513/04 | (2006.01) |
| C07D 417/04 | (2006.01) |
| C07D 417/14 | (2006.01) |

(52) U.S. Cl.
CPC ......... C07D 513/04 (2013.01); C07D 417/04 (2013.01); C07D 417/12 (2013.01); C07D 417/14 (2013.01)

(58) Field of Classification Search
CPC ... C07D 277/20; C07D 277/56; C07D 417/12
See application file for complete search history.

(56) References Cited

U.S. PATENT DOCUMENTS 6,455,520 B1   9/2002  Brown et al.
6,821,965 B1  11/2004  Brown et al.
7,060,700 B2   6/2006  Brown et al.
(Continued)

FOREIGN PATENT DOCUMENTS

WO    WO 99/054286 A2   10/1999
WO    WO 00/056737 A2    9/2000
(Continued)

OTHER PUBLICATIONS

Extended European Search Report for EP 14869351.8, dated Jul. 31, 2017.
(Continued)

Primary Examiner — Bruck Kifle
(74) Attorney, Agent, or Firm — Wolf, Greenfield & Sacks, P.C.

(57) ABSTRACT

The present disclosure provides thiazolyl-containing compounds of Formula (I), (II), or (III). The compounds described herein may be able to inhibit protein kinases (e.g., Src family kinases (e.g., hemopoietic cell kinase (HCK)), Bruton's tyrosine kinase (BTK)) and may be useful in treating and/or preventing proliferative diseases (e.g., myelodysplasia, leukemia, lymphoma (e.g., Waldenström's macroglobulinemia)) and in inducing apoptosis in a cell (e.g., malignant blood cell). Also provided in the present disclosure are pharmaceutical compositions, kits, methods, and uses including or using a compound described herein.

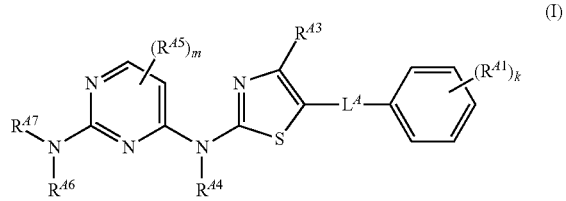

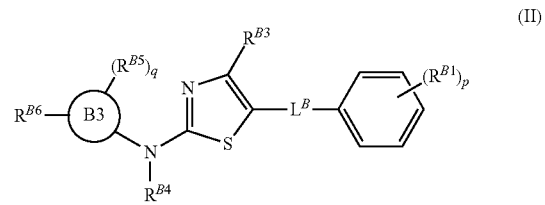

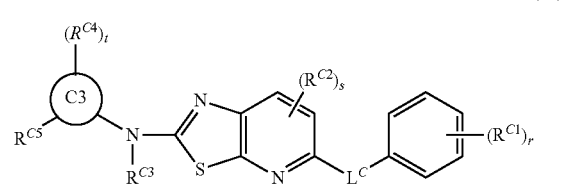

35 Claims, No Drawings
Specification includes a Sequence Listing.

(56) References Cited

U.S. PATENT DOCUMENTS

| | | |
|---|---|---|
| 9,856,223 B2 | 1/2018 | Treon et al. |
| 2004/0106615 A1 | 6/2004 | Cochran et al. |
| 2007/0060619 A1 | 3/2007 | Burns et al. |
| 2007/0072862 A1 | 3/2007 | Dimauro et al. |
| 2007/0155746 A1 | 7/2007 | Lang et al. |
| 2008/0269215 A1 | 10/2008 | Goldsmith et al. |
| 2009/0054405 A1 | 2/2009 | Booker et al. |
| 2009/0118297 A1 | 5/2009 | Simo et al. |
| 2009/0312396 A1 | 12/2009 | Byth et al. |
| 2011/0053905 A1 | 3/2011 | Guo et al. |
| 2012/0108572 A1 | 5/2012 | Wagner et al. |
| 2013/0040949 A1 | 2/2013 | Gray et al. |
| 2014/0162983 A1 | 6/2014 | Hodous et al. |
| 2016/0311807 A1 | 10/2016 | Treon et al. |
| 2016/0318878 A1 | 11/2016 | Treon et al. |

FOREIGN PATENT DOCUMENTS

| | | |
|---|---|---|
| WO | WO 03/030902 A1 | 4/2003 |
| WO | WO 2006/067445 A2 | 6/2006 |
| WO | WO 2006/067446 A1 | 6/2006 |
| WO | WO 2006/081172 A2 | 8/2006 |
| WO | WO 2007/019191 A2 | 2/2007 |
| WO | WO 2008/039218 A2 | 4/2008 |
| WO | WO 2008/144253 A1 | 11/2008 |
| WO | WO 2008/150446 A1 | 12/2008 |
| WO | WO 2009/076373 A1 | 6/2009 |
| WO | WO 2009/137596 A1 | 11/2009 |
| WO | WO 2010/026095 A1 | 3/2010 |
| WO | WO 2010/056875 A1 | 5/2010 |
| WO | WO 2011/029043 A1 | 3/2011 |
| WO | WO 2011/090738 A2 | 7/2011 |
| WO | WO 2012/007375 A1 | 1/2012 |
| WO | WO 2012/062704 A1 | 5/2012 |
| WO | WO 2012/068096 A2 | 5/2012 |
| WO | WO 2012/161877 A1 | 11/2012 |
| WO | WO 2012/170976 A2 | 12/2012 |
| WO | WO 2013/010380 A1 | 1/2013 |
| WO | WO 2013/052699 A2 | 4/2013 |
| WO | WO 2013/067277 A1 | 5/2013 |
| WO | WO 2013/074986 A1 | 5/2013 |
| WO | WO 2013/088404 A1 | 6/2013 |

OTHER PUBLICATIONS

Extended European Search Report for EP 14869964.8, dated Nov. 16, 2017.
Chen et al., Discovery of a potent and selective c-Kit inhibitor for the treatment of inflammatory diseases. Bioorg Med Chem Lett. Jul. 15, 2008;18(14):4137-41. doi: 10.1016/j.bmcl.2008.05.089. Epub May 28, 2008.
Dijkgraaf et al., Small Molecule Inhibition of GDC-0449 Refractory Smoothened Mutants and Downstream Mechanisms of Drug Resistance. Cancer Res Jan. 2011;71(2):435-44. DOI: 10.1158/0008-5472.CAN-10-2876.
Hellwig et al., Small-molecule inhibitors of the c-Fes protein-tyrosine kinase.Chem Biol. Apr. 20, 2012;19(4):529-40. doi: 10.1016/j.chembiol.Jan. 20, 2012.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Tan et al., Discovery of type II inhibitors of TGFβ-activated kinase 1 (TAK1) and mitogen-activated protein kinase kinase kinase 2 (MAP4K2). J Med Chem. Jan. 8, 2015;58(1):183-96. doi: 10.1021/jm500480k. Epub Jul. 30, 2014.
International Search Report and Written Opinion for PCT/US2014/70167, dated Mar. 11, 2015.
International Preliminary Report on Patentability for PCT/US2014/70167, dated Jun. 23, 2016.
International Search Report and Written Opinion for PCT/US2014/70162, dated Mar. 11, 2015.
International Preliminary Report on Patentability for PCT/US2014/70162, dated Jun. 23, 2016.
International Search Report and Written Opinion for PCT/US2015/56899, dated Jan. 29, 2016.
International Preliminary Report on Patentability for PCT/US2015/56899, dated May 4, 2017.
CAS Registry No. 1298854-20-2, STN Entry Date May 22, 2011.
CAS Registry No. 1319879-27-0, STN Entry Date Aug. 19, 2011.
CAS Registry No. 1388492-05-4, STN Entry Date Aug. 9, 2012.
CAS Registry No. 1320831-41-1, STN Entry Date Aug. 21, 2011.
Banker et al., Prodrugs. Modem Pharmaceuticals. 1996;3:596.
Buckley, et al., IRAK-4 inhibitors. Part I: A series of amides, Bioorganic & Medicinal Chemistry Letters, vol. 18, Issue 11, pp. 3211-3214.
Buckley et al., IRAK-4 inhibitors. Part III: A series of imidazo[1,2-a]pyridines, Bioorganic & Medicinal Chemistry Letters, vol. 18, Issue 12, pp. 3656-3660.
Chawla et al., Challenges in polymorphism of pharmaceuticals. CRIPS. 2004;5(1):9-12.
Cheng et al., Binding of Bruton's tyrosine kinase to Fyn, Lyn, or Hck through a Src homology 3 domain-mediated interaction, Proc. Natl. Acad. Sci. USA Aug. 1994; 91:8152-5.
Choi et al., Discovery and structural Bioorg Med Chem. Bioorg Med Chem Lett. Aug. 1, 2009;19(15):4467-70. doi: 10.1016/j.bmcl. May 29, 2009. Epub May 13, 2009.
Davis et al., Comprehensive analysis of kinase inhibitor selectivity. Nat. Biotechnol. 2011, 29(11): 1046-1051.
Ding et al., Constitutively activated STAT3 promotes cell proliferation and survival in the activated B-cell subtype of diffuse large B-cell lymphomas. Blood. Feb. 1, 2008; 111(3): 1515-23.
Ditzel et al., Establishment of BVWM.1 cell line for Waldenstrom's macroglobulinemia with productive in vivo engraftment in SCID-hu mice, Experimental Hematology 35 (2007) 1366-1375.
Fabian et al., A small molecule-kinase interaction map for clinical kinase inhibitors. Nat. Biotechnol. 2005, 23(3): 329-336.
Hodge et al., Establishment and characterization of a novel Waldenstrom macroglobulinemia cell line, MWCL-1, Blood. 2011;117(19):e190-e197, doi:10.1182/blood-2010-12-326868.
Horwood et al., Bruton's tyrosine kinase is required for lipopolysaccharide-induced tumor necrosis factor alpha production, J. Exp. Med., Jun. 16, 2003;197(12):1603-11.
Iwaki et al., Btk Plays a Crucial Role in the Amplification of Fc RI-mediated Mast Cell Activation by Kit, J. Biol. Chem., 2005, 280(48), 40261-40270.
Jeffries et al., Bruton's Tyrosine Kinase Is a Toll/Interleukin-1 Receptor Domain-binding Protein That Participates in Nuclear Factor B Activation by Toll-like Receptor 4, J.Biol. Chem., 2003, 278, 26258-26264.
Koshiol et al., Chronic immune stimulation and subsequent Waldenstrom's macroglobulinemia, Arch Intern Med. Sep. 22, 2008; 168(17): 1903-1909. doi:10.1001/archinternmed.2008.4.
Kurosaki, Functional dissection of BCR signaling pathways, Curr Opin Immunol. Jun. 2000;12(3):276-81.
Kwarcinski et al., Irreversible inhibitors of c-Src kinase that target a nonconserved cysteine. ACS Chem Biol. Nov. 16, 2012;7(11):1910-7. doi: 10.1021/cb300337u. Epub Sep. 5, 2012.
Lam et al., Cooperative signaling through the signal transducer and activator of transcription 3 and nuclear factor-{kappa}B pathways in subtypes of diffuse large B-cell lymphoma. Blood. Apr. 1, 2008; 111(7): 3701-13.
Li et al., Creating chemical diversity to target protein kinases. Comb Chem High Throughput Screen. Aug. 2004;7(5):453-72.
Lim et al., Oncogenic MYD88 mutants require Toll-like receptors. In: Proceedings of the 104th Annual Meeting of the American Association for Cancer Research; Apr. 6-10, 2013; Washington, DC. Philadelphia: AACR; Cancer Res; (2013) 73(8 Suppl): Abst 2332. 10.1158/1538-7445.AM2013-2332.
Liu et al., Intracellular MHC class II molecules promote TLR-triggered innate immune responses by maintaining activation of the kinase Btk, Nature Immunology 12, 416-424 (2011) doi:10.1038/ni.2015.

(56) References Cited

OTHER PUBLICATIONS

Neparidze et al., Waldenstrom's Macroglobulinemia: Recent Advances in Biology and Therapy, Clin Adv Hematol Oncol. Oct. 2009 ; 7(10): 677-690.

Newman et al., Solid-state analysis of the active pharmaceutical ingredient in drug products. Drug Discov Today. Oct. 1, 2003;8(19):898-905.

Ngo et al., Oncogenically active MYD88 mutations in human lymphoma. Nature. Feb. 3, 2011; 470(7332): 115-9.

Patricelli et al., Functional interrogation of the kinome using nucleotide acyl phosphates. Biochemistry, 2007, 46(2): 350-358.

Peng-Cheng et al., Synthesis, molecular docking and evaluation of thiazolyl-pyrazoline derivatives as EGFR TK inhibitors and potential anticancer agents. Bioorg Med Chem Letts. 2011; 21:5374-5377.

Quek et al., A role for Bruton's tyrosine kinase (Btk) in platelet activation by Collagen, Curr. Biol., 1998, 8(20), 1137-1140.

Sawasdikosol et al., HPK1 as a novel target for cancer immunotherapy, Immunol Res (2012) 54:262-265, DOI 10.1007/s12026-012-8319-1.

Schaeffer et al., Tec family kinases in lymphocyte signaling and function, Curr Opin Immunol. Jun. 2000; 12(3): 282-88.

Vassilev et al., Bruton's tyrosine kinase as an inhibitor of the Fas/CD95 death-inducing signaling complex, J. Biol. Chem., Jan. 15, 1999, 275(3): 1646-56.

Wang et al., Emerging targets in human lymphoma: targeting the MYD88 mutation. Blood Lymphat Cancer (2013) 2013:53-61.

Wang et al., Consequences of the recurrent MYD88(L265P) somatic mutation for B cell tolerance. J Exp Med. Mar. 10, 2014; 211(3): 413-26.

Wesche et al., MyD88: An Adapter That Recruits IRAK to the IL-1 Receptor Complex, Immunity, 1997, vol. 7, Issue 6, 837-847.

Wolff et al., Some reconsiderations for prodrug design. Burger's Medicinal Chemistry Drug Discovery. 1995;5(1):975-7.

Yang et al., A Mutation in MYD88 (L265P) supports the survival of lymphoplasmacytic cells by activation of Bruton tyrosine kinase in Waldenstrom macroglobulinemia, Blood, Aug. 15, 2013;122(7):1222-32. doi: 10.1182/blood-2012-12-475111. Epub Jul. 8, 2013.

Partial Supplementary European Search Report for EP 15 85 2450, dated Mar. 22, 2018.

Li et al., Characterization of dasatinib and its structural analogs as CYP3A4 mechanism-based inactivators and the proposed bioactivation pathways. Drug Metab Dispos. Jun. 2009;37(6):1242-50. doi: 10.1124/dmd.108.025932. Epub Mar. 12, 2009.

SEQUENCE LISTING

<160> NUMBER OF SEQ ID NOS: 235

<210> SEQ ID NO 1
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1

Leu Met Thr Gly Asp Thr Tyr Thr Ala His Ala Gly Ala Lys Phe Pro
1               5                   10                  15

Ile Lys

<210> SEQ ID NO 2
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 2

Tyr Ser Leu Thr Val Ala Val Lys Thr Leu Lys Glu Asp Thr Met Glu
1               5                   10                  15

Val Glu Glu Phe Leu Lys
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 3

Thr Val Ser Val Ala Val Lys Cys Leu Lys Pro Asp Val Leu Ser Gln
1               5                   10                  15

Pro Glu Ala Met Asp Asp Phe Ile Arg
            20                  25

<210> SEQ ID NO 4
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 4

Ala Thr Val Phe Leu Asn Pro Ala Ala Cys Lys Gly Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Gly Thr Phe Gly Lys Val Ile Leu Val Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 6

Gly Thr Phe Gly Lys Val Ile Leu Val Arg
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 7

Asp Leu Lys Pro Glu Asn Val Leu Leu Asp Ala His Met Asn Ala Lys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 8

Asp Leu Lys Ser Asn Asn Ile Phe Leu His Glu Gly Leu Thr Val Lys
1               5                   10                  15

<210> SEQ ID NO 9
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 9

Gln Leu Val Lys Gly Arg Asp Asp Leu Arg Gln Asp Ala Val Met Gln
1               5                   10                  15

Gln Val Phe Gln Met Cys Asn Thr Leu Leu Gln Arg
                20                  25

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 10

Phe Tyr Ile Met Met Cys Lys Pro Lys
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 11

Phe Ile Leu Ala Leu Lys Val Leu Phe Lys
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 12

Asp Ile Lys Pro Glu Asn Leu Leu Leu Gly Ser Ala Gly Glu Leu Lys
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 13

Gly Lys Phe Gly Asn Val Tyr Leu Ala Arg
1               5                   10

<210> SEQ ID NO 14
<211> LENGTH: 12

```
<212> TYPE: PRT
<213> ORGANISM: Artificial Sequence
<220> FEATURE:
<223> OTHER INFORMATION: Synthetic Polypeptide

<400> SEQUENCE: 14

Ser His Phe Ile Val Ala Leu Lys Val Leu Phe Lys
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 15

Ile Ile Asp Ser Glu Tyr Thr Ala Gln Glu Gly Ala Lys Phe Pro Ile
1               5                   10                  15

Lys

<210> SEQ ID NO 16
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 16

Asp Leu Lys Ser Asn Asn Ile Phe Leu His Glu Asp Leu Thr Val Lys
1               5                   10                  15

<210> SEQ ID NO 17
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 17

Tyr Val Leu Asp Asp Glu Tyr Thr Ser Ser Val Gly Ser Lys Phe Pro
1               5                   10                  15

Val Arg

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Leu Phe Ala Val Lys Cys Ile Pro Lys
1               5

<210> SEQ ID NO 19
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 19

Ile Pro Thr Gly Gln Glu Tyr Ala Ala Lys Ile Ile Asn Thr Lys Lys
1               5                   10                  15
```

<210> SEQ ID NO 20
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 20

Thr Ser Thr Gln Glu Tyr Ala Ala Lys Ile Ile Asn Thr Lys
1               5                   10

<210> SEQ ID NO 21
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 21

Asp Leu Lys Pro Glu Asn Leu Leu Tyr Ala Thr Pro Ala Pro Asp Ala
1               5                   10                  15

Pro Leu Lys

<210> SEQ ID NO 22
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 22

Asp Ile Lys Pro Ser Asn Leu Leu Val Gly Glu Asp Gly His Ile Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 23

Glu Thr Gly Gln Gln Phe Ala Val Lys Ile Val Asp Val Ala Lys
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 24

Asp Leu Lys Pro Gln Asn Leu Leu Ile Asp Asp Lys Gly Thr Ile Lys
1               5                   10                  15

<210> SEQ ID NO 25
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 25

Asp Val Lys Pro Ser Asn Phe Leu Tyr Asn Arg
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 26

Asp Leu Lys Pro Ala Asn Ile Leu Val Met Gly Glu Gly Pro Glu Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 27

Asp Leu Lys Pro Gln Asn Leu Leu Ile Asn Thr Glu Gly Ala Ile Lys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 28

Asp Leu Lys Pro Glu Asn Ile Leu Val Thr Ser Gly Gly Thr Val Lys
1               5                   10                  15

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 29

Asp Leu Lys Pro Gln Asn Leu Leu Ile Asn Arg
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 30

Asp Leu Lys Pro Gln Asn Ile Leu Val Thr Ser Ser Gly Gln Ile Lys
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 31

Asp Leu Lys Pro Asn Asn Leu Leu Leu Asp Glu Asn Gly Val Leu Lys
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 32

Asp Met Lys Ala Ala Asn Val Leu Ile Thr Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 33

Asp Ile Lys Cys Ser Asn Ile Leu Leu Asn Asn Arg
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 34

Asp Ile Lys Pro Glu Asn Leu Leu Leu Asp Glu Arg
1               5                   10

<210> SEQ ID NO 35
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 35

Asp Leu Lys Pro Glu Asn Val Leu Leu Ser Ser Gln Glu Glu Asp Cys
1               5                   10                  15

Leu Ile Lys

<210> SEQ ID NO 36
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 36

Asp Ile Lys Pro Asp Asn Phe Leu Met Gly Ile Gly Arg
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 37

Asp Val Lys Pro Asp Asn Phe Leu Met Gly Leu Gly Lys Lys
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 38

Lys Ile Gly Cys Gly Asn Phe Gly Glu Leu Arg
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 39

Asp Val Lys Pro Glu Asn Phe Leu Val Gly Arg Pro Gly Thr Lys
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 40

Asp Val Lys Pro His Asn Val Met Ile Asp His Gln Gln Lys
1               5                   10

<210> SEQ ID NO 41
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 41

Leu Thr His Thr Asp Leu Lys Pro Glu Asn Ile Leu Phe Val Gln Ser
1               5                   10                  15

Asp Tyr Thr Glu Ala Tyr Asn Pro Lys
            20                  25

<210> SEQ ID NO 42
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 42

Leu Thr His Thr Asp Leu Lys Pro Glu Asn Ile Leu Phe Val Asn Ser
1               5                   10                  15

Asp Tyr Glu Leu Thr Tyr Asn Leu Glu Lys
            20                  25

<210> SEQ ID NO 43
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 43

Tyr Glu Ile Val Gly Asn Leu Gly Glu Gly Thr Phe Gly Lys Val Val
1               5                   10                  15

Glu Cys Leu Asp His Ala Arg
            20

<210> SEQ ID NO 44
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 44

Gly Ala Phe Gly Lys Val Tyr Leu Ala Gln Asp Ile Lys
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 45

Asp Ile Lys Cys Ser Asn Ile Leu Leu Asn Asn Ser Gly Gln Ile Lys
1               5                   10                  15

<210> SEQ ID NO 46
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 46

Val Ser Asp Phe Gly Leu Thr Lys Glu Ala Ser Ser Thr Gln Asp Thr
1               5                   10                  15

Gly Lys Leu Pro Val Lys
            20

<210> SEQ ID NO 47
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 47

Ile Asp Pro Val Pro Asn Thr His Pro Leu Leu Val Phe Val Asn Pro
1               5                   10                  15

Lys Ser Gly Gly Lys
            20

<210> SEQ ID NO 48
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 48

Ala Thr Phe Ser Phe Cys Val Ser Pro Leu Leu Val Phe Val Asn Ser
1               5                   10                  15

```
Lys Ser Gly Asp Asn Gln Gly Val Lys
            20              25

<210> SEQ ID NO 49
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 49

Asp Leu Lys Ser Pro Asn Met Leu Ile Thr Tyr Asp Asp Val Val Lys
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 50

Lys Gly Gly Ser Trp Ile Gln Glu Ile Asn Val Ala Glu Lys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 51

Glu His Pro Phe Leu Val Lys Gly Gly Glu Asp Leu Arg
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 52

Tyr Ile Lys Tyr Asn Ser Asn Ser Gly Phe Val Arg
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 53

Ile Pro Val Ala Ile Lys Glu Leu Arg
1               5

<210> SEQ ID NO 54
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 54
```

-continued

```
Tyr Leu Gln Asp Asp Thr Ser Asp Pro Thr Tyr Thr Ser Ser Leu Gly
1               5                   10                  15

Gly Lys Ile Pro Val Arg
            20

<210> SEQ ID NO 55
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 55

Phe Leu Glu Asp Asp Thr Ser Asp Pro Thr Tyr Thr Ser Ala Leu Gly
1               5                   10                  15

Gly Lys Ile Pro Ile Arg
            20

<210> SEQ ID NO 56
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 56

Asp Leu Lys Pro Ser Asn Leu Leu Ile Asn Thr Thr Cys Asp Leu Lys
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 57

Asp Leu Lys Pro Ser Asn Leu Leu Leu Asn Thr Thr Cys Asp Leu Lys
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 58

Asp Leu Lys Pro Ala Asn Leu Phe Ile Asn Thr Glu Asp Leu Val Leu
1               5                   10                  15

Lys

<210> SEQ ID NO 59
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 59

Asp Leu Lys Pro Ser Asn Leu Leu Val Asn Glu Asn Cys Glu Leu Lys
1               5                   10                  15

<210> SEQ ID NO 60
<211> LENGTH: 17
```

<212> TYPE: PRT
<213> ORGANISM: Artificial Sequence
<220> FEATURE:
<223> OTHER INFORMATION: Synthetic Polypeptide

<400> SEQUENCE: 60

Thr Ser Val Ala Val Lys Thr Cys Lys Glu Asp Leu Pro Gln Glu Leu
1               5                   10                  15

Lys

<210> SEQ ID NO 61
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 61

Leu Arg Ala Asp Asn Thr Leu Val Ala Val Lys Ser Cys Arg
1               5                   10

<210> SEQ ID NO 62
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 62

Leu Ile Lys Asp Asp Glu Tyr Asn Pro Cys Gln Gly Ser Lys Phe Pro
1               5                   10                  15

Ile Lys

<210> SEQ ID NO 63
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 63

Ile Gln Ser Ile Ala Pro Ser Leu Gln Val Ile Thr Ser Lys Gln Arg
1               5                   10                  15

Pro Arg

<210> SEQ ID NO 64
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 64

His Glu Ile Lys Leu Pro Val Lys
1               5

<210> SEQ ID NO 65
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 65

Val Ala Ile Lys Thr Leu Lys Pro Gly Thr Met Ser Pro Glu Ser Phe

```
1               5                   10                  15

Leu Glu Glu Ala Gln Ile Met Lys
            20

<210> SEQ ID NO 66
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 66

Gln Gly Ala Lys Phe Pro Ile Lys Trp Thr Ala Pro Glu Ala Ala Leu
1               5                   10                  15

Tyr Gly Arg

<210> SEQ ID NO 67
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 67

Asp Leu Lys Val Glu Asn Leu Leu Leu Ser Asn Gln Gly Thr Ile Lys
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 68

Asp Ile Lys Gly Ala Asn Leu Leu Leu Thr Leu Gln Gly Asp Val Lys
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 69

Asp Leu Lys Pro Val Asn Ile Phe Leu Asp Ser Asp Asp His Val Lys
1               5                   10                  15

<210> SEQ ID NO 70
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 70

Asp Ile Lys Pro Gln Asn Leu Leu Val Asp Pro Asp Thr Ala Val Leu
1               5                   10                  15

Lys

<210> SEQ ID NO 71
<211> LENGTH: 17
<212> TYPE: PRT
<213> ORGANISM: Artificial Sequence
```

<220> FEATURE:
<223> OTHER INFORMATION: Synthetic Polypeptide

<400> SEQUENCE: 71

Asp Ile Lys Pro Gln Asn Leu Leu Leu Asp Pro Asp Thr Ala Val Leu
1               5                   10                  15

Lys

<210> SEQ ID NO 72
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 72

Asp Ile Lys Gly Ala Asn Ile Leu Ile Asn Asp Ala Gly Glu Val Arg
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 73

Asp Leu Lys Pro Glu Asn Ile Val Leu Gln Asp Val Gly Gly Lys
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 74

Asp Leu Lys Pro Glu Asn Ile Val Leu Gln Gln Gly Glu Gln Arg
1               5                   10                  15

<210> SEQ ID NO 75
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 75

Ser Gly Glu Leu Val Ala Val Lys Val Phe Asn Thr Thr Ser Tyr Leu
1               5                   10                  15

Arg Pro Arg

<210> SEQ ID NO 76
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 76

Trp Gln Gly Asn Asp Ile Val Val Lys Val Leu Lys
1               5                   10

<210> SEQ ID NO 77

```
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 77

Ile Ser Met Ala Asp Val Lys Phe Ser Phe Gln Cys Pro Gly Arg
1               5                   10                  15

<210> SEQ ID NO 78
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 78

Ala Ile Gln Phe Leu His Gln Asp Ser Pro Ser Leu Ile His Gly Asp
1               5                   10                  15

Ile Lys Ser Ser Asn Val Leu Leu Asp Glu Arg
            20                  25

<210> SEQ ID NO 79
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 79

Val Glu Ile Gln Asn Leu Thr Tyr Ala Val Lys Leu Phe Lys
1               5                   10

<210> SEQ ID NO 80
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 80

Asp Ile Lys Ser Ala Asn Ile Leu Leu Asp Glu Ala Phe Thr Ala Lys
1               5                   10                  15

<210> SEQ ID NO 81
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 81

Asp Leu Lys Pro His Asn Ile Leu Ile Ser Met Pro Asn Ala His Gly
1               5                   10                  15

Lys

<210> SEQ ID NO 82
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 82

Glu Ser Ile Phe Phe Asn Ser His Asn Val Ser Lys Pro Glu Ser Ser
```

-continued

```
                1               5                  10                 15
Ser Val Leu Thr Glu Leu Asp Lys Ile Glu Gly Val Phe Glu Arg Pro
                20                 25                 30

Ser Asp Glu Val Ile Arg
                35

<210> SEQ ID NO 83
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 83

Gln Leu Ala Ser Ala Leu Ser Tyr Leu Glu Asp Lys Asp Leu Val His
1               5                  10                 15

Gly Asn Val Cys Thr Lys Asn Leu Leu Leu Ala Arg
                20                 25

<210> SEQ ID NO 84
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 84

Ile Gly Asp Phe Gly Leu Thr Lys Ala Ile Glu Thr Asp Lys Glu Tyr
1               5                  10                 15

Tyr Thr Val Lys
                20

<210> SEQ ID NO 85
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 85

Tyr Asp Pro Glu Gly Asp Asn Thr Gly Glu Gln Val Ala Val Lys Ser
1               5                  10                 15

Leu Lys Pro Glu Ser Gly Gly Asn His Ile Ala Asp Leu Lys Lys
                20                 25                 30

<210> SEQ ID NO 86
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 86

Ile Ala Asp Phe Gly Leu Ala Lys Leu Leu Pro Leu Asp Lys Asp Tyr
1               5                  10                 15

Tyr Val Val Arg
                20

<210> SEQ ID NO 87
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 87

Asp Leu Lys Pro Ser Asn Ile Val Val Lys
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 88

Asn Val His Thr Gly Glu Leu Ala Ala Val Lys Ile Ile Lys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 89

Asn Val Asn Thr Gly Glu Leu Ala Ala Ile Lys Val Ile Lys
1               5                   10

<210> SEQ ID NO 90
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 90

Ser Lys Asn Val Phe Tyr Asp Asn Gly Lys Val Val Ile Thr Asp Phe
1               5                   10                  15

Gly Leu Phe Gly Ile Ser Gly Val Val Arg
            20                  25

<210> SEQ ID NO 91
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 91

Ser Lys Asn Val Phe Tyr Asp Asn Gly Lys
1               5                   10

<210> SEQ ID NO 92
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 92

Ala Leu Tyr Ala Thr Lys Thr Leu Arg
1               5

<210> SEQ ID NO 93
<211> LENGTH: 16
<212> TYPE: PRT
<213> ORGANISM: Artificial Sequence
```

```
<220> FEATURE:
<223> OTHER INFORMATION: Synthetic Polypeptide

<400> SEQUENCE: 93

Asp Ile Lys Pro Asp Asn Ile Leu Ile Asp Leu Asp Gly His Ile Lys
1               5                   10                  15

<210> SEQ ID NO 94
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 94

Glu Gly Ala Lys Phe Pro Ile Lys Trp Thr Ala Pro Glu Ala Ile Asn
1               5                   10                  15

Tyr Gly Thr Phe Thr Ile Lys
            20

<210> SEQ ID NO 95
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 95

Asp Ile Lys Pro Gly Asn Leu Leu Leu Thr Thr Gly Gly Thr Leu Lys
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 96

Asp Leu Lys Ala Gly Asn Val Leu Met Thr Leu Glu Gly Asp Ile Arg
1               5                   10                  15

<210> SEQ ID NO 97
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 97

Asp Leu Lys Pro His Asn Val Leu Leu Phe Thr Leu Tyr Pro Asn Ala
1               5                   10                  15

Ala Ile Ile Ala Lys
            20

<210> SEQ ID NO 98
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 98

Val Ala Val Lys Thr Leu Lys Pro Gly Thr Met Ser Val Gln Ala Phe
1               5                   10                  15
```

Leu Glu Glu Ala Asn Leu Met Lys
            20

<210> SEQ ID NO 99
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 99

Ile Met His Arg Asp Val Lys Pro Ser Asn Ile Leu Val Asn Ser Arg
1               5                   10                  15

<210> SEQ ID NO 100
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 100

Lys Leu Ile His Leu Glu Ile Lys Pro Ala Ile Arg
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 101

Asp Val Lys Pro Ser Asn Ile Leu Val Asn Ser Arg
1               5                   10

<210> SEQ ID NO 102
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 102

His Gln Ile Met His Arg Asp Val Lys Pro Ser Asn Ile Leu Val Asn
1               5                   10                  15

Ser Arg

<210> SEQ ID NO 103
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 103

Asp Val Lys Pro Ser Asn Val Leu Ile Asn Lys
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 104

```
Asp Ile Lys Pro Ser Asn Ile Leu Leu Asp Arg
1               5                   10
```

<210> SEQ ID NO 105
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 105

```
Asp Val Lys Pro Ser Asn Met Leu Val Asn Thr Arg
1               5                   10
```

<210> SEQ ID NO 106
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 106

```
Asp Val Lys Pro Ser Asn Val Leu Ile Asn Ala Leu Gly Gln Val Lys
1               5                   10                  15
```

<210> SEQ ID NO 107
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 107

```
Asp Val Lys Pro Ser Asn Ile Leu Leu Asp Glu Arg
1               5                   10
```

<210> SEQ ID NO 108
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 108

```
Asp Val Lys Gly Ala Asn Leu Leu Ile Asp Ser Thr Gly Gln Arg
1               5                   10                  15
```

<210> SEQ ID NO 109
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 109

```
Glu Leu Ala Val Lys Gln Val Gln Phe Asp Pro Asp Ser Pro Glu Thr
1               5                   10                  15

Ser Lys Glu Val Asn Ala Leu Glu Cys Glu Ile Gln Leu Leu Lys
                20                  25                  30
```

<210> SEQ ID NO 110
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 110

Asp Ile Lys Gly Ala Asn Ile Leu Arg
1               5

<210> SEQ ID NO 111
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 111

Glu Leu Ala Ser Lys Gln Val Gln Phe Asp Pro Asp Ser Pro Glu Thr
1               5                   10                  15

Ser Lys Glu Val Ser Ala Leu Glu Cys Glu Ile Gln Leu Leu Lys
            20                  25                  30

<210> SEQ ID NO 112
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 112

Asp Ile Lys Gly Ala Asn Ile Phe Leu Thr Ser Ser Gly Leu Ile Lys
1               5                   10                  15

<210> SEQ ID NO 113
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 113

Asp Ile Lys Gly Asp Asn Val Leu Ile Asn Thr Tyr Ser Gly Val Leu
1               5                   10                  15

Lys

<210> SEQ ID NO 114
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 114

Asp Ile Lys Gly Asp Asn Val Leu Ile Asn Thr Phe Ser Gly Leu Leu
1               5                   10                  15

Lys

<210> SEQ ID NO 115
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 115

Asp Leu Lys Ala Glu Asn Leu Leu Leu Asp Ala Asp Met Asn Ile Lys
1               5                   10                  15
```

```
<210> SEQ ID NO 116
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 116

Glu Val Ala Ile Lys Ile Ile Asp Lys Thr Gln Leu Asn Pro Thr Ser
1               5                   10                  15

Leu Gln Lys

<210> SEQ ID NO 117
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 117

Glu Val Ala Ile Lys Ile Ile Asp Lys
1               5

<210> SEQ ID NO 118
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 118

Asp Leu Lys Ala Glu Asn Leu Leu Leu Asp Ala Glu Ala Asn Ile Lys
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 119

Asp Leu Lys Pro Asp Asn Leu Leu Ile Thr Ser Met Gly His Ile Lys
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 120

Asp Leu Lys Pro Asp Asn Leu Leu Ile Thr Ser Leu Gly His Ile Lys
1               5                   10                  15

<210> SEQ ID NO 121
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 121

Gly Ala Phe Gly Lys Val Tyr Leu Gly Gln Lys
1               5                   10
```

```
<210> SEQ ID NO 122
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 122

Leu Tyr Ala Val Lys Val Val Lys
1               5

<210> SEQ ID NO 123
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 123

Asp Leu Lys Pro Glu Asn Leu Leu Phe Asp Glu Tyr His Lys
1               5                   10

<210> SEQ ID NO 124
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 124

Asn Cys Met Leu Arg Asp Asp Met Thr Val Cys Val Ala Asp Phe Gly
1               5                   10                  15

Leu Ser Lys Lys
            20

<210> SEQ ID NO 125
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 125

Lys Ile Tyr Ser Gly Asp Tyr Tyr Arg
1               5

<210> SEQ ID NO 126
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 126

Asp Met Tyr Asp Lys Glu Tyr Tyr Ser Val His Asn Lys
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 127

Asp Leu Lys Ser Ser Asn Ile Leu Ile Leu Gln Lys
```

```
<210> SEQ ID NO 128
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 128

Asp Leu Lys Ser Asn Asn Ile Leu Leu Leu Gln Pro Ile Glu Ser Asp
1               5                   10                  15

Asp Met Glu His Lys
            20

<210> SEQ ID NO 129
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 129

Asp Leu Lys Ser Ser Asn Ile Leu Leu Leu Glu Lys
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 130

Ala Pro Val Ala Ile Lys Val Phe Lys
1               5

<210> SEQ ID NO 131
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 131

Asp Leu Lys Pro Thr Asn Ile Leu Leu Gly Asp Glu Gly Gln Pro Val
1               5                   10                  15

Leu Met Asp Leu Gly Ser Met Asn Gln Ala Cys Ile His Val Glu Gly
            20                  25                  30

Ser Arg

<210> SEQ ID NO 132
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 132

Asp Ile Lys Leu Glu Asn Ile Leu Leu Asp Ser Asn Gly His Val Val
1               5                   10                  15

Leu Thr Asp Phe Gly Leu Ser Lys
            20
```

```
<210> SEQ ID NO 133
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 133

Asp Leu Lys Leu Glu Asn Val Leu Leu Asp Ser Glu Gly His Ile Val
1               5                   10                  15

Leu Thr Asp Phe Gly Leu Ser Lys
            20

<210> SEQ ID NO 134
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 134

Glu Thr Gly Gln Ile Val Ala Ile Lys Gln Val Pro Val Glu Ser Asp
1               5                   10                  15

Leu Gln Glu Ile Ile Lys
            20

<210> SEQ ID NO 135
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 135

Glu Ser Gly Gln Val Val Ala Ile Lys Gln Val Pro Val Glu Ser Asp
1               5                   10                  15

Leu Gln Glu Ile Ile Lys
            20

<210> SEQ ID NO 136
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 136

Asp Ile Lys Ala Ala Asn Val Leu Leu Ser Glu His Gly Glu Val Lys
1               5                   10                  15

<210> SEQ ID NO 137
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 137

Thr Gln Gln Val Val Ala Ile Lys Ile Ile Asp Leu Glu Glu Ala Glu
1               5                   10                  15

Asp Glu Ile Glu Asp Ile Gln Gln Glu Ile Thr Val Leu Ser Gln Cys
            20                  25                  30

Asp Ser Ser Tyr Val Thr Lys
        35
```

<210> SEQ ID NO 138
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 138

Asp Ile Lys Ala Ala Asn Val Leu Leu Ser Glu Gln Gly Asp Val Lys
1               5                   10                  15

<210> SEQ ID NO 139
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 139

Asp Ile Lys Pro Asp Asn Leu Leu Leu Asp Ser Lys
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 140

Asp Ile Lys Pro Asp Asn Leu Leu Leu Asp Ala Lys
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 141

Asp Ile Lys Ser Gln Asn Ile Phe Leu Thr Lys
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 142

Asp Leu Lys Pro Ala Asn Val Phe Leu Asp Gly Lys
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 143

Ser Lys Asn Ile Phe Leu Thr Gln Asn Gly Lys
1               5                   10

-continued

```
<210> SEQ ID NO 144
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 144

Asp Leu Lys Thr Gln Asn Val Phe Leu Thr Arg
1               5                   10

<210> SEQ ID NO 145
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 145

Asp Ile Lys Pro Ala Asn Val Phe Ile Thr Ala Thr Gly Val Val Lys
1               5                   10                  15

<210> SEQ ID NO 146
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 146

Ala Ala Cys Leu Leu Asp Gly Val Pro Val Ala Leu Lys Lys
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 147

Asp Leu Lys Thr Gln Asn Ile Leu Leu Asp Lys
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 148

Asp Ile Lys Thr Leu Asn Ile Phe Leu Thr Lys
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 149

Asp Ile Lys Pro Gly Asn Leu Leu Val Asn Ser Asn Cys Val Leu Lys
1               5                   10                  15

<210> SEQ ID NO 150
```

<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 150

Asp Val Lys Ala Gly Asn Ile Leu Leu Gly Glu Asp Gly Ser Val Gln
1               5                   10                  15

Ile Ala Asp Phe Gly Val Ser Ala Phe Leu Ala Thr Gly Gly Asp Ile
            20                  25                  30

Thr Arg

<210> SEQ ID NO 151
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 151

Asp Leu Lys Pro Ser Asn Leu Ala Val Asn Glu Asp Cys Glu Leu Lys
1               5                   10                  15

<210> SEQ ID NO 152
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 152

Gln Glu Leu Asn Lys Thr Ile Trp Glu Val Pro Glu Arg
1               5                   10

<210> SEQ ID NO 153
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 153

Asp Leu Lys Pro Gly Asn Leu Ala Val Asn Glu Asp Cys Glu Leu Lys
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 154

Asp Leu Lys Pro Glu Asn Ile Met Leu Asn His Gln Gly His Val Lys
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 155

Asp Leu Lys Pro Glu Asn Ile Met Leu Ser Ser Gln Gly His Ile Lys

<210> SEQ ID NO 156
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 156

Val Met Asp Pro Thr Lys Ile Leu Ile Thr Gly Lys
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 157

Ser Lys Leu Thr Asp Asn Leu Val Ala Leu Lys Glu Ile Arg
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 158

Ser Lys Leu Thr Glu Asn Leu Val Ala Leu Lys Glu Ile Arg
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 159

Glu Tyr Ala Ile Lys Ile Leu Glu Lys
1               5

<210> SEQ ID NO 160
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 160

Asp Leu Lys Pro Ser Asn Ile Phe Phe Thr Met Asp Asp Val Val Lys
1               5                   10                  15

<210> SEQ ID NO 161
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 161

Leu Val Ala Leu Lys Val Ile Arg
1               5

```
<210> SEQ ID NO 162
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 162

Asp Leu Lys Pro Glu Asn Ile Leu Leu Asp Asp Asn Met Asn Ile Lys
1               5                   10                  15

<210> SEQ ID NO 163
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 163

Ala Thr Gly His Glu Phe Ala Val Lys Ile Met Glu Val Thr Ala Glu
1               5                   10                  15

Arg

<210> SEQ ID NO 164
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 164

Ser Glu Glu Pro Tyr Gly Gln Leu Asn Pro Lys Trp Thr Lys
1               5                   10

<210> SEQ ID NO 165
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 165

Ser Gly Thr Pro Met Gln Ser Ala Ala Lys Ala Pro Tyr Leu Ala Lys
1               5                   10                  15

<210> SEQ ID NO 166
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 166

Val Pro His Thr Gln Ala Val Val Leu Asn Ser Lys Asp Lys
1               5                   10

<210> SEQ ID NO 167
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 167

Val Ile Phe Lys Cys Gly Asp Asp Leu Arg Gln Asp Met Leu Thr Leu
```

```
1               5                   10                  15

Gln Met Ile Arg
            20

<210> SEQ ID NO 168
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 168

Thr Glu Asp Gly Gly Lys Tyr Pro Val Ile Phe Lys His Gly Asp Asp
1               5                   10                  15

Leu Arg

<210> SEQ ID NO 169
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 169

Val Phe Gly Glu Asp Ser Val Gly Val Ile Phe Lys Asn Gly Asp Asp
1               5                   10                  15

Leu Arg Gln Asp Met Leu Thr Leu Gln Met Leu Arg
            20                  25

<210> SEQ ID NO 170
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 170

Val Asn Trp Leu Ala His Asn Val Ser Lys Asp Asn Arg Gln
1               5                   10

<210> SEQ ID NO 171
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 171

Lys Lys Pro Leu Trp Leu Glu Phe Lys
1               5

<210> SEQ ID NO 172
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 172

Ala Lys Glu Leu Pro Thr Leu Lys Asp Asn Asp Phe Ile Asn Glu Gly
1               5                   10                  15

Gln Lys

<210> SEQ ID NO 173
```

```
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 173

Ala Lys Asp Leu Pro Thr Phe Lys Asp Asn Asp Phe Leu Asn Glu Gly
1               5                   10                  15

Gln Lys

<210> SEQ ID NO 174
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 174

Thr Leu Val Ile Lys Glu Val Ser Ser Glu Asp Ile Ala Asp Met His
1               5                   10                  15

Ser Asn Leu Ser Asn Tyr His Gln Tyr Ile Val Lys
            20                  25

<210> SEQ ID NO 175
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 175

Glu Lys Pro Leu Pro Thr Phe Lys Asp Leu Asp Phe Leu Gln Asp Ile
1               5                   10                  15

Pro Asp Gly Leu Phe Leu Asp Ala Asp Met Tyr Asn Ala Leu Cys Lys
            20                  25                  30

<210> SEQ ID NO 176
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 176

Gly Gly Lys Ser Gly Ala Ala Phe Tyr Ala Thr Glu Asp Asp Arg Phe
1               5                   10                  15

Ile Leu Lys

<210> SEQ ID NO 177
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 177

Asp Leu Lys Thr Ser Asn Leu Leu Leu Ser His Ala Gly Ile Leu Lys
1               5                   10                  15

<210> SEQ ID NO 178
<211> LENGTH: 24
<212> TYPE: PRT
<213> ORGANISM: Artificial Sequence
<220> FEATURE:
```

```
<223> OTHER INFORMATION: Synthetic Polypeptide

<400> SEQUENCE: 178

Asp Leu Lys Pro Glu Asn Leu Leu Ile Asp Gln Gln Gly Tyr Ile Gln
1               5                   10                  15

Val Thr Asp Phe Gly Phe Ala Lys
            20

<210> SEQ ID NO 179
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 179

Asp Leu Lys Leu Asp Asn Val Met Leu Asp Ser Glu Gly His Ile Lys
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 180

Asp Leu Lys Leu Asp Asn Ile Leu Leu Asp Ala Glu Gly His Cys Lys
1               5                   10                  15

<210> SEQ ID NO 181
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 181

Ile Tyr Ala Met Lys Val Val Lys
1               5

<210> SEQ ID NO 182
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 182

Gly Ser Phe Gly Lys Val Phe Leu Ala Glu Phe Lys
1               5                   10

<210> SEQ ID NO 183
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 183

Asp Val Ala Val Lys Val Ile Asp Lys
1               5

<210> SEQ ID NO 184
<211> LENGTH: 9
<212> TYPE: PRT
```

```
<213> ORGANISM: Artificial Sequence
<220> FEATURE:
<223> OTHER INFORMATION: Synthetic Polypeptide

<400> SEQUENCE: 184

Asp Val Ala Ile Lys Val Ile Asp Lys
1               5

<210> SEQ ID NO 185
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 185

Val Leu Leu Ser Glu Phe Arg Pro Ser Gly Glu Leu Phe Ala Ile Lys
1               5                   10                  15

Ala Leu Lys

<210> SEQ ID NO 186
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 186

Asp Leu Lys Leu Asp Asn Leu Leu Leu Asp Thr Glu Gly Phe Val Lys
1               5                   10                  15

<210> SEQ ID NO 187
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 187

Asp Leu Lys Pro Ser Asn Ile Phe Leu Val Asp Thr Lys
1               5                   10

<210> SEQ ID NO 188
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 188

Cys Phe Glu Ile Ser Asp Ala Asp Thr Lys Glu Val Phe Ala Gly Lys
1               5                   10                  15

Ile Val Pro Lys
            20

<210> SEQ ID NO 189
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 189

Cys Asn Ile Leu His Ala Asp Ile Lys Pro Asp Asn Ile Leu Val Asn
1               5                   10                  15
```

Glu Ser Lys

<210> SEQ ID NO 190
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 190

Phe Leu Ser Gly Leu Glu Leu Val Lys Gln Gly Ala Glu Ala Arg
1               5                   10                  15

<210> SEQ ID NO 191
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 191

Tyr Ile Glu Asp Glu Asp Tyr Tyr Lys Ala Ser Val Thr Arg
1               5                   10

<210> SEQ ID NO 192
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 192

Asp Leu Lys Ala Glu Asn Leu Leu Leu Asp Ala Asn Leu Asn Ile Lys
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 193

Asp Met Lys Ser Asn Asn Ile Phe Leu His Glu Gly Leu Thr Val Lys
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 194

Asp Leu Lys Pro Ser Asn Val Leu Leu Asp Pro Glu Leu His Val Lys
1               5                   10                  15

<210> SEQ ID NO 195
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 195

Lys Leu Gln Leu Glu Leu Asn Gln Glu Arg
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 196

Asp Val Lys Pro Asp Asn Met Leu Leu Asp Lys
1               5                   10

<210> SEQ ID NO 197
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 197

Asp Leu Lys Pro Glu Asn Ile Leu Leu Asp Glu Glu Gly His Ile Lys
1               5                   10                  15

Leu Thr Asp Phe Gly Leu Ser Lys Glu Ala Ile Asp His Glu Lys
            20                  25                  30

<210> SEQ ID NO 198
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 198

Asp Leu Lys Pro Glu Asn Ile Leu Leu Asp Glu Glu Gly His Ile Lys
1               5                   10                  15

<210> SEQ ID NO 199
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 199

Asp Leu Lys Pro Ser Asn Ile Leu Tyr Val Asp Glu Ser Gly Asn Pro
1               5                   10                  15

Glu Cys Leu Arg
            20

<210> SEQ ID NO 200
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 200

Asp Leu Lys Pro Glu Asn Ile Leu Leu Asp Glu Glu Gly His Ile Lys
1               5                   10                  15

Leu Thr Asp Phe Gly Leu Ser Lys Glu Ser Ile Asp His Glu Lys
            20                  25                  30

<210> SEQ ID NO 201
<211> LENGTH: 20
<212> TYPE: PRT

```
<213> ORGANISM: Artificial Sequence
<220> FEATURE:
<223> OTHER INFORMATION: Synthetic Polypeptide

<400> SEQUENCE: 201

Asp Leu Lys Pro Ser Asn Ile Leu Tyr Val Asp Glu Ser Gly Asn Pro
1               5                   10                  15

Glu Ser Ile Arg
            20

<210> SEQ ID NO 202
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 202

Asp Leu Lys Pro Glu Asn Ile Leu Leu Asp Glu Glu Gly His Ile Lys
1               5                   10                  15

Ile Thr Asp Phe Gly Leu Ser Lys
            20

<210> SEQ ID NO 203
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 203

Asp Leu Lys Pro Glu Asn Ile Leu Leu Asp Glu Ile Gly His Ile Lys
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 204

Val Leu Gly Val Ile Asp Lys Val Leu Leu Val Met Asp Thr Arg
1               5                   10                  15

<210> SEQ ID NO 205
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 205

Phe Tyr Ala Val Lys Val Leu Gln Lys
1               5

<210> SEQ ID NO 206
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 206

Asp Leu Lys Ala Gly Asn Ile Leu Phe Thr Leu Asp Gly Asp Ile Lys
1               5                   10                  15
```

<210> SEQ ID NO 207
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 207

Asp Thr Val Thr Ile His Ser Val Gly Gly Thr Ile Thr Ile Leu Pro
1               5                   10                  15

Thr Lys Thr Lys Pro Lys
            20

<210> SEQ ID NO 208
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 208

Asp Leu Lys Pro Glu Asn Val Val Phe Phe Glu Lys
1               5                   10

<210> SEQ ID NO 209
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 209

Val Ala Ile Lys Thr Leu Lys Pro Gly Thr Met Ser Pro Glu Ala Phe
1               5                   10                  15

Leu Gln Glu Ala Gln Val Met Lys Lys
            20                  25

<210> SEQ ID NO 210
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 210

Ile Ile His Thr Asp Ile Lys Pro Glu Asn Ile Leu Leu Ser Val Asn
1               5                   10                  15

Glu Gln Tyr Ile Arg
            20

<210> SEQ ID NO 211
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 211

Phe Val Ala Met Lys Val Val Lys
1               5

<210> SEQ ID NO 212
<211> LENGTH: 10
<212> TYPE: PRT

```
<213> ORGANISM: Artificial Sequence
<220> FEATURE:
<223> OTHER INFORMATION: Synthetic Polypeptide

<400> SEQUENCE: 212

Asp Leu Lys Leu Glu Asn Ile Met Val Lys
1               5                   10

<210> SEQ ID NO 213
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 213

Tyr Ser Val Lys Val Leu Pro Trp Leu Ser Pro Glu Val Leu Gln Gln
1               5                   10                  15

Asn Leu Gln Gly Tyr Asp Ala Lys
            20

<210> SEQ ID NO 214
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 214

His Thr Pro Thr Gly Thr Leu Val Thr Ile Lys Ile Thr Asn Leu Glu
1               5                   10                  15

Asn Cys Asn Glu Glu Arg
            20

<210> SEQ ID NO 215
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 215

Ile Ser Asp Phe Gly Leu Ser Lys Ala Leu Arg
1               5                   10

<210> SEQ ID NO 216
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 216

Asp Leu Lys Pro Pro Asn Leu Leu Leu Val Ala Gly Gly Thr Val Leu
1               5                   10                  15

Lys

<210> SEQ ID NO 217
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 217
```

```
Asp Ile Lys Ala Gly Asn Ile Leu Leu Thr Glu Pro Gly Gln Val Lys
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 218

Asp Val Lys Ala Gly Asn Ile Leu Leu Ser Glu Pro Gly Leu Val Lys
1               5                   10                  15

<210> SEQ ID NO 219
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 219

Thr Gly Asp Leu Phe Ala Ile Lys Val Phe Asn Asn Ile Ser Phe Leu
1               5                   10                  15

Arg Pro Val Asp Val Gln Met Arg
            20

<210> SEQ ID NO 220
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 220

Tyr Val Leu Asp Asp Gln Tyr Thr Ser Ser Ser Gly Ala Lys Phe Pro
1               5                   10                  15

Val Lys

<210> SEQ ID NO 221
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 221

Tyr Leu Asn Glu Ile Lys Pro Pro Ile Ile His Tyr Asp Leu Lys Pro
1               5                   10                  15

Gly Asn Ile Leu Leu Val Asp Gly Thr Ala Cys Gly Glu Ile Lys
            20                  25                  30

<210> SEQ ID NO 222
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 222

Tyr Leu Asn Glu Ile Lys Pro Pro Ile Ile His Tyr Asp Leu Lys Pro
1               5                   10                  15

Gly Asn Ile Leu Leu Val Asn Gly Thr Ala Cys Gly Glu Ile Lys
            20                  25                  30
```

<210> SEQ ID NO 223
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 223

Ile Gly Asp Phe Gly Leu Ala Lys Ala Val Pro Glu Gly His Glu Tyr
1               5                   10                  15

Tyr Arg

<210> SEQ ID NO 224
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 224

Asp Leu Lys Pro Gln Asn Ile Leu Leu Ser Asn Pro Ala Gly Arg
1               5                   10                  15

<210> SEQ ID NO 225
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 225

Asn Ile Ser His Leu Asp Leu Lys Pro Gln Asn Ile Leu Leu Ser Ser
1               5                   10                  15

Leu Glu Lys Pro His Leu Lys
            20

<210> SEQ ID NO 226
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 226

Met Leu Asp Val Leu Glu Tyr Ile His Glu Asn Glu Tyr Val His Gly
1               5                   10                  15

Asp Ile Lys Ala Ala Asn Leu Leu Leu Gly Tyr Lys
            20                  25

<210> SEQ ID NO 227
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 227

Tyr Ile His Ser Met Ser Leu Val His Met Asp Ile Lys Pro Ser Asn
1               5                   10                  15

Ile Phe Ile Ser Arg
            20

<210> SEQ ID NO 228
<211> LENGTH: 8

```
<212> TYPE: PRT
<213> ORGANISM: Artificial Sequence
<220> FEATURE:
<223> OTHER INFORMATION: Synthetic Polypeptide

<400> SEQUENCE: 228

Gly Ser Phe Lys Thr Val Tyr Lys
1               5

<210> SEQ ID NO 229
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 229

Asp Leu Lys Cys Asp Asn Ile Phe Ile Thr Gly Pro Thr Gly Ser Val
1               5                   10                  15

Lys

<210> SEQ ID NO 230
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 230

Asp Val Lys Pro Asp Asn Ile Leu Leu Asp Glu Arg
1               5                   10

<210> SEQ ID NO 231
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 231

Glu Val Val Ala Ile Lys Ile Ile Asp Leu Glu Glu Ala Glu Asp Glu
1               5                   10                  15

Ile Glu Asp Ile Gln Gln Glu Ile Thr Val Leu Ser Gln Cys Asp Ser
            20                  25                  30

Pro Tyr Ile Thr Arg
        35

<210> SEQ ID NO 232
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 232

Trp Ile Ser Gln Asp Lys Glu Val Ala Val Lys Lys
1               5                   10

<210> SEQ ID NO 233
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 233
```

```
Thr Gly Gln Leu Ala Ala Ile Lys Val Met Asp Val Thr Glu Asp Glu
1               5                   10                  15

Glu Glu Glu Ile Lys Leu Glu Ile Asn Met Leu Lys Lys
            20                  25

<210> SEQ ID NO 234
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 234

Asp Ile Lys Gly Gln Asn Val Leu Leu Thr Glu Asn Ala Glu Val Lys
1               5                   10                  15

<210> SEQ ID NO 235
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 235

Thr Gly Gln Leu Ala Ala Ile Lys Val Met Asp Val Thr Gly Asp Glu
1               5                   10                  15

Glu Glu Glu Ile Lys Gln Glu Ile Asn Met Leu Lys Lys
            20                  25
```

THIAZOLYL-CONTAINING COMPOUNDS FOR TREATING PROLIFERATIVE DISEASES

RELATED APPLICATIONS

This application is a national stage filing under 35 U.S.C. § 371 of international PCT application, PCT/US2015/056899, filed Oct. 22, 2015, which claims priority under 35 U.S.C. § 119(e) to U.S. Provisional Application Ser. No., 62/067,178, filed Oct. 22, 2014, each of which is incorporated herein by reference.

GOVERNMENT SUPPORT

This invention was made with government support under grant number 2 P50 CA100707-11A1 awarded by the National Institutes of Health. The government has certain rights in the invention.

BACKGROUND OF THE INVENTION

Hematological malignancies are types of cancers that affect the blood, the bone marrow, and/or the lymph nodes. Hematological malignancies derive from either of the two major blood cell lineages: the myeloid and lymphoid lineages. The myeloid lineage normally produces granulocytes, erythrocytes, thrombocytes, macrophages, and mast cells; and the lymphoid lineage produces B, T, Natural Killer (NK), and plasma cells. Acute and chronic myelogenous leukemia, myelodysplasia, and myeloproliferative diseases are examples of hematological malignancies of myeloid origin; and lymphomas, lymphocytic leukemias, and myeloma are examples of hematological malignancies of the lymphoid lineage.

Myelodysplasia, also known as myelodysplastic syndrome (MDS), is a hematological malignancy with ineffective production (or dysplasia) of the myeloid class of blood cells.

Lymphomas include Hodgkin lymphoma (HL), non-Hodgkin lymphoma (NHL), multiple myeloma, and immunoproliferative diseases. Waldenström's macroglobulinemia (WM) is a rare, slow-growing, non-Hodgkin lymphoma. WM is also called lymphoplasmacytic lymphoma. Lymphoplasmacytic cells are cells that are in the process of maturing from B cells to plasma cells. In WM, abnormal lymphoplasmacytic cells multiply out of control, producing large amounts of a protein called monoclonal immunoglobulin M (IgM or "macroglobulin") antibody. High levels of IgM in the blood cause hyperviscosity (thickness or gumminess).

Diffuse large B-cell lymphoma (DLBCL or DLBL) is a malignancy of B cells. Usually DLBCL arises from normal B cells, but it can also represent a malignant transformation of other types of lymphoma or leukemia. An underlying immunodeficiency is a significant risk factor.

Central nervous system (CNS) lymphoma is a rare non-Hodgkin lymphoma in which malignant cells from lymph tissue form in the brain, spinal cord, meninges, and/or eye (primary CNS lymphoma) or spread from other parts of the body to the brain and/or spinal cord (secondary CNS lymphoma).

Lymphomas of an immune privileged site include, but are not limited to, cerebral lymphoma, ocular lymphoma, lymphoma of the placenta, lymphoma of the fetus, and testicular lymphoma.

Marginal zone lymphomas are a group of slow-growing, non-Hodgkin B-cell lymphomas presenting primarily in the marginal zone. There are three types of marginal zone lymphomas: Splenic marginal zone lymphoma, extranodal marginal zone B cell lymphoma (mucosa-associated lymphoid tissue (MALT) lymphoma), and nodal marginal zone B cell lymphoma (NMZL).

Leukemias are malignancies of the white blood cells (leukocytes). Chronic lymphoid leukemia (CLL) is the most common type of leukemia in adults. CLL affects B cell lymphocytes. In a subject with CLL, B cells grow out of control, accumulate in the bone marrow and blood, and crowd out healthy blood cells.

There is a need for novel therapies of hematological malignancies.

SUMMARY OF THE INVENTION

The present disclosure provides thiazolyl-containing compounds, such as compounds of Formula (I), (II), or (III). In certain embodiments, the compounds described herein are able to inhibit of protein kinases (e.g., Src family kinases (e.g., hemopoietic cell kinase (HCK)), Bruton's tyrosine kinase (BTK)). The compounds may be useful in treating and/or preventing proliferative diseases (e.g., myelodysplasia, leukemia, lymphoma (e.g., Waldenström's macroglobulinemia)). Without wishing to be bound by any particular theory, the compounds may act by inducing apoptosis of a cell (e.g., malignant blood cell). Also provided in the present disclosure are pharmaceutical compositions, kits, methods, and uses including a compound described herein.

In one aspect, the present disclosure provides compounds of Formula (I):

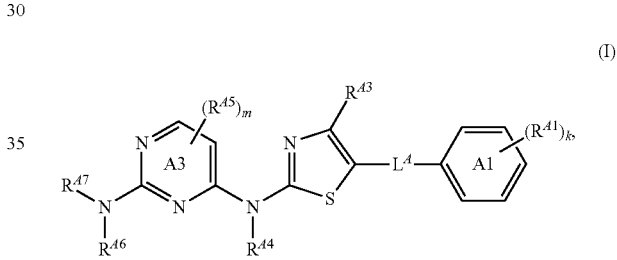

and pharmaceutically acceptable salts, solvates, hydrates, polymorphs, co-crystals, tautomers, stereoisomers, isotopically labeled derivatives, and prodrugs thereof, wherein Ring A1, $R^{A1}$, k, $L^A$, $R^{A3}$, Ring A3, $R^{A4}$, $R^{A5}$, m, $R^{A6}$, and $R^{A7}$ are described herein.

Exemplary compounds of Formula (I) include, but are not limited to:

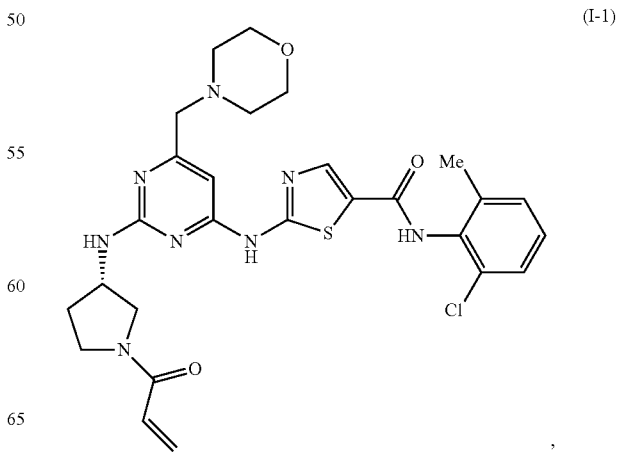

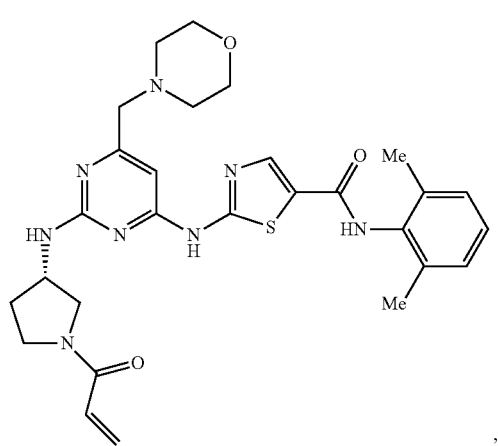
(I-2)
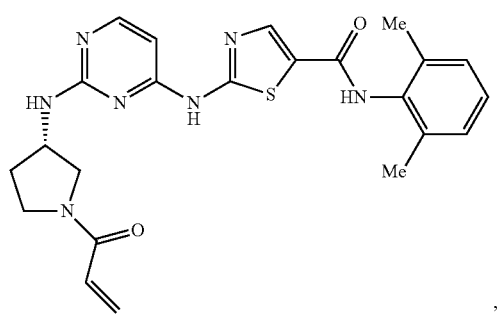
(I-3)
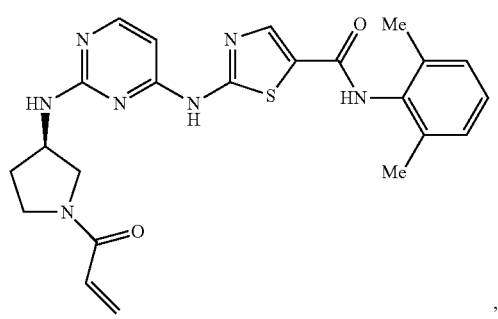
(I-4)
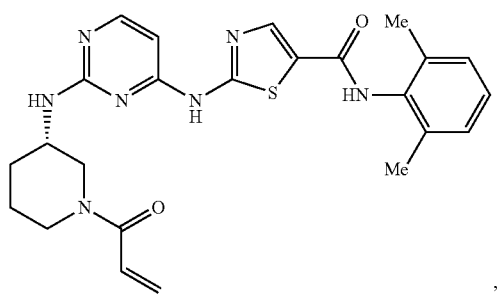
(I-5)
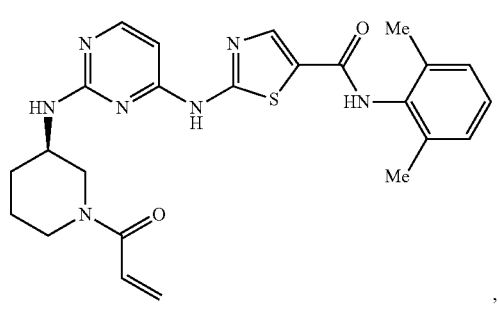
(I-6)
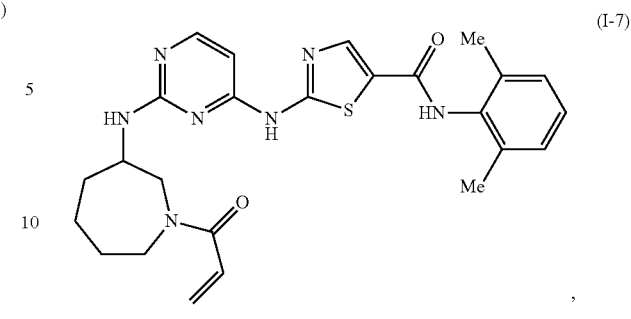
(I-7)
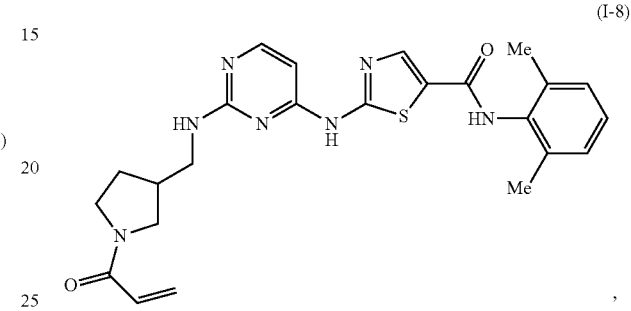
(I-8)
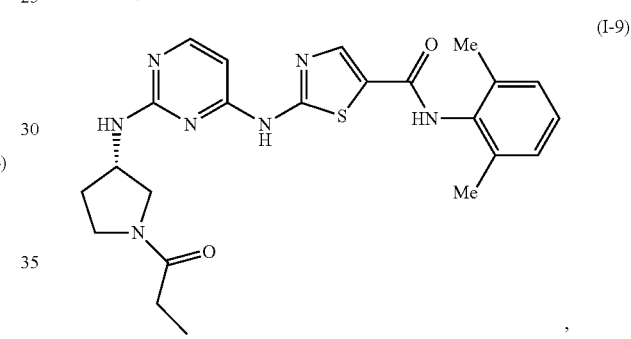
(I-9)
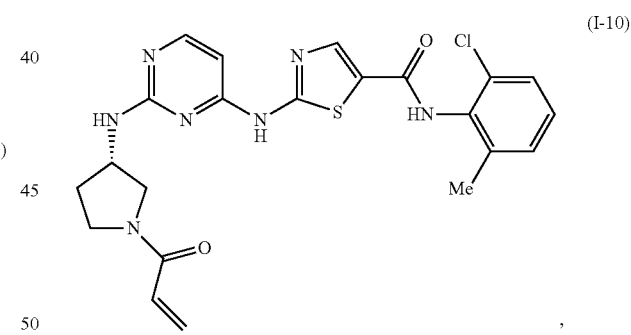
(I-10)
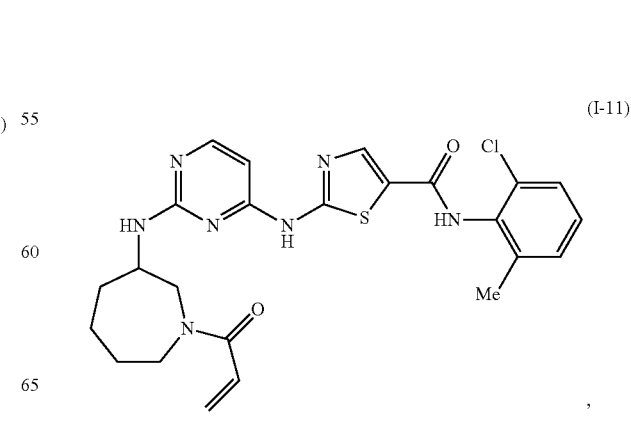
(I-11)

(I-12)

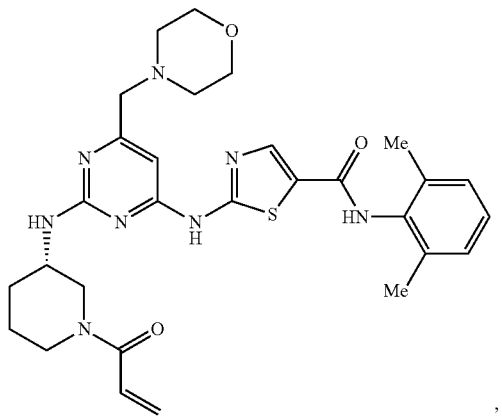

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (II):

(II)

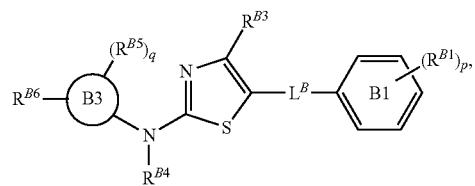

and pharmaceutically acceptable salts, solvates, hydrates, polymorphs, co-crystals, tautomers, stereoisomers, isotopically labeled derivatives, and prodrugs thereof, wherein Ring B1, $R^{B1}$, p, $L^B$, $R^{B3}$, $R^{B4}$, Ring B3, $R^{B5}$, q, and $R^{B6}$ are described herein.

Exemplary compounds of Formula (II) include, but are not limited to:

(II-1)

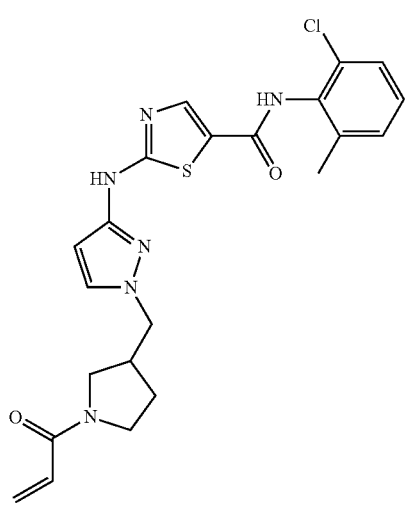

(II-2)

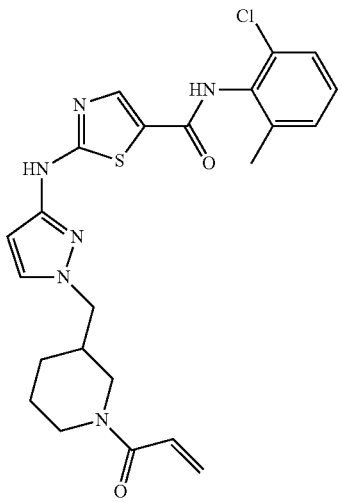

(II-3)

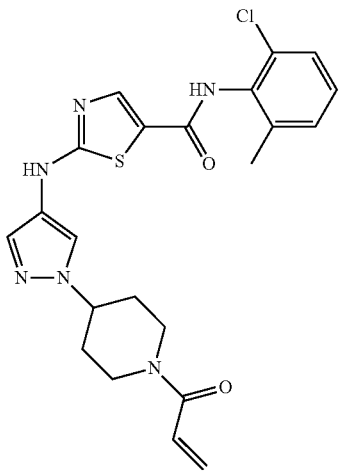

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (III):

(III)

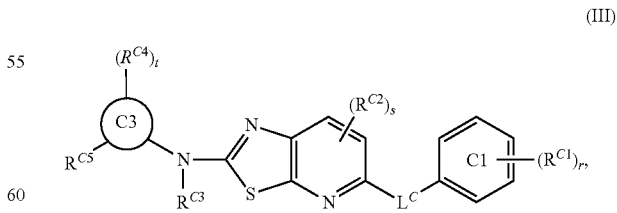

and pharmaceutically acceptable salts, solvates, hydrates, polymorphs, co-crystals, tautomers, stereoisomers, isotopically labeled derivatives, and prodrugs thereof, wherein Ring C1, $R^{C1}$, r, $L^C$, $R^{C2}$, s, $R^{C3}$, Ring C3, $R^{C4}$, t, and $R^{C5}$ are described herein.

Exemplary compounds of Formula (III) include, but are not limited to:
(III-1)
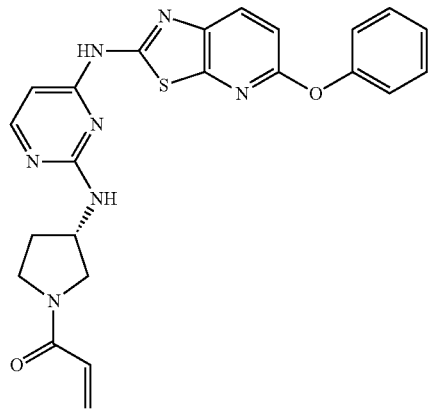
(III-2)
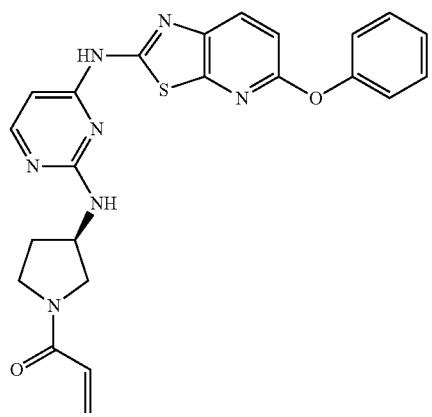
(III-3)
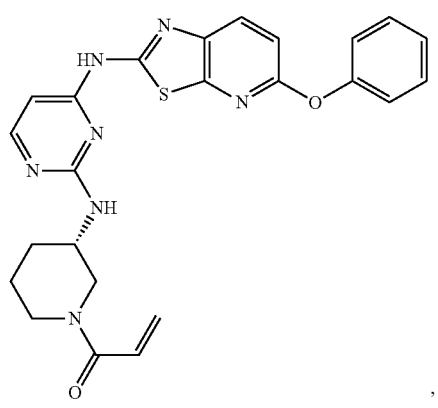
(III-4)
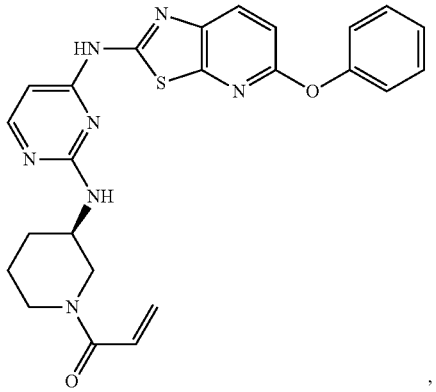
(III-5)
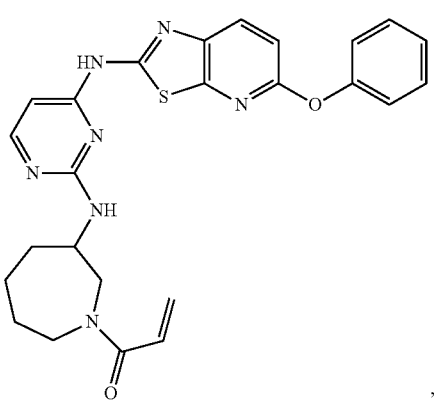
(III-6)
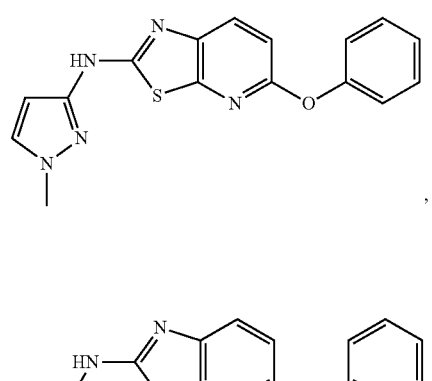
(III-7)
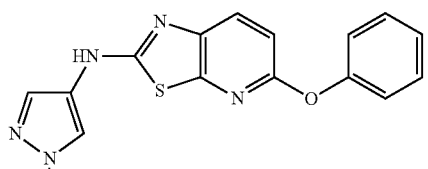
(III-8)
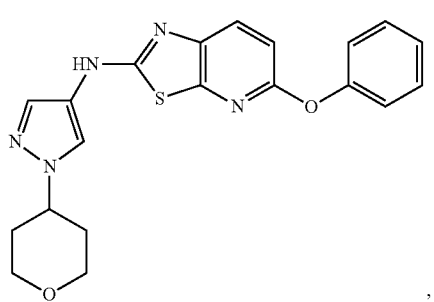

-continued

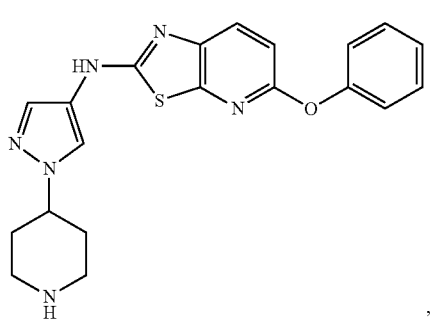

(III-9)

and pharmaceutically acceptable salts, solvates, hydrates, polymorphs, co-crystals, tautomers, stereoisomers, isotopically labeled derivatives, and prodrugs thereof.

In still another aspect, the present disclosure provides pharmaceutical compositions including a compound described herein, and optionally a pharmaceutically acceptable excipient. In certain embodiments, the pharmaceutical compositions described herein include an effective amount of a compound described herein. An effective amount described herein may be a therapeutically effective amount or prophylactically effective amount. The pharmaceutical composition may be useful for treating a proliferative disease in a subject in need thereof, preventing a proliferative disease in a subject in need thereof, inhibiting the activity of a protein kinase in a subject, biological sample, tissue, or cell, and/or inducing apoptosis in a cell.

In certain embodiments, a proliferative disease described herein is myelodysplasia, leukemia (e.g., chronic lymphocytic leukemia (CLL)), lymphoma (e.g., Waldenström's macroglobulinemia, activated B-cell (ABC) diffuse large B-cell lymphoma (DLBCL), central nervous system (CNS) lymphoma, lymphoma of an immune privileged site, testicular lymphoma, or marginal zone lymphoma).

In certain embodiments, the subject is a mammal (e.g., human or non-human mammal). In certain embodiments, the cell is in vitro or in vivo. In certain embodiments, the cell is a malignant blood cell.

In certain embodiments, the protein kinase is a Src family kinase (e.g., HCK) or BTK.

Another aspect of the present disclosure relates to methods of treating a proliferative disease in a subject in need thereof.

In another aspect, the present disclosure provides methods of preventing a proliferative disease in a subject in need thereof.

In another aspect, the present disclosure provides methods of inhibiting the activity (e.g., aberrant activity or increased activity) of a protein kinase in a subject, biological sample, tissue, or cell. In certain embodiments, the activity of the protein kinase is selectively inhibited, compared to the activity of a different protein kinase.

In yet another aspect, the present disclosure provides methods of inducing apoptosis in a cell.

In certain embodiments, a method described herein includes administering to the subject an effective amount of a compound or pharmaceutical composition described herein. In certain embodiments, a method described herein includes contacting a cell with an effective amount of a compound or pharmaceutical composition described herein. In certain embodiments, a method described herein further includes administering to the subject an additional pharmaceutical agent. In certain embodiments, a method described herein further includes contacting the cell with an additional pharmaceutical agent. In certain embodiments, a method described herein further includes performing a radiotherapy, immunotherapy, and/or transplantation on the subject.

Another aspect of the disclosure relates to methods of screening a library of compounds to identify a compound that is useful in a method of the disclosure.

Another aspect of the present disclosure relates to kits comprising a container with a compound or pharmaceutical composition described herein. The kits described herein may include a single dose or multiple doses of the compound or pharmaceutical composition. The kits may be useful in a method of the disclosure. In certain embodiments, the kit further includes instructions for using the compound or pharmaceutical composition.

In yet another aspect, the present disclosure provides compounds and pharmaceutical compositions described herein for use in a method of the disclosure.

The details of one or more embodiments of the disclosure are set forth herein. Other features, objects, and advantages of the disclosure will be apparent from the Detailed Description, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{r}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw—Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight—chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight—chain or branched hydrocarbon group having from 2 to 20 carbon atoms, one or more carbon—carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon—carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

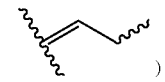
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon—carbon triple bonds can be internal (such as in 2-butynyl) or terminal (such as in 1-butynyl). Examples of $C_{2-4}$ alkynyl groups include, without limitation, ethynyl ($C_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl") . In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1] heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or Spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix —ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, -NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid -2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(Rcc)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o -nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro 4 pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H5)$— is a $C_1$ hydrocarbon chain, and

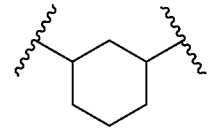 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

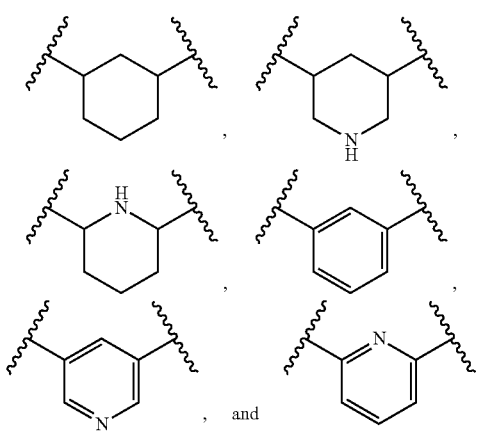

are all examples of a hydrocarbon chain. In contrast, in certain embodiments,

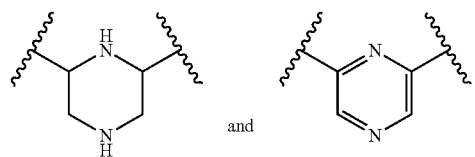 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

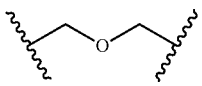 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. Exemplary leaving groups include, but are not limited to, activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF2)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate -containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$$^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., activity of a bromodomain and/or a bromodomain-containing protein) in a cell relative to vehicle.

When a compound, pharmaceutical composition, method, use, or kit is referred to as "selectively," "specifically," or "competitively" binding a first protein or a first chromatin, the compound, pharmaceutical composition, method, use, or kit binds the first protein or the first chromatin with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin. When a compound, pharmaceutical composition, method, use, or kit is referred to as "selectively," "specifically," or "competitively" modulating (e.g., increasing or inhibiting) the activity of a bromodomain-containing protein, the compound, pharmaceutical composition, method, use, or kit modulates the activity of the bromodomain-containing protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the bromodomain-containing protein.

The term "aberrant activity" refers to activity deviating from normal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, $CDC_2$, $CDC_7$, CDK10, CDK11, CDK2, CDK3, CDK4, CDK4ps, CDKS, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEKS, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PIP4K2C, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK(e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK. In certain embodiments, the protein kinase is a protein kinase shown in Table 2 or Table 3.

The term "SRC family kinase" refers to a family of non-receptor tyrosine protein kinases that includes nine members: SRCA subfamily that includes c-SRC (proto-oncogene tyrosine-protein kinase SRC), YES (proto-oncogene tyrosine-protein kinase Yes), FYN (proto-oncogene tyrosine-protein kinase FYN), and FGR (Gardner-Rasheed feline sarcoma viral (v-FGR) oncogene homolog); SRCB subfamily that includes LCK (lymphocyte-specific protein tyrosine kinase), HCK (tyrosine-protein kinase HCK, hemopoietic cell kinase), BLK (tyrosine-protein kinase BLK), and LYN (tyrosine-protein kinase LYN); and FRK (Fyn -related kinase).

DETAILED DESCRIPTION OF CERTAIN EMBODIMENTS OF THE INVENTION

The present disclosure provides thiazolyl-containing compounds, such as compounds of Formula (I), (II), or (III). In certain embodiments, the compounds described herein are able to inhibit protein kinases (e.g., Src family kinases (e.g., hemopoietic cell kinase (HCK)), Bruton's tyrosine kinase (BTK)). Therefore, the compounds may be useful in treating and/or preventing proliferative diseases (e.g., myelodysplasia, leukemia, lymphoma (e.g., Waldenström's macroglobulinemia)). The compounds may act by inducing apoptosis in a cell (e.g., malignant blood cell). Also provided in the present disclosure are pharmaceutical compositions, kits, methods, and uses including a compound described herein.

Compounds

One aspect of the present disclosure relates to the compounds described herein. The compounds described herein are thiazolyl-containing compounds that may be useful in treating and/or preventing proliferative diseases in a subject, inhibiting the activity of a protein kinase (e.g., HCK, BTK) in a subject, biological sample, tissue, or cell, and/or inducing apoptosis in a cell. In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof. In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II), or a pharmaceutically acceptable salt thereof. In certain embodiments, a compound described herein is a compound of Formula (III), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (III), or a pharmaceutically acceptable salt thereof.

Compounds of Formula (I)

In certain embodiments, a compound described herein is of Formula (I):

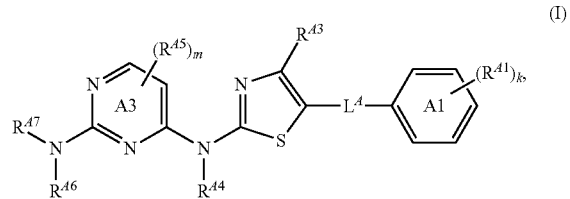

or a pharmaceutically acceptable salt, solvate, hydrate, polymorph, co-crystal, tautomer, stereoisomer, isotopically labeled derivative, or prodrug thereof, wherein:

each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —NO$_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

each instance of Ra is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

k is 0, 1, 2, 3, 4, or 5;

$L^A$ is —C(=O)—$NR^{A2}$— or —$NR^{A2}$—C(=O)—, wherein $R^{A2}$ is hydrogen, substituted or unsubstituted $C_{1-6}$ alkyl, or a nitrogen protecting group;

$R^{A3}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

$R^{A4}$ is hydrogen, substituted or unsubstituted $C_{1-6}$ alkyl, or a nitrogen protecting group;

each instance of $R^{A5}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

m is 0, 1, or 2;

$R^{A6}$ is hydrogen, substituted or unsubstituted $C_{1-6}$ alkyl, or a nitrogen protecting group; and $R^{A7}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, —C(=O)$R^a$, —C(=O)$OR^a$, —C(=O)N($R^a$)$_2$, or a nitrogen protecting group.

Formula (I) includes as Ring A1 a phenyl ring that is unsubstituted (e.g., when k is 0) or substituted (e.g., when k is 1, 2, 3, 4, or 5) with one or more substituents $R^{A1}$. In certain embodiments, Ring A1 is of the formula:

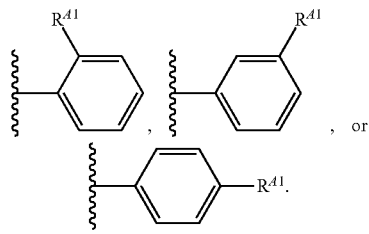

In certain embodiments, Ring A1 is of the formula:

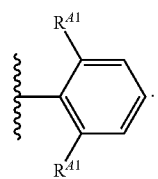

In certain embodiments, Ring A1 is of the formula:

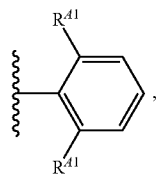

wherein each instance of $R^{A1}$ is independently substituted or unsubstituted alkyl (e.g., substituted or unsubstituted $C_{1-6}$ alkyl, such as —$CH_3$, —$CF_3$, Bn, unsubstituted ethyl, perfluoroethyl, unsubstituted propyl, perfluoropropyl, unsubstituted butyl, or perfluorobutyl) or halogen (e.g., F, Cl, Br, or I). In certain embodiments, Ring A1 is of the formula:

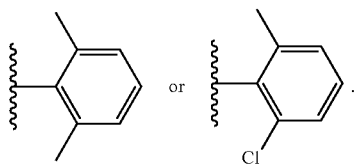

In certain embodiments, Ring A1 is of the formula:

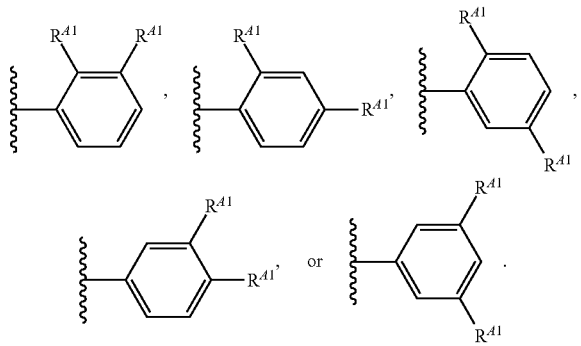

In Formula (I), Ring A1 may include one or more substituents $R^{A1}$. In certain embodiments, all instances of $R^{A1}$ are the same. In certain embodiments, two instances of $R^{A1}$ are different from each other. In certain embodiments, at least one instance of $R^{A1}$ is halogen (e.g., F, Cl, Br, or I). In certain embodiments, at least one instance of $R^{A1}$ is substituted or unsubstituted alkyl (e.g., substituted or unsubstituted $C_{1-6}$ alkyl). In certain embodiments, at least one instance of $R^{A1}$ is —CH3. In certain embodiments, at least one instance of $R^{A1}$ is —CF3, Bn, unsubstituted ethyl, perfluoroethyl, unsubstituted propyl, perfluoropropyl, unsubstituted butyl, or perfluorobutyl. In certain embodiments, at least one instance of $R^{A1}$ is substituted or unsubstituted alkenyl (e.g., substituted or unsubstituted $C_{2-6}$ alkenyl). In certain embodiments, at least one instance of $R^{A1}$ is substituted or unsubstituted alkynyl (e.g., substituted or unsubstituted $C_{1-6}$ alkynyl). In certain embodiments, at least one instance of RAI is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{A1}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{41}$ is substituted or unsubstituted aryl (e.g., substituted or unsubstituted, 6- to 10-membered aryl). In certain embodiments, at least one instance of $R^{41}$ is substituted or unsubstituted phenyl. In certain embodiments, at least one instance of $R^{41}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{41}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{41}$ is —SRa (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{41}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —$NMe_2$)). In certain embodiments, at least one instance of $R^{41}$ is —CN, —SCN, or —$NO_2$. In certain embodiments, at least one instance of $R^{41}$ is —$C(=NR^a)R^a$, —$C(=NR^a)OR^a$, or —$C(=NR^a)N(R^a)_2$. In certain embodiments, at least one instance of $R^{41}$ is —$C(=O)R^a$ (e.g., —$C(=O)$(substituted or unsubstituted alkyl) or —$C(=O)$(substituted or unsubstituted phenyl)), —$C(=O)OR^a$ (e.g., —$C(=O)O$(substituted or unsubstituted alkyl) or —$C(=O)O$(substituted or unsubstituted phenyl)), or —$C(=O)N(R^a)_2$ (e.g., —$C(=O)NH_2$, —$C(=O)NH$(substituted or unsubstituted alkyl), —$C(=O)NH$(substituted or unsubstituted phenyl), —$C(=O)N$(substituted or unsubstituted alkyl)—(substituted or unsubstituted alkyl), or —$C(=O)N$(substituted or unsubstituted phenyl)—(substituted or unsubstituted alkyl)). In certain embodiments, at least one instance of $R^{41}$ is —$NR^aC(=O)R^a$, —$NR^aC(=O)ORa$, or —$NR^aC(=O)N(R^a)_2$. In certain embodiments, at least one instance of $R^{41}$ is —$OC(=O)R^a$, —$OC(=O)OR^a$, or —$OC(=O)N(R^a)_2$.

When Formula (I) includes two or more instances of substituent $R^a$, any two instances of $R^a$ may be the same or different from each other. In certain embodiments, at least one instance of $R^a$ is H. In certain embodiments, each instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted $C_{1-6}$ alkyl). In certain embodiments, at least one instance of $R^a$ is —CH3. In certain embodiments, at least one instance of $R^a$ is —$CF_3$, Bn, unsubstituted ethyl, perfluoroethyl, unsubstituted propyl, perfluoropropyl, unsubstituted butyl, or perfluorobutyl. In certain embodiments, at least one instance of $R^a$ is substituted or unsubstituted alkenyl (e.g., substituted or unsubstituted $C_{2-6}$ alkenyl). In certain embodiments, at least one instance of $R^a$ is substituted or unsubstituted alkynyl (e.g., substituted or unsubstituted $C_{1-6}$ alkynyl). In certain embodiments, at least one instance of $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^a$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^a$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$ are joined to form a substituted or unsubstituted, heterocyclic ring (e.g., substituted or unsubstituted, 5- to 6-membered, monocyclic heterocyclic ring comprising zero, one, or two double bonds in the heterocyclic ring system, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, 5- to 6-membered, monocyclic heteroaryl ring, wherein one, two, three, or four atoms in the heteroaryl ring system are independently nitrogen, oxygen, or sulfur).

In certain embodiments, k is 0. In certain embodiments, k is 1. In certain embodiments, k is 2. In certain embodiments, k is 3. In certain embodiments, k is 4. In certain embodiments, k is 5.

In certain embodiments, k is 1; and $R^{41}$ is substituted or unsubstituted alkyl (e.g., substituted or unsubstituted $C_{1-6}$ alkyl, such as —$CH_3$, —$CF_3$, Bn, unsubstituted ethyl, perfluoroethyl, unsubstituted propyl, perfluoropropyl, unsubstituted butyl, or perfluorobutyl) or halogen (e.g., F, Cl, Br, or I). In certain embodiments, k is 2; and each of the two instances of $R^{41}$ is independently substituted or unsubstituted alkyl (e.g., substituted or unsubstituted $C_{1-6}$ alkyl, such as —$CH_3$, —$CF_3$, Bn, unsubstituted ethyl, perfluoroethyl, unsubstituted propyl, perfluoropropyl, unsubstituted butyl, or perfluorobutyl) or halogen (e.g., F, Cl, Br, or I).

Formula (I) includes divalent linker $L^A$ connecting Ring A1 to the thiazolyl ring. In certain embodiments, $L^A$ is —$C(=O)$—$N(R^{42})$— (e.g., —$C(=O)$—NH—). In certain embodiments, $L^A$ is —$N(R^{42})$—$C(=O)$— (e.g., —NH—C(=O)—).

In certain embodiments, $R^{42}$ is H. In certain embodiments, $R^{42}$ is substituted or unsubstituted $C_{1-6}$ alkyl (e.g., —$CH_3$, Bn, —$CF_3$, unsubstituted ethyl, perfluoroethyl, unsubstituted propyl, perfluoropropyl, unsubstituted butyl, or perfluorobutyl). In certain embodiments, $R^{42}$ is a nitrogen protecting group (e.g., Bn, Boc, Cbz, Fmoc, trifluoroacetyl, triphenylmethyl, acetyl, or Ts).

The thiazolyl ring of Formula (I) includes substituent $R^{43}$. In certain embodiments, $R^{43}$ is H. In certain embodiments, $R^{43}$ is halogen (e.g., F, Cl, Br, or I). In certain embodiments, $R^{43}$ is substituted or unsubstituted alkyl (e.g., substituted or unsubstituted $C_{1-6}$ alkyl). In certain embodiments, $R^{43}$ is —CH3. In certain embodiments, $R^{43}$ is —CF3, Bn, unsubstituted ethyl, perfluoroethyl, unsubstituted propyl, perfluoropropyl, unsubstituted butyl, or perfluorobutyl. In certain embodiments, $R^{43}$ is substituted or unsubstituted alkenyl (e.g., substituted or unsubstituted $C_{2-6}$ alkenyl). In certain embodiments, $R^{43}$ is substituted or unsubstituted alkynyl (e.g., substituted or unsubstituted $C_{1-6}$ alkynyl). In certain embodiments, $R^{43}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{43}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{43}$ is substituted or unsubstituted aryl (e.g., substituted or unsubstituted, 6- to 10-membered aryl). In certain embodiments, $R^{43}$ is substituted or unsubstituted phenyl. In certain embodiments, $R^{43}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{43}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{43}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{43}$ is —$N(R^a)_2$ (e.g., —$NH_2$, —NH(substituted or unsubstituted $C_{1-6}$ alkyl) (e.g., —NHMe), or N(substituted or unsubstituted $C_{1-6}$ alkyl)—(substituted or unsubstituted $C_{1-6}$ alkyl) (e.g., —$NMe_2$)). In certain embodiments, $R^{43}$ is —CN, —SCN, or —$NO_2$. In certain embodiments, $R^{43}$ is —C(=$NR^a$)$R^a$, —C(=$NR^a$)$OR^a$, or —C(=$NR^a$)$N(R^a)_2$. In certain embodiments, $R^{43}$ is —C(=O)$R^a$ (e.g., —C(=O)(substituted or unsubstituted alkyl) or —C(=O)(substituted or unsubstituted phenyl)), —C(=O)$OR^a$ (e.g., —C(=O)O(substituted or unsubstituted alkyl) or —C(=O)O(substituted or unsubstituted phenyl)), or —C(=O)$N(R^a)_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{43}$ is —$NR^a$C(=O)$R^a$, —$NR^a$C(=O)$OR^a$, or —$NR^a$C(=O)$N(R^a)_2$. In certain embodiments, $R^{43}$ is —OC(=O)$R^a$, —OC(=O)$OR^a$, or —OC(=O)$N(R^a)_2$.

Formula (I) includes substituent $R^{44}$ on a nitrogen atom attached to the thiazolyl ring. In certain embodiments, $R^{44}$ is H. In certain embodiments, $R^{44}$ is substituted or unsubstituted $C_{1-6}$ alkyl (e.g., —CH3, Bn, —CF3, unsubstituted ethyl, perfluoroethyl, unsubstituted propyl, perfluoropropyl, unsubstituted butyl, or perfluorobutyl). In certain embodiments, $R^{44}$ is a nitrogen protecting group (e.g., Bn, Boc, Cbz, Fmoc, trifluoroacetyl, triphenylmethyl, acetyl, or Ts).

Formula (I) includes as Ring A3 a pyrimidinyl ring that is unsubstituted (e.g., when m is 0) or substituted (e.g., when m is 1 or 2) with one or more substituents $R^{45}$. In certain embodiments, Ring A3 is of the formula:

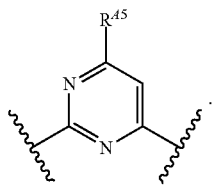

In certain embodiments, Ring A3 is of the formula:

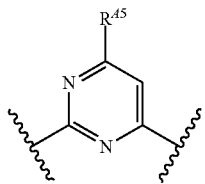

wherein $R^{45}$ is substituted or unsubstituted alkyl (e.g., substituted or unsubstituted $C_{1-6}$ alkyl, such as —$CH_3$, —$CF_3$, Bn, unsubstituted ethyl, perfluoroethyl, unsubstituted propyl, perfluoropropyl, unsubstituted butyl, or perfluorobutyl).

In certain embodiments, Ring A3 is of the formula:

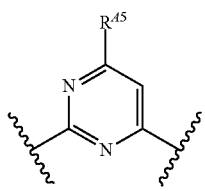

wherein $R^{45}$ is $C_{1-6}$ alkyl substituted independently with at least one substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, Ring A3 is of the formula:

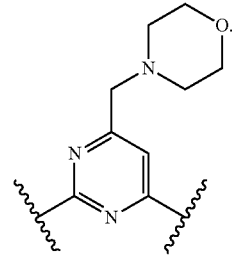 [SMILES: *c1cc(CN2CCOCC2)nc(*)n1]

In certain embodiments, Ring A3 is of the formula:

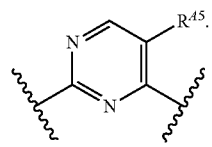

In certain embodiments, Ring A3 is of the formula:

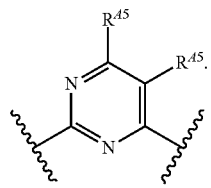

In Formula (I), Ring A3 may include one or two substituents $R^{45}$. In certain embodiments, two instances of $R^{45}$ are the same. In certain embodiments, two instances of $R^{45}$ are different from each other. In certain embodiments, at least one instance of $R^{45}$ is halogen (e.g., F, Cl, Br, or I). In certain embodiments, at least one instance of $R^{45}$ is substituted or unsubstituted alkyl (e.g., substituted or unsubstituted $C_{1-6}$ alkyl). In certain embodiments, at least one instance of $R^{45}$ is —$CH_3$. In certain embodiments, at least one instance of $R^{45}$ is —$CF_3$, Bn, unsubstituted ethyl, perfluoroethyl, unsubstituted propyl, perfluoropropyl, unsubstituted butyl, or perfluorobutyl. In certain embodiments, at least one instance of $R^{45}$ is $C_{1-6}$ alkyl substituted with at least one substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{45}$ is methyl substituted at least with substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^{45}$ is of the formula:

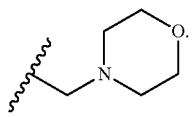

In certain embodiments, at least one instance of $R^{45}$ is substituted or unsubstituted alkenyl (e.g., substituted or unsubstituted $C_{2-6}$ alkenyl). In certain embodiments, at least one instance of $R^{45}$ is substituted or unsubstituted alkynyl (e.g., substituted or unsubstituted $C_{1-6}$ alkynyl). In certain embodiments, at least one instance of $R^{45}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{45}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{45}$ is substituted or unsubstituted aryl (e.g., substituted or unsubstituted, 6- to 10-membered aryl). In certain embodiments, at least one instance of $R^{45}$ is substituted or unsubstituted phenyl. In certain embodiments, at least one instance of $R^{45}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{45}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{45}$ is —SRa (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{45}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —$NMe_2$)). In certain embodiments, at least one instance of $R^{45}$ is —CN, —SCN, or —$NO_2$. In certain embodiments, at least one instance of $R^{45}$ is —C(=$NR^a$)$R^a$, —C(=$NR^a$)$OR^a$, or —C(=$NR^a$)$N(R^a)_2$. In certain embodiments, at least one instance of $R^{45}$ is —C(=O)$R^a$ (e.g., —C(=O)(substituted or unsubstituted alkyl) or —C(=O)(substituted or unsubstituted phenyl)), —C(=O)$OR^a$ (e.g., —C(=O)O(substituted or unsubstituted alkyl) or —C(=O)O(substituted or unsubstituted phenyl)), or —C(=O)$N(R^a)_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, at least one instance of $R^{45}$ is —$NR^a$C(=O)Ra, —$NR^a$C(=O)$OR^a$, or —$NR^a$C(=O)$N(R^a)_2$. In certain embodiments, at least one instance of $R^{45}$ is —OC(=O)$R^a$, —OC(=O)$OR^a$, or —OC(=O)$N(R^a)_2$.

In certain embodiments, m is 0. In certain embodiments, m is 1. In certain embodiments, m is 2.

Formula (I) includes substituent $R^{46}$ on a nitrogen atom attached to Ring A3. In certain embodiments, $R^{46}$ is H. In certain embodiments, $R^{46}$ is substituted or unsubstituted $C_{1-6}$ alkyl (e.g., —$CH_3$, Bn, —$CF_3$, unsubstituted ethyl, perfluoroethyl, unsubstituted propyl, perfluoropropyl, unsubstituted butyl, or perfluorobutyl). In certain embodiments, $R^{46}$ is a nitrogen protecting group (e.g., Bn, Boc, Cbz, Fmoc, trifluoroacetyl, triphenylmethyl, acetyl, or Ts).

Formula (I) includes substituent $R^{47}$ on a nitrogen atom attached to Ring A3. In certain embodiments, $R^{47}$ is H. In certain embodiments, $R^{47}$ is substituted or unsubstituted alkyl (e.g., substituted or unsubstituted $C_{1-6}$ alkyl). In certain embodiments, $R^{47}$ is —$CH_3$. In certain embodiments, $R^{47}$ is —$CF_3$, Bn, unsubstituted ethyl, perfluoroethyl, unsubstituted propyl, perfluoropropyl, unsubstituted butyl, or perfluorobutyl. In certain embodiments, $R^{47}$ is substituted or unsubstituted alkenyl (e.g., substituted or unsubstituted $C_{2-6}$ alkenyl). In certain embodiments, $R^{47}$ is substituted or unsubstituted alkynyl (e.g., substituted or unsubstituted $C_{1-6}$ alkynyl). In certain embodiments, $R^{47}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{47}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{47}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{A7}$ is —C(=O)$R^a$ (e.g., —C(=O)(substituted or unsubstituted alkyl) or —C(=O)(substituted or unsubstituted phenyl)), —C(=O)OR$^a$ (e.g., —C(=O)O(substituted or unsubstituted alkyl) or —C(=O)O(substituted or unsubstituted phenyl)), or —C(=O)N(R$^a$)$_2$ (e.g., —C(=O)NH$_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{A7}$ is a nitrogen protecting group (e.g., Bn, Boc, Cbz, Fmoc, trifluoroacetyl, triphenylmethyl, acetyl, or Ts). In certain embodiments, $R^{A7}$ is of the formula:

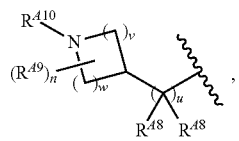

wherein:
each instance of $R^{A8}$ is independently hydrogen, halogen, or substituted or unsubstituted $C_{1-6}$ alkyl;
u is 0, 1, 2, 3, or 4;
v is 1, 2, or 3;
w is 1, 2, or 3;
each instance of $R^{A9}$ is independently halogen, or substituted or unsubstituted $C_{1-6}$ alkyl;
n is an integer between 0 and 13, inclusive; and
$R^{A10}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, —C(=O)R$^a$, —C(=O)OR$^a$, —C(=O)N(R$^a$)$_2$, a nitrogen protecting group, or of any one of Formulae (ii-1) to (ii-42):

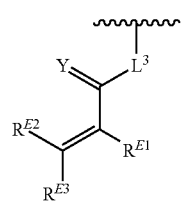 (ii-1)

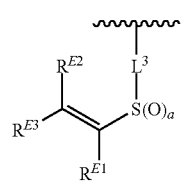 (ii-2)

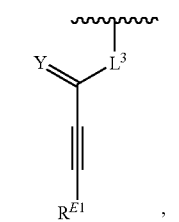 (ii-3)

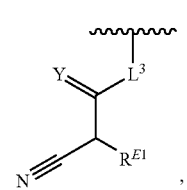 (ii-4)

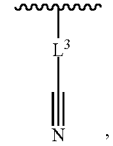 (ii-5)

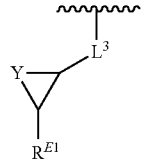 (ii-6)

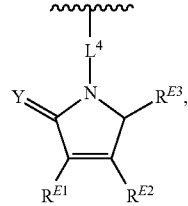 (ii-7)

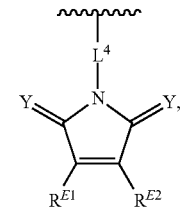 (ii-8)

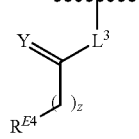 (ii-9)

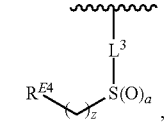 (ii-10)

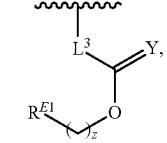 (ii-11)

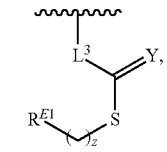 (ii-12)

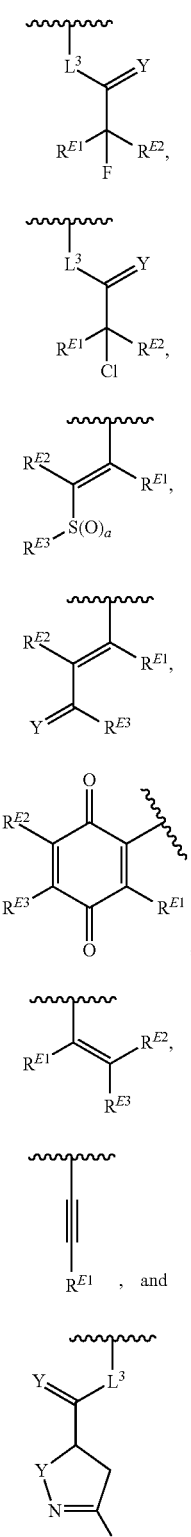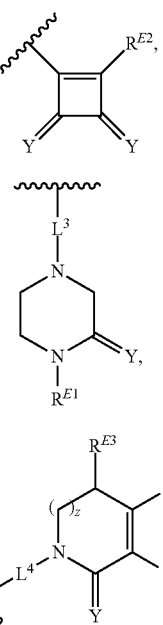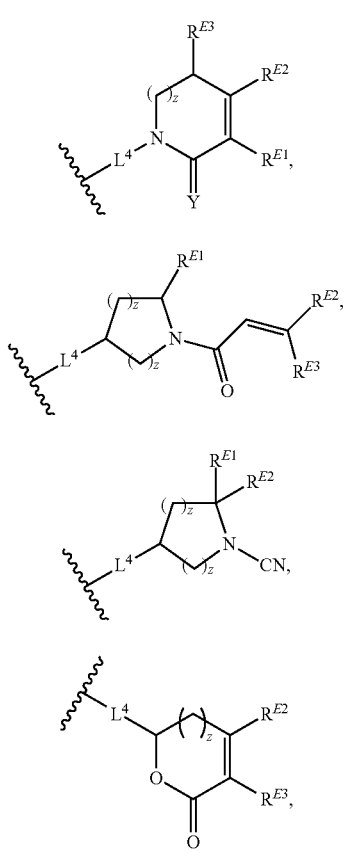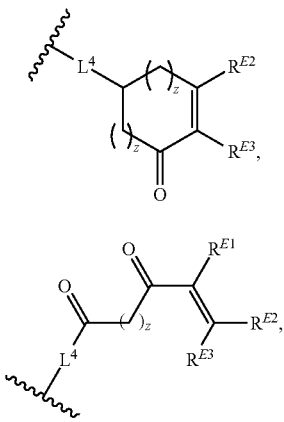

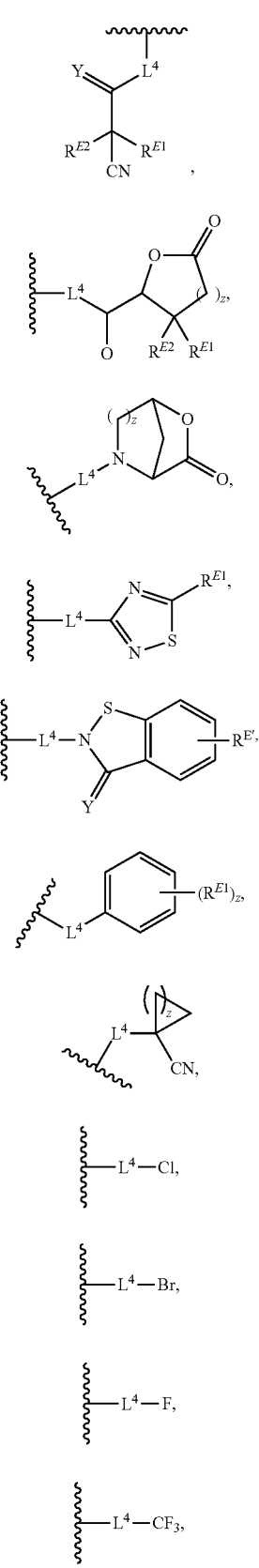

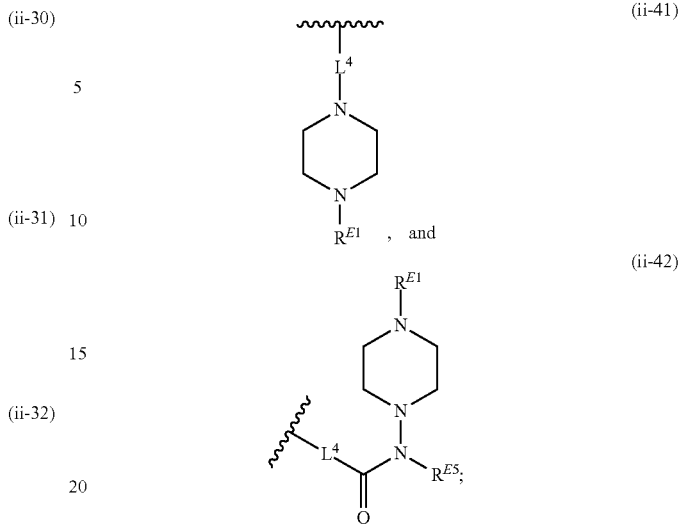

wherein:

$L^3$ is a bond or an optionally substituted $C_{1-4}$ hydrocarbon chain, optionally wherein one or more carbon units of the hydrocarbon chain are independently replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans—CR$^{L3b}$=CR$^{L3b}$—, cis—CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring; or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or NR$^{E6}$, wherein $R^{E6}$ is hydrogen, substituted or unsubstituted C$_{1-6}$ alkyl, or a nitrogen protecting group;

a is 1 or 2; and each instance of z is independently 0, 1, 2, 3, 4, 5, or 6.

In certain embodiments, $R^{A7}$ is of the formula:

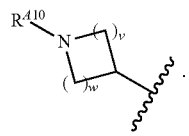

In certain embodiments, $R^{A7}$ is of the formula:

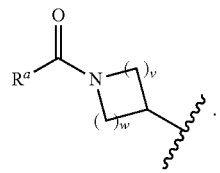

In certain embodiments, $R^{A7}$ is of the formula:

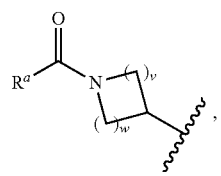

wherein $R^a$ is substituted or unsubstituted C$_{2-6}$ alkenyl. In certain embodiments, $R^{A7}$ is of the formula:

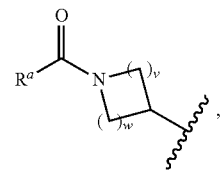

wherein $R^a$ is substituted or unsubstituted C$_{1-6}$ alkyl. In certain embodiments, $R^{A7}$ is of the formula:

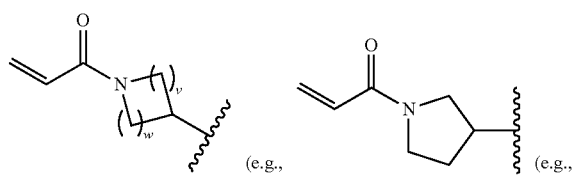

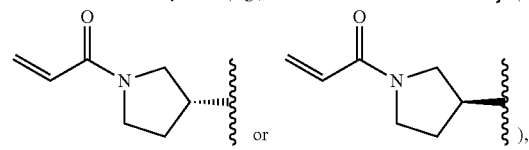

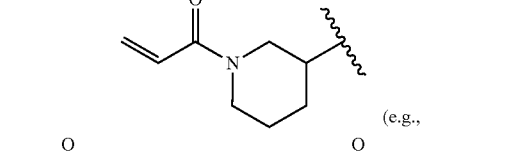

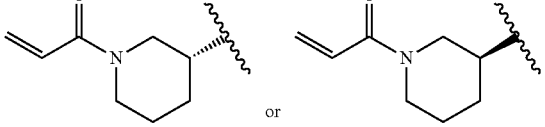

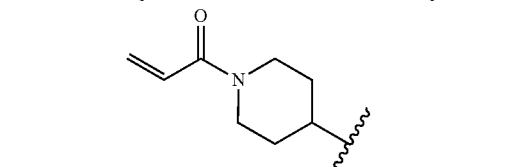

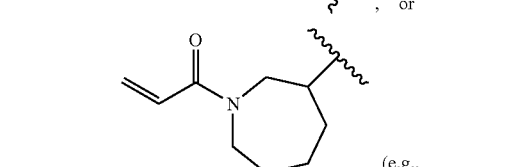

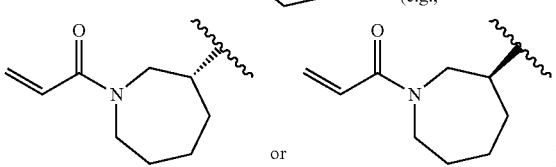

In certain embodiments, $R^{A7}$ is of the formula

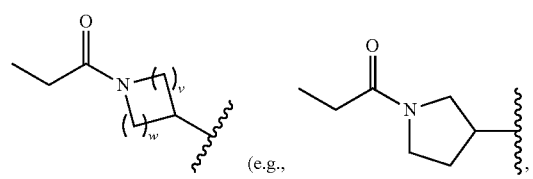

53

-continued

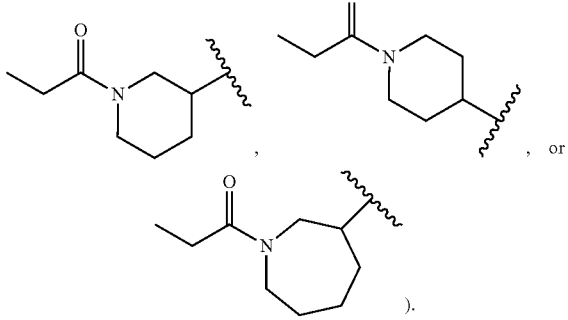

In certain embodiments, $R^{A7}$ is of the formula:

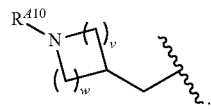

In certain embodiments, $R^{A7}$ is of the formula:

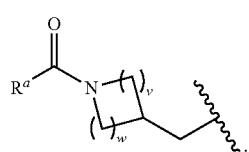

In certain embodiments, $R^{A7}$ is of the formula:

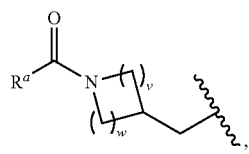

wherein $R^a$ is substituted or unsubstituted $C_{2-6}$ alkenyl. In certain embodiments, $R^{A7}$ is of the formula:

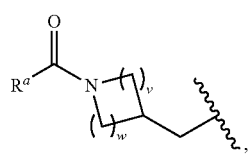

wherein $R^a$ is substituted or unsubstituted $C_{1-6}$ alkyl. In certain embodiments, $R^{A7}$ is of the formula:

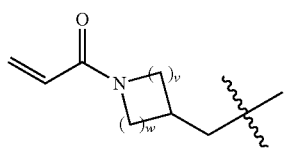

54

-continued

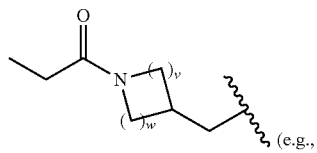

In certain embodiments, $R^{A7}$ is of the formula:

-continued

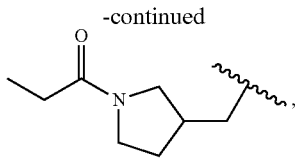

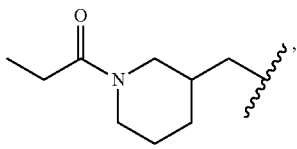

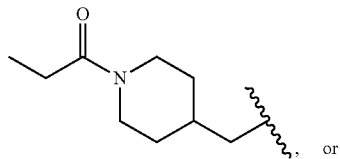, or

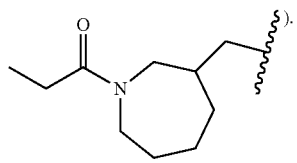.

In certain embodiments, all instances of $R^{48}$ are the same. In certain embodiments, two instances of $R^{48}$ are different from each other. In certain embodiments, at least one instance of $R^{48}$ is H. In certain embodiments, each instance of $R^{48}$ is H. In certain embodiments, at least one instance of $R^{48}$ is halogen (e.g., F, Cl, Br, or I). In certain embodiments, at least one instance of $R^{48}$ is substituted or unsubstituted alkyl (e.g., substituted or unsubstituted $C_{1-6}$ alkyl). In certain embodiments, at least one instance of $R^{48}$ is —$CH_3$. In certain embodiments, at least one instance of $R^{48}$ is —$CF_3$, Bn, unsubstituted ethyl, perfluoroethyl, unsubstituted propyl, perfluoropropyl, unsubstituted butyl, or perfluorobutyl.

In certain embodiments, u is 0. In certain embodiments, u is 1. In certain embodiments, u is 2. In certain embodiments, u is 3. In certain embodiments, u is 4.

In certain embodiments, v is 1. In certain embodiments, v is 2. In certain embodiments, v is 3. In certain embodiments, v is 4.

In certain embodiments, w is 1. In certain embodiments, w is 2. In certain embodiments, w is 3.

In certain embodiments, v is 2; and w is 1. In certain embodiments, v is 3; and w is 1. In certain embodiments, v is 4; and w is 1.

In certain embodiments, all instances of $R^{49}$ are the same. In certain embodiments, two instances of $R^{49}$ are different from each other. In certain embodiments, at least one instance of $R^{49}$ is halogen (e.g., F, Cl, Br, or I). In certain embodiments, at least one instance of $R^{49}$ is substituted or unsubstituted alkyl (e.g., substituted or unsubstituted $C_{1-6}$ alkyl). In certain embodiments, at least one instance of $R^{49}$ is —$CH_3$. In certain embodiments, at least one instance of $R^{49}$ is —$CF_3$, Bn, unsubstituted ethyl, perfluoroethyl, unsubstituted propyl, perfluoropropyl, unsubstituted butyl, or perfluorobutyl.

In certain embodiments, n is 0. In certain embodiments, n is 1, 2, 3, 4, 5, 6, 7, 8, 9, 10, 11, 12, or 13.

In certain embodiments, $R^{A10}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, —C(=O)$R^a$, —C(=O)O$R^a$, —C(=O)N($R^a$)$_2$, a nitrogen protecting group, or of any one of Formulae (ii-1) to (ii-23). In certain embodiments, $R^{A10}$ is H. In certain embodiments, $R^{A10}$ is substituted or unsubstituted $C_{1-6}$ alkyl (e.g., $C_{1-6}$ alkyl substituted with one or more substituents independently selected from the group consisting of oxo; halogen; substituted or unsubstituted $C_{2-6}$ alkenyl; substituted or unsubstituted cyclopropyl; substituted or unsubstituted, 4- to 7-membered monocyclic carbocyclyl comprising 1 or 2 double bonds in the carbocyclic ring system; substituted or unsubstituted oxiranyl; substituted or unsubstituted, 5- to 10-membered, monocyclic or bicyclic heteroaryl, wherein 1, 2, 3, or 4 atoms in the heteroaryl ring system are independently oxygen, nitrogen, or sulfur; —CN; —(C=O)$R^a$; —N($R^a$)(C=O)$R^a$; —O(C=O)$R^a$; —O$R^a$; and —N($R^a$)$_2$). In certain embodiments, $R^{A10}$ is substituted or unsubstituted $C_{2-6}$ alkenyl (e.g., substituted or unsubstituted vinyl). In certain embodiments, $R^{A10}$ is substituted or unsubstituted $C_{2-6}$ alkynyl (e.g., substituted or unsubstituted ethynyl). In certain embodiments, $R^{A10}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{A10}$ is —C(=O)$R^a$. In certain embodiments, $R^{A10}$ is —C(=O)(substituted or unsubstituted alkyl) (e.g., —C(=O)(substituted or unsubstituted $C_{1-6}$ alkyl), such as —C(=O)Et). In certain embodiments, $R^{A10}$ is —C(=O)(substituted or unsubstituted alkenyl) (e.g., —C(=O)(substituted or unsubstituted $C_{2-6}$ alkenyl), such as —C(=O)—CH=CH$_2$). In certain embodiments, $R^{A10}$ is —C(=O)(substituted or unsubstituted carbocyclyl). In certain embodiments, $R^{A10}$ is —C(=O)(substituted or unsubstituted heterocyclyl). In certain embodiments, $R^{A10}$ is —C(=O)(substituted or unsubstituted phenyl). In certain embodiments, $R^{A10}$ is —C(=O)(substituted or unsubstituted heteroaryl). In certain embodiments, $R^{A10}$ is —C(=O)O$R^a$ (e.g., —C(=O)O(substituted or unsubstituted alkyl) or —C(=O)O(substituted or unsubstituted phenyl)) or —C(=O)N($R^a$)$_2$ (e.g., —C(=O)NH$_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{A10}$ is a nitrogen protecting group (e.g., Bn, Boc, Cbz, Fmoc, trifluoroacetyl, triphenylmethyl, acetyl, or Ts). In certain embodiments, $R^{A10}$ is of any one of Formulae (ii-1) to (ii-23). In certain embodiments, $R^{A10}$ is of any one of Formulae (ii-24) to (ii-42). In certain embodiments, $R^{A10}$ is of Formula (ii-1) (e.g., of the formula:

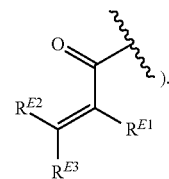).

In certain embodiments, $R^{410}$ is of Formula (ii-3) (e.g., of the formula:
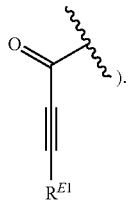
In certain embodiments, $R^{410}$ is of any one of the formulae shown in Table 1A.
TABLE 1A
| Exemplary moieties. |
|---|
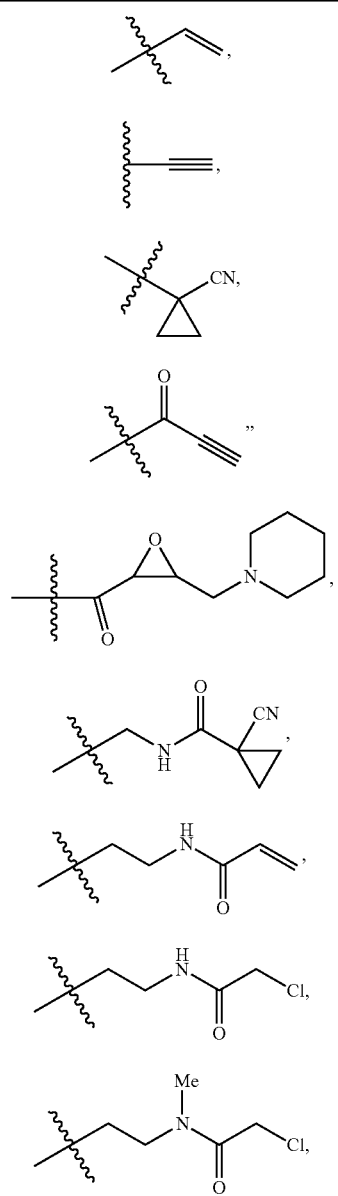
TABLE 1A-continued
| Exemplary moieties. |
|---|
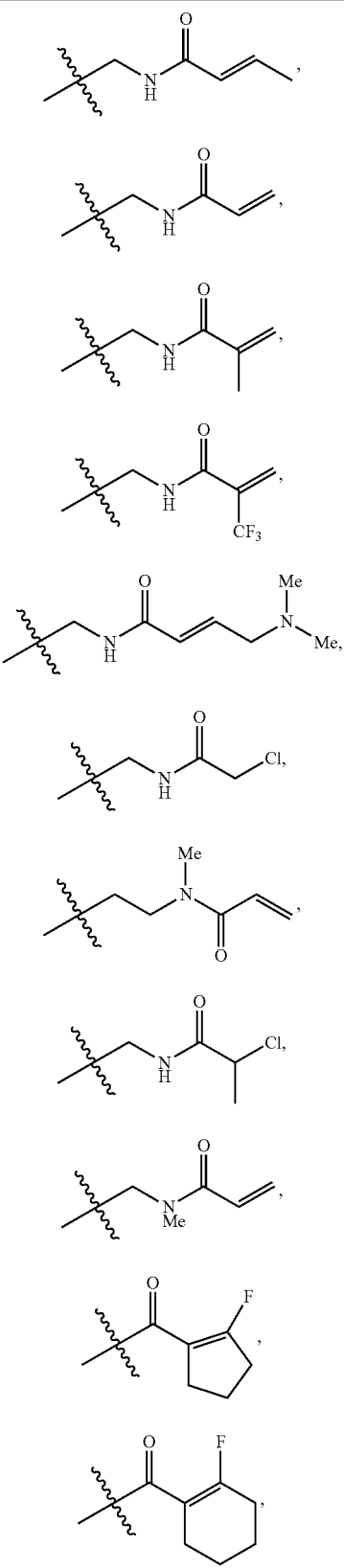

TABLE 1A-continued
Exemplary moieties.
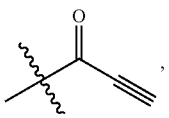
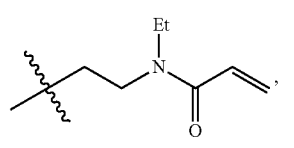 [SMILES: *CCN(CC)C(=O)C=C]
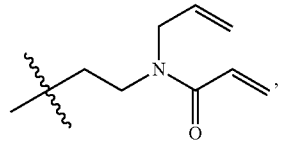 [SMILES: *CCN(CC=C)C(=O)C=C]
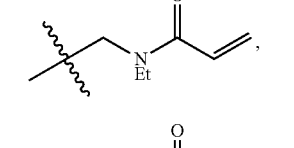
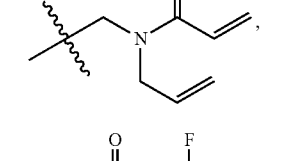
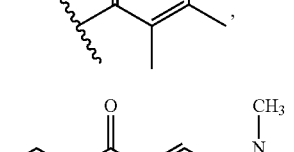
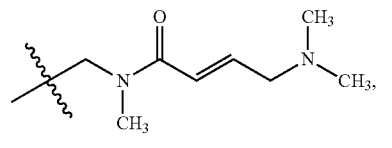 [SMILES: *CN(C)C(=O)/C=C/CN(C)C]
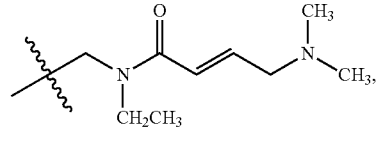
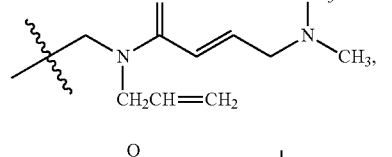
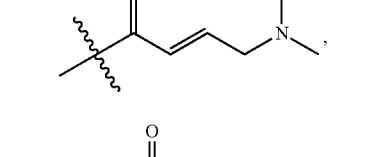
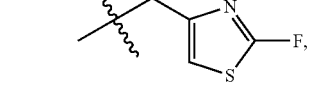
TABLE 1A-continued
Exemplary moieties.
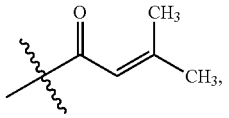 [SMILES: *C(=O)C=C(C)C]
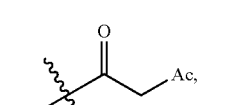
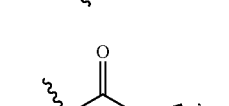
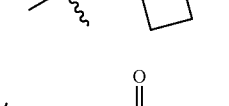
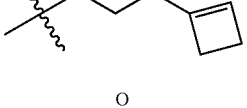
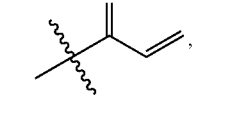
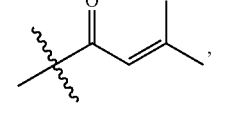
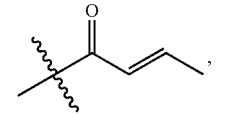 [SMILES: *C(=O)/C=C/C]
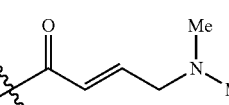
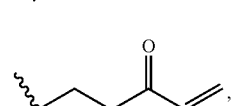
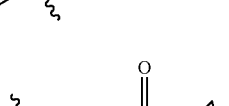

TABLE 1A-continued

Exemplary moieties.

TABLE 1A-continued

Exemplary moieties.

TABLE 1A-continued

Exemplary moieties.

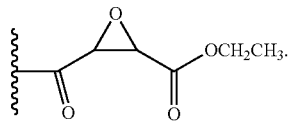 [SMILES: *C(=O)C1OC1C(=O)OCC]

In certain embodiments, $L^3$ is a bond. In certain embodiments, $L^3$ is an optionally substituted $C_{1-4}$ hydrocarbon chain. In certain embodiments, $L^3$ is an optionally substituted $C_{1-4}$ hydrocarbon chain, wherein one or more carbon units of the hydrocarbon chain are independently replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans—CR$^{L3b}$=CR$^{L3b}$—, cis—CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—. In certain embodiments, $L^3$ is an optionally substituted $C_{1-4}$ hydrocarbon chain, wherein one carbon unit of the hydrocarbon chain is replaced with —NR$^{L3a}$— (e.g., —NH—). In certain embodiments, $L^3$ is of the formula: —(CH$_2$)$_{1-4}$—NR$^{L3a}$— (e.g., —(CH$_2$)$_{1-4}$—NH—) or —NR$^{L3a}$—(CH$_2$)$_{1-4}$— (e.g., —NH—(CH$_2$)$_{1-4}$—).

In certain embodiments, $R^{L3a}$ is hydrogen.

In certain embodiments, at least one instance of $R^{L3b}$ is hydrogen. In certain embodiments, each instance of $R^{L3b}$ is hydrogen. In certain embodiments, at least one instance of $R^{L3b}$ is halogen (e.g., F or Cl). In certain embodiments, each instance of $R^{L3b}$ is halogen (e.g., F or Cl). In certain embodiments, at least one instance of $R^{L3b}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, two $R^{L3b}$ groups are joined to form an optionally substituted carbocyclic or optionally substituted heterocyclic ring.

In certain embodiments, $L^4$ is a bond. In certain embodiments, $L^4$ is an optionally substituted $C_{1-4}$ hydrocarbon chain.

In certain embodiments, $R^{E1}$ is hydrogen. In certain embodiments, $R^{E1}$ is halogen. In certain embodiments, $R^{E1}$ is optionally substituted alkyl (e.g., substituted or unsubstituted $C_{1-6}$ alkyl). In certain embodiments, $R^{E1}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, or —SR$^{E1a}$.

In certain embodiments, $R^{E2}$ is hydrogen. In certain embodiments, $R^{E2}$ is halogen. In certain embodiments, $R^{E2}$ is optionally substituted alkyl (e.g., substituted or unsubstituted $C_{1-6}$ alkyl). In certain embodiments, $R^{E2}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, or —SR$^{E2a}$.

In certain embodiments, $R^{E3}$ is hydrogen. In certain embodiments, $R^{E3}$ is halogen. In certain embodiments, $R^{E3}$ is optionally substituted alkyl (e.g., substituted or unsubstituted $C_{1-6}$ alkyl). In certain embodiments, $R^{E3}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, or —SR$^{E3a}$.

In certain embodiments, $R^{E1}$ and $R^{E3}$ are joined to form an optionally substituted carbocyclic ring. In certain embodiments, $R^{E1}$ and $R^{E3}$ are joined to form an optionally substituted heterocyclic ring. In certain embodiments, $R^{E2}$ and $R^{E3}$ are joined to form an optionally substituted carbocyclic ring. In certain embodiments, $R^{E2}$ and $R^{E3}$ are joined to form an optionally substituted heterocyclic ring. In certain embodiments, $R^{E1}$ and $R^{E2}$ are joined to form an optionally substituted carbocyclic ring. In certain embodiments, $R^{E1}$ and $R^{E2}$ are joined to form an optionally substituted heterocyclic ring.

In certain embodiments, $R^{E4}$ is halogen (e.g., F, Cl, Br, or I). In certain embodiments, $R^{E4}$ is —OS(=O)R$^{E4a}$ or —OS(=O)$_2$R$^{E4a}$, wherein $R^{E4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{E4}$ is —OMs, —OTf, —OTs, —OBs, or 2-nitrobenzenesulfonyloxy. In certain embodiments, $R^{E4}$ is —OR$^{E4a}$. In certain embodiments, $R^{E4}$ is —OMe, —OCF$_3$, or —OPh. In certain embodiments, $R^{E4}$ is —OC(=O)R$^{E4a}$. In certain embodiments, $R^{E4}$ is —OC(=O)Me, —OC(=O)CF$_3$, —OC(=O)Ph, or —OC(=O)Cl. In certain embodiments, $R^{E4}$ is —OC(=O)OR$^{E4a}$. In certain embodiments, $R^{E4}$ is —OC(=O)OMe or —OC(=O)O(t-Bu).

In certain embodiments, $R^{E5}$ is F, Cl, Br, or I.

In certain embodiments, Y is O. In certain embodiments, Y is S. In certain embodiments, Y is NR$^{E6}$ (e.g., NH).

In certain embodiments, $R^{E6}$ is H.

In certain embodiments, a is 1. In certain embodiments, a is 2.

In certain embodiments, at least one instance of z is 0. In certain embodiments, at least one instance of z is 1. In certain embodiments, at least one instance of z is 2, 3, 4, 5, or 6. In certain embodiments, two instacnes of z are the same. In certain embodiments, two instacnes of z are different from each other.

In certain embodiments, a compound of Formula (I) is of the formula:

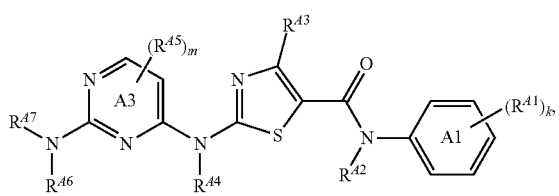

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

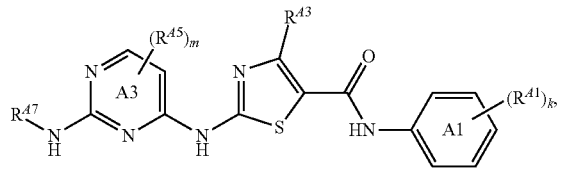

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

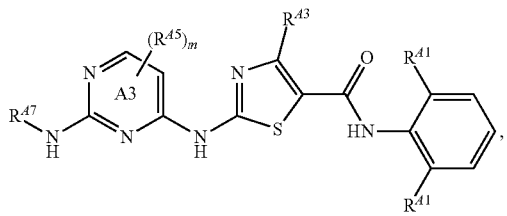

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

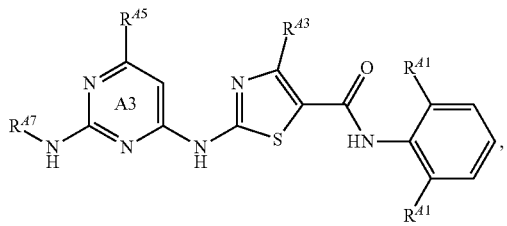

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

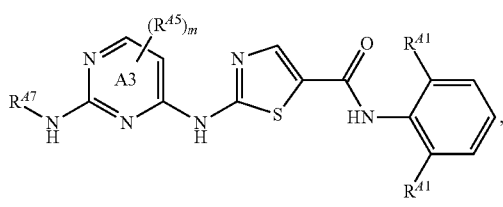

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

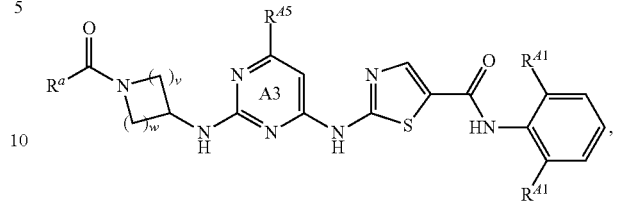

or a pharmaceutically acceptable salt, solvate, hydrate, polymorph, co-crystal, tautomer, stereoisomer, isotopically labeled derivative, or prodrug thereof, wherein $R^a$ is substituted or unsubstituted $C_{1-6}$ alkyl or substituted or unsubstituted $C_{2-6}$ alkenyl.

In certain embodiments, a compound of Formula (I) is of the formula:

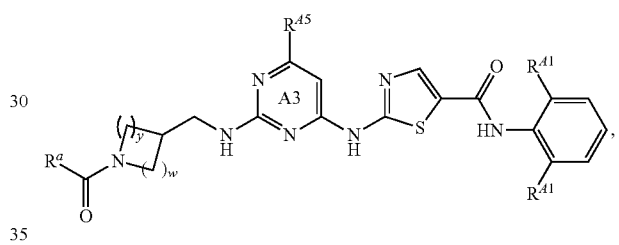

or a pharmaceutically acceptable salt, solvate, hydrate, polymorph, co-crystal, tautomer, stereoisomer, isotopically labeled derivative, or prodrug thereof, wherein $R^a$ is substituted or unsubstituted $C_{1-6}$ alkyl or substituted or unsubstituted $C_{2-6}$ alkenyl.

Exemplary compounds of Formula (I) include, but are not limited to:

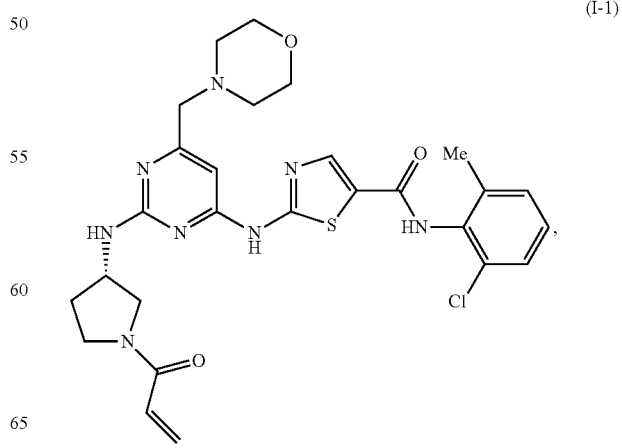

(I-1)

(I-2)
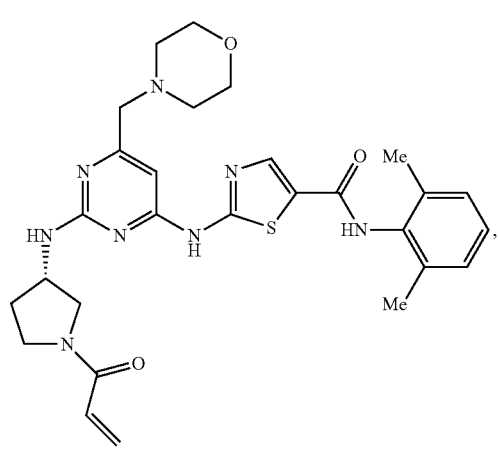
(I-3)
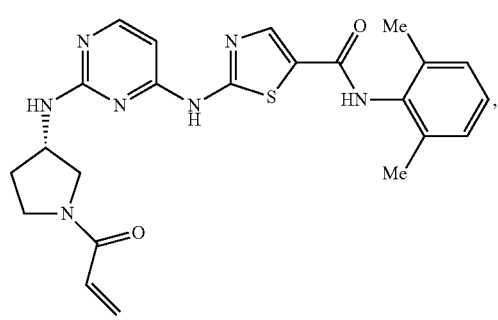
(I-4)
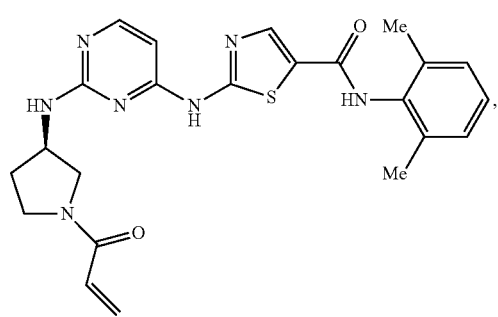
(I-5)
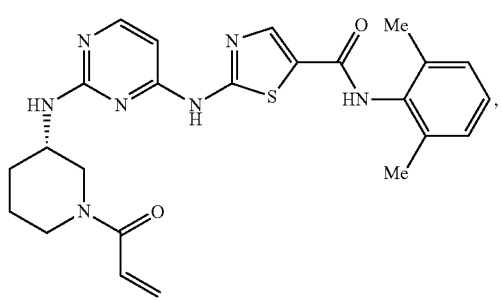
(I-6)
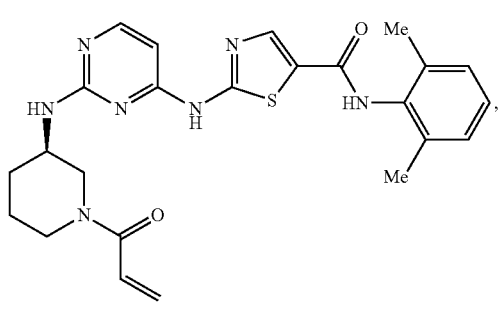
(I-7)
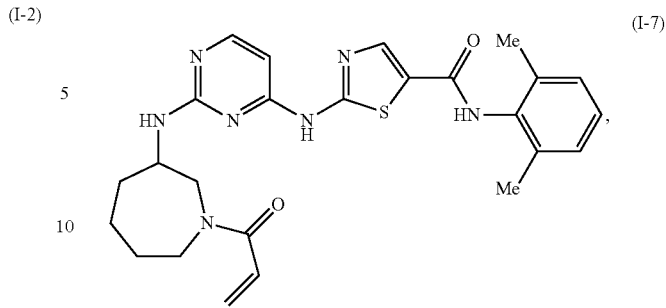
(I-8)
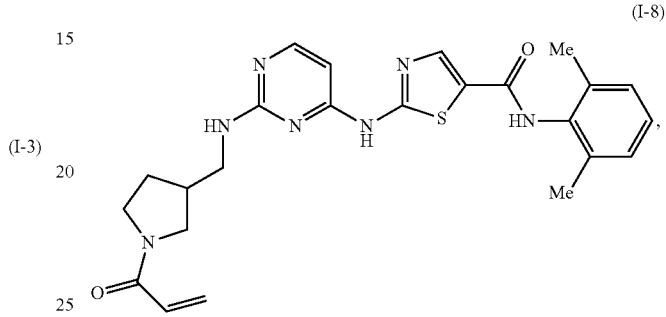
(I-9)
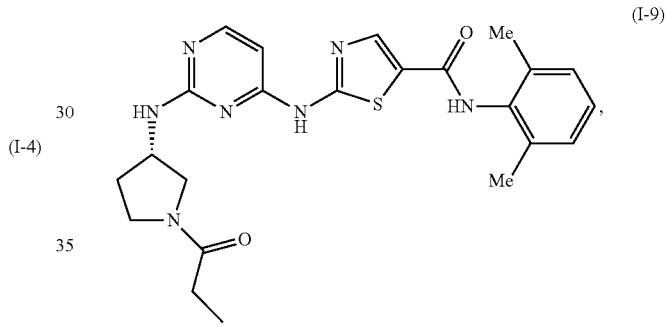
(I-10)
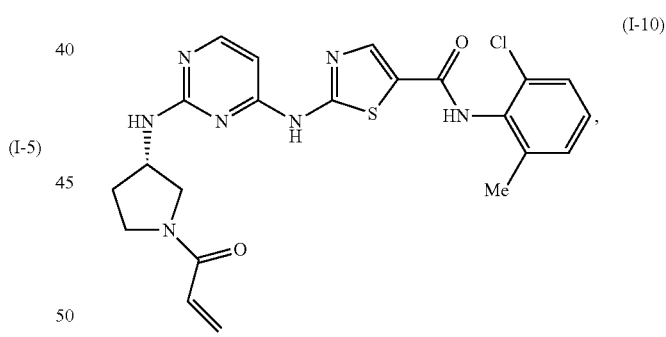
(I-11)
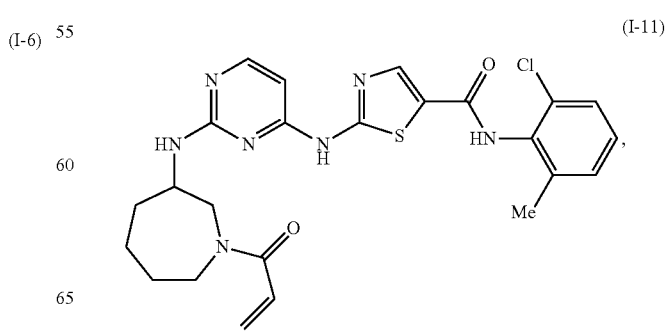

-continued (I-12)

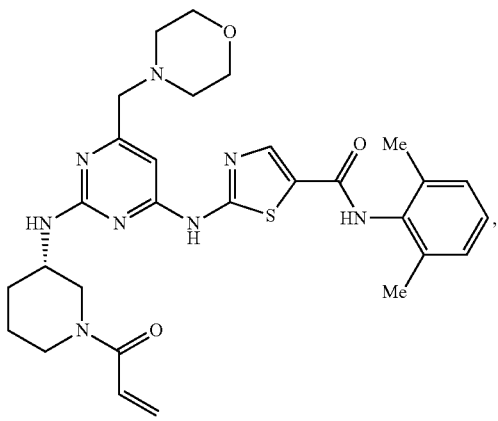

and pharmaceutically acceptable salts, solvates, hydrates, polymorphs, co-crystals, tautomers, stereoisomers, isotopically labeled derivatives, and prodrugs thereof.

Compounds of Formula (II)

In certain embodiments, a compound described herein is of Formula (II):

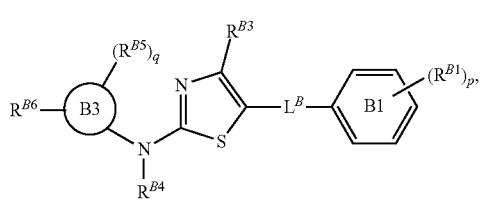

(II)

or a pharmaceutically acceptable salt, solvate, hydrate, polymorph, co-crystal, tautomer, stereoisomer, isotopically labeled derivative, or prodrug thereof, wherein:

each instance of $R^{B1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^b$, —$N(R^b)_2$, —$SR^b$, —CN, —SCN, —$C(=NR^b)R^b$, —$C(=NR^b)OR^b$, —$C(=NR^b)N(R^b)_2$, —$C(=O)R^b$, —$C(=O)OR^b$, —$C(=O)N(R^b)_2$, —$NO_2$, —$NR^bC(=O)R^b$, —$NR^bC(=O)OR^b$, —$NR^bC(=O)N(R^b)_2$, —$OC(=O)R^b$, —$OC(=O)OR^b$, or —$OC(=O)N(R^b)_2$;

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^b$ are joined to form a substituted or unsubstituted, heterocyclic ring, or substituted or unsubstituted, heteroaryl ring;

p is 0, 1, 2, 3, 4, or 5;

$L^B$ is —C(=O)—$NR^{B2}$— or —$NR^{B2}$—C(=O)—, wherein $R^{B2}$ is hydrogen, substituted or unsubstituted $C_{1-6}$ alkyl, or a nitrogen protecting group;

$R^{B3}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^b$, —$N(R^b)_2$, —$SR^b$, —CN, —SCN, —$C(=NR^b)R^b$, —$C(=NR^b)OR^b$, —$C(=NR^b)N(R^b)_2$, —$C(=O)R^b$, —$C(=O)OR^b$, —$C(=O)N(R^b)_2$, —$NO_2$, —$NR^bC(=O)R^b$, —$NR^bC(=O)OR^b$, —$NR^bC(=O)N(R^b)_2$, —$OC(=O)R^b$, —$OC(=O)OR^b$, or —$OC(=O)N(R^b)_2$;

$R^{B4}$ is hydrogen, substituted or unsubstituted $C_{1-6}$ alkyl, or a nitrogen protecting group;

Ring B3 is a substituted or unsubstituted pyrazolyl ring;

each instance of $R^{B5}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^b$, —$N(R^b)_2$, —$SR^b$, —CN, —SCN, —$C(=NR^b)R^b$, —$C(=NR^b)OR^b$, —$C(=NR^b)N(R^b)_2$, —$C(=O)R^b$, —$C(=O)OR^b$, —$C(=O)N(R^b)_2$, —$NO_2$, —$NR^bC(=O)R^b$, —$NR^bC(=O)OR^b$, —$NR^bC(=O)N(R^b)_2$, —$OC(=O)R^b$, —$OC(=O)OR^b$, or —$OC(=O)N(R^b)_2$;

q is 0, 1, or 2;

$R^{B6}$ is substituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$C(=O)R^b$, —$C(=O)OR^b$, or —$C(=O)N(R^b)_2$.

Formula (II) includes as Ring B1 a phenyl ring that is unsubstituted (e.g., when p is 0) or substituted (e.g., when p is 1, 2, 3, 4, or 5) with one or more substituents $R^{B1}$.

In certain embodiments, Ring B1 is of the formula:

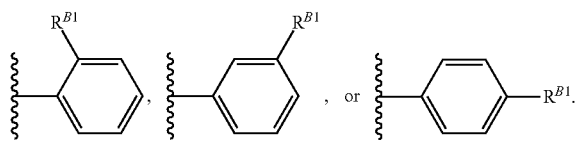

In certain embodiments, Ring B1 is of the formula:

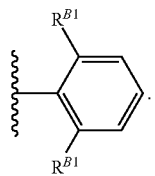

In certain embodiments, Ring B1 is of the formula:

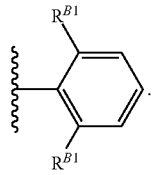

wherein each instance of $R^{B1}$ is independently substituted or unsubstituted alkyl (e.g., substituted or unsubstituted $C_{1-6}$ alkyl, such as —CH3, —CF3, Bn, unsubstituted ethyl, perfluoroethyl, unsubstituted propyl, perfluoropropyl, unsubstituted butyl, or perfluorobutyl) or halogen (e.g., F, Cl, Br, or I). In certain embodiments, Ring B1 is of the formula:

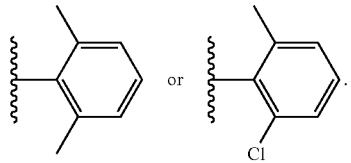

In certain embodiments, Ring B1 is of the formula:

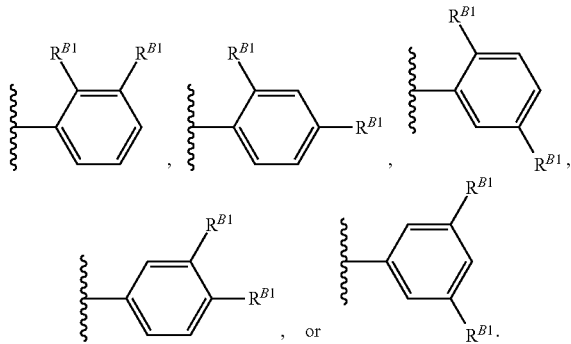

In Formula (II), Ring B1 may include one or more substituents $R^{B1}$. In certain embodiments, all instances of $R^{B1}$ are the same. In certain embodiments, two instances of $R^{B1}$ are different from each other. In certain embodiments, at least one instance of $R^{B1}$ is halogen (e.g., F, Cl, Br, or I). In certain embodiments, at least one instance of $R^{B1}$ is substituted or unsubstituted alkyl (e.g., substituted or unsubstituted $C_{1-6}$ alkyl). In certain embodiments, at least one instance of $R^{B1}$ is —CH$_3$. In certain embodiments, at least one instance of $R^{B1}$ is —CF3, Bn, unsubstituted ethyl, perfluoroethyl, unsubstituted propyl, perfluoropropyl, unsubstituted butyl, or perfluorobutyl. In certain embodiments, at least one instance of $R^{B1}$ is substituted or unsubstituted alkenyl (e.g., substituted or unsubstituted $C_{2-6}$ alkenyl). In certain embodiments, at least one instance of $R^{B1}$ is substituted or unsubstituted alkynyl (e.g., substituted or unsubstituted $C_{1-6}$ alkynyl). In certain embodiments, at least one instance of $R^{B1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{B1}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{B1}$ is substituted or unsubstituted aryl (e.g., substituted or unsubstituted, 6- to 10-membered aryl). In certain embodiments, at least one instance of $R^{B1}$ is substituted or unsubstituted phenyl. In certain embodiments, at least one instance of $R^{B1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{B1}$ is —OR$^b$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{B1}$ is —SR$^b$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{B1}$ is —N(R$^b$)$_2$ (e.g., —NH$_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —NMe$_2$)). In certain embodiments, at least one instance of $R^{B1}$ is —CN, —SCN, or —NO$_2$. In certain embodiments, at least one instance of $R^{B1}$ is —C(=NR$^b$)R$^b$, —C(=NR$^b$)OR$^b$, or —C(=NR$^b$)N(R$^b$)$_2$. In certain embodiments, at least one instance of $R^{B1}$ is —C(=O)R$^b$ (e.g., —C(=O)(substituted or unsubstituted alkyl) or —C(=O)(substituted or unsubstituted phenyl)), —C(=O)OR$^b$ (e.g., —C(=O)O(substituted or unsubstituted alkyl) or —C(=O)O(substituted or unsubstituted phenyl)), or —C(=O)N(R$^b$)$_2$ (e.g., —C(=O)NH$_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, at least one instance of $R^{B1}$ is —NR$^b$C(=O)R$^b$, —NR$^b$C(=O)OR$^b$, or —NR$^b$C(=O)N(R$^b$)$_2$. In certain embodiments, at least one instance of $R^{B1}$ is —OC(=O)R$^b$, —OC(=O)OR$^b$, or —OC(=O)N(R$^b$)$_2$.

When Formula (II) includes two or more instances of substituent $R^b$, any two instances of $R^b$ may be the same or different from each other. In certain embodiments, at least one instance of $R^b$ is H. In certain embodiments, each instance of $R^b$ is H. In certain embodiments, at least one instance of $R^b$ is substituted or unsubstituted acyl (e.g., acetyl). In certain embodiments, at least one instance of $R^b$ is substituted or unsubstituted alkyl (e.g., substituted or unsubstituted $C_{1-6}$ alkyl). In certain embodiments, at least one instance of $R^b$ is —CH3. In certain embodiments, at least one instance of $R^b$ is —CF$_3$, Bn, unsubstituted ethyl, perfluoroethyl, unsubstituted propyl, perfluoropropyl, unsubstituted butyl, or perfluorobutyl. In certain embodiments, at least one instance of $R^b$ is substituted or unsubstituted alkenyl (e.g., substituted or unsubstituted $C_{2-6}$ alkenyl). In certain embodiments, at least one instance of $R^b$ is substituted or unsubstituted alkynyl (e.g., substituted or unsubstituted $C_{1-6}$ alkynyl). In certain embodiments, at least one instance of $R^b$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^b$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^b$ is substituted or unsubstituted aryl (e.g., substituted or unsubstituted, 6- to 10-membered aryl). In certain embodiments, at least one instance of $R^b$ is substituted or unsubstituted phenyl. In certain embodiments, at least one instance of $R^b$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^b$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^b$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^b$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^b$ are joined to form a substituted or unsubstituted, heterocyclic ring (e.g., substituted or unsubstituted, 5- to 6-membered, monocyclic heterocyclic ring comprising zero, one, or two double bonds in the heterocyclic ring system, wherein one, two, or three atoms in the heterocyclic ring system are independently nitrogen, oxygen, or sulfur). In certain embodiments, two instances of $R^b$ are joined to form a substituted or unsubstituted heteroaryl ring (e.g., substituted or unsubstituted, 5- to 6-membered, monocyclic heteroaryl ring, wherein one, two, three, or four atoms in the heteroaryl ring system are independently nitrogen, oxygen, or sulfur).

In certain embodiments, p is 0. In certain embodiments, p is 1. In certain embodiments, p is 2. In certain embodiments, p is 3. In certain embodiments, p is 4. In certain embodiments, p is 5.

In certain embodiments, p is 1; and $R^{B1}$ is substituted or unsubstituted alkyl (e.g., substituted or unsubstituted $C_{1-6}$ alkyl, such as —$CH_3$, —$CF_3$, Bn, unsubstituted ethyl, perfluoroethyl, unsubstituted propyl, perfluoropropyl, unsubstituted butyl, or perfluorobutyl) or halogen (e.g., F, Cl, Br, or I). In certain embodiments, p is 2; and each of the two instances of $R^{B1}$ is independently substituted or unsubstituted alkyl (e.g., substituted or unsubstituted $C_{1-6}$ alkyl, such as —$CH_3$, —$CF_3$, Bn, unsubstituted ethyl, perfluoroethyl, unsubstituted propyl, perfluoropropyl, unsubstituted butyl, or perfluorobutyl) or halogen (e.g., F, Cl, Br, or I).

Formula (II) includes divalent linker $L^B$ connecting Ring B1 to the thiazolyl ring. In certain embodiments, $L^B$ is —C(=O)—N($R^{B2}$)— (e.g., —C(=O)—NH—). In certain embodiments, $L^B$ is —N($R^{B2}$)—C(=O)— (e.g., —NH—C(=O)—).

In certain embodiments, $R^{B2}$ is H. In certain embodiments, $R^{B2}$ is substituted or unsubstituted $C_{1-6}$ alkyl (e.g., —$CH_3$, Bn, —$CF_3$, unsubstituted ethyl, perfluoroethyl, unsubstituted propyl, perfluoropropyl, unsubstituted butyl, or perfluorobutyl). In certain embodiments, $R^{B2}$ is a nitrogen protecting group (e.g., Bn, Boc, Cbz, Fmoc, trifluoroacetyl, triphenylmethyl, acetyl, or Ts).

The thiazolyl ring of Formula (II) includes substituent $R^{B3}$. In certain embodiments, $R^{B3}$ is H. In certain embodiments, $R^{B3}$ is halogen (e.g., F, Cl, Br, or I). In certain embodiments, $R^{B3}$ is substituted or unsubstituted alkyl (e.g., substituted or unsubstituted $C_{1-6}$ alkyl). In certain embodiments, $R^{B3}$ is —$CH_3$. In certain embodiments, $R^{B3}$ is —$CF_3$, Bn, unsubstituted ethyl, perfluoroethyl, unsubstituted propyl, perfluoropropyl, unsubstituted butyl, or perfluorobutyl. In certain embodiments, $R^{B3}$ is substituted or unsubstituted alkenyl (e.g., substituted or unsubstituted $C_{2-6}$ alkenyl). In certain embodiments, $R^{B3}$ is substituted or unsubstituted alkynyl (e.g., substituted or unsubstituted $C_{1-6}$ alkynyl). In certain embodiments, $R^{B3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B3}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{B3}$ is substituted or unsubstituted aryl (e.g., substituted or unsubstituted, 6- to 10-membered aryl). In certain embodiments, $R^{B3}$ is substituted or unsubstituted phenyl. In certain embodiments, $R^{B3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{B3}$ is —$OR^b$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{B3}$ is —$SR^b$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{B3}$ is —N($R^b$)$_2$ (e.g., —$NH_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —$NMe_2$)). In certain embodiments, $R^{B3}$ is —CN, —SCN, or —$NO_2$. In certain embodiments, $R^{B3}$ is —C(=$NR^b$)$R^b$, —C(=$NR^b$)$OR^b$, or —C(=$NR^b$)N($R^b$)$_2$. In certain embodiments, $R^{B3}$ is —C(=O)$R^b$ (e.g., —C(=O)(substituted or unsubstituted alkyl) or —C(=O)(substituted or unsubstituted phenyl)), —C(=O)$OR^b$ (e.g., —C(=O)O(substituted or unsubstituted alkyl) or —C(=O)O(substituted or unsubstituted phenyl)), or —C(=O)N($R^b$)$_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{B3}$ is —$NR^b$C(=O)$R^b$, —$NR^b$C(=O)$OR^b$, or —$NR^b$C(=O)N($R^b$)$_2$. In certain embodiments, $R^{B3}$ is —OC(=O)$R^b$, —OC(=O)$OR^b$, or —OC(=O)N($R^b$)$_2$.

Formula (II) includes substituent $R^{B4}$ on a nitrogen atom attached to the thiazolyl ring. In certain embodiments, $R^{B4}$ is H. In certain embodiments, $R^{B4}$ is substituted or unsubstituted $C_{1-6}$ alkyl (e.g., —CH3, Bn, —$CF_3$, unsubstituted ethyl, perfluoroethyl, unsubstituted propyl, perfluoropropyl, unsubstituted butyl, or perfluorobutyl). In certain embodiments, $R^{B4}$ is a nitrogen protecting group (e.g., Bn, Boc, Cbz, Fmoc, trifluoroacetyl, triphenylmethyl, acetyl, or Ts).

Formula (II) includes as Ring B3 a pyrazolyl ring that is unsubstituted (e.g., when q is 0) or substituted (e.g., when q is 1 or 2) with one or more substituents $R^{B5}$. In certain embodiments, Ring B3 is of the formula:

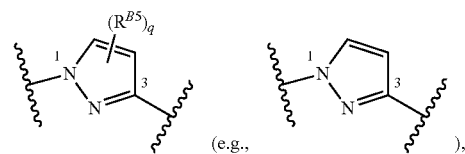

wherein the nitrogen atom labeled with "1" is attached to $R^{B6}$, and the carbon atom labeled with "3" is attached to the nitrogen atom to which $R^{B4}$ is attached. In certain embodiments, Ring B3 is of the formula:

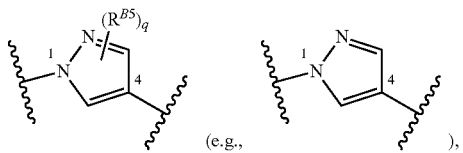

(e.g., ), wherein the nitrogen atom labeled with "1" is attached to $R^{B6}$, and the carbon atom labeled with "4" is attached to the nitrogen atom to which $R^{B4}$ is attached.

In Formula (II), Ring B3 may include one or two substituents $R^{B5}$. In certain embodiments, two instances of $R^{B5}$ are the same. In certain embodiments, two instances of $R^{B5}$ are different from each other. In certain embodiments, at least one instance of $R^{B5}$ is halogen (e.g., F, Cl, Br, or I). In certain embodiments, at least one instance of $R^{B5}$ is substituted or unsubstituted alkyl (e.g., substituted or unsubstituted $C_{1-6}$ alkyl). In certain embodiments, at least one instance of $R^{B5}$ is $-CH_3$. In certain embodiments, at least one instance of $R^{B5}$ is $-CF_3$, Bn, unsubstituted ethyl, perfluoroethyl, unsubstituted propyl, perfluoropropyl, unsubstituted butyl, or perfluorobutyl. In certain embodiments, at least one instance of $R^{B5}$ is substituted or unsubstituted alkenyl (e.g., substituted or unsubstituted $C_{2-6}$ alkenyl). In certain embodiments, at least one instance of $R^{B5}$ is substituted or unsubstituted alkynyl. (e.g., substituted or unsubstituted $C_{1-6}$ alkynyl). In certain embodiments, at least one instance of $R^{B5}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{B5}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{B5}$ is substituted or unsubstituted aryl (e.g., substituted or unsubstituted, 6- to 10-membered aryl). In certain embodiments, at least one instance of $R^{B5}$ is substituted or unsubstituted phenyl. In certain embodiments, at least one instance of $R^{B5}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{B5}$ is $-OR^b$ (e.g., $-OH$, $-O$(substituted or unsubstituted $C_{1-6}$ alkyl) (e.g., $-OMe$, $-OEt$, $-OPr$, $-OBu$, or $-OBn$), or $-O$(substituted or unsubstituted phenyl) (e.g., $-OPh$)). In certain embodiments, at least one instance of $R^{B5}$ is $-SR^b$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)). In certain embodiments, at least one instance of $R^{B5}$ is $-N(R^b)_2$ (e.g., $-NH_2$, $-NH$(substituted or unsubstituted $C_{1-6}$ alkyl) (e.g., $-NHMe$), or $-N$(substituted or unsubstituted $C_{1-6}$ alkyl)—(substituted or unsubstituted $C_{1-6}$ alkyl) (e.g., $-NMe_2$)). In certain embodiments, at least one instance of $R^{B5}$ is $-CN$, $-SCN$, or $-NO_2$. In certain embodiments, at least one instance of $R^{B5}$ is $-C(=NR^b)R^b$, $-C(=NR^b)OR^b$, or $-C(=NR^b)N(R^b)_2$. In certain embodiments, at least one instance of $R^{B5}$ is $-C(=O)R^b$ (e.g., $-C(=O)$(substituted or unsubstituted alkyl) or $-C(=O)$(substituted or unsubstituted phenyl)), $-C(=O)OR^b$ (e.g., $-C(=O)O$(substituted or unsubstituted alkyl) or $-C(=O)O$(substituted or unsubstituted phenyl)), or $-C(=O)N(R^b)_2$ (e.g., $-C(=O)NH_2$, $-C(=O)NH$(substituted or unsubstituted alkyl), $-C(=O)NH$(substituted or unsubstituted phenyl), $-C(=O)N$(substituted or unsubstituted alkyl)—(substituted or unsubstituted alkyl), or $-C(=O)N$(substituted or unsubstituted phenyl)—(substituted or unsubstituted alkyl)). In certain embodiments, at least one instance of $R^{B5}$ is $-NR^bC(=O)R^b$, $-NR^bC(=O)OR^b$, or $-NR^bC(=O)N(R^b)_2$. In certain embodiments, at least one instance of $R^{B5}$ is $-OC(=O)R^b$, $-OC(=O)OR^b$, or $-OC(=O)N(R^b)_2$.

In certain embodiments, q is 0. In certain embodiments, q is 1. In certain embodiments, q is 2.

Formula (II) includes substituent $R^{B6}$ on a nitrogen atom attached to Ring B3. In certain embodiments, $R^{B6}$ is substituted alkyl (e.g., substituted $C_{1-6}$ alkyl). In certain embodiments, $R^{B6}$ is $-CF_3$, Bn, perfluoroethyl, perfluoropropyl, or perfluorobutyl. In certain embodiments, $R^{B6}$ is substituted or unsubstituted alkenyl (e.g., substituted or unsubstituted $C_{2-6}$ alkenyl). In certain embodiments, $R^{B6}$ is substituted or unsubstituted alkynyl (e.g., substituted or unsubstituted $C_{1-6}$ alkynyl). In certain embodiments, $R^{B6}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B6}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{B6}$ is substituted or unsubstituted aryl (e.g., substituted or unsubstituted, 6- to 10-membered aryl). In certain embodiments, $R^{B6}$ is substituted or unsubstituted phenyl. In certain embodiments, $R^{B6}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{B6}$ is $-C(=O)R^b$ (e.g., $-C(=O)$(substituted or unsubstituted alkyl) or $-C(=O)$(substituted or unsubstituted phenyl)), $-C(=O)OR^b$ (e.g., $-C(=O)O$(substituted or unsubstituted alkyl) or $-C(=O)O$(substituted or unsubstituted phenyl)), or $-C(=O)N(R^b)_2$ (e.g., $-C(=O)NH_2$, $-C(=O)NH$(substituted or unsubstituted alkyl), $-C(=O)NH$(substituted or unsubstituted phenyl), $-C(=O)N$(substituted or unsubstituted alkyl)—(substituted or unsubstituted alkyl), or $-C(=O)N$(substituted or unsubstituted phenyl)—(substituted or unsubstituted alkyl)). In certain embodiments, $R^{B6}$ is of the formula:
wherein:

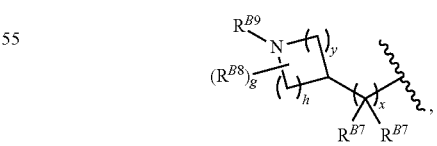

each instance of $R^{B7}$ is independently hydrogen, halogen, or substituted or unsubstituted $C_{1-6}$ alkyl;
x is 0, 1, 2, 3, or 4;
y is 1, 2, 3, or 4;
h is 1, 2, or 3;
each instance of $R^{B8}$ is independently halogen, or substituted or unsubstituted $C_{1-6}$ alkyl;

g is an integer between 0 and 13, inclusive; and $R^{B9}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, —C(=O)R$^a$, —C(=O)OR$^a$, —C(=O)N(R$^a$)$_2$, a nitrogen protecting group, or of any one of Formulae (ii-1) to (ii-42):

(ii-1)
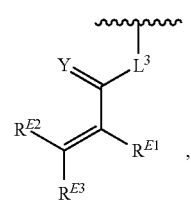

(ii-2)
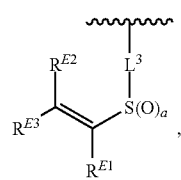

(ii-3)
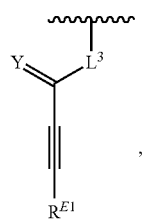

(ii-4)
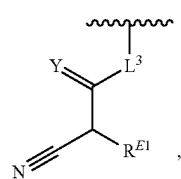

(ii-5)
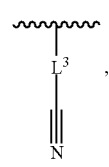

(ii-6)
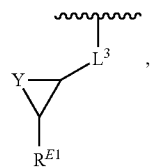

(ii-7)
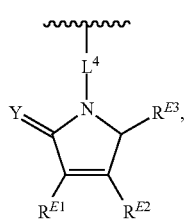

-continued (ii-8)
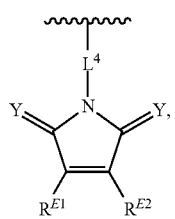

(ii-9)
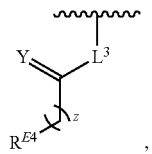

(ii-10)
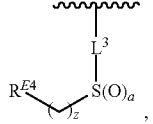

(ii-11)
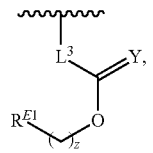

(ii-12)
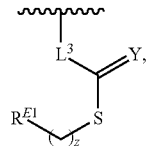

(ii-13)
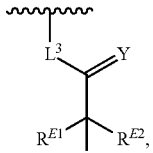

(ii-14)
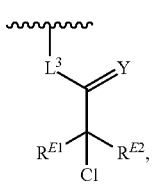

(ii-15)
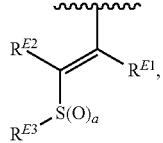

(ii-16)
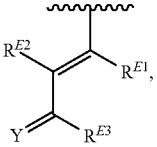

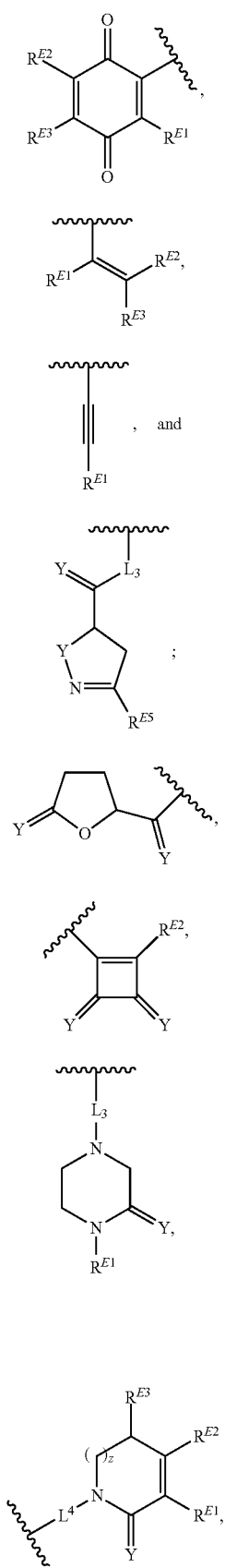
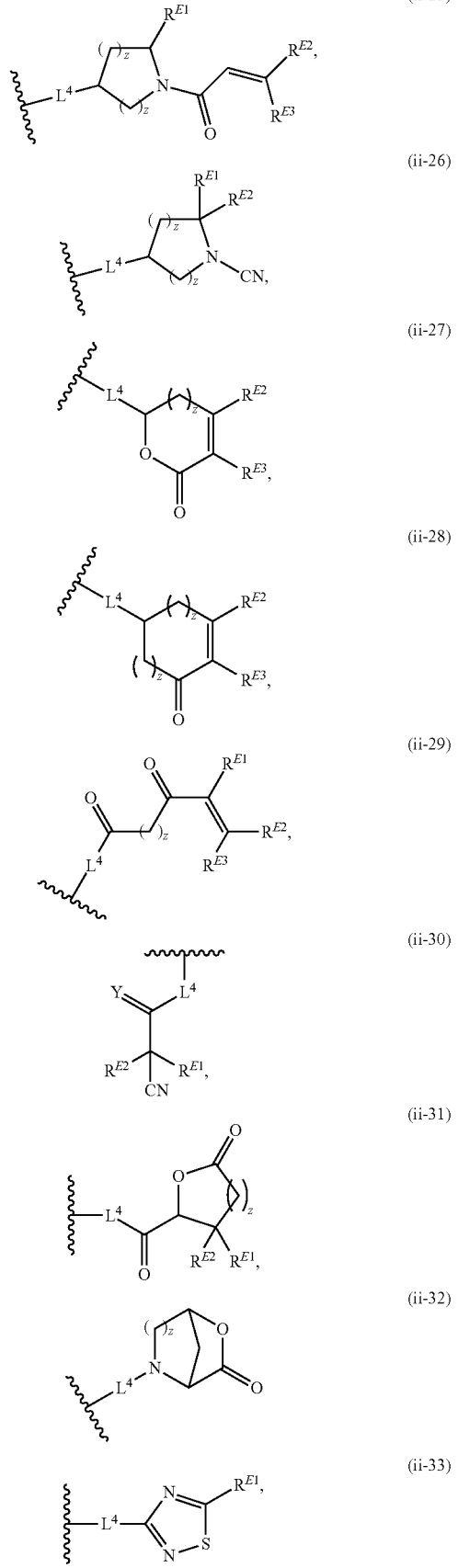

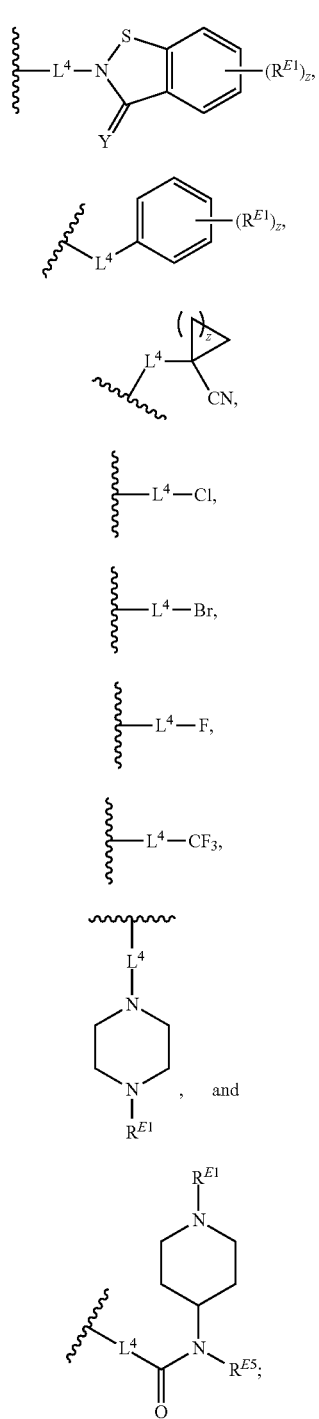

wherein:
L³ is a bond or an optionally substituted C₁ hydrocarbon chain, optionally wherein one or more carbon units of the hydrocarbon chain are independently replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans—CR$^{L3b}$=CR$^{L3b}$—, cis—CR$^{L3b}$=CR$^{L3b}$—, —C≡C—, —S(=O)—, —S(=O)O—, —OS(=O)—, —S(=O)₂—, —S(=O)NR$^{L3a}$—, —NR$^{L3a}$S(=O)—, —S(=O)₂—, —S(=O)₂O—, —OS(=O)₂—, —S(=O)₂NR$^{L3a}$—, or —NR$^{L3a}$S(=O)₂—, wherein R$^{L3}$a is hydrogen, substituted or unsubstituted C₁₋₆ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

L⁴ is a bond or an optionally substituted C₁₋₄ hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR$^{E1a}$, —CH₂N(R$^{E1a}$)₂, —CH₂SR$^{E1a}$, —OR$^{E1a}$, —N(R$^{E1a}$)₂, —Si(R$^{E1a}$)₃, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR$^{E2a}$, —CH₂N(R$^{E2a}$)₂, —CH₂SR$^{E2a}$, —OR$^{E2a}$, —N(R$^{E2a}$)₂, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR$^{E3a}$, —CH₂N(R$^{E3a}$)₂, —CH₂SR$^{E3a}$, —OR$^{E3a}$, —N(R$^{E3a}$)₂, and —SR$^{E3a}$, wherein each occurrence of R$^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

Y is O, S, or NR$^{E6}$, wherein R$^{E6}$ is hydrogen, substituted or unsubstituted C₁₋₆ alkyl, or a nitrogen protecting group;

a is 1 or 2; and each instance of z is independently 0, 1, 2, 3, 4, 5, or 6.

In certain embodiments, R$^{B6}$ is of the formula:

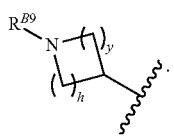

In certain embodiments, $R^{B6}$ is of the formula:

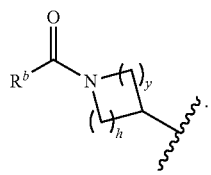

In certain embodiments, $R^{B6}$ is of the formula:

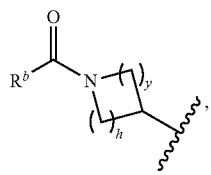

wherein $R^b$ is substituted or unsubstituted $C_{2-6}$ alkenyl. In certain embodiments, $R^{B6}$ is of the formula:

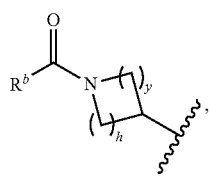

wherein $R^b$ is substituted or unsubstituted $C_{1-6}$ alkyl. In certain embodiments, $R^{B6}$ is of the formula:

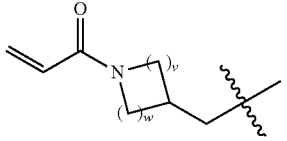

(e.g., 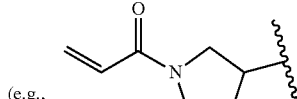

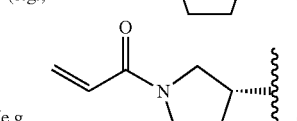

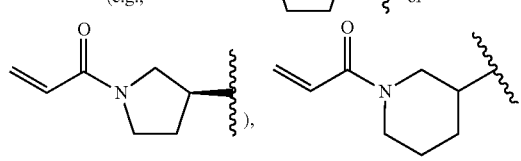

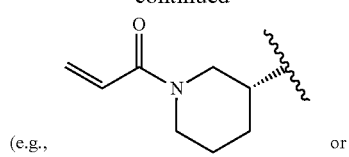

(e.g., or

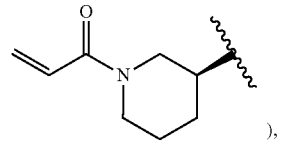

),

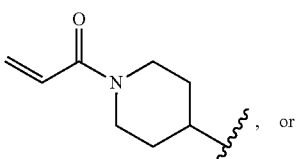

, or

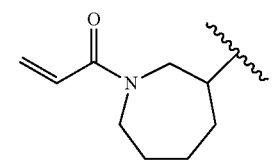

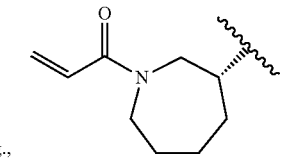

(e.g., or

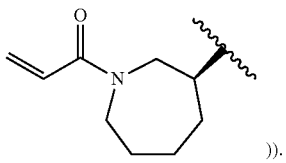

)).

In certain embodiments, $R^{B6}$ is of the formula:

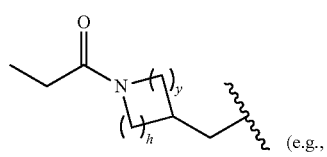 (e.g.,

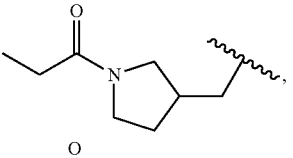,

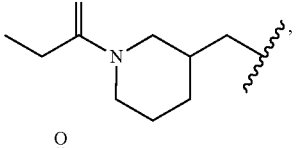,

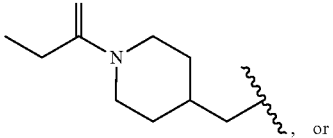, or

-continued

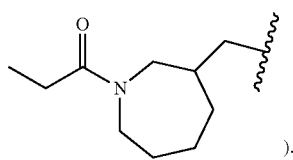

In certain embodiments, $R^{B6}$ is of the formula:

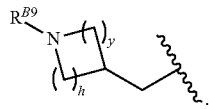

In certain embodiments, $R^{B6}$ is of the formula:

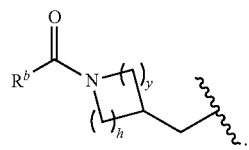

In certain embodiments, $R^{B6}$ is of the formula:

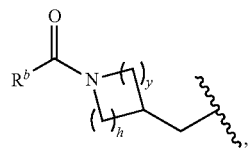

wherein $R^b$ is substituted or unsubstituted $C_{2-6}$ alkenyl. In certain embodiments, $R^{B6}$ is of the formula:

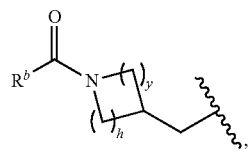

wherein $R^b$ is substituted or unsubstituted $C_{1-6}$ alkyl. In certain embodiments, $R^{B6}$ is of the formula:

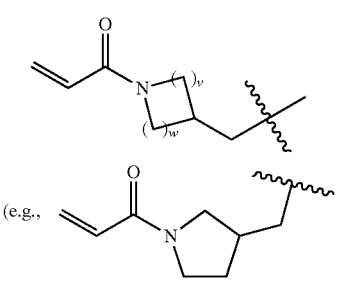

-continued

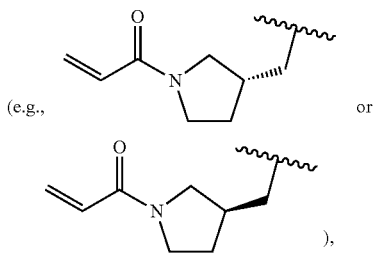

In certain embodiments, $R^{B6}$ is of the formula:

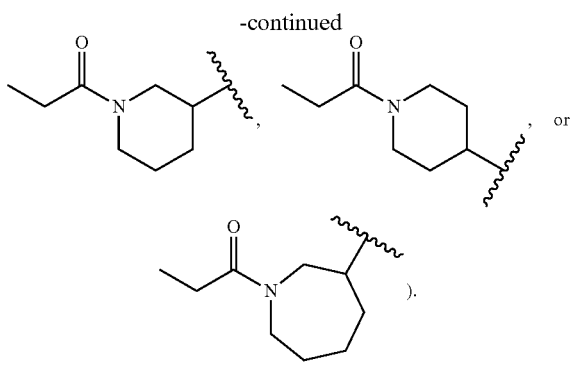

In certain embodiments, all instances of $R^{B7}$ are the same. In certain embodiments, two instances of $R^{B7}$ are different from each other. In certain embodiments, at least one instance of $R^{B7}$ is H. In certain embodiments, each instance of $R^{B7}$ is H. In certain embodiments, at least one instance of $R^{B7}$ is halogen (e.g., F, Cl, Br, or I). In certain embodiments, at least one instance of $R^{B7}$ is substituted or unsubstituted alkyl (e.g., substituted or unsubstituted $C_{1-6}$ alkyl). In certain embodiments, at least one instance of $R^{B7}$ is —CH3. In certain embodiments, at least one instance of $R^{B7}$ is —CF$_3$, Bn, unsubstituted ethyl, perfluoroethyl, unsubstituted propyl, perfluoropropyl, unsubstituted butyl, or perfluorobutyl.

In certain embodiments, x is 0. In certain embodiments, x is 1. In certain embodiments, x is 2. In certain embodiments, x is 3. In certain embodiments, x is 4.

In certain embodiments, y is 1. In certain embodiments, y is 2. In certain embodiments, y is 3. In certain embodiments, y is 4.

In certain embodiments, h is 1. In certain embodiments, h is 2. In certain embodiments, h is 3.

In certain embodiments, y is 2; and h is 1. In certain embodiments, y is 3; and h is 1. In certain embodiments, y is 4; and h is 1.

In certain embodiments, all instances of $R^{B8}$ are the same. In certain embodiments, two instances of $R^{B8}$ are different from each other. In certain embodiments, at least one instance of $R^{B8}$ is halogen (e.g., F, Cl, Br, or I). In certain embodiments, at least one instance of $R^{B8}$ is substituted or unsubstituted alkyl (e.g., substituted or unsubstituted $C_{1-6}$ alkyl). In certain embodiments, at least one instance of $R^{B8}$ is —CH$_3$. In certain embodiments, at least one instance of $R^{B8}$ is —CF$_3$, Bn, unsubstituted ethyl, perfluoroethyl, unsubstituted propyl, perfluoropropyl, unsubstituted butyl, or perfluorobutyl.

In certain embodiments, g is 0. In certain embodiments, g is 1, 2, 3, 4, 5, 6, 7, 8, 9, 10, 11, 12, or 13.

In certain embodiments, $R^{B9}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, —C(=O)R$^a$, —C(=O)OR$^a$, —C(=O)N(R$^a$)$_2$, a nitrogen protecting group, or of any one of Formulae (ii-1) to (ii-23). In certain embodiments, $R^{B9}$ is H. In certain embodiments, $R^{B9}$ is substituted or unsubstituted $C_{1-6}$ alkyl (e.g., $C_{1-6}$ alkyl substituted with one or more substituents independently selected from the group consisting of oxo; halogen; substituted or unsubstituted $C_{2-6}$ alkenyl; substituted or unsubstituted cyclopropyl; substituted or unsubstituted, 4- to 7-membered monocyclic carbocyclyl comprising 1 or 2 double bonds in the carbocyclic ring system; substituted or unsubstituted oxiranyl; substituted or unsubstituted, 5- to 10-membered, monocyclic or bicyclic heteroaryl, wherein 1, 2, 3, or 4 atoms in the heteroaryl ring system are independently oxygen, nitrogen, or sulfur; —CN; —(C=O)R$^a$; —N(R$^a$)(C=O)R$^a$; —O(C=O)R$^a$; —OR$^a$; and —N(R$^a$)$_2$). In certain embodiments, $R^{B9}$ is substituted or unsubstituted $C_{2-6}$ alkenyl (e.g., substituted or unsubstituted vinyl). In certain embodiments, $R^{B9}$ is substituted or unsubstituted $C_{2-6}$ alkynyl (e.g., substituted or unsubstituted ethynyl). In certain embodiments, $R^{B9}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B9}$ is —C(=O)R$^a$. In certain embodiments, $R^{B9}$ is —C(=O) (substituted or unsubstituted alkyl) (e.g., —C(=O)(substituted or unsubstituted $C_{1-6}$ alkyl), such as —C(=O)Et). In certain embodiments, $R^{B9}$ is —C(=O)(substituted or unsubstituted alkenyl) (e.g., —C(=O)(substituted or unsubstituted $C_{2-6}$ alkenyl), such as —C(=O)—CH=CH2). In certain embodiments, $R^{B9}$ is —C(=O)(substituted or unsubstituted carbocyclyl). In certain embodiments, $R^{B9}$ is —C(=O)(substituted or unsubstituted heterocyclyl). In certain embodiments, $R^{B9}$ is —C(=O)(substituted or unsubstituted phenyl). In certain embodiments, $R^{B9}$ is —C(=O) (substituted or unsubstituted heteroaryl). In certain embodiments, $R^{B9}$ is —C(=O)OR$^a$ (e.g., —C(=O)O(substituted or unsubstituted alkyl) or —C(=O)O(substituted or unsubstituted phenyl)) or —C(=O)N(R$^a$)$_2$ (e.g., —C(=O) NH$_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{B9}$ is a nitrogen protecting group (e.g., Bn, Boc, Cbz, Fmoc, trifluoroacetyl, triphenylmethyl, acetyl, or Ts). In certain embodiments, $R^{B9}$ is of any one of Formulae (ii-1) to (ii-23). In certain embodiments, $R^{B9}$ is of any one of Formulae (ii-24) to (ii-42). In certain embodiments, $R^{B9}$ is of Formula (ii-1) (e.g., of the formula:

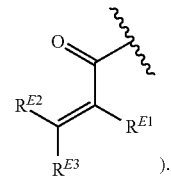

In certain embodiments, $R^{B9}$ is of Formula (ii-3) (e.g., of the formula:

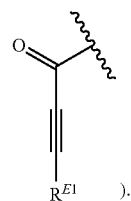

In certain embodiments, $R^{B9}$ is of any one of the formulae shown in Table 1A. The moieties included in $R^{B9}$ are as described herein.

In certain embodiments, a compound of Formula (II) is of the formula:

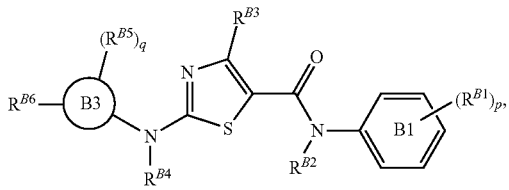

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

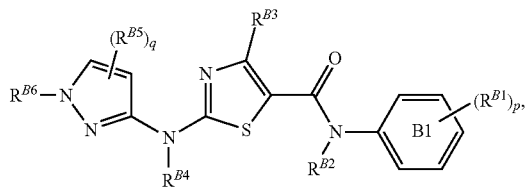

or a pharmaceutically acceptable salt, solvate, hydrate, polymorph, co-crystal, tautomer, stereoisomer, isotopically labeled derivative, or prodrug thereof.

In certain embodiments, a compound of Formula (H) is of the formula:

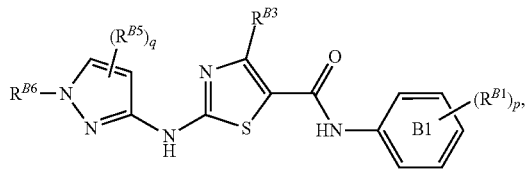

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

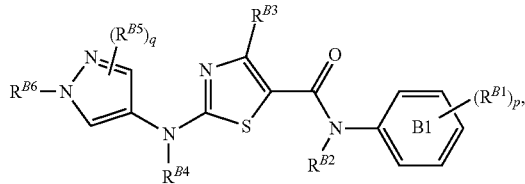

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

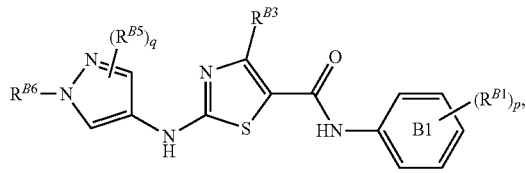

or a pharmaceutically acceptable salt, solvate, hydrate, polymorph, co-crystal, tautomer, stereoisomer, isotopically labeled derivative, or prodrug thereof.

In certain embodiments, a compound of Formula (H) is of the formula:

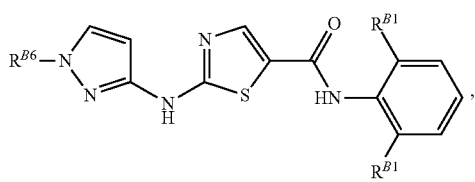

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

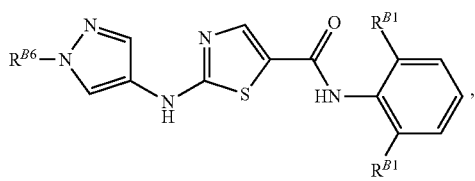

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

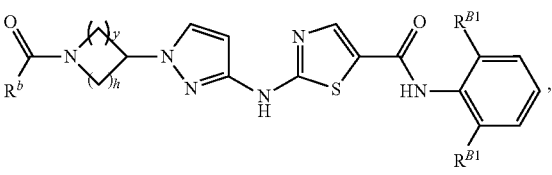

or a pharmaceutically acceptable salt, solvate, hydrate, polymorph, co-crystal, tautomer, stereoisomer, isotopically labeled derivative, or prodrug thereof, wherein $R^b$ is substituted or unsubstituted $C_{2-6}$ alkenyl.

In certain embodiments, a compound of Formula (II) is of the formula:

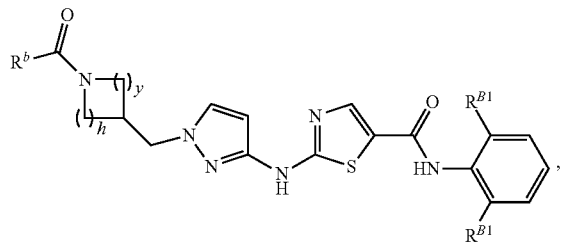

or a pharmaceutically acceptable salt, solvate, hydrate, polymorph, co-crystal, tautomer, stereoisomer, isotopically labeled derivative, or prodrug thereof, wherein $R^b$ is substituted or unsubstituted $C_{2-6}$ alkenyl.

In certain embodiments, a compound of Formula (II) is of the formula:

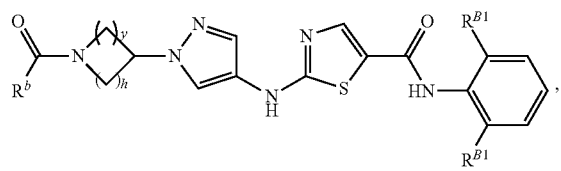

or a pharmaceutically acceptable salt, solvate, hydrate, polymorph, co-crystal, tautomer, stereoisomer, isotopically labeled derivative, or prodrug thereof, wherein $R^b$ is substituted or unsubstituted $C_{2-6}$ alkenyl.

In certain embodiments, a compound of Formula (II) is of the formula:

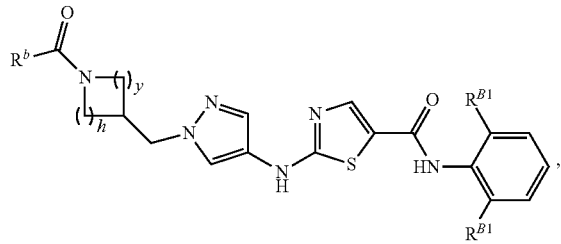

or a pharmaceutically acceptable salt, solvate, hydrate, polymorph, co-crystal, tautomer, stereoisomer, isotopically labeled derivative, or prodrug thereof, wherein $R^b$ is substituted or unsubstituted $C_{2-6}$ alkenyl.

Exemplary compounds of Formula (II) include, but are not limited to:

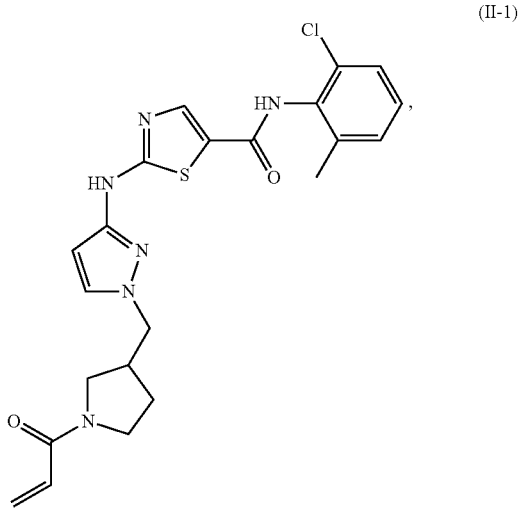

(II-1)

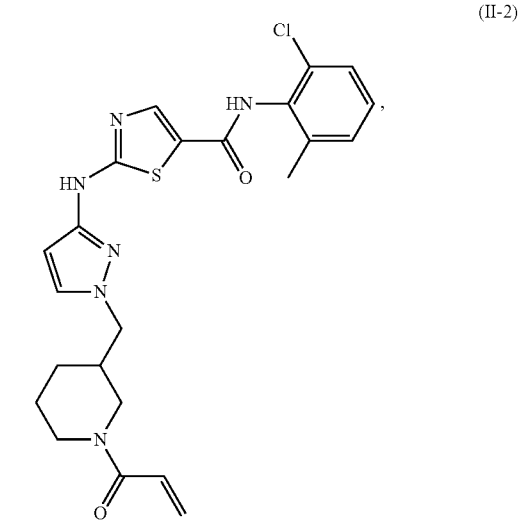

(II-2)

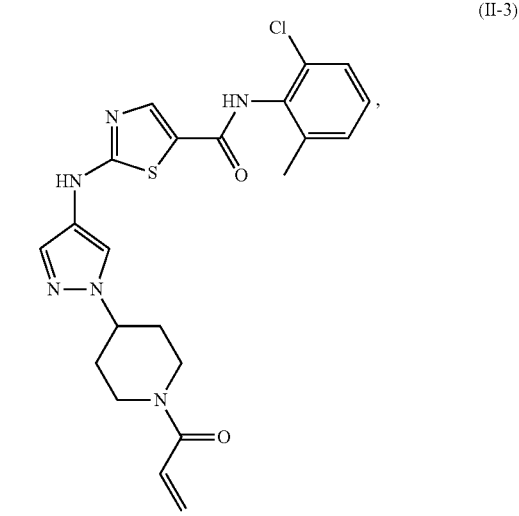

(II-3)

and pharmaceutically acceptable salts, solvates, hydrates, polymorphs, co-crystals, tautomers, stereoisomers, isotopically labeled derivatives, and prodrugs thereof.

Compounds of Formula (III)

In certain embodiments, a compound described herein is of Formula (III):

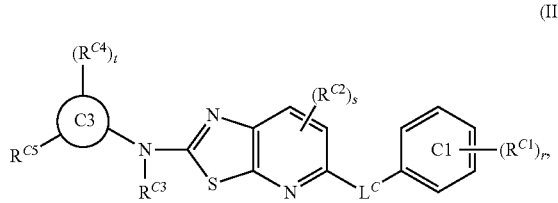

(III)

or a pharmaceutically acceptable salt, solvate, hydrate, polymorph, co-crystal, tautomer, stereoisomer, isotopically labeled derivative, or prodrug thereof, wherein:

each instance of $R^{C1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^e$, —$N(R^e)_2$, —$SR^e$, —CN, —SCN, —C(=$NR^e$)$R^e$, —C(=$NR^e$)$OR^e$, —C(=$NR^e$)N($R^e$)$_2$, —C(=O)$R^e$, —C(=O)$OR^e$, —C(=O)N($R^e$)$_2$, —$NO_2$, —$NR^e$C(=O)$R^e$, —$NR^e$C(=O)$OR^e$, —$NR^e$C(=O)N($R^e$)$_2$, —OC(=O)$R^e$, —OC(=O)$OR^e$, or —OC(=O)N($R^e$)$_2$;

each instance of $R^e$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^e$ are joined to form a substituted or unsubstituted, heterocyclic ring, or substituted or unsubstituted, heteroaryl ring;

r is 0, 1, 2, 3, 4, or 5;

$L^c$ is —O— or —S—;

each instance of $R^{C2}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^e$, —$N(R^e)_2$, —$SR^e$, —CN, —SCN, —C(=$NR^e$)$R^e$, —C(=$NR^e$)$OR^e$, —C(=$NR^e$)N($R^e$)$_2$, —C(=O)$R^e$, —C(=O)$OR^e$, —C(=O)N($R^e$)$_2$, —$NO_2$, —$NR^e$C(=O)$R^e$, —$NR^e$C(=O)$OR^e$, —$NR^e$C(=O)N($R^e$)$_2$, —OC(=O)$R^e$, —OC(=O)$OR^e$, or —OC(=O)N($R^e$)$_2$;

s is 0, 1, or 2;

$R^{C3}$ is hydrogen, substituted or unsubstituted $C_{1-6}$ alkyl, or a nitrogen protecting group;

Ring C3 is a substituted or unsubstituted, pyrimidinyl ring or substituted or unsubstituted, pyrazolyl ring;

each instance of $R^{C4}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^e$, —$N(R^e)_2$, —$SR^e$, —CN, —SCN, —C(=$NR^e$)$R^e$, —C(=$NR^e$)$OR^e$, —C(=$NR^e$)N($R^e$)$_2$, —C(=O)$R^e$, —C(=O)$OR^e$, —C(=O)N($R^e$)$_2$, —$NO_2$, —$NR^e$C(=O)$R^e$, —$NR^e$C(=O)$OR^e$, —$NR^e$C(=O)N($R^e$)$_2$, —OC(=O)$R^e$, —OC(=O)$OR^e$, or —OC(=O)N($R^e$)$_2$;

t is 0, 1, or 2; and $R^{C5}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^e$, —$N(R^e)_2$, —$SR^e$, —CN, —SCN, —C(=$NR^e$)$R^e$, —C(=$NR^e$)$OR^e$, —C(=$NR^e$)N($R^e$)$_2$, —C(=O)$R^e$, —C(=O)$OR^e$, —C(=O)N($R^e$)$_2$, —$NO_2$, —$NR^e$C(=O)$R^e$, —$NR^e$C(=O)$OR^e$, —$NR^e$C(=O)N($R^e$)$_2$, —OC(=O)$R^e$, —OC(=O)$OR^e$, or —OC(=O)N($R^e$)$_2$.

Formula (III) includes as Ring C1 a phenyl ring that is unsubstituted (e.g., when r is 0) or substituted (e.g., when r is 1, 2, 3, 4, or 5) with one or more substituents $R^{C1}$. In certain embodiments, Ring C1 is unsubstituted phenyl. In certain embodiments, Ring C1 is of the formula:

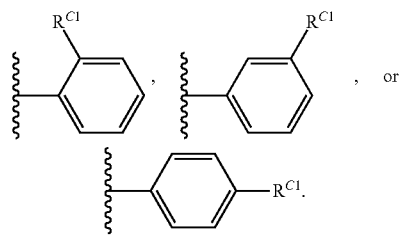

In certain embodiments, Ring C1 is of the formula:

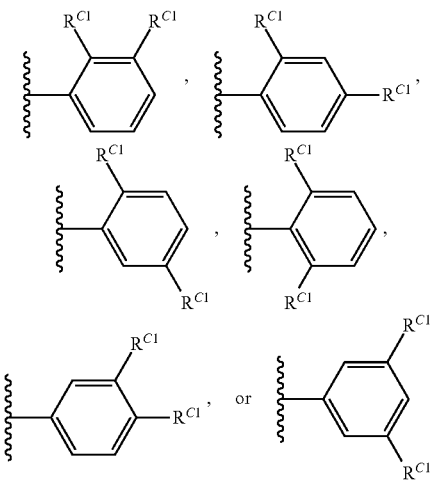

In Formula (III), Ring C1 may include one or more substituents $R^{C1}$. In certain embodiments, all instances of $R^{C1}$ are the same. In certain embodiments, two instances of $R^{C1}$ are different from each other. In certain embodiments, at least one instance of $R^{C1}$ is halogen (e.g., F, Cl, Br, or I). In certain embodiments, at least one instance of $R^{C1}$ is substituted or unsubstituted alkyl (e.g., substituted or unsubstituted $C_{1-6}$ alkyl). In certain embodiments, at least one instance of $R^{C1}$ is —$CH_3$. In certain embodiments, at least one instance of $R^{C1}$ is —$CF_3$, Bn, unsubstituted ethyl, perfluoroethyl, unsubstituted propyl, perfluoropropyl, unsubstituted butyl, or perfluorobutyl. In certain embodiments, at least one instance of $R^{C1}$ is substituted or unsubstituted alkenyl (e.g., substituted or unsubstituted $C_{2-6}$ alkenyl). In certain embodiments, at least one instance of $R^{C1}$ is substituted or unsubstituted alkynyl (e.g., substituted or unsubstituted $C_{1-6}$ alkynyl). In certain embodiments, at least one instance of $R^{C1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{C1}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{C1}$ is substituted or unsubstituted aryl (e.g., substituted or unsubstituted, 6- to 10-membered aryl). In certain embodiments, at least one instance of $R^{C1}$ is substituted or unsubstituted phenyl. In certain embodiments, at least one instance of $R^{C1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{C1}$ is —$OR^c$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{C1}$ is —$SR^c$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{C1}$ is —$N(R^c)_2$ (e.g., —$NH_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —$NMe_2$)). In certain embodiments, at least one instance of $R^{C1}$ is —CN, —SCN, or —$NO_2$. In certain embodiments, at least one instance of $R^{C1}$ is —C(=$NR^c$)$R^c$, —C(=$NR^c$)$OR^c$, or —C(=$NR^c$)$N(R^c)_2$. In certain embodiments, at least one instance of $R^{C1}$ is —C(=O)$R^c$ (e.g., —C(=O)(substituted or unsubstituted alkyl) or —C(=O)(substituted or unsubstituted phenyl)), —C(=O)$OR^c$ (e.g., —C(=O)O(substituted or unsubstituted alkyl) or —C(=O)O(substituted or unsubstituted phenyl)), or —C(=O)$N(R^c)_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, at least one instance of $R^{C1}$ is —$NR^c$C(=O)$R^c$, —$NR^c$C(=O)$OR^c$, or —$NR^c$C(=O)N$(R^c)_2$. In certain embodiments, at least one instance of $R^{C1}$ is —OC(=O)W, —OC(=O)$OR^c$, or —OC(=O)$N(R^c)_2$.

When Formula (III) includes two or more instances of substituent $R^c$, any two instances of $R^c$ may be the same or different from each other. In certain embodiments, at least one instance of $R^c$ is H. In certain embodiments, each instance of $R^c$ is H. In certain embodiments, at least one instance of $R^c$ is substituted or unsubstituted acyl (e.g., acetyl). In certain embodiments, at least one instance of $R^c$ is substituted or unsubstituted alkyl (e.g., substituted or unsubstituted $C_{1-6}$ alkyl). In certain embodiments, at least one instance of $R^c$ is —$CH_3$. In certain embodiments, at least one instance of $R^c$ is —$CF_3$, Bn, unsubstituted ethyl, perfluoroethyl, unsubstituted propyl, perfluoropropyl, unsubstituted butyl, or perfluorobutyl. In certain embodiments, at least one instance of $R^c$ is substituted or unsubstituted alkenyl (e.g., substituted or unsubstituted $C_{2-6}$ alkenyl). In certain embodiments, at least one instance of $R^c$ is substituted or unsubstituted alkynyl (e.g., substituted or unsubstituted $C_{1-6}$ alkynyl). In certain embodiments, at least one instance of $R^c$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^c$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^c$ is substituted or unsubstituted aryl (e.g., substituted or unsubstituted, 6- to 10-membered aryl). In certain embodiments, at least one instance of $R^c$ is substituted or unsubstituted phenyl. In certain embodiments, at least one instance of $R^c$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^c$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^c$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^c$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^c$ are joined to form a substituted or unsubstituted, heterocyclic ring (e.g., substituted or unsubstituted, 5- to 6-membered, monocyclic heterocyclic ring comprising zero, one, or two double bonds in the heterocyclic ring system, wherein one, two, or three atoms in the heterocyclic ring system are independently nitrogen, oxygen, or sulfur). In certain embodiments, two instances of $R^c$ are joined to form a substituted or unsubstituted heteroaryl ring (e.g., substituted or unsubstituted, 5- to 6-membered, monocyclic heteroaryl ring, wherein one, two, three, or four atoms in the heteroaryl ring system are independently nitrogen, oxygen, or sulfur).

In certain embodiments, r is 0. In certain embodiments, r is 1. In certain embodiments, r is 2. In certain embodiments, r is 3. In certain embodiments, r is 4. In certain embodiments, r is 5.

Formula (III) includes divalent linker $L^C$ connecting Ring C1 to the 7-azabenzothiazolyl ring. In certain embodiments, $L^C$ is —O—. In certain embodiments, $L^C$ is —S—.

In Formula (III), the 7-azabenzothiazolyl ring may include one or two substituents $R^{C2}$. In certain embodiments, two instances of $R^{C2}$ are the same. In certain embodiments, two instances of $R^{C2}$ are different from each other. In certain embodiments, at least one instance of $R^{C2}$ is halogen (e.g., F, Cl, Br, or I). In certain embodiments, at least one instance of $R^{C2}$ is substituted or unsubstituted alkyl (e.g., substituted or unsubstituted $C_{1-6}$ alkyl). In certain embodiments, at least one instance of $R^{C2}$ is —$CH_3$. In certain embodiments, at least one instance of $R^{C2}$ is —$CF_3$, Bn, unsubstituted ethyl, perfluoroethyl, unsubstituted propyl, perfluoropropyl, unsubstituted butyl, or perfluorobutyl. In certain embodiments, at least one instance of $R^{C2}$ is substituted or unsubstituted alkenyl (e.g., substituted or unsubstituted $C_{2-6}$ alkenyl). In certain embodiments, at least one instance of $R^{C2}$ is substituted or unsubstituted alkynyl (e.g., substituted or unsubstituted $C_{1-6}$ alkynyl). In certain embodiments, at least one instance of $R^{C2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{C2}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{C2}$ is substituted or unsubstituted aryl (e.g., substituted or unsubstituted, 6- to 10-membered aryl). In certain embodiments, at least one instance of $R^{C2}$ is substituted or unsubstituted phenyl. In certain embodiments, at least one instance of $R^{C2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{C2}$ is —$O^e$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{C2}$ is —$SR^e$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{C2}$ is —$N(R^e)_2$ (e.g., —$NH_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —$NMe_2$)). In certain embodiments, at least one instance of $R^{C2}$ is —CN, —SCN, or —$NO_2$. In certain embodiments, at least one instance of $R^{C2}$ is —C(=$NR^e$)$R^e$, —C(=$NR^e$)$OR^e$, or —C(=$NR^e$)N($R^e$)$_2$. In certain embodiments, at least one instance of $R^{C2}$ is —C(=O)$R^e$ (e.g., —C(=O)(substituted or unsubstituted alkyl) or —C(=O) (substituted or unsubstituted phenyl)), —C(=O)$OR^e$ (e.g., —C(=O)O(substituted or unsubstituted alkyl) or —C(=O)O(substituted or unsubstituted phenyl)), or —C(=O)N($R^e$)$_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, at least one instance of $R^{C2}$ is —$NR^e$C(=O)$R^e$, —$NR^e$C(=O)$OR^e$, or —$NR^e$C(=O)N($R^e$)$_2$. In certain embodiments, at least one instance of $R^{C2}$ is —OC(=O)$R^e$, —OC(=O)$OR^e$, or —OC(=O)N($R^e$)$_2$.

In certain embodiments, s is 0. In certain embodiments, s is 1. In certain embodiments, s is 2.

Formula (III) includes substituent $R^{C3}$ on a nitrogen atom attached to the 7-azabenzothiazolyl ring. In certain embodiments, $R^{C3}$ is H. In certain embodiments, $R^{C3}$ is substituted or unsubstituted $C_{1-6}$ alkyl (e.g., —$CH_3$, Bn, —$CF_3$, unsubstituted ethyl, perfluoroethyl, unsubstituted propyl, perfluoropropyl, unsubstituted butyl, or perfluorobutyl). In certain embodiments, $R^{C3}$ is a nitrogen protecting group (e.g., Bn, Boc, Cbz, Fmoc, trifluoroacetyl, triphenylmethyl, acetyl, or Ts).

Formula (III) includes Ring C3. In certain embodiments, Ring C3 is a pyrimidinyl ring that is unsubstituted (e.g., when t is 0) or substituted (e.g., when t is 1 or 2) with one or more substituents $R^{C4}$. In certain embodiments, Ring C3 is of the formula:

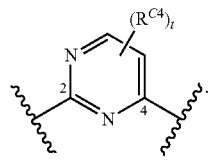

In certain embodiments, in Formula (III), when Ring C3 is a substituted or unsubstituted pyrimidinyl ring, the carbon atom labeled with "2" is attached to $R^{C5}$, and the carbon atom labeled with "4" is attached to the nitrogen atom to which $R^{C3}$ is attached. In certain embodiments, Ring C3 is of the formula:

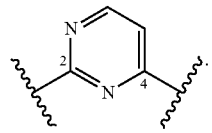 [SMILES: *c1ccnc(*)n1]

In certain embodiments, Ring C3 is of the formula:

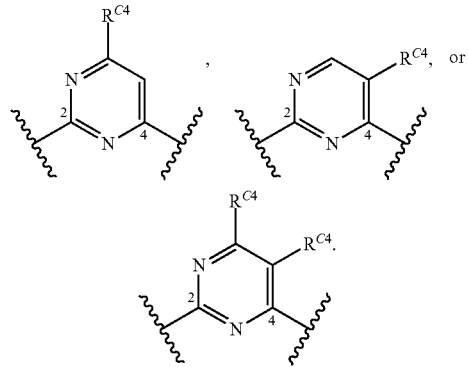

In certain embodiments, Ring C3 is a pyrazolyl ring that is unsubstituted (e.g., when t is 0) or substituted (e.g., when t is 1 or 2) with one or more substituents $R^{C4}$. In certain embodiments, Ring C3 is of the formula:

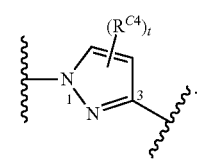

In certain embodiments, in Formula (III), when Ring C3 is a substituted or unsubstituted pyrazolyl ring, the nitrogen atom labeled with "1" is attached to $R^{C5}$, and the carbon atom labeled with "3" is attached to the nitrogen atom to which $R^{C3}$ is attached. In certain embodiments, Ring C3 is of the formula:

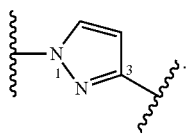 [SMILES: *c1ccn(*)n1]

In certain embodiments, Ring C3 is of the formula:

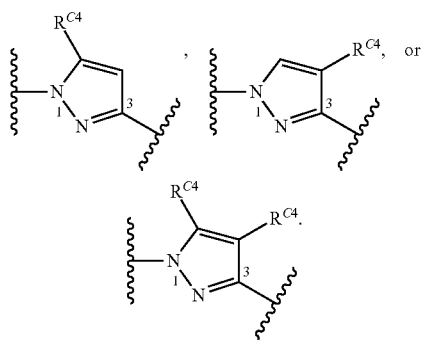

In certain embodiments, Ring C3 is of the formula:

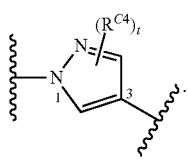

In certain embodiments, Ring C3 is of the formula:

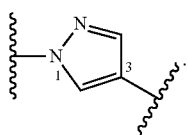 [SMILES: *c1cnn(*)c1]

In certain embodiments, Ring C3 is of the formula:

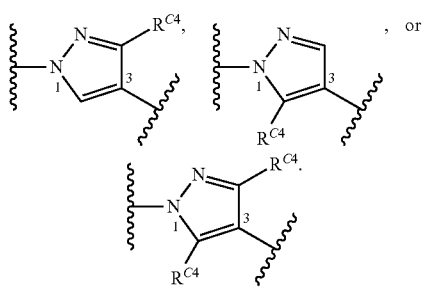

In Formula (III), Ring C3 may include one or two substituents $R^{C4}$. In certain embodiments, two instances of $R^{C4}$ are the same. In certain embodiments, two instances of $R^{C4}$ are different from each other. In certain embodiments, at least one instance of $R^{C4}$ is halogen (e.g., F, Cl, Br, or I). In certain embodiments, at least one instance of $R^{C4}$ is substituted or unsubstituted alkyl (e.g., substituted or unsubstituted $C_{1-6}$ alkyl). In certain embodiments, at least one instance of $R^{C4}$ is —CH3. In certain embodiments, at least one instance of $R^{C4}$ is —CF3, Bn, unsubstituted ethyl, perfluoroethyl, unsubstituted propyl, perfluoropropyl, unsubstituted butyl, or perfluorobutyl. In certain embodiments, at least one instance of $R^{C4}$ is substituted or unsubstituted alkenyl (e.g., substituted or unsubstituted $C_{2-6}$ alkenyl). In certain embodiments, at least one instance of $R^{C4}$ is substituted or unsubstituted alkynyl (e.g., substituted or unsubstituted $C_{3-6}$ alkynyl). In certain embodiments, at least one instance of $R^{C4}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{C4}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{C4}$ is substituted or unsubstituted aryl (e.g., substituted or unsubstituted, 6- to 10-membered aryl). In certain embodiments, at least one instance of $R^{C4}$ is substituted or unsubstituted phenyl. In certain embodiments, at least one instance of $R^{C4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{C4}$ is —OW (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{C4}$ is —SRC (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{C4}$ is —N(Rc)$_2$ (e.g., —NH$_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —NMe$_2$)). In certain embodiments, at least one instance of $R^{C4}$ is —CN, —SCN, or —NO$_2$. In certain embodiments, at least one instance of $R^{C4}$ is —C(=NR$^c$)R$^c$, —C(=NR$^c$)OR$^c$, or —C(=NR$^c$)N(R$^c$)$_2$. In certain embodiments, at least one instance of $R^{C4}$ is —C(=O)R$^c$ (e.g., —C(=O)(substituted or unsubstituted alkyl) or —C(=O)(substituted or unsubstituted phenyl)), —C(=O)OR$^c$ (e.g., —C(=O)O(substituted or unsubstituted alkyl) or —C(=O)O(substituted or unsubstituted phenyl)), or —C(=O)N(R$^c$)$_2$ (e.g., —C(=O)NH$_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, at least one instance of $R^{C4}$ is —NR$^c$C(=O)R$^c$, —NR$^c$C(=O)OR$^c$, or —NR$^c$C(=O)N(R$^c$)$_2$. In certain embodiments, at least one instance of $R^{C4}$ is —OC(=O)R$^c$, —OC(=O)OR$^c$, or —OC(=O)N(R$^c$)$_2$.

In certain embodiments, t is 0. In certain embodiments, t is 1. In certain embodiments, t is 2.

Formula (III) includes substituent $R^{C5}$ on a nitrogen atom attached to Ring C3. In certain embodiments, $R^{C5}$ is H. In certain embodiments, $R^{C5}$ is halogen (e.g., F, Cl, Br, or I). In certain embodiments, $R^{C5}$ is substituted or unsubstituted alkyl (e.g., substituted or unsubstituted $C_{1-6}$ alkyl). In certain embodiments, $R^{C5}$ is —CH$_3$. In certain embodiments, $R^{C5}$ is —CF$_3$, Bn, unsubstituted ethyl, perfluoroethyl, unsubstituted propyl, perfluoropropyl, unsubstituted butyl, or perfluorobutyl. In certain embodiments, $R^{C5}$ is substituted or unsubstituted alkenyl (e.g., substituted or unsubstituted $C_{2-6}$ alkenyl). In certain embodiments, $R^{C5}$ is substituted or unsubstituted alkynyl (e.g., substituted or unsubstituted $C_{1-6}$ alkynyl). In certain embodiments, $R^{C5}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{C5}$ is substituted or unsubstituted heterocyclyl (e.g., substituted or unsubstituted, 3- to 9-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{C5}$ is substituted or unsubstituted tetrahydropyranyl or substituted or unsubstituted piperidinyl. In certain embodiments, $R^{C5}$ is of the formula:

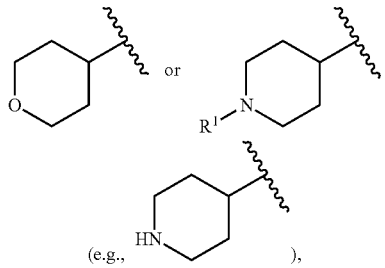

(e.g., ), wherein $R^1$ is H, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{C5}$ is substituted or unsubstituted oxetanyl, substituted or unsubstituted azetidinyl, substituted or unsubstituted tetrahydrofuranyl, substituted or unsubstituted pyrrolidinyl, substituted or unsubstituted morpholinyl, or substituted or unsubstituted piperazinyl. In certain embodiments, $R^{C5}$ is substituted or unsubstituted aryl (e.g., substituted or unsubstituted, 6- to 10-membered aryl). In certain embodiments, $R^{C5}$ is substituted or unsubstituted phenyl. In certain embodiments, $R^{C5}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{C5}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{C5}$ is —SRa (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{C5}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)—(substituted or unsubstituted $C_{1-6}$ alkyl) (e.g., —$NMe_2$)). In certain embodiments, $R^{C5}$ is —CN, —SCN, or —$NO_2$. In certain embodiments, $R^{C5}$ is —C(=$NR^a$)$R^a$, —C(=$NR^a$)$OR^a$, or —C(=$NR^a$)N($R^a$)$_2$. In certain embodiments, $R^{C5}$ is —C(=O)$R^a$ (e.g., —C(=O)(substituted or unsubstituted alkyl) or —C(=O)(substituted or unsubstituted phenyl)), —C(=O)$OR^a$ (e.g., —C(=O)O(substituted or unsubstituted alkyl) or —C(=O)O(substituted or unsubstituted phenyl)), or —C(=O)N($R^a$)$_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{C5}$ is —$NR^aC$(=O)$R^a$, —$NR^aC$(=O)$OR^a$, or —$NR^aC$(=O)N($R^a$)$_2$. In certain embodiments, $R^{C5}$ is —OC(=O)$R^a$, —OC(=O)$OR^a$, or —OC(=O)N($R^a$)$_2$. In certain embodiments, $R^{C5}$ is of the formula:

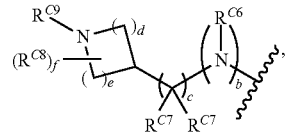

wherein:

$R^{C6}$ is hydrogen, substituted or unsubstituted $C_{1-6}$ alkyl, or a nitrogen protecting group;

b is 0 or 1;

each instance of $R^{C6}$ is independently hydrogen, halogen, or substituted or unsubstituted $C_{1-6}$ alkyl;

c is 0, 1, 2, 3, or 4;

d is 1, 2, 3, or 4;

e is 1, 2, or 3;

each instance of $R^{C8}$ is independently halogen, or substituted or unsubstituted $C_{1-6}$ alkyl;

f is an integer between 0 and 13, inclusive; and $R^{C9}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, —C(=O)$R^a$, —C(=O)$OR^a$, —C(=O)N($R^a$)$_2$, a nitrogen protecting group, or of any one of Formulae (ii-1) to (ii-42):

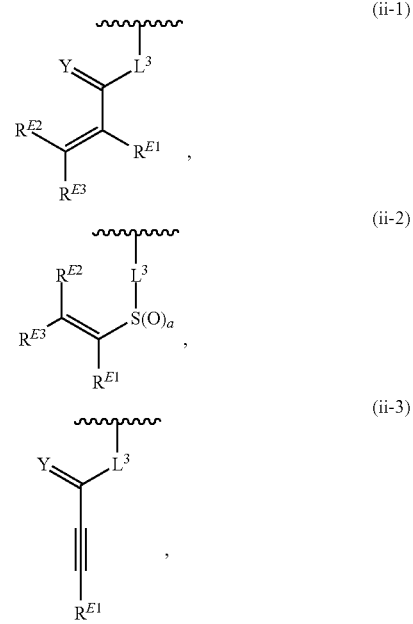

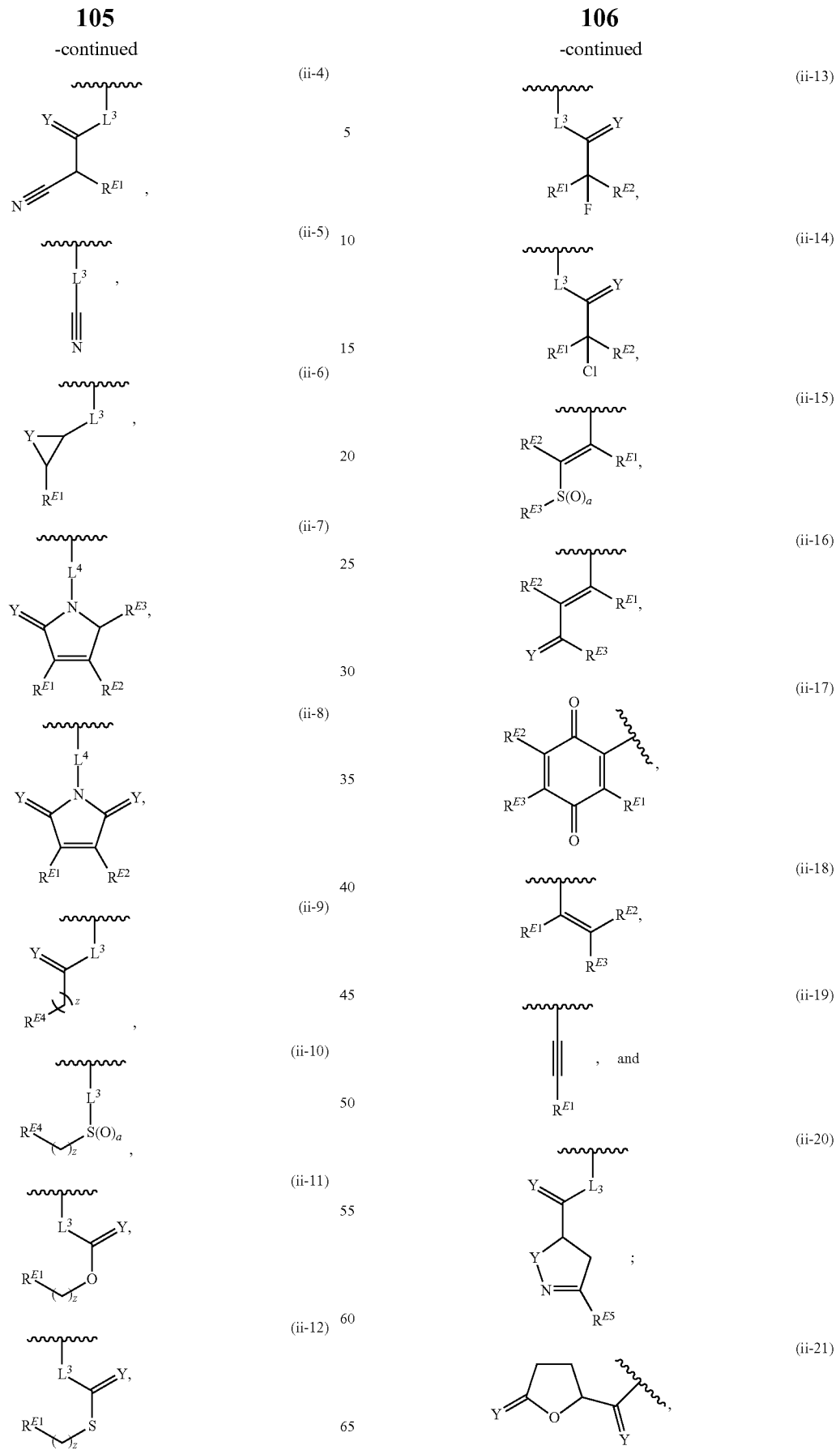

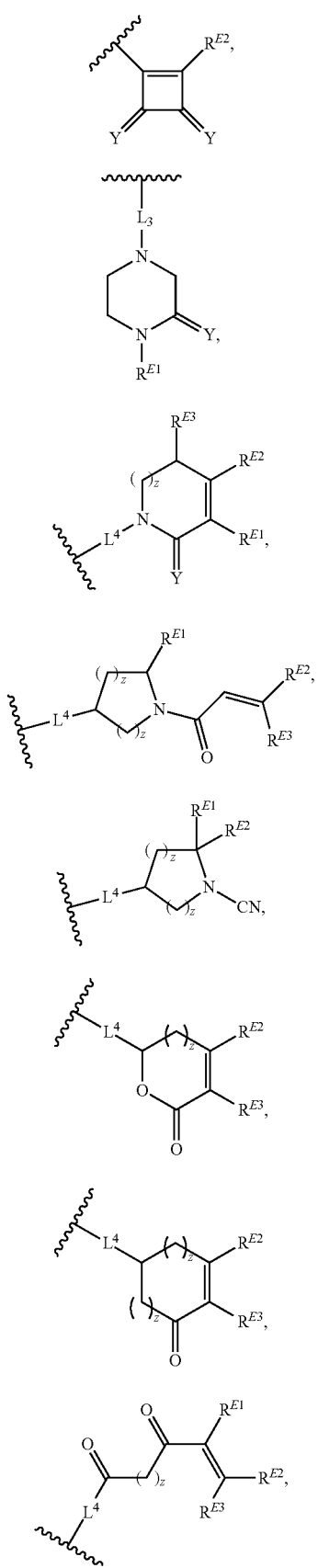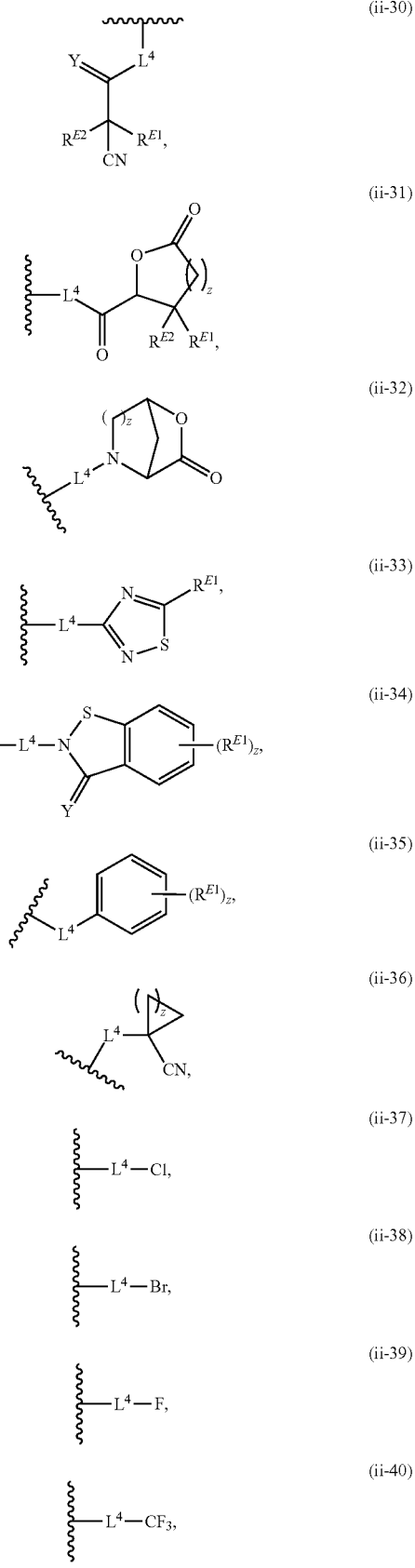

-continued

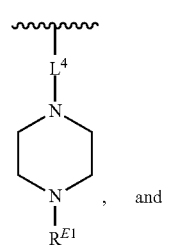
(ii-41)

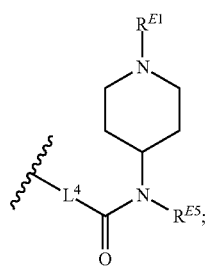
(ii-42)

wherein:

$L^3$ is a bond or an optionally substituted $C_{1-4}$ hydrocarbon chain, optionally wherein one or more carbon units of the hydrocarbon chain are independently replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans—CR$^{L3b}$=CR$^{L3b}$—, cis—CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

$L^4$ is a bond or an optionally substituted $C_{1-4}$ hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, and —SR$^{E1a}$, wherein in each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ a groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2}$a is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

Y is O, S, or NR$^{E6}$, wherein R$^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

In certain embodiments, R$^{C5}$ is of the formula:

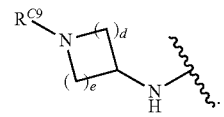

In certain embodiments, R$^{C5}$ is of the formula:

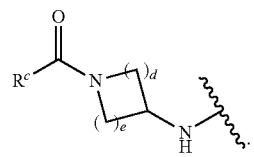

In certain embodiments, R$^{C5}$ is of the formula:

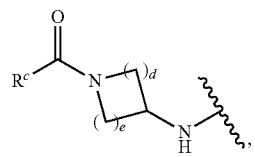

wherein R$^c$ is substituted or unsubstituted $C_{2-6}$ alkenyl. In certain embodiments, R$^{C5}$ is of the formula:

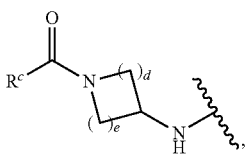
wherein $R^c$ is substituted or unsubstituted $C_{1-6}$ alkyl. In certain embodiments, $R^{C5}$ is of the formula:
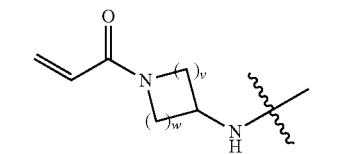
(e.g., 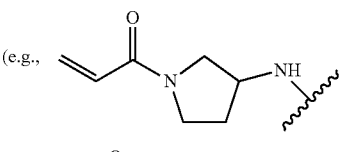
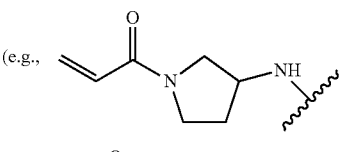
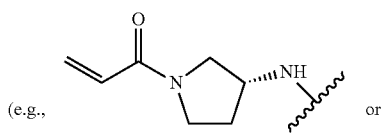),
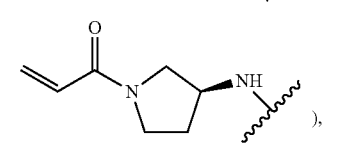
(e.g., 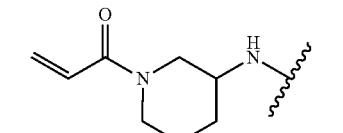
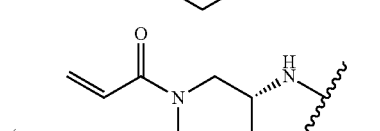),
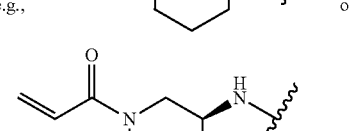 or
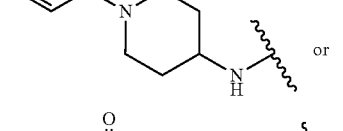
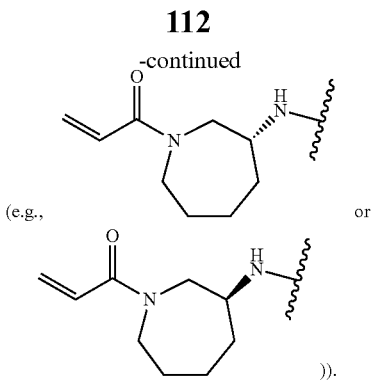
(e.g., 
or
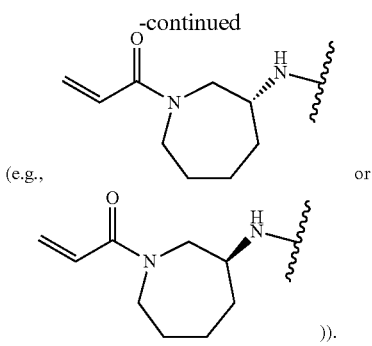
)).
In certain embodiments, $R^{C5}$ is of the formula:
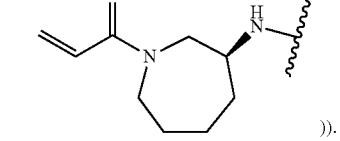
(e.g.,
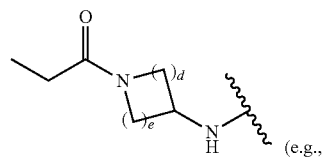
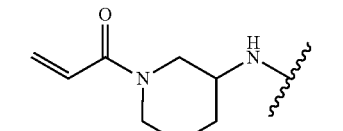
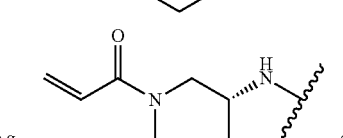, or
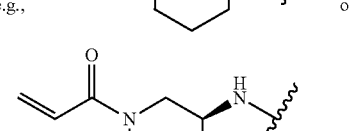
).
In certain embodiments, $R^{C5}$ is of the formula:
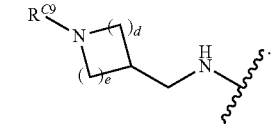.

In certain embodiments, $R^{C5}$ is of the formula:

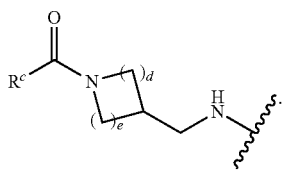

In certain embodiments, $R^{C5}$ is of the formula:

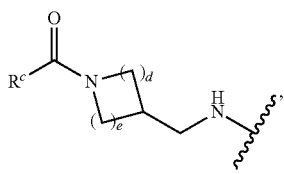

wherein $R^c$ is substituted or unsubstituted $C_{2-6}$ alkenyl. In certain embodiments, $R^{C5}$ is of the formula:

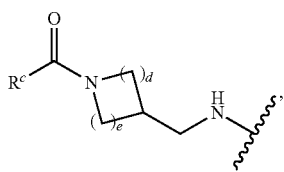

wherein $R^c$ is substituted or unsubstituted $C_{1-6}$ alkyl. In certain embodiments, $R^{C5}$ is of the formula:

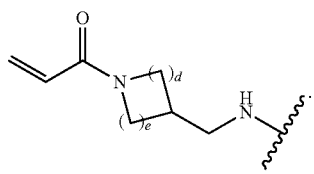

In certain embodiments, $R^{C5}$ is of the formula:

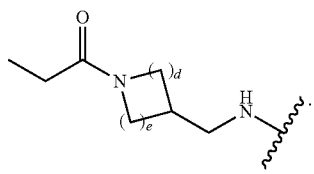

In certain embodiments, $R^{C6}$ is H. In certain embodiments, $R^{C6}$ is substituted or unsubstituted $C_{1-6}$ alkyl (e.g., —$CH_3$, Bn, —$CF_3$, unsubstituted ethyl, perfluoroethyl, unsubstituted propyl, perfluoropropyl, unsubstituted butyl, or perfluorobutyl). In certain embodiments, $R^{C6}$ is a nitrogen protecting group (e.g., Bn, Boc, Cbz, Fmoc, trifluoroacetyl, triphenylmethyl, acetyl, or Ts).

In certain embodiments, b is 0. In certain embodiments, b is 1.

In certain embodiments, b is 1; and $R^{C6}$ is H.

In certain embodiments, all instances of $R^{C7}$ are the same. In certain embodiments, two instances of $R^{C7}$ are different from each other. In certain embodiments, at least one instance of $R^{C7}$ is H. In certain embodiments, each instance of $R^{C7}$ is H. In certain embodiments, at least one instance of $R^{C7}$ is halogen (e.g., F, Cl, Br, or I). In certain embodiments, at least one instance of $R^{C7}$ is substituted or unsubstituted alkyl (e.g., substituted or unsubstituted $C_{i-6}$ alkyl). In certain embodiments, at least one instance of $R^{C7}$ is —$CH_3$. In certain embodiments, at least one instance of $R^{C7}$ is —$CF_3$, Bn, unsubstituted ethyl, perfluoroethyl, unsubstituted propyl, perfluoropropyl, unsubstituted butyl, or perfluorobutyl.

In certain embodiments, c is 0. In certain embodiments, c is 1. In certain embodiments, c is 2. In certain embodiments, c is 3. In certain embodiments, c is 4.

In certain embodiments, d is 1. In certain embodiments, d is 2. In certain embodiments, d is 3. In certain embodiments, d is 4.

In certain embodiments, e is 1. In certain embodiments, e is 2. In certain embodiments, e is 3.

In certain embodiments, d is 2; and e is 1. In certain embodiments, d is 3; and e is 1. In certain embodiments, d is 4; and e is 1.

In certain embodiments, all instances of $R^{C8}$ are the same. In certain embodiments, two instances of $R^{C8}$ are different from each other. In certain embodiments, at least one instance of $R^{C8}$ is halogen (e.g., F, Cl, Br, or I). In certain embodiments, at least one instance of $R^{C8}$ is substituted or unsubstituted alkyl (e.g., substituted or unsubstituted $C_{1-6}$ alkyl). In certain embodiments, at least one instance of $R^{C8}$ is —$CH_3$. In certain embodiments, at least one instance of $R^{C8}$ is —$CF_3$, Bn, unsubstituted ethyl, perfluoroethyl, unsubstituted propyl, perfluoropropyl, unsubstituted butyl, or perfluorobutyl.

In certain embodiments, f is 0. In certain embodiments, f is 1, 2, 3, 4, 5, 6, 7, 8, 9, 10, 11, 12, or 13.

In certain embodiments, $R^{C9}$ is hydrogen, substituted or unsubstituted CI-6 alkyl, substituted or unsubstituted $C_{2-6}$ alkenyl, substituted or unsubstituted $C_{2-6}$ alkynyl, substituted or unsubstituted carbocyclyl, —C(=O)$R^a$, —C(=O)O$R^a$, —C(=O)N($R^a$)$_2$, a nitrogen protecting group, or of any one of Formulae (ii-1) to (ii-23). In certain embodiments, $R^{C9}$ is H. In certain embodiments, $R^{C9}$ is substituted or unsubstituted $C_{1-6}$ alkyl (e.g., $C_{1-6}$ alkyl substituted with one or more substituents independently selected from the group consisting of oxo; halogen; substituted or unsubstituted $C_{2-6}$ alkenyl; substituted or unsubstituted cyclopropyl; substituted or unsubstituted, 4- to 7-membered monocyclic carbocyclyl comprising 1 or 2 double bonds in the carbocyclic ring system; substituted or unsubstituted oxiranyl; substituted or unsubstituted, 5- to 10-membered, monocyclic or bicyclic heteroaryl, wherein 1, 2, 3, or 4 atoms in the heteroaryl ring system are independently oxygen, nitrogen, or sulfur; —CN; —(C=O)$R^a$; —N($R^a$)(C=O)$R^a$; —O(C=O)$R^a$; —O$R^a$; and —N($R^a$)$_2$). In certain embodiments, $R^{C9}$ is substituted or unsubstituted $C_{2-6}$ alkenyl (e.g., substituted or unsubstituted vinyl). In certain embodiments, $R^{C9}$ is substituted or unsubstituted $C_{2-6}$ alkynyl (e.g., substituted or unsubstituted ethynyl). In certain embodiments, $R^{C9}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{C9}$ is —C(=O)$R^a$. In certain embodiments, $R^{C9}$ is —C(=O)(substituted or unsubstituted alkyl) (e.g., —C(=O)(substituted or unsubstituted $C_{1-6}$ alkyl), such as —C(=O)Et). In certain embodiments, $R^{C9}$ is —C(=O)(substituted or unsubstituted alkenyl) (e.g., —C(=O)(substituted or unsubstituted $C_{2-6}$ alkenyl), such as —C(=O)—CH=CH2). In certain embodiments, $R^{C9}$ is —C(=O)(substituted or unsubstituted carbocyclyl). In certain embodiments, $R^{C9}$ is —C(=O)(substituted or unsubstituted heterocyclyl). In certain embodiments, $R^{C9}$ is —C(=O)(substituted or unsubstituted phenyl). In certain embodiments, $R^{C9}$ is —C(=O) (substituted or unsubstituted heteroaryl). In certain embodiments, $R^{C9}$ is —C(=O)OR$^a$ (e.g., —C(=O)O(substituted or unsubstituted alkyl) or —C(=O)O(substituted or unsubstituted phenyl)) or —C(=O)N(R$^a$)$_2$ (e.g., —C(=O) NH$_2$, —C(=O)NH(substituted or unsubstituted alkyl), —C(=O)NH(substituted or unsubstituted phenyl), —C(=O)N(substituted or unsubstituted alkyl)—(substituted or unsubstituted alkyl), or —C(=O)N(substituted or unsubstituted phenyl)—(substituted or unsubstituted alkyl)). In certain embodiments, $R^{C9}$ is a nitrogen protecting group (e.g., Bn, Boc, Cbz, Fmoc, trifluoroacetyl, triphenylmethyl, acetyl, or Ts). In certain embodiments, $R^{C9}$ is of any one of Formulae (ii-1) to (ii-23). In certain embodiments, $R^{C9}$ is of any one of Formulae (ii-24) to (ii-42). In certain embodiments, $R^{C9}$ is of Formula (ii-1) (e.g., of the formula:

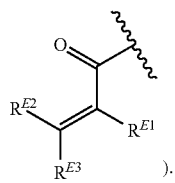
).

In certain embodiments, $R^{C9}$ is of Formula (ii-3) (e.g., of the formula:

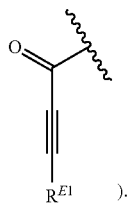
).

In certain embodiments, $R^{C9}$ is of any one of the formulae shown in Table 1A. The moieties included in $R^{C9}$ are as described herein.

In certain embodiments, a compound of Formula (III) is of the formula:

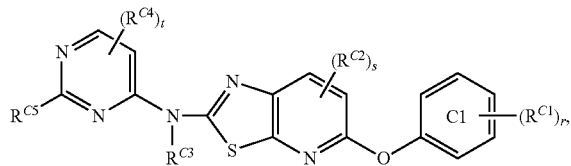

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

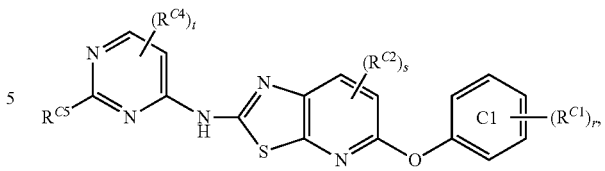

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

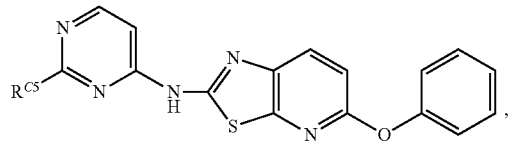
, or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

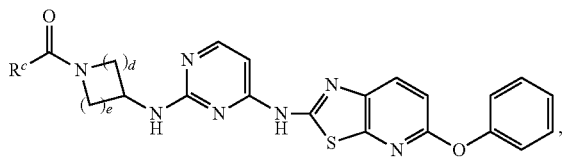
, or a pharmaceutically acceptable salt, solvate, hydrate, polymorph, co-crystal, tautomer, stereoisomer, isotopically labeled derivative, or prodrug thereof, wherein $R^c$ is substituted or unsubstituted $C_{2-6}$ alkenyl.

In certain embodiments, a compound of Formula (III) is of the formula:

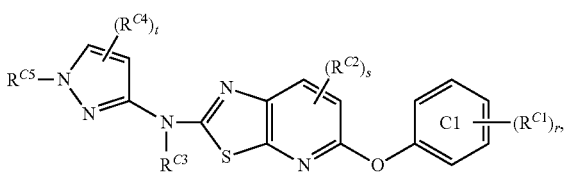

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

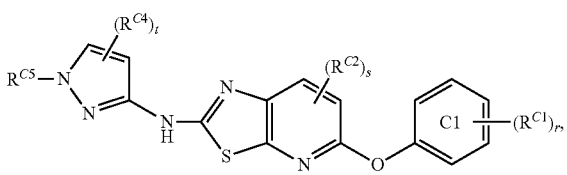

In certain embodiments, a compound of Formula (III) is of the formula:

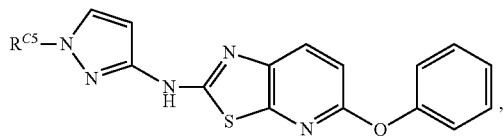

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

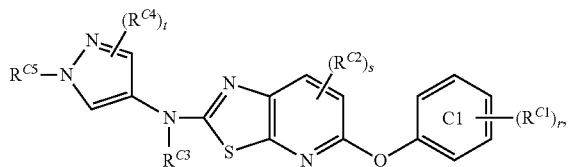

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

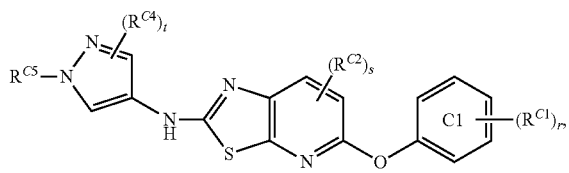

or a pharmaceutically acceptable salt, solvate, hydrate, polymorph, co-crystal, tautomer, stereoisomer, isotopically labeled derivative, or prodrug thereof.

In certain embodiments, a compound of Formula (III) is of the formula:

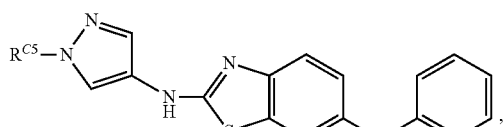

or a pharmaceutically acceptable salt, solvate, hydrate, polymorph, co-crystal, tautomer, stereoisomer, isotopically labeled derivative, or prodrug thereof.

Exemplary compounds of Formula (III) include, but are not limited to:

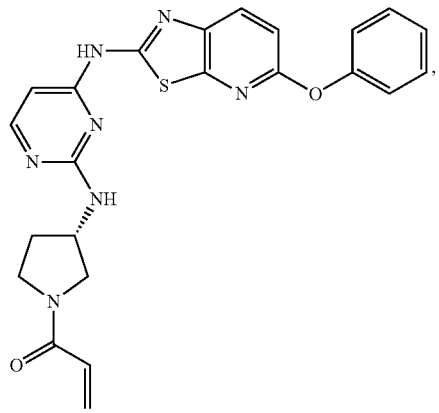

(III-1)

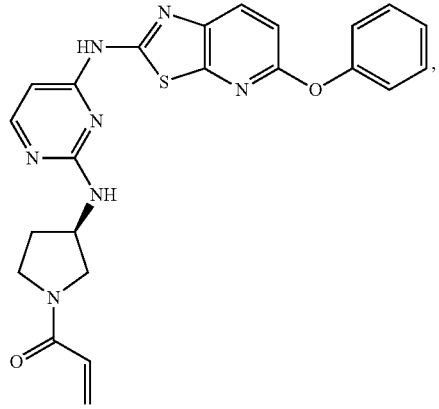

(III-2)

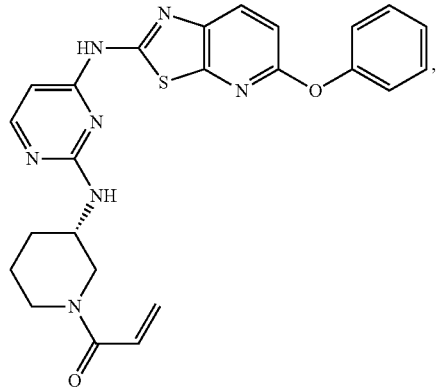

(III-3)

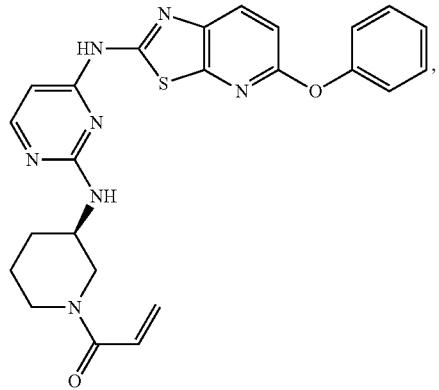

(III-4)

-continued

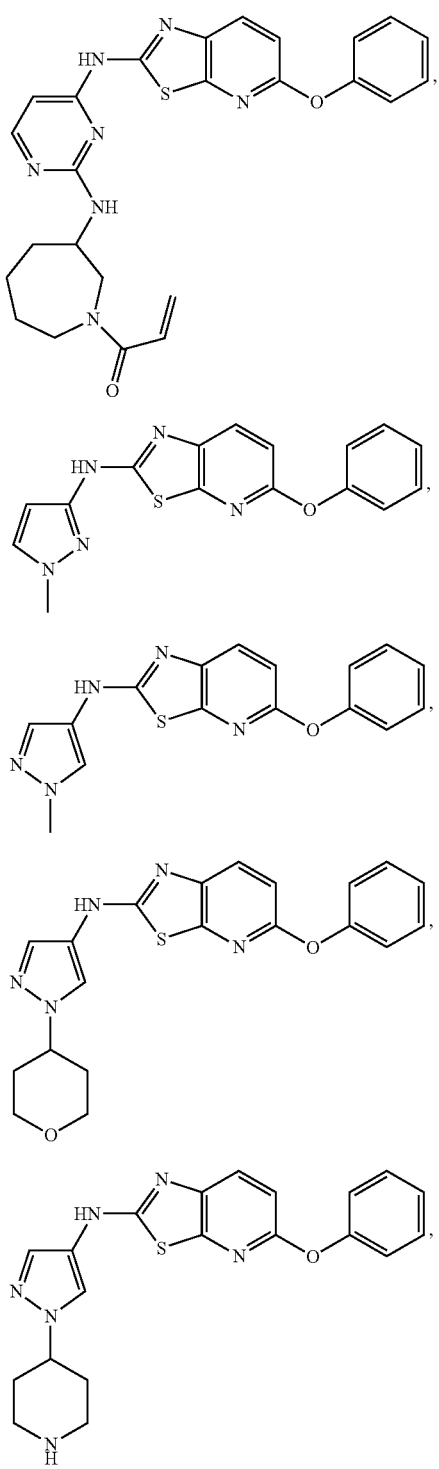

and pharmaceutically acceptable salts, solvates, hydrates, polymorphs, co-crystals, tautomers, stereoisomers, isotopically labeled derivatives, and prodrugs thereof.

Pharmaceutical Compositions, Kits, and Administration

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein may be useful in treating and/or preventing proliferative diseases (e.g., myelodysplasia, leukemia, lymphoma (e.g., Waldenström's macroglobulinemia)) in a subject, inhibiting the activity of a protein kinase (e.g., HCK, BTK) in a subject, biological sample, tissue, or cell, and/or inducing apoptosis in a cell.

In certain embodiments, a subject described herein is an animal. The animal may be of either sex and may be at any stage of development. In certain embodiments, a subject described herein described herein is a human. In certain embodiments, a subject described herein is a non-human animal. In certain embodiments, a subject described herein is a mammal (e.g., non-human mammal). In certain embodiments, a subject described herein is a domesticated animal, such as a dog, cat, cow, pig, horse, sheep, or goat. In certain embodiments, a subject described herein is a companion animal such as a dog or cat. In certain embodiments, a subject described herein is a livestock animal such as a cow, pig, horse, sheep, or goat. In certain embodiments, a subject described herein is a zoo animal. In another embodiment, a subject described herein is a research animal such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, a subject described herein is a fish or reptile.

In certain embodiments, a biological sample described herein is bone marrow, lymph node, spleen, or blood.

In certain embodiments, a tissue described herein is blood. In certain embodiments, a tissue described herein is bone marrow. In certain embodiments, a tissue described herein is a central nervous system (CNS) tissue (e.g., brain, spinal cord, meninges). In certain embodiments, a tissue described herein is an immune privileged tissue. In certain embodiments, a tissue described herein is the placenta or testicle. In certain embodiments, a tissue described herein is a fetus. In certain embodiments, a tissue described herein is the eye. In certain embodiments, a tissue described herein is the spleen. In certain embodiments, a tissue described herein is the marginal zone.

In certain embodiments, a cell described herein is in vitro. In certain embodiments, a cell described herein is ex vivo. In certain embodiments, a cell described herein is in vivo. In certain embodiments, a cell described herein is a malignant cell (e.g., malignant blood cell). In certain embodiments, a cell described herein is a malignant hematopoietic stem cell (e.g., malignant myeloid cell or malignant lymphoid cell). In certain embodiments, a cell described herein is a malignant lymphocyte (e.g., malignant T-cell or malignant B-cell). In certain embodiments, a cell described herein is a malignant red blood cell, malignant white blood cell, or malignant platelet. In certain embodiments, a cell described herein is a malignant neutrophil, malignant macrophage, or malignant plasma cell.

In certain embodiments, the compound described herein is provided in an effective amount in the pharmaceutical composition. In certain embodiments, the effective amount is a therapeutically effective amount (e.g., amount effective for treating a proliferative disease in a subject in need thereof). In certain embodiments, the effective amount is an amount effective for inhibiting the activity of a protein kinase (e.g., HCK, BTK) in a subject in need thereof. In certain embodiments, the effective amount is an amount effective for inhibiting the activity of a protein kinase (e.g., HCK, BTK) in a cell. In certain embodiments, the effective amount is an amount effective for inducing apoptosis in a cell. In certain embodiments, the effective amount is a prophylactically effective amount (e.g., amount effective for preventing a proliferative disease in a subject in need thereof and/or for keeping a subject in need thereof in remission of a proliferative disease).

In certain embodiments, a protein kinase described herein is HCK. In certain embodiments, a protein kinase described herein is BTK. In certain embodiments, a protein kinase described herein is IRAK1 or IRAK4. In certain embodiments, a protein kinase described herein is BMX. In certain embodiments, a protein kinase described herein is a PI3K. In certain embodiments, a protein kinase described herein is ABL, ACK, ARG, BLK, CSK, EphB1, EphB2, FGR, FRK, FYN, SRC, YES, LCK, LYN, MAP2K5, NLK, PIP4K2C, p38a, SNRK, SRC, or TEC. In certain embodiments, a protein kinase described herein is ABL1(H396P)-phosphorylated, ABL1-phosphorylated, BLK, EPHA4, EPHB2, EPHB3, EPHB4, FGR, JAK3(JH1domain-catalytic), KIT, KIT(L576P), KIT(V559D), PDGFRB, SRC, YES, ABL1 (H396P)-nonphosphorylated, ABL1(Y253F)-phosphorylated, ABL1-nonphosphorylated, FRK, LYN, ABL1 (Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1 (F317L)-nonphosphorylated, FYN, LCK, EPHA2, ABL1 (M351T)-phosphorylated, TXK, EGFR(L858R), EGFR (L861Q), ERBB2, ERBB3, EPHA5, ABL1(F317I)-nonphosphorylated, EGFR(L747-E749del, A750P), CSK, EPHA1, ABL1(F317L)-phosphorylated, BRAF(V600E), EGFR, KIT-autoinhibited, or EGFR(E746-A750del). In certain embodiments, a protein kinase described herein is ABL1(F317L) -nonphosphorylated, ABL1(H396P)-nonphosphorylated, ABL1(H396P)-phosphorylated, ABL1-phosphorylated, BLK, EPHA4, EPHB2, EPHB3, EPHB4, JAK3(JHldomain -catalytic), KIT, KIT(L576P), KIT (V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1 (Q252H)-nonphosphorylated, ABL2, FYN, EPHB1, ABL1 (E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT(D816V), KIT-autoinhibited, EGFR(L747-T751del,Sins), EGFR(L858R), EGFR(L747-E749de1, A750P), or CSF1R.

In certain embodiments, the effective amount is an amount effective for inhibiting the activity of a protein kinase (e.g., HCK, BTK) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a protein kinase (e.g., HCK, BTK) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a protein kinase (e.g., HCK, BTK) by a range between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, rhea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65 ° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents) useful in treating and/or preventing a proliferative disease. The compounds or compositions can be administered in combination with additional pharmaceutical agents that improve their activity (e.g., activity (e.g., potency and/or efficacy) in treating a proliferative disease in a subject in need thereof, in preventing a proliferative disease in a subject in need thereof, and/or in inhibiting the activity of a protein kinase (e.g., HCK, BTK) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent useful in inhibiting the activity of a protein kinase (e.g., HCK, BTK) in a subject, biological sample, tissue, or cell. In certain embodiments, the additional pharmaceutical agent is a pharmaceutical agent useful in inducing apoptosis in a cell. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is an anti-myelodysplasia agent. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), or a combination thereof.

In certain embodiments, the additional pharmaceutical agent is an anti-macroglobulinemia agent.

In certain embodiments, the additional pharmaceutical agent is LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI , FOLFIRI -BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL -AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VELP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a protein kinase inhibitor (e.g., tyrosine protein kinase inhibitor). In certain embodiments, the additional pharmaceutical agent is an inhibitor of a Src family kinase. In certain embodiments, the additional pharmaceutical agent is an HCK inhibitor or BTK inhibitor. In certain embodiments, the additional pharmaceutical agent is an inhibitor of one or more protein kinases selected from the group consisting of IRAK1, IRAK4, BMX, and PI3K. In certain embodiments, the additional pharmaceutical agent is an inhibitor of one or more protein kinases selected from the group consisting of ABL, ACK, ARG, BLK, CSK, EphB1, EphB2, FGR, FRK, FYN, SRC, YES, LCK, LYN, MAP2K5, NLK, PIP4K2C, p38a, SNRK, SRC, and TEC. In certain embodiments, the additional pharmaceutical agent is an inhibitor of one or more protein kinases selected from the group consisting of ABL1(H396P) -phosphorylated, ABL1-phosphorylated, BLK, EPHA4, EPHB2, EPHB3, EPHB4, FGR, JAK3(JH1domain-catalytic), KIT, KIT(L576P), KIT (V559D), PDGFRB, SRC, YES, ABL1(H396P)-nonphosphorylated, ABL1(Y253F)-phosphorylated, ABL1-nonphosphorylated, FRK, LYN, ABL1(Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1(F317L)-nonphosphorylated, FYN, LCK, EPHA2, ABL1(M351T)-phosphorylated, TXK, EGFR(L858R), EGFR(L861Q), ERBB2, ERBB3, EPHA5, ABL1(F317I)-nonphosphorylated, EGFR(L747-E749del, A750P), CSK, EPHA1, ABL1 (F317L)-phosphorylated, BRAF(V600E), EGFR, KIT-autoinhibited, and EGFR(E746-A750del). In certain embodiments, the additional pharmaceutical agent is an inhibitor of one or more protein kinases selected from the group consisting of ABL1(F317L) -nonphosphorylated, ABL1(H396P)-nonphosphorylated, ABL1(H396P)-phosphorylated, ABL1-phosphorylated, BLK, EPHA4, EPHB2, EPHB3, EPHB4, JAK3(JH1domain -catalytic), KIT, KIT (L576P), KIT(V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1(Q252H)-nonphosphorylated, ABL2, FYN, EPHB1, ABL1(E255K)-phosphorylated, ABL1(F317L)-phosphorylated, EPHAl, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT (D816V), KIT-autoinhibited, EGFR(L747-T751del,Sins), EGFR(L858R), EGFR(L747-E749del, A750P), and CSF1R. In certain embodiments, the additional pharmaceutical agent is an anti-angiogenesis agent, anti-inflammatory agent, immunosuppressant, anti-bacterial agent, anti-viral agent, cardiovascular agent, cholesterol- lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a proliferative disease (e.g., myelodysplasia, leukemia, lymphoma (e.g., Waldenström's macroglobulinemia)) in a subject in need thereof, preventing a proliferative disease in a subject in need thereof, inhibiting the activity of a protein kinase (e.g., HCK, BTK) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a proliferative disease in a subject in need thereof, inhibiting the activity of a protein kinase (e.g., HCK, BTK) in a subject, biological sample, tissue, or cell, and/or inducing apoptosis in a cell. A kit described herein may include one or more additional pharmaceutical agents described herein as a separate composition.

Methods of Treatment

The compounds described herein may:
- exhibit kinase inhibitory activity,
- exhibit the ability to inhibit transforming growth factor b-activated kinase-1 (TAK1), hemopoietic cell kinase (HCK) or both TAK1 and HCK,
- exhibit the ability to inhibit Bruton's tyrosine kinase (BTK), v-src sarcoma (Schmidt-Ruppin A-2) viral oncogene homolog (SRC) family of kinases or both BTK and SRC,
- exhibit cytotoxic or growth inhibitory effect on Waldenstrom's macroglobulinemia (WM) cell lines maintained in vitro or in animal studies using a scientifically acceptable cancer cell xenograft model; and/or
- exhibit a therapeutic profile (e.g., optimum safety and curative effect) that is superior to existing chemotherapeutic agents.

Without wishing to be bound by any particular theory, the compounds described herein may be able to attach (e.g., covalently attach) to a protein kinase described herein. In certain embodiments, the $R^{A10}$, $R^{B9}$, or $R^{C9}$ group of a compound described herein is able to attach (e.g., covalently attach) to the protein kinase.

In another aspect, the present disclosure provides methods of inhibiting the activity of a protein kinase in a subject, the methods comprising administering to the subject an effective amount (e.g., therapeutically effective amount) of a compound or pharmaceutical composition described herein.

In another aspect, the present disclosure provides methods of inhibiting the activity of a protein kinase in a biological sample, the methods comprising contacting the biological sample with an effective amount of a compound or pharmaceutical composition described herein.

In another aspect, the present disclosure provides methods of inhibiting the activity of a protein kinase in a tissue, the methods comprising contacting the tissue with an effective amount of a compound or pharmaceutical composition described herein.

In another aspect, the present disclosure provides methods of inhibiting the activity of a protein kinase in a cell, the methods comprising contacting the cell with an effective amount of a compound or pharmaceutical composition described herein.

In some embodiments, the protein kinase is involved in the myeloid differentiation primary response gene (88) (MYD88) signaling pathway. In certain embodiments, the protein kinase is a Src family kinase, such as hemopoietic cell kinase (HCK). In certain embodiments, the protein kinase is Bruton's tyrosine kinase (BTK). In certain embodiments, the protein kinase is IRAK1, IRAK4, BMX, or a PI3K.

MYD88 is an adaptor molecule for Toll-like receptors (TLR) with the exception of TLR-3 and interleukin-1 receptor (IL-1R) signaling. Following TLR or IL-1R stimulation, MYD88 is recruited to the activated receptor complex as a homodimer which then complexes with interleukin-1 receptor-associated kinase 4 (IRAK4) and activates IRAK1 and IRAK2. Tumor necrosis factor receptor associated factor 6 (TRAF6) is then activated by IRAK1 leading to NFKB activation via IKBa phosphorylation.

Transforming growth factor b-activated kinase-1 (TAK1; also known as MAP3K7), is a member of the serine/threonine protein kinase family. This kinase mediates the signaling transduction induced by TGF beta and morphogenetic protein (BMP), and controls a variety of cell functions including transcription regulation and apoptosis. TAK1 knockout is embryonic lethal to mice. Conditional knockdown of TAK1 in adult mice results in systemic inflammation, spenomegaly, degeneration in heart, kidneys and liver and increased proliferation and differentiation of myeloid progenitor cells. TAK1 is located downstream of Myd88, Bruton's tyrosine kinase (BTK) and interleukin-1 receptor-associated kinase (IRAK), and is being investigated for its role in innate immunity, inflammatory response and Ras dependent cancers.

HCK is a non-receptor tyrosine-protein kinase found in hematopoietic cells and is known to interact with Bruton's tyrosine kinase (BTK) upon activation by B cell receptors (Proc Natl Acad Sci U S A. 1994 Aug. 16; 91(17): 8152-8155). HCK transmits signals from cell surface receptors and plays an important role in the regulation of innate immune responses, including neutrophil, monocyte, macrophage and mast cell functions, phagocytosis, cell survival and proliferation, cell adhesion and migration. It acts downstream of receptors that bind the Fc region of immunoglobulins, such as FCGR1A and FCGR2A, but also CSF3R, PLAUR, the receptors for IFNG, IL2, IL6 and IL8, and integrins, such as ITGB1 and ITGB2. During the phagocytic process, it mediates mobilization of secretory lysosomes, degranulation, and activation of NADPH oxidase to bring about the respiratory burst. It also plays a role in the release of inflammatory molecules, promotes reorganization of the actin cytoskeleton and actin polymerization, and formation of podosomes and cell protrusions.

BTK is a key signaling enzyme expressed in all hematopoietic cells types except T lymphocytes and natural killer cells. BTK plays an essential role in the B cell signaling pathway linking cell surface B cell receptor BCR stimulation to downstream intracellular responses. BTK is a key regulator of B cell development activation signaling and survival (Kurosaki, *Curr. Op. Imm.*, 2000, 276-281; Schaeffer and Schwartzberg, *Curr. Op. Imm.*, 2000, 282-288). In addition BTK plays a role in a number of other hematopoietic cell signaling pathways, e.g., Toll like receptor (TLR) and cytokine receptor-mediated TNF-α production in macrophages, IgE receptor (FcepsilonRI) signaling in mast cells, inhibition of Fas/APO-1 apoptotic signaling in B-lineage lymphoid cells, and collagen stimulated platelet aggregation. See e.g., C. A. Jeffries, et al., *J. Biol. Chem.*, 2003, 278, 26258-26264; N.J. Horwood, et al., *J. Exp. Med.*, 2003, 197, 1603-1611; Iwaki et al., *J. Biol. Chem.*, 2005, 280(48), 40261-40270; Vassilev et al., *J. Biol. Chem.*, 1999, 274(3), 1646-1656; and Quek et al., *Curr. Biol.*, 1998, 8(20),1137-1140. Activated Btk interacts with MyD88 and TRW, promoting the activation of MyD88-dependent and TRW-dependent pathways (*Nature Immunology*, 2011, 12, 416-424). BTK inhibitors are well-known in the art, and include, for example, ibrutinib and benzonaphthyridinones (see U.S. provisional patent application Ser. No. 61/716,273, filed Oct. 19, 2012). Additional non-limiting examples of BTK inhibitors are disclosed in WO 1999/054286, WO 2013/010380, WO 2009/137596, WO 2011/029043, WO 2010/056875, WO 2000/056737, and WO 2013/067277.

IRAK1 and IRAK4 are serine/threonine-protein kinases that play a critical role in initiating innate immune response against foreign pathogens. They are involved in Toll-like receptor (TLR) and IL-1R signaling pathways, and are rapidly recruited by MYD88 to the receptor-signaling complex upon TLR activation. Association with MYD88 leads to IRAK1 phosphorylation by IRAK4 and subsequent autophosphorylation and kinase activation of IRAK1 (*Immunity*, 1997, 7(6), 837-47). IRAK4-/—mice have abolished cellular responses to various IL-1 and TLR ligands and are severely impaired in their response to viral and bacterial challenges.

IRAK1-/—mice show a similar but partial response. IRAK1 and IRAK4 inhibitors are well-known in the art, and include, for example, those disclosed in WO 2003/030902, WO 2012/007375, GM Buckely et al. *Biorg. Med. Chem. Lett.* 2008 18 3211-3214, and GM Buckely et al. *Biorg. Med. Chem. Lett.* 2008 18 3656-3660, WO2013/074986, and U.S. 61/727,640.

"Bone Marrow on X chromosome" kinase (BMX, also termed ETK) is a non -receptor tyrosine kinase and is activated downstream of phosphatidylinositol-3 kinase (PI -3K) and v-src sarcoma (Schmidt-Ruppin A-2) viral oncogene homolog (SRC), but its substrates are unknown. Positional scanning peptide library screening revealed a marked preference for a priming phosphotyrosine (pY) in the −1 position. Potential substrates include multiple tyrosine kinases with kinase domain pYpY sites required for full activity. BMX has been found to phosphorylate residue Y577 of focal adhesion kinase (FAK) subsequent to Y576 phosphorylation by SRC. In addition, BMX loss by RNA interference and mouse embryonic fibroblasts (MEFs) from Bmx negative (Bmx$^-$) mice displayed impaired FAK signaling. Insulin receptor (IR) phosphorylation similarly was decreased by BMX loss, as was hepatic IR phosphorylation in Bmx$^-$ mice. However, glucose tolerance was increased, reflecting a marked compensatory decrease in the activity of the AKT phosphatase PHLPP. These findings reveal a mechanism through which BMX functions as a central regulator of multiple kinase pathways. BMX inhibitors are well-known in the art, and include, for example, those disclosed in U.S. Ser. Nos. 61/716,273 and 61/717,345, the contents of both of which are incorporated herein by reference.

Phosphatidylinositol 3-kinases (PI3-kinases or PI3Ks) are a family of enzymes involved in cellular functions such as cell growth, proliferation, differentiation, motility, survival and intracellular trafficking, which in turn are involved in cancer. PI3Ks are a family of related intracellular signal transducer enzymes capable of phosphorylating the 3 position hydroxyl group of the inositol ring of phosphatidylinositol (Ptdlns). Phosphatidylinositol 3-kinase is composed of an 85 kDa regulatory subunit and a 110 kDa catalytic subunit. The protein encoded by PI3KCA gene represents the catalytic subunit, which uses ATP to phosphorylate phosphatidylinositols (Ptdlns), Ptdlns4P and Ptdlns(4,5)P2. PI3K inhibitors are well-known in the art, and include, for example, those disclosed in WO 2013/088404, WO 2012/068096, and WO 2013/052699, which are incorporated herein by reference.In certain embodiments, the activity of the protein kinase is inhibited by the compounds or pharmaceutical compositions described herein by at least 10%, at least 20%, at least 30%, at least 40%, at least 50%, at least 60%, at least 70%, at least 80%, at least 90%, or at least 95%. In certain embodiments, the activity of the protein kinase is inhibited by the compounds or pharmaceutical compositions described herein by not more than 90%, not more than 80%, not more than 70%, not more than 60%, not more than 50%, not more than 40%, not more than 30%, not more than 20%, or not more than 10%. Combinations of the above-referenced ranges (e.g., at least 10% and not more than 50%) are also within the scope of the disclosure.

In some embodiments, the activity of a protein kinase described herein is selectively inhibited by the compounds or pharmaceutical compositions described herein, compared to the activity of a different protein (e.g., a different protein kinase). In certain embodiments, the activity of a Src family kinase (e.g., HCK) is selectively inhibited by a compound or pharmaceutical composition described herein, compared to the activity of a different protein. In certain embodiments, the activity of BTK is selectively inhibited by a compound or pharmaceutical composition described herein, compared to the activity of a different protein.

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the Ka value of an adduct of the compound or pharmaceutical composition and the different protein over the Ka value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In some embodiments, the activity of a protein kinase is non-selectively inhibited by the compounds or pharmaceutical compositions described herein.

In certain embodiments, the activity of a protein kinase described herein is aberrant. In certain embodiments, the activity of a protein kinase described herein is increased. In certain embodiments, the activity of a protein kinase described herein is increased compared to normal (i.e., non-cancerous) cells.

In some proliferative diseases, such as MYD88 L265P driven Waldenstrom's macroglobulinemia, certain protein kinase (e.g., a Src family kinase (e.g., HCK), BTK) is activated. Thus the compounds and pharmaceutical compositions may be useful in treating and/or preventing proliferative diseases by, e.g., inhibiting the activity of protein kinases.

Another aspect of the present disclosure relates to methods of treating a proliferative disease in a subject in need thereof, the methods comprising administering to the subject an effective amount (e.g., therapeutically effective amount) of a compound or pharmaceutical composition described herein.

Another aspect of the present disclosure relates to methods of preventing proliferative disease in a subject in need thereof, the methods comprising administering to the subject an effective amount (e.g., prophylactically effective amount) of a compound or pharmaceutical composition described herein.

In certain embodiments, the compounds and pharmaceutical compositions are useful in treating and/or preventing proliferative diseases, such as proliferative diseases associated with MYD88. MYD88 gene has been implicated in many proliferative diseases. Activated B cell type diffuse large B cell lymphoma (ABC-DLBCL), a particularly aggressive subtype of DLBCL whose pathogenesis relies on constitutively active NFκB, is frequently associated with MYD88 mutations. 39% of tumor samples contain mutations in MYD88, and 29% of those mutations result in a single nucleotide change from leucine into proline at position 265 (L265P) (Ngo et al., Nature. 2011 Feb. 3; 470 (7332):115-9). shRNA knockdown of MYD88 in lymphoma cell lines demonstrated that MYD88 mutations are critical for their survival and high NFκB transcription factor activity (Ngo et al., Nature. 2011 Feb. 3; 470(7332):115-9). A hyperphosphorylated isoform of IRAK1 was strongly associated with the L265P mutant form of MYD88, suggesting that this mutation is a gain-of-function mutation that leads to the constitutive activation of downstream IRAKs (Ngo et al., Nature. 2011 Feb 3; 470(7332):115-9). The effects of the L265P mutation include increased NFKB activity as well as increased JAK-STAT3 signaling and the production of pro-inflammatory cytokines such as IL-6, IL-10, and IFN-I3 (Ngo et al., Nature. 2011 Feb. 3; 470(7332):115-9). The production of these cytokines further activates JAK-STAT3 signaling as part of an autocrine loop that enhances the survival of the lymphoma cells (Lam et al., Blood. 2008 Apr. 1; 111(7):3701-13; Ding et al., Blood. 2008 Feb. 1; 111(3): 1515-23).

MYD88 mutations have since been seen in a number of other human malignancies, with the L265P mutation found in almost 100% of Waldenström's macroglobulinemia (WM), 2-10% of chronic lymphocytic leukemia (CLL), 69% of cutaneous diffuse large B cell lymphoma (CBCL), and 38% of primary central nervous system lymphoma (PCNSL) (Wang et al., Blood Lymphat Cancer (2013) 2013:53-6110). However, the effect of single MYD88 L265P mutation on tumor growth is confounded by the accumulation of other potential damaging mutations in the same malignant clones. Recently, a retroviral gene transfer strategy to study the effects of single MYD88 mutation in otherwise normal mature B cells found that the MYD88 L265P mutation alone was able to drive limited rounds of mitogen independent B cell proliferation both in vitro and in vivo (Wang et al., J Exp Med. 2014 Mar 10; 211(3):413-26). Nevertheless, the drive for B cell proliferation was dependent on intact nucleic acid sensing toll-like receptor (TLR) activity since Unc93b13d mutation or Tlr9 deficiency inhibited the proliferation of MYD88 L265P B cells in vitro (Wang et al., J Exp Med (2014) 211:413-2610). Other studies have also shown that oncogenic MYD88 depends on TLRs by using the depletion of $UNC_{91}B1$, PRAT4A, and CD14 in ABC-DLBCL lines as well as by using pharmacological inhibitors to TLR7 and TLR9 (Lim et al. In: Proceedings of the 104th Annual Meeting of the American Association for Cancer Research; 2013 Apr. 6-10; Washington, D.C. Philadelphia: AACR; Cancer Res; (2013) 73(8 Suppl):Abst 2332.10.1158/1538-7445.AM2013-2332). Given that intact TLR activity is critical for lymphoma cells carrying MYD88 mutations, targeting this pathway appears to be attractive for treating these malignancies. Indeed, blocking endosome acidification using chloroquine selectively inhibits MYD88 L265P mutation driven B cell proliferation in vitro (Wang et al., J Exp Med (2014) 211:413-2610).

In certain embodiments, a subject described herein is diagnosed as having WM. The subject may present one or more signs, symptoms, or clinical features of WM including anemia, hyper-viscosity, neuropathy, coagulopathies, splenomegaly, hepatomegaly, adenopathy, and an IgM serum paraprotein. In certain embodiments, the subject is diagnosed as having WM on the basis that the subject has a mutation at position 38182641 of chromosome 3p22.2. In some embodiments, the mutation results in a single nucleotide change from T to C in the MYD88 gene. In some embodiments, the mutation results in an amino acid change from leucine to proline at position 265 in the MYD88 gene.

The mutation may be detected in a biological sample obtained from the subject using any suitable method known in the art, including but not limited to, direct sequencing of nucleic acid molecules, HPLC analysis, DNA chip technologies, and mass spectroscopy.

In certain embodiments, a proliferative disease that is treated and/or prevented by a method described herein is a proliferative disease associated with an MYD88 mutation (e.g., MYD88 L265P mutation). In certain embodiments, the proliferative disease is cancer. In certain embodiments, the proliferative disease is a hematological malignancy. In certain embodiments, the proliferative disease is myelodysplasia. In certain embodiments, the proliferative disease is leukemia. In certain embodiments, the proliferative disease is chronic lymphocytic leukemia (CLL). In certain embodiments, the proliferative disease is lymphoma. In certain embodiments, the proliferative disease is Waldenström's macroglobulinemia. In certain embodiments, the proliferative disease is activated B-cell (ABC) diffuse large B-cell lymphoma (DLBCL), central nervous system (CNS) lymphoma (e.g., primary CNS lymphoma, secondary CNS lymphoma), lymphoma of an immune privileged site, testicular lymphoma, or marginal zone lymphoma. In certain embodiments, the proliferative disease is cerebral lymphoma, ocular lymphoma, lymphoma of the placenta, or lymphoma of the fetus. In certain embodiments, the proliferative disease is a benign neoplasm. In certain embodiments, the proliferative disease is pathological angiogenesis. In certain embodiments, the proliferative disease is an inflammatory disease. In certain embodiments, the proliferative disease is an autoimmune disease.

In certain embodiments, a method described herein further includes administering to the subject an additional pharmaceutical agent. In certain embodiments, a method described herein further includes contacting the biological sample with an additional pharmaceutical agent. In certain embodiments, a method described herein further includes contacting the tissue with an additional pharmaceutical agent. In certain embodiments, a method described herein further includes contacting the cell with an additional pharmaceutical agent. In certain embodiments, a method described herein further includes radiotherapy, immunotherapy, and/or transplantation (e.g., bone marrow transplantation).

Another aspect of the present disclosure relates to methods of inducing apoptosis in a cell, the methods comprising contacting the cell with an effective amount of a compound or pharmaceutical composition described herein. Without wishing to be bound by any particular theory, the compounds and pharmaceutical compositions described herein may be able to inhibit the proliferation of and/or to kill cells, such as malignant cells (e.g., malignant cells whose proliferation and/or survival are driven by MYD88 L265P expression). In certain embodiments, a compound or pharmaceutical composition described herein inhibits the proliferation of a cell by at least 10%, at least 20%, at least 30%, at least 40%, at least 50%, at least 70%, or at least 90%. In certain embodiments, a compound or pharmaceutical composition described herein inhibits the proliferation of a cell by not more than 10%, not more than 20%, not more than 30%, not more than 40%, not more than 50%, not more than 70%, or not more than 90%. In certain embodiments, a compound or pharmaceutical composition described herein kills at least 10%, at least 20%, at least 30%, at least 40%, at least 50%, at least 70%, or at least 90% cells. In certain embodiments, a compound or pharmaceutical composition described herein kills not more than 10%, not more than 20%, not more than 30%, not more than 40%, not more than 50%, not more than 70%, or not more than 90% cells. Combinations of the above-referenced ranges (e.g., at least 10% and not more than 50%) are also within the scope of the disclosure.

Methods of Screening a Library of Compounds

Another aspect of the disclosure relates to methods of screening a library of compounds, and pharmaceutical acceptable salts thereof, to identify a compound, or a pharmaceutical acceptable salt thereof, that is useful in the methods of the disclosure. In certain embodiments, the methods of screening a library include obtaining at least two different compounds described herein; and performing at least one assay using the different compounds described herein. In certain embodiments, at least one assay is useful in identifying a compound that is useful in the described methods.

Typically, the methods of screening a library of compounds involve at least one assay. In certain embodiments, the assay is performed to detect one or more characteristics associated with the treatment of a proliferative disease (e.g., myelodysplasia, leukemia, lymphoma (e.g., Waldenström's macroglobulinemia)) in a subject in need thereof, with the prevention of a proliferative disease (e.g., myelodysplasia, leukemia, lymphoma (e.g., Waldenström's macroglobulinemia)) in a subject in need thereof, with the inhibition of the activity of a protein kinase (e.g., HCK, BTK) in a subject, biological sample, tissue, or cell, and/or with the induction of apoptosis in a cell. The characteristics may be desired characteristics (e.g., a proliferative disease in a subject having been treated, a subject having been prevented from having a proliferative disease, the activity of a protein kinase (e.g., HCK, BTK) in a subject, biological sample, tissue, or cell having been inhibited, and/or the apoptosis in a cell having been induced). The characteristics may be undesired characteristics (e.g., a proliferative disease in a subject having not been treated, a subject having not been prevented from having not a proliferative disease, the activity of a protein kinase (e.g., HCK, BTK) in a subject, biological sample, tissue, or cell having not been inhibited, and/or the apoptosis in a cell having not been induced). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with a protein kinase; and (b) detecting the binding of the library of compounds to the protein kinase. In certain embodiments, the assay comprises detecting the specific binding of the library of compounds to the protein kinase. In certain embodiments, the detected binding of the library of compounds to the protein kinase is useful in identifying the compound that is useful in the methods of the disclosure. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell in vitro, ex vivo, or in vivo. In certain embodiments, the step of performing at least one assay is performed in a cell in vitro. In certain embodiments, the assay comprises (a) contacting a library of compounds with a cell; and (b) detecting a decrease in cell proliferation, an increase in cell death, and/or an increase in cell differentiation.

Uses

In another aspect, the present disclosure provides the compounds described herein for use in a method of the disclosure.

In still another aspect, the present disclosure provides the pharmaceutical compositions described herein for use in a method of the disclosure.

In still another aspect, the present disclosure provides uses of the compounds described herein in a method of the disclosure.

In further another aspect, the present disclosure provides uses of the pharmaceutical compositions described herein in a method of the disclosure.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation of the Compounds

The compounds provided herein can be prepared from readily available starting materials using the following general methods and procedures (e.g., Examples 1 to 21). Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

General Methods and Materials for Preparing Exemplary Compounds Described Herein The following general methods and materials may be independently applicable to any one of Examples 1 to 21. Commercially available reagents and solvents were used without further purification. All reactions were monitored by thin layer chromatography (TLC) with 0.25 mm E. Merck pre-coated silica gel plates (60 F254) and/or Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 µm particle size): Method A; solvent gradient =97% A at 0 min, 0% A at 5 min; solvent A=0.035% TFA in Water; solvent B=0.035% TFA in MeOH; flow rate: 2.5 mL/min. Purification of reaction products was carried out by flash chromatography using CombiFlash® Rf with Teledyne Isco RediSep® Rf High Performance Gold or Silicycle SiliaSep™ High Performance columns (4 g, 12 g, or 24 g) and Waters LCMS system using SunFire™ Prep C18 column (19×50 mm, 5 µm particle size): solvent gradient=100% A at 0 min, 20% A at 6 min; solvent A=0.035% TFA in Water; solvent B=0.035% TFA in MeOH; flow rate: 25 mL/min. The purity of all compounds was over 95% and was analyzed with Waters LCMS system. $^1$H NMR spectra were obtained using a Varian Inova-500 or 600 (500 or 600 MHz for $^1$H NMR) spectrometer. Chemical shifts are reported relative to chloroform ($\delta$=7.26) or dimethyl sulfoxide ($\delta$=2.50) for $^1$H NMR. Data are reported as (br=broad, s=singlet, d=doublet, t=triplet, q=quartet, m=multiplet).

General Procedure I for the Aromatic Nucleophilic Displacement Reaction

The following General procedure I may be independently applicable to any one of Examples 1 to 21. A microwave vial was charged with 2-((2-chloropyrimidin-4-yl)amino)-N-(2,6-dimethylphenyl)thiazole-5-carboxamide (1 eq), the amine analogue (2 eq) and anhydrous sec-butanol (0.05 M). The vial was sealed and was heated in the Biotage Initiator microwave at 160° C. until the reaction had reached completion. The solvent was removed under reduced pressure and the residue redissolved in DCM, and TFA was added and the reaction mixture was stirred at ambient temperature for 2 h. The solvent was removed under reduced pressure and the residue was purified by preparative HPLC.

General Procedure II for the Acrylamide Formation

The following General procedure II may be independently applicable to any one of Examples 1 to 21. The amine intermediate (1 eq) was dissolved in a 1:1 mixture of THF and saturated NaHCO₃ aqueous solution, and cooled to 0° C. To the stirring mixture was added a dilute solution of acryloyl chloride (3 eq) in THF, the reaction was stirred at 0° C. and gradually warmed to ambient temperature. After 30 min, the reaction was extracted with ethyl acetate twice, the organic extracts were combined and concentrated under reduced pressure. The residue was directly purified by preparative HPLC.

Example 1. Preparation of (S)-2-((2-((1-acryloylpyrrolidin-3-yl)amino)pyrimidin-4-yl)amino)-N-(2,6-dimethylphenyl)thiazole-5-carboxamide

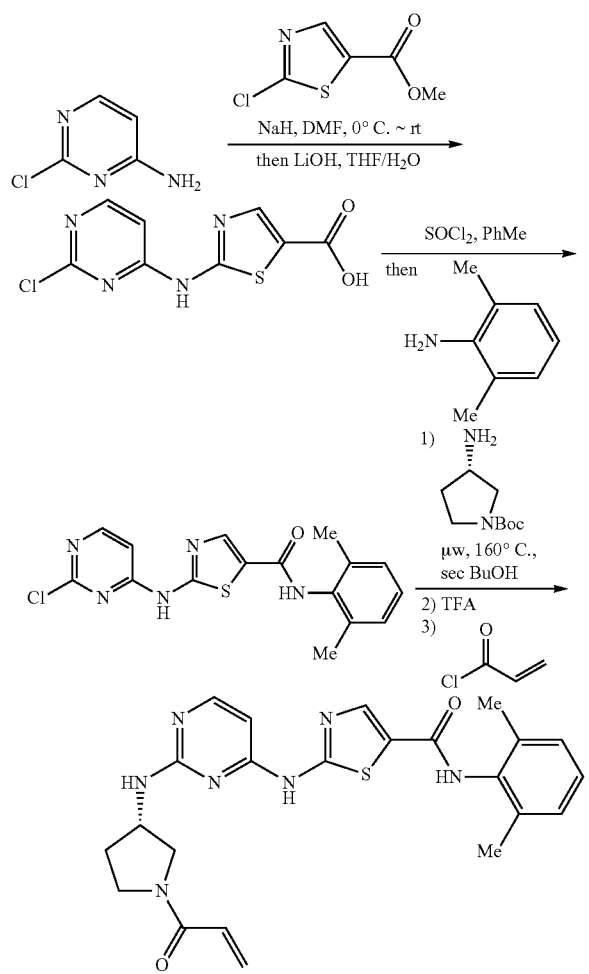

Methyl 2-((2-chloropyrimidin-4-yl)amino)thiazole-5-carboxylate

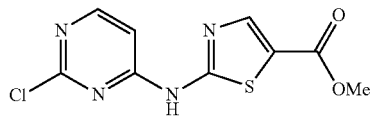 [SMILES: COC(=O)c1cnc(Nc2ccnc(Cl)n2)s1]

A solution of a mixture of 2-chloropyrimidin-4-amine (5.0 g, 38.5 mmol) and methyl 2-chlorothiazole-5-carboxylate (6.85 g, 38.5 mmol, 1 equivalent (eq)) in dry N,N-dimethylformamide (75 ml) was cooled to 0° C. and was treated portionwise over 5 min with sodium hydride (60% w/w in mineral oil, 3.1 g, 76.9 mmol, 2 eq). The reaction mixture was stirred at 0° C. for 1 h and warmed to ambient temperature for a further 1 h. The mixture was treated with saturated ammonium chloride, followed by saturated aqueous Na₂CO₃ solution to reach pH 9, and the resulting mixture was extracted with 1:1 mixture of dichloromethane and ethyl acetate. The organic extracts were combined, dried using a hydrophobic frit, and evaporated under reduced pressure. The residue was purified by chromatography on silica to afford the title compound as an off-white solid. LCMS retention time (RT): 2.70 (Method A), Mass m/z: 270.99 (M+1).

2-((2-Chloropyrimidin-4-yl)amino)thiazole-5-carboxylic acid

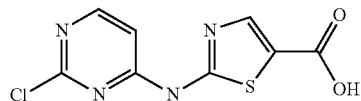

To a solution of methyl 2-((2-chloropyrimidin-4-yl)amino)thiazole-5-carboxylate (1 g, 3.7 mmol) in 1:1 mixture of THF/H₂O (15 mL) was added LiOH monohydrate (2.6 g, 29.6 mmol, 8 eq), and the reaction mixture was stirred at ambient temperature for 12 h. After 12 h, the reaction mixture was concentrated under reduced pressure and cooled to 0° C., and concentrated HCl was added dropwise to reach pH 6. The precipitate was filtered, washed with cold water, and dried using a hydrophobic frit to afford the titled compound as a white solid. LCMS RT: 2.13 (Method A), Mass m/z: 257.05 (M+1).

2-((2-Chloropyrimidin-4-yl)amino)-N-(2,6-dimethylphenyl)thiazole-5-carboxamide

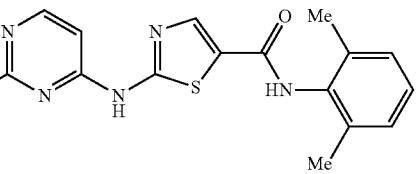

To a solution of 2-((2-chloropyrimidin-4-yl)amino)thiazole-5-carboxylic acid (50 mg, 0.195 mmol) in toluene (1 mL) was added thionyl chloride (2.26 mL, 1.95 mmol, 10 eq). The reaction mixture was stirred at 90° C. for 3 h, cooled to room temperature (rt), and concentrated under reduced pressure. The crude was dissolved in 1,2-dichloroethane (DCE, 1 mL), and 2,6-dimethylaniline (48 µL, 0.390 mmol, 2 eq) and DIPEA (N,N-diisopropylethylamine, 68 µL, 0.390 mmol, 2 eq) was added. The reaction mixture was stirred at 80° C. for 12 h and cooled to ambient temperature, and water was added. The mixture was extracted with isopropanol/chloroform (1:4) three times, the organic extracts were combined, washed with brine, dried over Na$_2$SO4, and concentrated under reduced pressure. The residue was purified by chromatography on silica to afford the title compound as a yellowish solid. LCMS RT: 2.95 (Method A), Mass m/z: 360.22 (M+1).

N-(2-Chloro-6-methylphenyl)-2-((2-chloropyrimidin-4-yDamino)thiazole-5-carboxamide

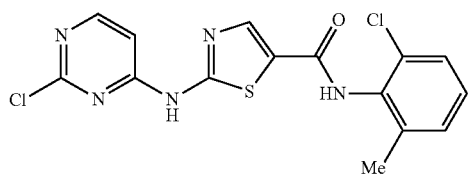 [SMILES: Cc1cccc(Cl)c1NC(=O)c1cnc(Nc2ccnc(Cl)n2)s1]

N-(2-chloro-6-methylphenyl)-2-(2-chloropyrimidin-4-yl) amino)thiazole-5-carboxamide was prepared from 2-((2-chloropyrimidin-4-yl)amino)thiazole-5-carboxylic acid and 2-chloro-6-methylaniline using the same procedure. LCMS RT: 2.98 (Method A), Mass m/z: 380.26 (M+1).

(S)-2-((2-((1-acryloylpyrrolidin-3-yl)amino)pyrimidin-4-yl)amino)-N-(2,6-dimethylphenyl)thiazole-5-carboxamide

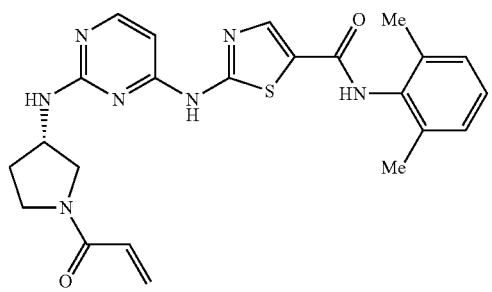 [SMILES: C=CC(=O)N1CC[C@H](Nc2nccc(Nc3ncc(C(=O)Nc4c(C)cccc4C)s3)n2)C1]

(S)-24(24(1-acryloylpyrrolidin-3-yl)amino)pyrimidin-4-yl)amino)-N-(2,6-dimethylphenyl)thiazole-5-carboxamide was prepared from 2-((2-chloropyrimidin-4-yl)amino)-N-(2,6-dimethylphenyl)thiazole-5-carboxamide and tert-butyl (S)-3-aminopyrrolidine-1-carboxylate using general procedures I and II. LCMS RT: 2.23 (Method A), Mass m/z: 464.48 (M+1).

Example 2. Preparation of (S)-N-(2,6-dimethylphenyl)-24(2-((1-propionylpyrrolidin-3-yl)amino)pyrimidin-4-yl)amino)thiazole-5-carboxamide

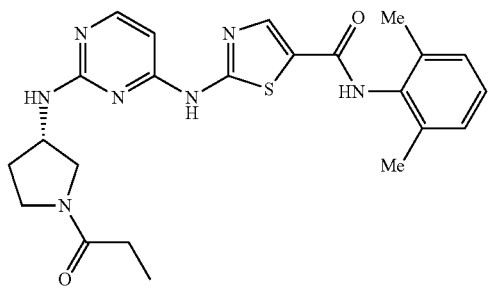 [SMILES: CCC(=O)N1CC[C@H](Nc2nccc(Nc3ncc(C(=O)Nc4c(C)cccc4C)s3)n2)C1]

(S)-N-(2,6-dimethylphenyl)-2-((2-((1-propionylpyrrolidin-3-yl)amino)pyrimidin-4-yl)amino)thiazole-5-carboxamidewas prepared from 2-((2-chloropyrimidin-4-yl) amino)-N-(2,6-dimethylphenyl)thiazole-5-carboxamide, tert-butyl (S) -3-aminopyrrolidine-1-carboxylate and propionyl chloride using general procedures I and II. LCMS RT: 2.28 (Method A), Mass m/z: 466.62 (M+1). 1H NMR (400 MHz,) δ12.47 (s, 1H), 9.77 (s, 1H), 8.53 (s, 1H), 8.38-8.28 (m, 1H), 8.08 (dd, J=6.4, 3.1 Hz, 1H), 7.13 (d, J =1.8 Hz, 3H), 6.44 (t, J=5.5 Hz, 1H), 4.51 (d, J=98.4 Hz, 1H), 3.97-2.94 (m, 3H), 2.28-2.21 (m, 1H), 2.19 (d, J=2.0 Hz, 6H), 2.08 (t, J=7.5 Hz, 1H), 1.97 (d, J=8.8 Hz, 1H), 1.01-0.91 (m, 3H), 0.91-0.78 (m, 2H).

Example 3. Preparation of (R)-2-((2-((1-acryloylpyrrolidin-3-yl)amino)pyrimidin-4-yl)amino)-N-(2,6-dimethylphenyl)thiazole-5-carboxamide

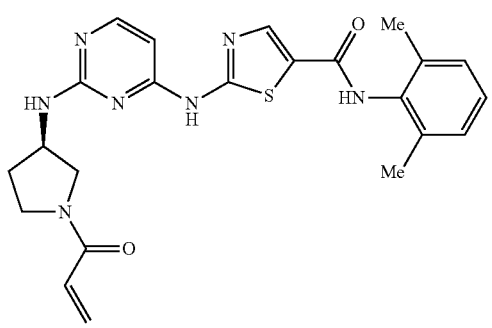 [SMILES: C=CC(=O)N1CC[C@@H](Nc2nccc(Nc3ncc(C(=O)Nc4c(C)cccc4C)s3)n2)C1]

(R)-2-((2-((1-acryloylpyrrolidin-3-yl)amino)pyrimidin-4-yl)amino)-N-(2,6-dimethylphenyl)thiazole-5-carboxamide was prepared from 2-((2-chloropyrimidin-4-yl)amino)-N-(2, 6-dimethylphenyl)thiazole-5-carboxamide and tert-butyl (R)-3-aminopyrrolidine-1-carboxylate using general procedures I and II. LCMS RT: 2.23 (Method A), Mass m/z: 464.54 (M+1). 1H NMR (400 MHz,) δ12.47 (s, 1H), 9.77 (s, 1H), 8.46 (s, 1H), 8.33 (d, J=5.3 Hz, 1H), 8.08 (d, J=6.6 Hz, 1H), 7.12 (s, 3H), 6.66-6.40 (m, 2H), 6.12 (ddd, J=17.3, 5.8, 2.5 Hz, 1H), 5.71-5.59 (m, 1H), 4.57 (d, J=69.4 Hz, 1H), 4.04-2.75 (m, 3H), 2.19 (s, 6H), 2.35-1.93 (m, 1H), 1.33-0.66 (m, 2H).

Example 4. Preparation of (R)-2-((2-((1-acryloylpiperidin-3-yl)amino)pyrimidin-4-yl)amino)-N-(2,6-dimethylphenyl)thiazole-5-carboxamide

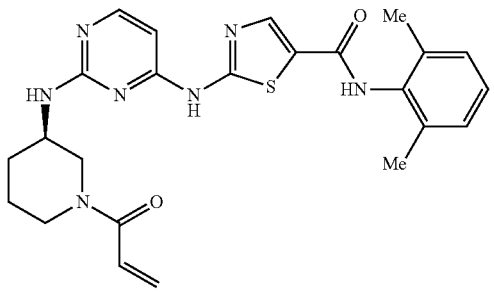 [SMILES: C=CC(=O)N1CCC[C@@H](Nc2nccc(Nc3ncc(C(=O)Nc4c(C)cccc4C)s3)n2)C1]

(R)-2-((2-((1-acryloylpiperidin-3-yl)amino)pyrimidin-4-yl)amino)-N-(2,6-dimethylphenyl)thiazole-5-carboxamide was prepared from 2-((2-chloropyrimidin-4-yl)amino)-N-(2,6-dimethylphenyl)thiazole-5-carboxamide and tert-butyl (R)-3-aminopiperidine-1-carboxylate using general procedures I and II. LCMS RT: 2.10 (Method A), Mass m/z: 478.53 (M+1).

Example 5. Preparation of 2-((2-((1-acryloylazepan-3-yl)amino)pyrimidin-4-yl)amino)-N-(2,6-dimethylphenyl)thiazole-5-carboxamide

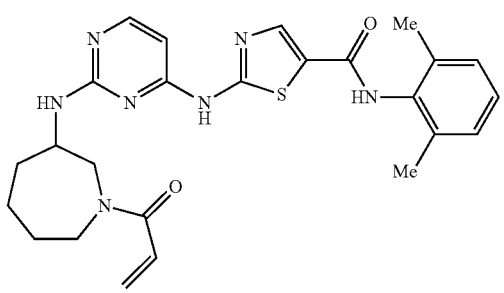 [SMILES: C=CC(=O)N1CCCCC(Nc2nccc(Nc3ncc(C(=O)Nc4c(C)cccc4C)s3)n2)C1]

2-((2-((1-acryloylazepan-3-yl)amino)pyrimidin-4-yl)amino)-N-(2,6-dimethylphenyl)thiazole-5-carboxamide was prepared from 2-((2-chloropyrimidin-4-yl)amino)-N-(2,6-dimethylphenyl)thiazole-5-carboxamide and tert-butyl 3-aminoazepane-1-carboxylate using general procedures I and II. LCMS RT: 2.50 (Method A), Mass m/z: 492.59 (M+1). 1H NMR (400 MHz, DMSO-d6) δ9.80 (s, 1H), 8.34 (s, 1H), 8.23 (s, 1H), 8.09 (d, J=6.5 Hz, 1H), 7.13 (s, 3H), 6.78 (dd, J=16.6, 10.5 Hz, 1H), 6.45 (d, J=6.7 Hz, 1H), 6.06 (d, J=16.6 Hz, 1H), 5.64 (d, J=10.6 Hz, 1H), 4.48 (s, 1H), 3.42 (s, 5H), 2.19 (s, 6H), 1.80-1.50 (m, 4H), 1.23 (m, 1H), 0.84 (m, 1H).

Example 6. Preparation of 2-((2-(((1-acryloylpyrrolidin-3-yl)methyl)amino)pyrimidin-4-yl)amino)-N-(2,6-dimethylphenyl)thiazole-5-carboxamide

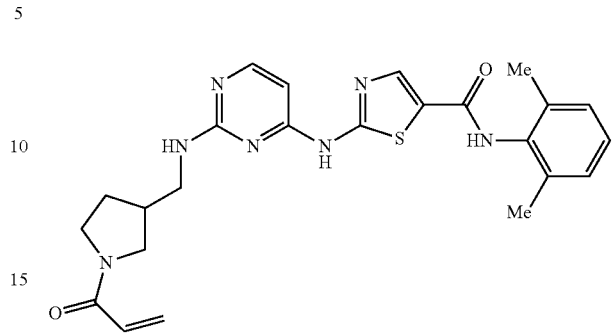

2-((2-(((1-acryloylpyrrolidin-3-yl)methyl)amino)pyrimidin-4-yl)amino)-N-(2,6-dimethylphenyl)thiazole-5-carboxamide was prepared from 2-((2-chloropyrimidin-4-yl)amino)-N-(2,6-dimethylphenyl)thiazole-5-carboxamide and tert-butyl 3-(aminomethyl)pyrrolidine-1-carboxylate using general procedures I and II. LCMS RT: 2.25 (Method A), Mass m/z: 478.60 (M+1). 1H NMR (400 MHz, DMSO-d6) δ12.56 (s, 1H), 9.83 (d, J=8.8 Hz, 1H), 8.48 (s, 1H), 8.35 (s, 1H), 8.06 (d, J=6.5 Hz, 1H), 7.14 (s, 3H), 6.52 (dd, J=16.8, 9.2 Hz, 1H), 6.42 (t, J=5.6 Hz, 1H), 6.11-5.99 (m, 1H), 5.60-5.40 (m, 1H), 4.00-2.97 (m, 4H), 2.82-2.54 (m, 1H), 2.20 (s, 6H, overlap), 2.17-1.97 (m, 1H), 1.87-1.55 (m, 1H), 1.24 (m, 1H), 0.85 (d, J=7.2 Hz, 1H).

Example 7. Preparation of (S)-2-((2-((1-acryloylpyrrolidin-3-yl)amino)pyrimidin-4-yl)amino)-N-(2-chloro-6-methylphenyl)thiazole-5-carboxamide

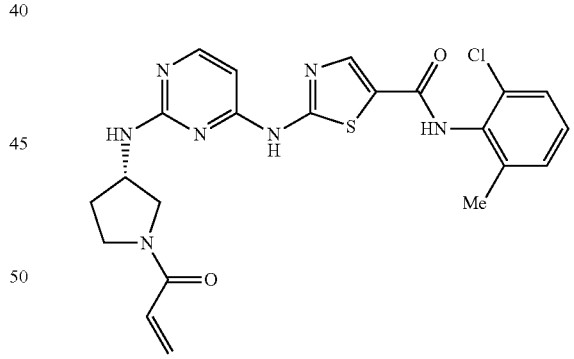

(S)-2-((2-((1-acryloylpyrrolidin-3-yl)amino)pyrimidin-4-yl)amino)-N-(2-chloro-6-methylphenyl)thiazole-5-carboxamide was prepared from N-(2-chloro-6-methylphenyl)-2-((2-chloropyrimidin-4-yl)amino)thiazole-5-carboxamide and tert-butyl (S)-3-aminopyrrolidine-1-carboxylate using general procedures I and II. LCMS RT: 2.25 (Method A), Mass m/z: 484.52 (M+1). 1H NMR (400 MHz, DMSO-d6) δ9.99 (s, 1H), 8.43 (d, J=6.7 Hz, 1H), 8.30 (s, 1H), 8.06 (s, 1H), 7.44 —7.31 (m, 1H), 7.31 —7.17 (m, 2H), 6.34 (d, J=6.2 Hz, 1H), 6.23-6.02 (m, 2H), 5.58 (d, J=9.9 Hz, 1H), 3.43 (s, 4H), 2.21 (s, 4H), 1.95 (s, 1H), 1.36-1.02 (m, 1H), 0.82 (s, 1H).

Example 8. Preparation of 2-((2-((1-acryloylazepan-3-yl)amino)pyrimidin-4-yl)amino)-N-(2-chloro-6-methylphenyl)thiazole-5-carboxamide

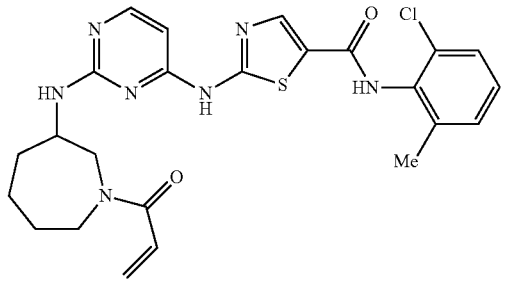 [SMILES: C=CC(=O)N1CCCCC(Nc2nccc(Nc3ncc(C(=O)Nc4c(C)cccc4Cl)s3)n2)C1]

2-((2-((1-acryloylazepan-3-yl)amino)pyrimidin-4-yl)amino)-N-(2-chloro-6-methylphenyl)thiazole-5-carboxamide was prepared from N-(2-chloro-6-methylphenyl)-2-((2-chloropyrimidin-4-yl)amino)thiazole-5-carboxamide and tert-butyl 3-aminoazepane-1-carboxylate using general procedures I and II. LCMS RT: 2.50 (Method A), Mass m/z: 512.69 (M+1).

Example 9. Preparation of (S)-2-((2-((1-acryloylpyrrolidin-3-yl)amino)-6-(morpholinomethyl)pyrimidin-4-yl)amino)-N-(2,6-dimethylphenyl)thiazole-5-carboxamide

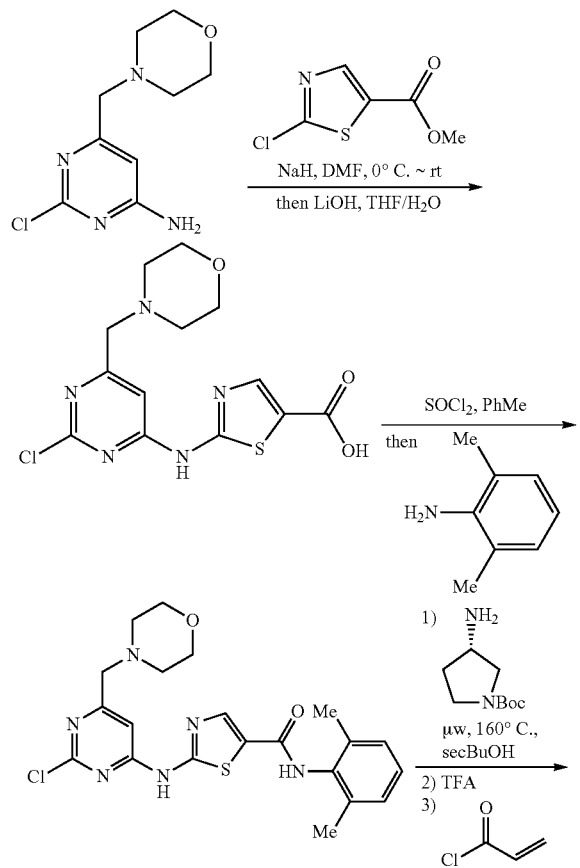

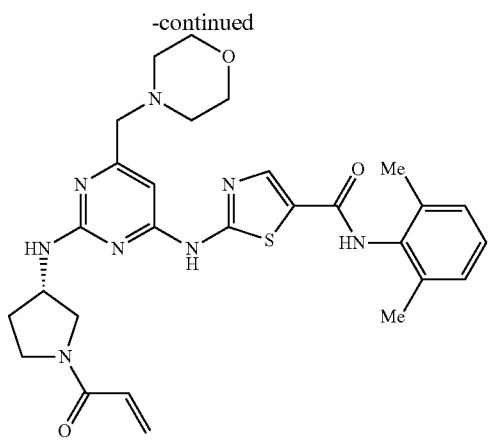

Methyl 2-((2-chloro-6-(morpholinomethyl)pyrimidin-4-yl)amino)thiazole-5-carboxylate

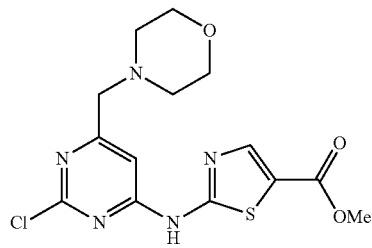 [SMILES: COC(=O)c1cnc(Nc2cc(CN3CCOCC3)nc(Cl)n2)s1]

A solution of a mixture of 2-chloropyrimidin-4-amine (730 mg, 3.2 mmol) and methyl 2-chlorothiazole-5-carboxylate (626 mg, 3.5 mmol, 1.1 eq) in dry N,N-dimethylformamide (15 ml) was cooled to 0° C. and was treated portionwise over 5 min with sodium hydride (60% w/w in mineral oil, 256 mg, 6.4 mmol, 2 eq). The reaction mixture was stirred at 0° C. for 1 h and warmed to ambient temperature for a further 1 h. The mixture was treated with saturated ammonium chloride, followed by saturated aqueous $Na_2CO_3$ solution to reach pH 9 and the product was extracted with 1:1 mixture of dichloromethane and ethyl acetate. The organic extracts were combined, dried using a hydrophobic frit and evaporated under reduced pressure. The residue was purified by chromatography on silica to afford the title compound as an off-white solid. LCMS RT: 2.07 (Method A), Mass m/z: 370.37 (M+1).

2-((2-chloro-6-(morpholinomethyl)pyrimidin-4-yl)amino)thiazole-5-carboxylic acid

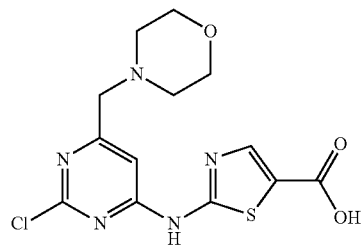 [SMILES: O=C(O)c1cnc(Nc2cc(CN3CCOCC3)nc(Cl)n2)s1]

To a solution of methyl 2-((2-chloro-6-(morpholinomethyl)pyrimidin-4-yl)amino)thiazole-5-carboxylate (190 mg, 0.51 mmol) in THF/H₂O (1:2 mixture, 6 mL), was added LiOH monohydrate (32 mg, 0.77 mmol, 1.5 eq) in one portion and the reaction mixture was stirred at ambient temperature for 12 h. After 12 h, the reaction mixture was concentrated under reduced pressure and cooled to 0° C. and concentrated HCl was added dropwise to reach pH 6. The precipitate was filtered, washed with cold water, dried using a hydrophobic frit to afford the titled compound as a white solid. LCMS RT: 1.67 (Method A), Mass m/z: 356.24 (M+1).

2-((2-chloro-6-(morpholinomethyl)pyrimidin-4-yl)amino)-N-(2,6-dimethylphenyl)thiazole-5-carboxamide

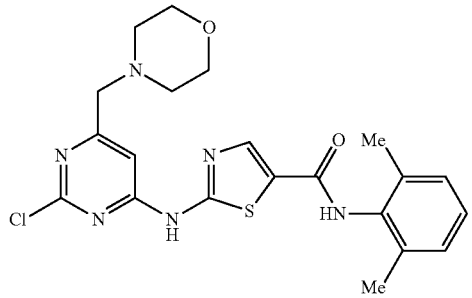 [SMILES: Cc1cccc(C)c1NC(=O)c1cnc(Nc2cc(CN3CCOCC3)nc(Cl)n2)s1]

To a solution of 2-((2-chloro-6-(morpholinomethyl)pyrimidin-4-yl)amino)thiazole-5-carboxylic acid (175 mg, 0.49 mmol) in toluene (3 mL) was added thionyl chloride (5.68 mL, 4.9 mmol, 10 eq). The reaction mixture was stirred at 90° C. for 3 h before cooled to room temperature and concentrated under reduced pressure. The crude was dissolved in DCE and 2,6-dimethylaniline and DIPEA was added. The reaction mixture was stirred at 80° C. for 12 h before cooled to ambient temperature and water was added. The mixture was extracted with isopropanol/chloroform (1:4) three times, the organic extracts were combined, washed with brine and dried over Na₂SO₄ and concentrated under reduced pressure. The residue was purified by chromatography on silica to afford the title compound as a yellowish solid. LCMS RT: 2.23 (Method A), Mass m/z: 479.48 (M+1).

2-((2-chloro-6-(morpholinomethyl)pyrimidin-4-yl)amino)-N-(2-chloro-6-methylphenyl)thiazole-5-carboxamide

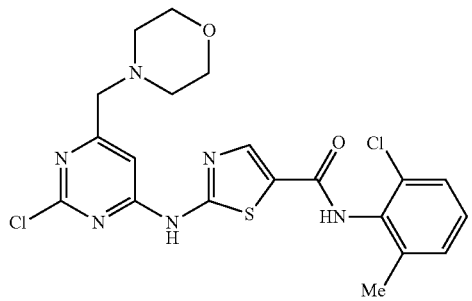 [SMILES: Cc1cccc(Cl)c1NC(=O)c1cnc(Nc2cc(CN3CCOCC3)nc(Cl)n2)s1]

2-((2-chloro-6-(morpholinomethyl)pyrimidin-4-yl)amino)-N-(2-chloro-6-methylphenyl)thiazole-5-carboxamide was prepared from 2-((2-chloro-6-(morpholinomethyl)pyrimidin-4-yl)amino)thiazole-5-carboxylic acid and 2-chloro-6-methylaniline using the same procedure.

(S)-2-((2-((1-acryloylpyrrolidin-3-yl)amino)-6-(morpholinomethyl)pyrimidin-4-yl)amino)-N-(2,6-dimethylphenyl)thiazole-5-carboxamide

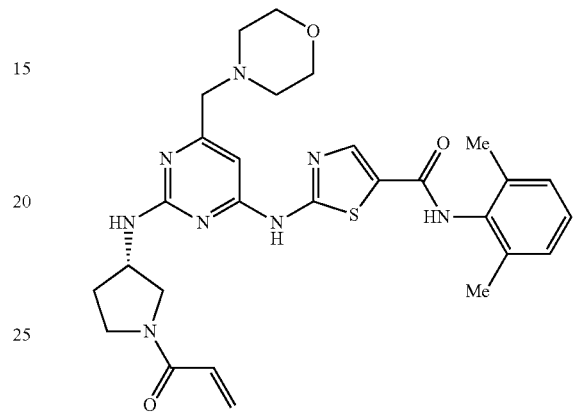

(S)-2-((2-((1-acryloylpyrrolidin-3-yl)amino)-6-(morpholinomethyl)pyrimidin -4-yl)amino)-N-(2,6-dimethylphenyl)thiazole-5-carboxamide was prepared from 2-((2-chloro -6-(morpholinomethyl)pyrimidin-4-yl)amino)-N-(2,6-dimethylphenyl)thiazole-5-carboxamide and tert-butyl (S)-3-aminopyrrolidine-1-carboxylate following general procedures I and II. LCMS RT: 2.10 (Method A), Mass m/z: 563.55 (M+1).

Example 10. Preparation of (S)-2-((2-((1-acryloylpyrrolidin-3-yl)amino)-6-(morpholinomethyl)pyrimidin-4-yl)amino)-N-(2-chloro-6-methylphenyl)thiazole-5-carboxamide

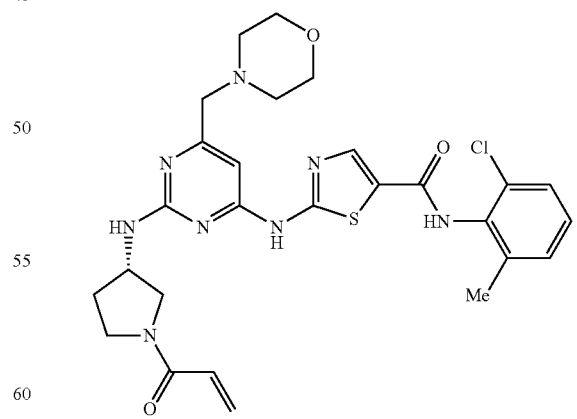

(S)-2-((2-((1-acryloylpyrrolidin-3-yl)amino)-6-(morpholinomethyl)pyrimidin -4-yl)amino)-N-(2-chloro-6-methylphenyl)thiazole-5-carboxamide was prepared from 2-((2-chloro-6-(morpholinomethyl)pyrimidin-4-yl)amino)-N-(2-chloro-6-methylphenyl)thiazole-5-carboxamide and tert-butyl (S)-3-aminopyrrolidine-1-carboxylate following general procedures I and II. LCMS RT: 2.17 (Method A), Mass m/z: 583.52 (M+1).

Example 11. Preparation of 2-((1-((1-acryloylpyrrolidin-3-yl)methyl)-1H-pyrazol-3-yl)amino)-N-(2-chloro-6-methylphenyl)thiazole-5-carboxamide

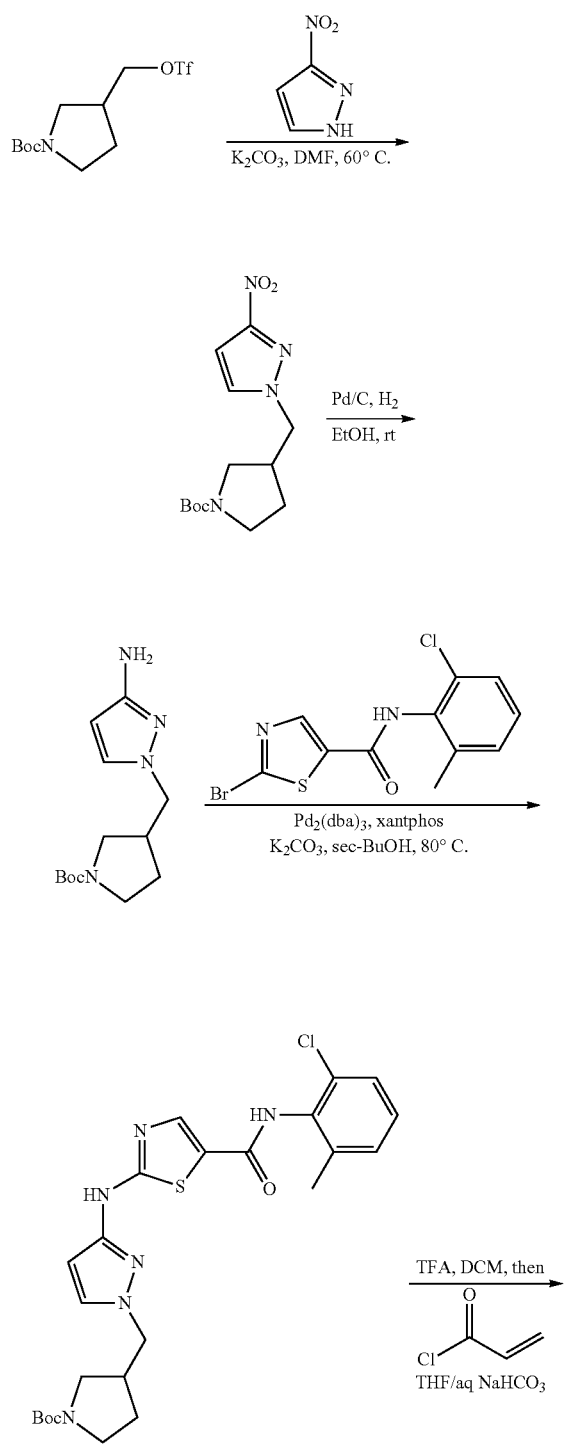

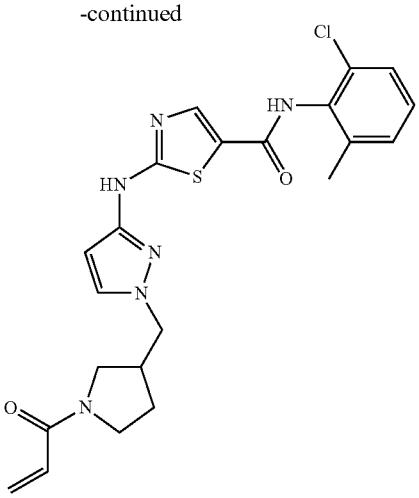

tert-butyl 3-((3-nitro-1H-pyrazol-1-yl)methyl)pyrrolidine-1-carboxylate

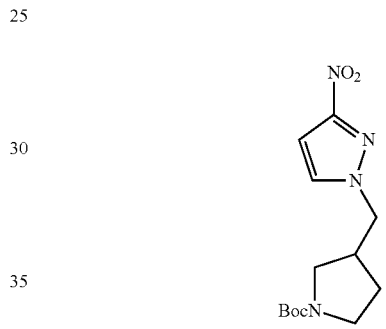

To a solution of tert-butyl 3-(((((trifluoromethyl)sulfonyl)oxy)methyl)pyrrolidine-1-carboxylate (1.47 g, 4.98 mmol) and 3-nitro-1H-pyrazole (619 mg, 5.48 mmol, 1.1 eq) in DMF (25 mL) was added K2CO3 (2.06 g, 14.94 mmol, 3 eq) in one portion, the reaction mixture was stirred at 60° C. for 12 h. The mixture was cooled to ambient temperature and extracted with ethyl acetate, the combined extracts were washed with water, 1N HCl and brine, dried over Na2SO4 and concentrated under reduced pressure to yield the title compound, as a crude and used directly in the next step. LCMS RT: 3.78 (Method A), Mass m/z: 300.06 (M+1).

tert-butyl 3-((3-amino-1H-pyrazol-1-yl)methyl)pyrrolidine-1-carboxylate

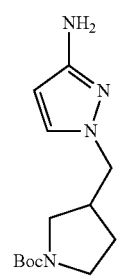 [SMILES: CC(C)(C)OC(=O)N1CCC(Cn2ccc(N)n2)C1]

tert-butyl 3-((3-nitro-1H-pyrazol-1-yl)methyl)pyrrolidine-1-carboxylate was dissolved in ethanol, 10 wt % Pd/C was added to the solution and the reaction mixture was stirred under H$_2$ atmosphere at ambient temperature for 3 h. The suspension was filtered through a pad of celite and the filtrate concentrated under reduced pressure to afford the title compound. LCMS RT: 1.97 (Method A), Mass m/z: 267.33 (M+1).

tert-butyl 3-((3-amino-1H-pyrazol-1-yl)methyl)piperidine-1-carboxylate

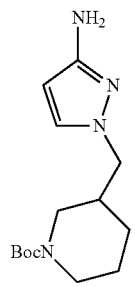

tert-butyl 3-((3-amino-1H-pyrazol-1-yl)methyl)piperidine-1-carboxylate was prepared using tert-butyl 3-((((trifluoromethyl)sulfonyl)oxy)methyl)piperidine-1-carboxylate and 3-nitro-1H-pyrazole following the same procedure. LCMS RT: 2.18 (Method A), Mass m/z: 281.21 (M+1).

tert-butyl 3-((3-((5-((2-chloro-6-methylphenyl)carbamoyl)thiazol-2-yl)amino)-1H-pyrazol-1-ypmethyppyrrolidine-1-carboxylate

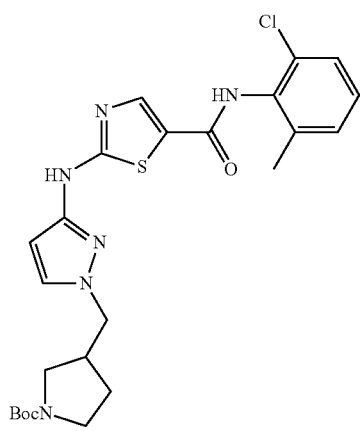 [SMILES: Cc1cccc(Cl)c1NC(=O)c1cnc(Nc2ccn(CC3CCN(C(=O)OC(C)(C)C)C3)n2)s1]

To a solution of 2-bromo-N-(2-chloro-6-methylphenyl)thiazole-5-carboxamide (75 mg, 0.23 mmol) and tert-butyl 3-((3-amino-1H-pyrazol-1-yl)methyl)pyrrolidine-1-carboxylate (120 mg, 0.45 mmol, 2 eq) in sec-butanol (1 mL) was added K$_2$CO$_3$ (94 mg, 0.68 mmol, 3 eq). The reaction mixture was degassed via sonication, before Pd$_2$(dba)$_3$ (12.4 mg, 0.014 mmol, 0.06 eq) and xantphos (12.0 mg, 0.020 mmol, 0.09 eq) were added to the mixture. The reaction was stirred at 80° C. for 3 h, filtered and dried under reduced pressure, and the residue was purified by preparative HPLC to yield the title compound. LCMS RT: 3.57 (Method A), Mass m/z: 517.61 (M+1).

tert-butyl 3-((3-((5-((2-chloro-6-methylphenyl)carbamoyl)thiazol-2-yl)amino)-1H-pyrazol-1-yl)methyl)piperidine-1-carboxylate

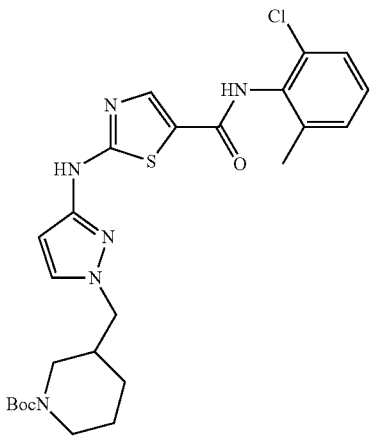 [SMILES: Cc1cccc(Cl)c1NC(=O)c1cnc(Nc2ccn(CC3CCCN(C(=O)OC(C)(C)C)C3)n2)s1]

tert-butyl 3-((3-((5-((2-chloro-6-methylphenyl)carbamoyl)thiazol-2-yl)amino)-1H-pyrazol-1-yl)methyl)piperidine-1-carboxylate was prepared from tert-butyl 3-((3-amino-1H-pyrazol-1-yl)methyl)piperidine-1-carboxylate and 2-bromo-N-(2-chloro-6-methylphenyl)thiazole-5-carboxamide following the same procedure. LCMS RT: 3.65 (Method A), Mass m/z: 531.66 (M+1).

tert-butyl 4-(4-((5-((2-chloro-6-methylphenyl)carbamoyl)thiazol-2-yl)amino)-1H-pyrazol-1-yl)piperidine-1-carboxylate

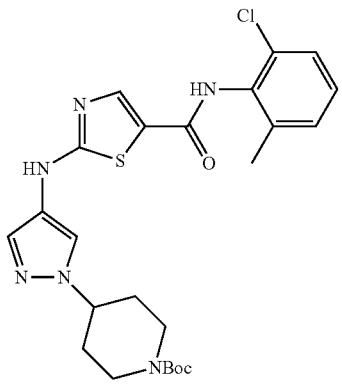 [SMILES: Cc1cccc(Cl)c1NC(=O)c1cnc(Nc2cnn(C3CCN(C(=O)OC(C)(C)C)CC3)c2)s1]

tert-butyl 4-(4-((5-((2-chloro-6-methylphenyl)carbamoyl)thiazol-2-yl)amino) -1H-pyrazol-1-yl)piperidine-1-carboxylate was prepared from tert-butyl 4-(4-amino-1H-pyrazol-1-yl)piperidine-1-carboxylate and 2-bromo-N-(2-chloro-6-methylphenyl)thiazole-5-carboxamide following the same procedure. LCMS RT: 3.28 (Method A), Mass m/z: 517.61 (M+1).

2-((1-((1-acryloylpyrrolidin-3-yl)methyl)-1H-pyrazol-3-yl)amino)-N-(2-chloro-6-methylphenyl)thiazole-5-carboxamide

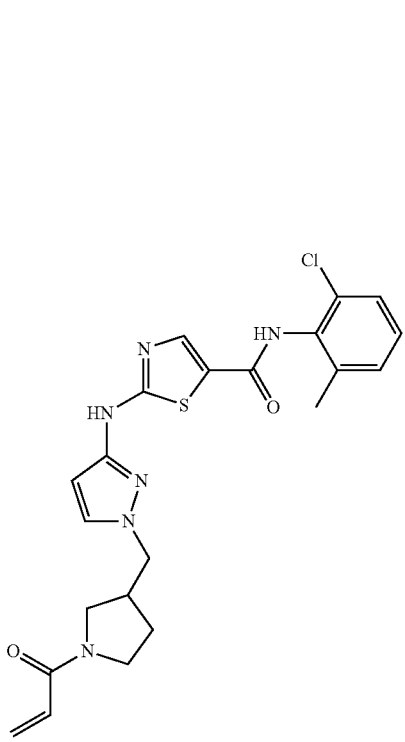 [SMILES: C=CC(=O)N1CCC(Cn2ccc(Nc3ncc(C(=O)Nc4c(C)cccc4Cl)s3)n2)C1]

tert-butyl 3-((3-((5-((2-chloro-6-methylphenyl)carbamoyl)thiazol-2-yl)amino)-1H-pyrazol-1-yl)methyl)pyrrolidine-1-carboxylate was dissolved in a 1:1 mixture of DCM and TFA. The reaction was stirred at ambient temperature for 2 h and dried under reduced pressure. The residue was dissolved in a 1:1 mixture of THF and saturated NaHCO$_3$ aqueous solution and cooled to 0° C. To the stirring mixture was added a dilute solution of acryloyl chloride in THF, the reaction was stirred at 0° C. and gradually warmed to ambient temperature. After 30min, the reaction was extracted with Ethyl acetate twice, the organic extracts combined and concentrated under reduced pressure. The residue was directly purified by preparative HPLC to yield the title compound. LCMS RT: 2.98 (Method A), Mass m/z: 485.47 (M+1). 1H NMR (400 MHz, DMSO-d6) δ11.12 (s, 1H), 9.78 (d, J=8.4 Hz, 1H), 8.13 (d, J=6.4 Hz, 1H), 7.69 (t, J=2.6 Hz, 1H), 7.43-7.19 (m, 3H), 6.54 (dd, J=16.8, 10.3 Hz, 1H), 6.07 (ddd, J=16.9, 5.1, 2.4 Hz, 1H), 5.95 (dd, J=9.7, 2.2 Hz, 1H), 5.61 (ddd, J=10.2, 7.8, 2.5 Hz, 1H), 4.11 (d, J=7.3 Hz, 1H), 3.57-3.40 (m, 3H), 3.25 (m, 1H), 2.80-2.60 (m, 1H), 2.23 (s, 3H), 1.97 (ddt, J=41.2, 12.5, 6.3 Hz, 1H), 1.67 (ddd, J=45.6, 12.8, 7.7 Hz, 1H).

Example 12. Preparation of 2-((1-((1-acryloylpiperidin-3-yl)methyl)-1H-pyrazol-3-yl)amino)-N-(2-chloro-6-methylphenyl)thiazole-5-carboxamide

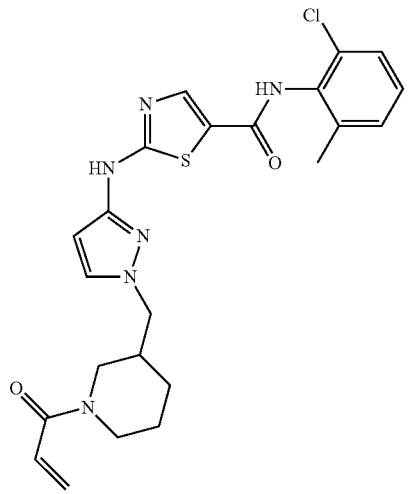 [SMILES: C=CC(=O)N1CCCC(Cn2ccc(Nc3ncc(C(=O)Nc4c(C)cccc4Cl)s3)n2)C1]

2-((1-((1-acryloylpiperidin-3-yl)methyl)-1H-pyrazol-3-yl)amino)-N-(2-chloro -6-methylphenyl)thiazole-5-carboxamide was prepared from tert-butyl 3-((3-((5-((2-chloro-6-methylphenyl)carbamoyl)thiazol-2-yl)amino)-1H-pyrazol-1-yl)methyl)piperidine-1-carboxylate following the same procedure. LCMS RT: 2.83 (Method A), Mass m/z: 471.60 (M+1). 1H NMR (400 MHz, DMSO-d6) δ11.10 (s, 1H), 9.79 (s, 1H), 8.13 (s, 1H), 7.67 (d, J =2.3 Hz, 1H), 7.38 (dd, J=7.5, 2.0 Hz, 1H), 7.32-7.16 (m, 2H), 6.70 (ddd, J=51.7, 16.7, 10.4 Hz, 1H), 6.02 (dd, J=16.7, 2.4 Hz, 1H), 5.96 (d, J=2.3 Hz, 1H), 5.59 (t, J=12.6 Hz, 1H), 4.22-3.91 (m, 4H), 3.14-2.80 (m, 2H), 2.23 (s, 3H), 1.98 (s, 1H), 1.68 (d, J=12.1 Hz, 2H), 1.44-1.16 (m, 2H).

Example 13. Preparation of 2-((1-(1-acryloylpiperidin-4-yl)-1H-pyrazol-4-yl)amino)-N-(2-chloro-6-methylphenyl)thiazole-5-carboxamide

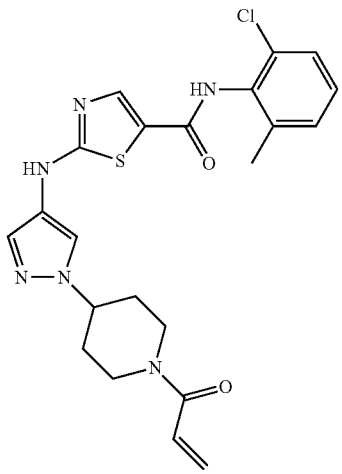 [SMILES: C=CC(=O)N1CCC(n2cc(Nc3ncc(C(=O)Nc4c(C)cccc4Cl)s3)cn2)CC1]

2-((1-(1-acryloylpiperidin-4-yl)-1H-pyrazol-4-yl)amino)-N-(2-chloro-6-methylphenyl)thiazole-5-carboxamide was prepared from tert-butyl 4-(4-(4-((5-((2-chloro-6-methylphenyl)carbamoyl)thiazol-2-yl)amino)-1H-pyrazol-1-yl)piperidine-1-carboxylate following the same procedure. LCMS RT: 2.67 (Method A), Mass m/z: 471.41 (M+1).

Example 14. Preparation of N-(1-methyl-1H-pyrazol-3-yl)-5-phenoxythiazolo[5,4-b]pyridin-2-amine

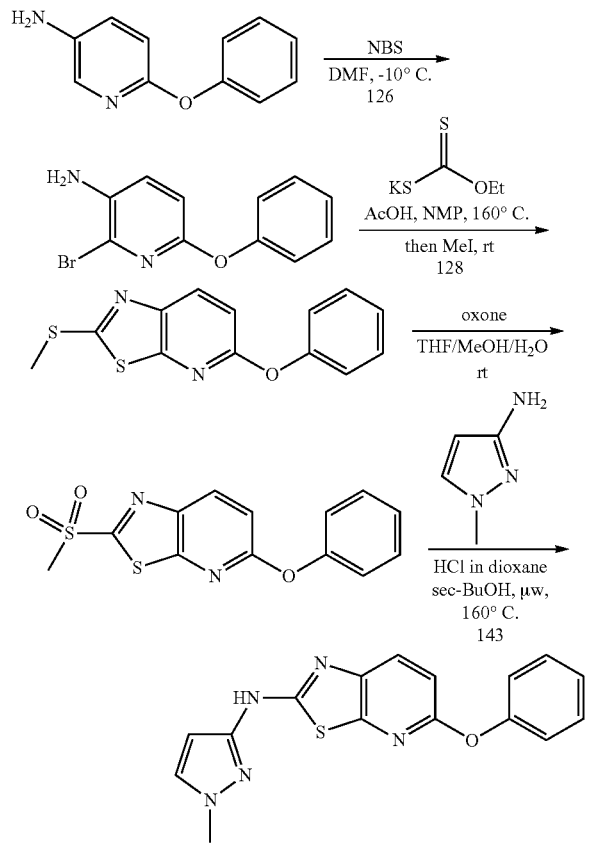

2-bromo-6-phenoxypyridin-3-amine

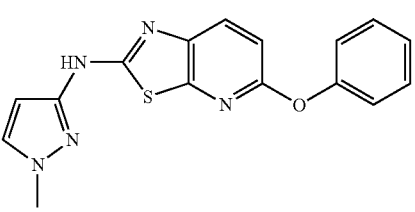

To a solution of 6-phenoxypyridin-3-amine (2 g, 10.8 mmol) in DMF (20 mL) was added N-bromosuccinimide (1.91 g, 10.8 mmol, 1 eq) at −10° C. for 5 min. The reaction mixture was quenched with saturated. NaHCO3 solution at -10° C. The mixture was partitioned between ethyl acetate and water. The organic layer was separated and the aqueous layer was extracted with ethyl acetate. The combined organic extracts were washed with brine, dried over Na2SO4 and concentrated under reduced pressure. The crude product was purified by flash column chromatography to afford title compound as a reddish brown solid. LCMS RT: 3.33 (Method A), Mass m/z: 261.21 (M+1).

2-(methylthio)-5-phenoxythiazolo[5,4-b]pyridine

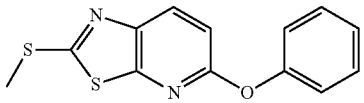 [SMILES: CSc1nc2ccc(Oc3ccccc3)nc2s1]

To a solution of 2-bromo-6-phenoxypyridin-3-amine (2.29 g, 8.64 mmol) in NMP (80 mL) was added potassium ethyl xanthogenate (6.9 g, 43.2 mmol, 5 eq) and acetic acid (3.1 mL, 43.2 mmol, 5 eq). The reaction mixture was heated at 150° C. for 16 hours. The mixture was cooled to 50° C. and iodomethane (538 µL, 86.4 mmol, 10 eq) was added. The reaction mixture was further stirred for 30 minutes and partitioned between ethyl acetate and water. The organic layer was separated and the aqueous layer was extracted with ethyl acetate. The combined organic extracts were washed with brine, dried over Na2SO4 and concentrated under reduced pressure. The residue was purified by flash column chromatography to afford title compound as a bright brown solid. LCMS RT: 3.95 (Method A), Mass m/z: 275.21 (M+1).

2-(methylsulfonyl)-5-phenoxythiazolo[5,4-b]pyridine

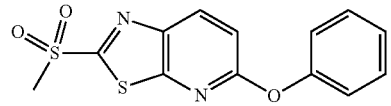 [SMILES: CS(=O)(=O)c1nc2ccc(Oc3ccccc3)nc2s1]

To a solution of 2-(methylthio)-5-phenoxythiazolo[5,4-b]pyridine (3.0 g, 11 mmol) in THF (18 mL) and methanol (18 mL) was added Oxone (6.66 g, 44 mmol, 4 eq) in water (18 mL). The reaction mixture was stirred for 16 hours at room temperature. The reaction mixture was filtered and concentrated under reduced pressure to give the title product as a bright brown solid. LCMS RT: 3.38 (Method A), Mass m/z: 307.19 (M+1).

N-(1-methyl-1H-pyrazol-3-yl)-5-phenoxythiazolo[5,4-b]pyridin-2-amine

To a solution of 2-(methylsulfonyl)-5-phenoxythiazolo[5,4-b]pyridine and 1-methyl-1H-pyrazol-3-amine (30 mg, 0.1 mmol) in sec-butanol (1 mL) was added HCl in dioxane (0.1 mL). The reaction mixture was heated in the Biotage Initiator microwave at 160° C. until the reaction had reached completion. The solvent was removed under reduced pressure and the residue purified directly by preparative HPLC. LCMS RT: 3.23 (Method A), Mass m/z: 324.09 (M+1).

Example 15. Preparation of N-(1-methyl-1H-pyrazol-4-yl)-5-phenoxythiazolo[5,4-b]pyridin-2-amine

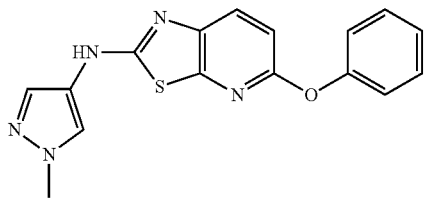 [SMILES: Cn1cc(Nc2nc3ccc(Oc4ccccc4)nc3s2)cn1]

N-(1-methyl-1H-pyrazol-4-yl)-5-phenoxythiazolo[5,4-b]pyridin-2-amine was prepared from 2-(methylsulfonyl)-5-phenoxythiazolo[5,4-b]pyridine and 1-methyl-1H-pyrazol-4-amine following the same procedure. LCMS RT: 3.18 (Method A), Mass m/z: 324.15 (M+1).

Example 16. Preparation of 5-phenoxy-N-(1-(tetrahydro-2H-pyran-4-yl)-1H-pyrazol-4-yl)thiazolo[5,4-b]pyridin-2-amine

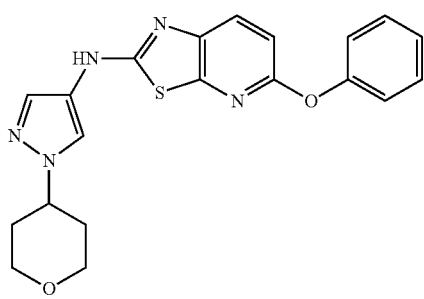 [SMILES: c1ccc(Oc2ccc3nc(Nc4cnn(C5CCOCC5)c4)sc3n2)cc1]

5-phenoxy-N-(1-(tetrahydro-2H-pyran-4-yl)-1H-pyrazol-4-yl)thiazolo[5,4-b]pyridin-2-amine was prepared from 2-(methylsulfonyl)-5-phenoxythiazolo[5,4-b]pyridine and 1-(tetrahydro-2H-pyran-4-yl)-1H-pyrazol-4-amine following the same procedure. LCMS RT: 3.22 (Method A), Mass m/z: 394.45 (M+1).

Example 17. Preparation of (S)-1-(3-((4-((5-phenoxythiazolo[5,4-b]pyridin-2-yl)amino)pyrimidin-2-yl)amino)pyrrolidin-1-yl)prop-2-en-1-one

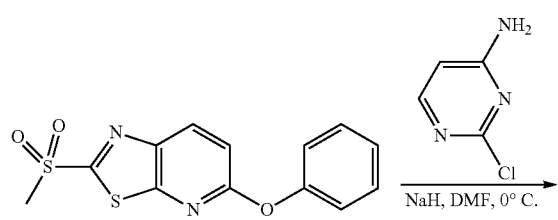

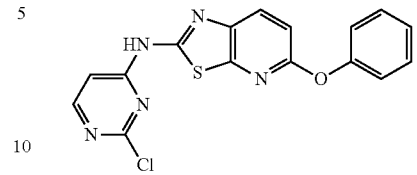

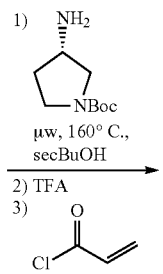

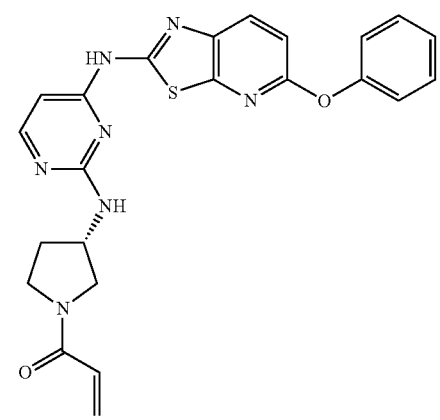

N-(2-chloropyrimidin-4-yl)-5-phenoxythiazolo[5,4-b]pyridin-2-amine

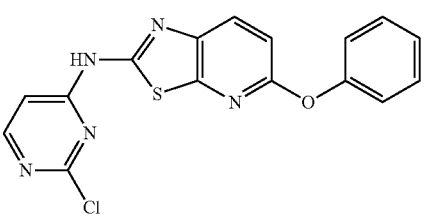 [SMILES: Clc1nccc(Nc2nc3ccc(Oc4ccccc4)nc3s2)n1]

A solution of 2-(methylsulfonyl)-5-phenoxythiazolo[5,4-b]pyridine and 2-chloropyrimidin-4-amine (192 mg, 1.49 mmol) in DMF (9 mL) was cooled to 0° C. and NaH (184 mg, 4.47 mmol, 3 eq, 60% in mineral) was added to the stirring mixture. The reaction was warmed to ambient temperature and stirred for a further 2 h. The mixture was treated with saturated ammonium chloride. Saturated aqueous Na2CO3 was added to reach pH 9 and the product was extracted with 1:1 mixture of dichloromethane and ethyl acetate. The organic extracts were combined, dried using a hydrophobic frit and evaporated to dryness. The residue was purified by chromatography on silica to afford the title compound as an off-white solid. LCMS RT: 3.62 (Method A), Mass m/z: 356.24 (M+1).

(S)-1-(3-((4-((5-phenoxythiazolo[5,4-b]pyridin-2-yl)amino)pyrimidin-2-yl)amino)pyrrolidin-1-yl)prop-2-en-1-one

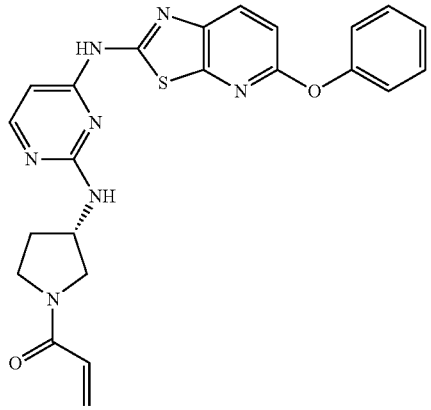 [SMILES: C=CC(=O)N1CC[C@H](Nc2nccc(Nc3nc4ccc(Oc5ccccc5)nc4s3)n2)C1]

(S)-1-(3-((4-((5-phenoxythiazolo [5,4-b]pyridin-2-yl)amino)pyrimidin-2-yl)amino)pyrrolidin-1-yl)prop-2-en-1-one was prepared from N-(2-chloropyrimidin-4-yl)-5-phenoxythiazolo[5,4-b]pyridin-2-amine and tert-butyl (S)-3-aminopyrrolidine-1-carboxylate following general procedures I and II. LCMS RT: 2.62 (Method A), Mass m/z: 460.51 (M+1).

Example 18. Preparation of (R)-1-(3-((4-((5-phenoxythiazolo[5,4-b]pyridin-2-yl)amino)pyrimidin-2-yl)amino)pyrrolidin-1-yl)prop-2-en-1-one

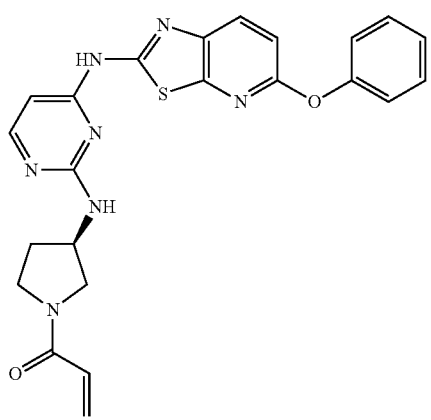 [SMILES: C=CC(=O)N1CC[C@@H](Nc2nccc(Nc3nc4ccc(Oc5ccccc5)nc4s3)n2)C1]

(R)-1-(3-((4-((5-phenoxythiazolo[5,4-b]pyridin-2-yl)amino)pyrimidin-2-yl)amino)pyrrolidin-1-yl)prop-2-en-1-one was prepared from N-(2-chloropyrimidin-4-yl)-5-phenoxythiazolo[5,4-b]pyridin-2-amine and tert-butyl (R)-3-aminopyrrolidine-1-carboxylate following general procedures I and II. LCMS RT: 2.47 (Method A), Mass m/z: 460.51 (M+1).

Example 19. Preparation of (S)-1-(3-((4-((5-phenoxythiazolo[5,4-b]pyridin-2-yl)amino)pyrimidin-2-yl)amino)piperidin-1-yl)prop-2-en-1-one

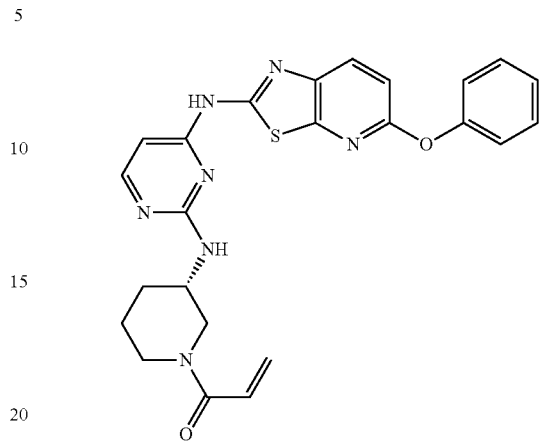

(S)-1-(3-((4-((5 -phenoxythiazolo[5,4-b]pyridin-2-yl)amino)pyrimidin-2-yl)amino)piperidin-1-yl)prop-2-en-1-one was prepared from N-(2-chloropyrimidin-4-yl)-5-phenoxythiazolo[5,4-b]pyridin-2-amine and tert-butyl (S)-3-aminopiperidine-1-carboxylate following general procedures I and II. LCMS RT: 2.57 (Method A), Mass m/z: 474.56 (M+1).

Example 20. Preparation of (R)-1-(3-((4-((5-phenoxythiazolo[5,4-b]pyridin-2-yl)amino)pyrimidin-2-yl)amino)piperidin-1-yl)prop-2-en-1-one

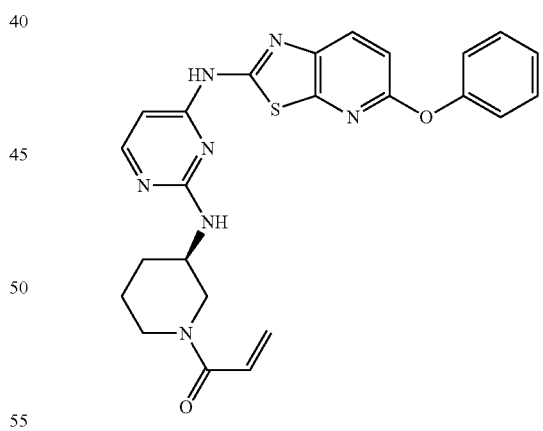

(R)-1-(3-((4-((5-phenoxythiazolo[5,4-b]pyridin-2-yl)amino)pyrimidin-2-yl)amino)piperidin-1-yl)prop-2-en-1-one was prepared from N-(2-chloropyrimidin-4-yl)-5-phenoxythiazolo[5,4-b]pyridin-2-amine and tert-butyl (R)-3-aminopiperidine-1-carboxylate following general procedures I and II. LCMS RT: 2.55 (Method A), Mass m/z: 474.50 (M+1).

Example 21. Preparation of 1-(3-((4-((5-phenoxythiazolo[5,4-b]pyridin-2-yl)amino)pyrimidin-2-yl)amino)azepan-1-yl)prop-2-en-1-one

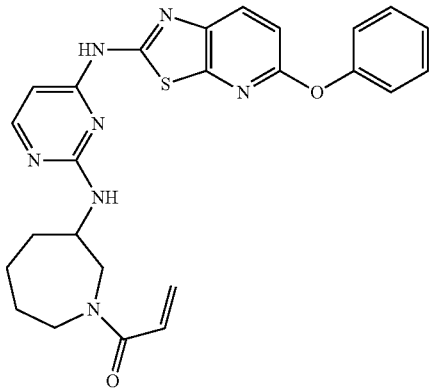 [SMILES: C=CC(=O)N1CCCCC(Nc2nccc(Nc3nc4ccc(Oc5ccccc5)nc4s3)n2)C1]

1-(3-((4-(5-phenoxythiazolo[5,4-b]pyridin-2-yl)amino)pyrimidin-2-yl)amino)azepan-1-yl)prop-2-en-1-one was prepared from N-(2-chloropyrimidin-4-yl)-5-phenoxythiazolo[5,4-b]pyridin-2-amine and tert-butyl 3-aminoazepane-1-carboxylate following general procedures I and II. LCMS RT: 2.73 (Method A), Mass m/z: 488.49 (M+1).

Example 22. Inhibitory activities of exemplary compounds described herein against select protein kinases and cells The inhibitory activities of exemplary compounds described herein against select protein kinases and cells were determined. Cell survival following treatment of exemplary compounds described herein was assessed by CellTiter-Glo® Luminescent cell viability assay (Promega). The cells were seeded into 384 well plates with the EL406 Combination Washer Dispenser (BioTek Instruments, Inc.), and a series diluted exemplary compounds (20–0.0006 μM) were injected into the culture media with the JANUS Automated Workstation (PerkinElmer Inc.). The cells were treated for 72 hours at 37° C. with 5% CO2. Luminescent measurement is performed using the 2104 Envision® Multilabel Reader (PerkinElmer Inc.). $EC_{50}$ values were calculated with GRAPHPAD PRISM software. Exemplary results are shown in Table 1B.

TABLE 1B

Exemplary biological data of exemplary compounds described herein.

| Compound | BTK $IC_{50}$ (nM) | HCK $IC_{50}$ (nM) | BCWM.1 $EC_{50}$ (nM) | MWCL-1 $EC_{50}$ (nM) | TMD-8 $EC_{50}$ (nM) | HBL-1 $EC_{50}$ (nM) |
|---|---|---|---|---|---|---|
| Dasatinib |  |  | 1.20 | 7.41 | 18.70 | 190.00 |
| I-1 | 1.61 | 0.59 | 73.40 | 50.00 | 301.00 | 522.00 |
| I-3 | 0.60 | <0.495 | 19.30 | 55.20 | 158.00 | 669.00 |
| I-6 | 1.90 | 4.24 | 69.60 | 93.70 | 80.20 | 229.00 |
| I-2 | 1.63 | 0.73 | 41.00 | 67.00 | 311.00 | 1670.00 |
| I-4 | 1.38 | 0.59 | 53.00 | 85.00 | 315.00 | 449.00 |
| I-7 | <0.495 | <0.495 | 22.00 | 19.00 | 49.00 | 70.00 |
| I-8 | <0.495 | <0.495 | 75.00 | 103.00 | 301.00 | 522.00 |
| I-10 | 1.74 | 2.42 | 170.00 | 191.00 | 1010.00 | 1640.00 |
| I-11 | 5.52 | 3.99 | 129.00 | 245.00 | 500.00 | 623.00 |
| III-1 | 86.60 | 1820.00 | 1830.00 | 4080.00 | 3850.00 | 3200.00 |
| III-2 | 281.00 | 402.00 | 916.00 | 1350.00 | 2640.00 | 2960.00 |
| III-3 | 19.40 | 2150.00 | 2710.00 | 5750.00 | 4130.00 | 2960.00 |
| III-4 | 367 | 1150 | 808 | 2160 | 2120 | 2550 |
| III-5 | 9.06 | 1910 | 1190 | 3370 | 1230 | 896 |
| III-6 | 2580 | 4550 | 270 | 2170 | 467 | 450 |
| III-7 | >10000 | >10000 | >20000 | >20000 | >20000 | >20000 |
| III-8 | >10000 | >10000 | 7250 | >20000 | 14600 | >20000 |
| III-9 | 2660 | 7200 | 8290 | 16600 | 18300 | >20000 |
| II-1 | 1.1 | 1.64 | 84 | 121 | 573 | 735 |
| II-2 | <0.495 | 1.94 | 196 | 166 | 929 | 1000 |
| II-3 | 19.9 | 25.3 | 690 | 772 | 2540 | 3650 |
| I-9 | 0.5 | <0.495 | 9.84 | 25 | 70.9 | 220 |
| I-12 |  |  | 75.50 | 317.00 | 453.00 | 1200.00 |

| Compound | OCI-Ly3 $EC_{50}$ (nM) | OCI-Ly19 $EC_{50}$ (nM) | Ramos $EC_{50}$ (nM) | OCI-Ly7 $EC_{50}$ (nM) | RPMI-8226 $EC_{50}$ (nM) | OPM-2 $EC_{50}$ (nM) |
|---|---|---|---|---|---|---|
| Dasatinib | 8060.00 | 3860.00 | 4560.00 | 155.00 | 5390.00 | 7110.00 |
| I-1 | NA | NA | NA |  |  |  |
| I-3 | 39500.00 | 13000.00 | >20000 | 370.00 |  |  |
| I-6 | NA | NA | NA | 520.00 |  |  |
| I-2 | >20000 | >20000 | >20000 |  |  |  |
| I-4 |  | 4270 | >20000 |  |  |  |
| I-7 |  | 399 | 133 |  |  |  |
| I-8 |  | 3770 | 7970 |  |  |  |
| I-5 |  |  |  |  |  |  |
| I-10 |  | 5700 | 12 |  |  |  |
| I-11 |  | 3680 | 1580 |  |  |  |
| III-1 |  | 1250 | 3700 |  |  |  |
| III-2 |  | 1100 | 2300 |  |  |  |
| III-3 |  | 2500 | 8460 |  |  |  |
| III-4 |  | 1170 | 2190 |  |  |  |

TABLE 1B-continued

Exemplary biological data of exemplary compounds described herein.

| | | | |
|---|---|---|---|
| III-5 | | 1330 | 2720 |
| III-6 | | 321 | 749 |
| III-7 | | 9520 | >20000 |
| III-8 | | 12600 | >20000 |
| III-9 | | 7060 | 11800 |
| II-1 | | 7880 | >20000 |
| II-2 | | 6540 | >20000 |
| II-3 | | 9970 | >20000 |
| I-9 | 14500 | 10000 | >20000 |
| I-12 | | | 309.00 |

NA: Not available.

Example 23. KINATIV assay of compounds I-3 and I-9

BCWM.1 cells were treated with compound I-3 or I-9 (1 µM) for 90 minutes. The cells were harvested and lysed. The lysates were divided into two parts: one part was directly labeled with an ATP-biotin probe (no GENEFILTERS (GF)), and the other part was first gel-filtered, and, 15 minutes after gel-filtering, probe labeled (GENEFILTERS (GF)). Bound kinases were identified and quantitated by ACTIVX as described in Patricelli et al., *Biochemistry*, 2007, 46(2): 350-358. The compounds were tested in duplicates against duplicate or quadruplicate control samples. Exemplary results are shown in Table 2, where the % changes of MS (mass spectroscopy) signals of compounds I-3 or I-9, compared to the control samples, are reported. The results shown in Table 2 were statistically significant (Student T-test score <0.04). A compound inhibited the kinase activity when a % change of the MS signal shown in Table 2 is positive (e.g., greater than 0%) or increased the kinase activity when a % change of the MS signal shown in Table 2 is negative (e.g., lower than 0%).

TABLE 2

Exemplary KINATIV assay results of compounds I-3 and I-9.

| | | | | % change of MS signal compared to control sample | | | |
|---|---|---|---|---|---|---|---|
| Kinase | Reference | Sequence | Labeling Site | I-3 1 µM no GF | I-9 1 µM GF | I-3 1 µM no GF | I-9 1 µM GF |
| ABL, ARG | UniRef100_P00519, UniRef100_P42684 | LMTGDTYTAHAG AKFPIK | Activation Loop | 75.4 | 46.1 | 93.5 | 75.4 |
| ABL, ARG | UniRef100_P00519, UniRef100_P42684 | YSLTVAVKTLKE DTMEVEEFLK | Lys1 | 86.9 | 40.6 | 93.2 | 71.8 |
| ACK | UniRef100_Q07912 | TVSVAVKCLKPD VLSQPEAMDDFIR | Lys1 | 5.8 | 15.6 | 52.7 | 2.4 |
| AGK | UniRef100_Q53H12 | ATVFLNPAACKG K | ATP | -0.2 | | -12.4 | |
| AKT1 | UniRef100_P31749 | GTFGKVILVK | ATP Loop | -20.4 | -25.1 | -21.9 | -16.8 |
| AKT2, AKT3 | UniRef100_Q9Y243, UniRef100_P31751 | GTFGKVILVR | ATP Loop | -19.2 | -9.7 | -14.5 | 5.4 |
| AMPKa1, AMPKa2 | UniRef100_P54646, UniRef100_Q96E92 | DLKPENVLLDAH MNAK | Lys2 | -7.6 | 22.1 | 12.1 | 5.8 |
| ARAF | UniRef100_P10398 | DLKSNNIFLHEGL TVK | Lys2 | -152.4 | -56.6 | -402.1 | -95.1 |
| ATM | UniRef100_Q13315 | QLVKGRDDLRQD AVMQQVFQMCN TLLQR | ATP | 20.7 | | 19.5 | |
| ATR | UniRef100_Q13535 | FYIMMCKPK | ATP | -31.6 | 28.1 | 25.3 | 16.5 |
| AurA | UniRef100_O14965 | FILALKVLFK | Lys1 | 12 | -14.5 | -13 | 1.4 |
| AurA | UniRef100_O14965 | DIKPENLLLGSAG ELK | Lys2 | 12.7 | -6.6 | -5.9 | 1.2 |
| AurA, AurB, AurC | UniRef100_O14965, UniRef100_Q9UQB9, UniRef100_Q96GD4 | GKFGNVYLAR | ATP Loop | 7.7 | 5.5 | 4.7 | 2.8 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 µM no GF | I-9 1 µM GF | I-3 1 µM no GF | I-9 1 µM GF |
| AurB | UniRef100_Q96GD4 | SHFIVALKVLFK | Lys1 | -2.2 | -20.6 | -23.6 | -21.5 |
| BLK | UniRef100_P51451 | IIDSEYTAQEGAKFPIK | Activation Loop | >96 | 93.7 | >96 | 95.4 |
| BRAF | UniRef100_P15056 | DLKSNNIFLHEDLTVK | Lys2 | -7.6 | -18.3 | -48.9 | -12.9 |
| BTK | UniRef100_Q06187 | YVLDDEYTSSVGSKFPVR | Activation Loop | 94.7 | 96.7 | 95.2 | 70.7 |
| CaMK1d | UniRef100_Q8IU85 | LFAVKCIPK | Lys1 | -0.4 | -7.5 | -5 | -4.6 |
| CaMK2d | UniRef100_Q13557 | IPTGQEYAAKIINTKK | Lys1 | -1.3 | -8.1 | -25 | -8.2 |
| CaMK2g | UniRef100_Q13555 | TSTQEYAAKIINTK | Lys1 | 13.7 | -17.7 | -12 | -4.4 |
| CaMK4 | UniRef100_Q16566 | DLKPENLLYATPAPDAPLK | Lys2 | 6.8 | -10.3 | -0.1 | -13.1 |
| CaMKK2 | UniRef100_Q96RR4 | DIKPSNLLVGEDGHIK | Lys2 | -2.1 | -4.9 | 1.7 | 0.5 |
| CASK | UniRef100_O14936 | ETGQQFAVKIVDVAK | Lys1 | -1 | -10.4 | 0.5 | 3.9 |
| CDC2 | UniRef100_Q5H9N4 | DLKPQNLLIDDKGTIK | Protein Kinase Domain | -0.7 | -2.6 | -4.3 | -3.2 |
| CDC7 | UniRef100_O00311 | DVKPSNFLYNR | Lys2 | | -12.5 | | -2.2 |
| CDK11, CDK8 | UniRef100_P49336, UniRef100_Q9BWU1 | DLKPANILVMGEGPER | Lys2 | -15.2 | 28.6 | 20.4 | 11.8 |
| CDK2 | UniRef100_P24941 | DLKPQNLLINTEGAIK | Lys2 | 3.6 | -8.7 | 1.2 | -4.3 |
| CDK4 | UniRef100_P11802 | DLKPENILVTSGGTVK | Lys2 | 10.3 | 1.2 | 4.8 | 3.4 |
| CDK5 | UniRef100_Q00535 | DLKPQNLLINR | Lys2 | 11.8 | -1.1 | -1.8 | 7.7 |
| CDK6 | UniRef100_Q00534 | DLKPQNILVTSSGQIK | Lys2 | 12.4 | 2.7 | 3.6 | 3.5 |
| CDK7 | UniRef100_P50613 | DLKPNNLLLDENGVLK | Lys2 | 8.9 | 1.3 | 5.1 | 5.1 |
| CDK9 | UniRef100_P50750 | DMKAANVLITR | Lys2 | -1.7 | 32.7 | 25.9 | 23.1 |
| CHED | UniRef100_Q14004 | DIKCSNILLNNR | Lys2 | | 5.7 | | 15.3 |
| CHK1 | UniRef100_B4DT73 | DIKPENLLLDER | Lys2 | 9.7 | -25.9 | 5.6 | -2 |
| CHK2 | UniRef100_O96017 | DLKPENVLLSSQEEDCLIK | Lys2 | 8.2 | -13.1 | -11.9 | -2.5 |
| CK1a | UniRef100_P48729, | DIKPDNFLMGIGR | Lys2 | -18.2 | 32.6 | 30.6 | 12.5 |
| CK1d, CK1e | UniRef100_P49674, UniRef100_P48730 | DVKPDNFLMGLGKK | Lys2 | -16.5 | 26.3 | 10.8 | 12.8 |
| CK1g1, CK1g2, CK1g3 | UniRef100_Q9Y6M4, UniRef100_P78368, UniRef100_Q9HCP0 | KIGCGNFGELR | ATP Loop | | -8.2 | | -4.7 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 μM no GF | I-9 1 μM GF | I-3 1 μM no GF | I-9 1 μM GF |
| CK1g2 | UniRef100_P78368 | DVKPENFLVGRPGTK | Lys2 | −3.7 | −8.9 | −4.5 | −10.9 |
| CK2a2 | UniRef100_P19784 | DVKPHNVMIDHQQK | Lys2 | −8.7 | 7 | 4 | −1.8 |
| CLK1 | UniRef100_P49759 | LTHTDLKPENILFVQSDYTEAYNPK | Lys2 | | −25 | | −6.2 |
| CLK2 | UniRef100_P49760 | LTHTDLKPENILFVNSDYELTYNLEK | Lys2 | | −19.3 | | −10.6 |
| CLK3 | UniRef100_P49761 | YEIVGNLGEGTFGKVVECLDHAR | ATP Loop | 17.6 | −19 | 3.6 | −10.3 |
| COT | UniRef100_P41279 | GAFGKVYLAQDIK | ATP Loop | | −37.3 | | −40.3 |
| CRK7 | UniRef100_Q9NYV4 | DIKCSNILLNNSGQIK | Lys2 | | 13 | | 27.8 |
| CSK | UniRef100_P41240 | VSDFGLTKEASSTQDTGKLPVK | Activation Loop | 36 | −6 | 60.3 | 1.5 |
| DGKA | UniRef100_P23743 | IDPVPNTHPLLVFVNPKSGGK | ATP | −5.2 | −1.5 | −24 | −6.6 |
| DGKH | UniRef100_Q86XP1 | ATFSFCVSPLLVFVNSKSGDNQGVK | ATP | 15.2 | −21.2 | −44.1 | −12.5 |
| DLK | UniRef100_Q12852 | DLKSPNMLITYDDVVK | Lys2 | 10.2 | | −8 | |
| DNAPK | UniRef100_P78527 | KGGSWIQEINVAEK | ATP | −2.2 | −0.3 | 10.5 | −0.4 |
| DNAPK | UniRef100_P78527 | EHPFLVKGGEDLR | ATP | −15.1 | −35.1 | 11 | 3.4 |
| eEF2K | UniRef100_O00418 | YIKYNSNSGFVR | ATP | −18.9 | −51.4 | −27.8 | −48.7 |
| EGFR | UniRef100_P00533 | IPVAIKELR | Lys1 | 20 | | 17 | |
| EphB1 | UniRef100_P54762 | YLQDDTSDPTYTSSLGGKIPVR | Activation Loop | 92.9 | 53.3 | 95.7 | 78.9 |
| EphB2 | UniRef100_P29323 | FLEDDTSDPTYTSALGGKIPIR | Activation Loop | 91 | 81.7 | 91.6 | 85.6 |
| Erk1 | UniRef100_P27361 | DLKPSNLLINTTCDLK | Lys2 | −0.6 | −3.1 | 1.5 | 3.1 |
| Erk2 | UniRef100_P28482 | DLKPSNLLLNTTCDLK | Lys2 | −1.8 | −3.8 | 1.1 | 4 |
| Erk3 | UniRef100_Q16659 | DLKPANLFINTEDLVLK | Lys2 | 23.2 | 16.9 | 23.8 | 25.3 |
| Erk5 | UniRef100_Q13164 | DLKPSNLLVNENCELK | Lys2 | 3 | −1.8 | 8.3 | 1.1 |
| FER | UniRef100_P16591 | TSVAVKTCKEDLPQELK | Lys1 | 9.1 | −8.4 | −14 | 2.6 |
| FES | UniRef100_P07332 | LRADNTLVAVKSCR | Lys1 | 10.7 | −11.2 | −13.3 | −3.9 |
| FGR | UniRef100_P09769 | LIKDDEYNPCQGSKFPIK | Activation Loop | 95.7 | 84.7 | 95.4 | 72.1 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 μM no GF | I-9 1 μM no GF | I-3 1 μM GF | I-9 1 μM GF |
| FRAP | UniRef100_P42345 | IQSIAPSLQVITSKQRPR | ATP | 6.9 | -8.1 | -21.4 | 2.2 |
| FRK | UniRef100_P42685 | Activation HEIKLPVK | 92.4 Loop | 36.7 | 95.8 | 73.6 | |
| FYN | UniRef100_P06241 | VAIKTLKPGTMSPESFLEEAQIMK | Lys1 | | >91 | | >91 |
| FYN, SRC, YES | UniRef100_P12931, UniRef100_P07947, UniRef100_P06241 | QGAKFPIKWTAPEAALYGR | Activation Loop | 87.3 | 72.5 | 85.7 | 80.4 |
| GAK | UniRef100_O14976 | DLKVENLLLSNQGTIK | Lys2 | | -14.5 | | 33.8 |
| GCK | UniRef100_Q12851 | DIKGANLLLTLQGDVK | Lys2 | 18.1 | 4.5 | 17.8 | 16.4 |
| GCN2 | UniRef100_Q9P2K8 | DLKPVNIFLDSDDHVK | Lys2 | -2.8 | -18.8 | -14.3 | -10.7 |
| GSK3A | UniRef100_P49840 | DIKPQNLLVDPDTAVLK | Lys2 | 3.5 | 2.3 | 9 | 1.9 |
| GSK3B | UniRef100_P49841 | DIKPQNLLLDPDTAVLK | Lys2 | 9.4 | -9.8 | -0.5 | -1.3 |
| HPK1 | UniRef100_Q92918 | DIKGANILINDAGEVR | Lys2 | 18.8 | -2.9 | 5.9 | 7.3 |
| IKKa | UniRef100_O15111 | DLKPENIVLQDVGGK | Lys2 | 14.6 | -3.3 | -4.4 | -0.4 |
| IKKb | UniRef100_O14920 | DLKPENIVLQQGEQR | Lys2 | 3.6 | 0.4 | -6.4 | -1.4 |
| IKKe | UniRef100_Q14164 | SGELVAVKVFNTTSYLRPR | Lys1 | 5.5 | -12.6 | -21.5 | -6.1 |
| ILK | UniRef100_Q13418 | WQGNDIVVKVLK | Lys1 | 3.2 | -1.9 | -9.7 | 1.2 |
| ILK | UniRef100_Q13418 | ISMADVKFSFQCPGR | Protein Kinase Domain | 3.6 | 24.5 | 9.7 | 12.4 |
| IRAK1 | UniRef100_P51617 | AIQFLHQDSPSLIHGDIKSSNVLLDER | Lys2 | -4.8 | -2.6 | -19.8 | -3.2 |
| IRAK3 | UniRef100_Q9Y616 | VEIQNLTYAVKLFK | Lys1 | -11.3 | 7.2 | -5.5 | -1.4 |
| IRAK4 | UniRef100_Q9NWZ3 | DIKSANILLDEAFTAK | Lys2 | 16.4 | -3.2 | -11 | 6.2 |
| IRE1 | UniRef100_O75460 | DLKPHNILISMPNAHGK | Lys2 | -12.1 | 24.3 | 13.2 | 2 |
| ITPK1 | UniRef100_Q13572 | ESIFFNSHNVSKPESSSVLTELDKIEGVFERPSDEVIR | ATP | 8.5 | -10 | 1.5 | 1.7 |
| JAK1 | UniRef100_P23458 | QLASALSYLEDKDLVHGNVCTKNLLLAR | Protein Kinase Domain | 12.3 | -11.5 | -25 | -6.7 |
| JAK1 domain2 | UniRef100_P23458 | IGDFGLTKAIETDKEYYTVK | Activation Loop | -2.9 | -15.6 | -1.6 | -13.9 |
| JAK1 domain2 | UniRef100_P23458 | YDPEGDNTGEQVAVKSLKPESGGNHIADLKK | Lys1 | -2.1 | -18.1 | -29.1 | -14.4 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 µM no GF | I-9 1 µM no GF | I-3 1 µM GF | I-9 1 µM GF |
| JAK3 domain2 | UniRef100_P52333 | IADFGLAKLLPLD KDYYVVR | Activation Loop | -1.5 | -21.6 | -0.6 | 13.5 |
| JNK1, JNK2, JNK3 | UniRef100_P45983, UniRef100_P53779, UniRef100_P45984 | DLKPSNIVVK | Lys2 | 14.9 | -7 | 4.7 | 0.5 |
| KHS1 | UniRef100_Q9Y4K4 | NVHTGELAAVKII K | Lys1 | -7.5 | -8.7 | | |
| KHS2 | UniRef100_Q8IVH8 | NVNTGELAAIKVI K | Lys1 | | -23.6 | | -22.7 |
| KSR1 | UniRef100_Q8IVT5 | SKNVFYDNGKVV ITDFGLFGISGVVR | Activation Loop | 7.1 | -8.7 | -41.8 | -25.6 |
| KSR1, KSR2 | UniRef100_Q6VAB6, UniRef100_Q8IVT5 | SKNVFYDNGK | Activation Loop | -4.3 | -14.6 | -24.2 | -16.2 |
| LATS1 | UniRef100_O95835 | ALYATKTLR | Lys1 | 14.6 | -2.8 | -5.2 | 5.4 |
| LATS2 | UniRef100_Q9NRM7 | DIKPDNILIDLDGH IK | Lys2 | 9.4 | -12.3 | -17.9 | -5.1 |
| LCK | UniRef100_P06239 | EGAKFPIKWTAPE AINYGTFTIK | Activation Loop | 92.6 | 61.6 | 92.7 | 82.8 |
| LKB1 | UniRef100_Q15831 | DIKPGNLLLTTGG TLK | Lys2 | -11.2 | -11.2 | -8.7 | -7.4 |
| LOK | UniRef100_O94804 | DLKAGNVLMTLE GDIR | Lys2 | -8.6 | 26.2 | 8.5 | 15.2 |
| LRRK2 | UniRef100_Q5S007 | DLKPHNVLLFTLY PNAAIIAK | Lys2 | 11.6 | -26.4 | -6.6 | -21.7 |
| LYN | UniRef100_P07948 | VAVKTLKPGTMS VQAFLEEANLMK | Lys1 | >98 | 85.2 | >98 | 94 |
| MAP2K1 | UniRef100_Q02750 | IMHRDVKPSNILV NSR | Lys2 | 0.1 | 28.5 | 25 | 3.5 |
| MAP2K1, MAP2K2 | UniRef100_P36507, UniRef100_Q02750 | KLIHLEIKPAIR | Lys1 | 13.5 | -9.2 | -5.7 | -1.1 |
| MAP2K1, MAP2K2 | UniRef100_P36507, UniRef100_Q02750 | DVKPSNILVNSR | Lys2 | 20.8 | -6.4 | -6.9 | -4.5 |
| MAP2K2 | UniRef100_P36507 | HQIMHRDVKPSNI LVNSR | Lys2 | -3.5 | 34.6 | 16.5 | 12.5 |
| MAP2K3 | UniRef100_P46734 | DVKPSNVLINK | Lys2 | 15.6 | -21.3 | 5.8 | -3.6 |
| MAP2K4 | UniRef100_P45985 | DIKPSNILLDR | Lys2 | -3.9 | -5.4 | 1.1 | -2.1 |
| MAP2K5 | UniRef100_Q13163 | DVKPSNMLVNTR | Lys2 | -2.2 | 16.8 | 44.4 | 16.3 |
| MAP2K6 | UniRef100_P52564 | DVKPSNVLINALG QVK | Lys2 | 10.6 | -22.1 | -2 | -5.9 |
| MAP2K7 | UniRef100_O14733 | DVKPSNILLDER | Lys2 | 1.5 | -2.8 | -9.1 | -0.3 |
| MAP3K1 | UniRef100_Q13233 | DVKGANLLIDSTG QR | Lys2 | 22.5 | 11.1 | 18.8 | 9.8 |
| MAP3K2 | UniRef100_Q9Y2U5 | ELAVKQVQFDPD SPETSKEVNALEC EIQLLK | Lys1 | -2.1 | -16.2 | -21.7 | -8.3 |

TABLE 2-continued

Exemplary KINATIV assay results of compounds I-3 and I-9.

| | | | | % change of MS signal compared to control sample | | | |
|---|---|---|---|---|---|---|---|
| Kinase | Reference | Sequence | Labeling Site | I-3 1 μM no GF | I-9 1 μM no GF | I-3 1 μM GF | I-9 1 μM GF |
| MAP3K2, MAP3K3 | UniRef100_Q9Y2U5, UniRef100_Q99759 | DIKGANILR | Lys2 | 15.3 | 0.7 | −12.6 | 6.8 |
| MAP3K3 | UniRef100_Q99759 | ELASKQVQFDPDS PETSKEVSALECEI QLLK | Lys1 | 13.2 | −13.7 | −40.9 | −19.7 |
| MAP3K4 | UniRef100_Q9Y6R4 | DIKGANIFLTSSGL IK | Lys2 | 16.8 | 3.2 | 1.2 | 10.9 |
| MAP3K5 | UniRef100_Q99683 | DIKGDNVLINTYS GVLK | Lys2 | 8.3 | −9 | −5.9 | 8.1 |
| MAP3K6 | UniRef100_O95382 | DIKGDNVLINTFS GLLK | Lys2 | 15.9 | −13.4 | −15.4 | −5 |
| MARK2, MARK3 | UniRef100_P27448, UniRef100_Q7KZI7 | DLKAENLLLDAD MNIK | Lys2 | −17.6 | 27.8 | 16.2 | 9.5 |
| MARK3 | UniRef100_P27448 | EVAIKIIDKTQLNP TSLQK | Lys1 | 7.9 | −6.4 | −12.9 | −4.8 |
| MARK3, MARK4 | UniRef100_Q96L34, UniRef100_P27448 | EVAIKIIDK | Lys1 | 2.5 | −10.4 | −4 | −7.1 |
| MARK4 | UniRef100_Q96L34 | DLKAENLLLDAE ANIK | Lys2 | −8.5 | −12.2 | −8.7 | −10.2 |
| MAST1, MAST2 | UniRef100_Q6P0Q8, UniRef100_Q9Y2H9 | DLKPDNLLITSMG HIK | Lys2 | −13.4 | 22 | 26.3 | −0.5 |
| MAST3 | UniRef100_O60307 | DLKPDNLLITSLG HIK | Lys2 | 8.1 | −22.1 | −11.9 | −11.9 |
| MASTL | UniRef100_Q96GX5 | GAFGKVYLGQK | ATP Loop | 5.3 | 0.4 | 6 | 1.8 |
| MASTL | UniRef100_Q96GX5 | LYAVKVVK | Lys1 | 16.4 | 2.4 | 9.8 | 8 |
| MELK | UniRef100_Q14680 | DLKPENLLFDEYH K | Lys2 | −12.1 | −9.6 | −10.6 | −9.5 |
| MER | UniRef100_Q12866 | NCMLRDDMTVCV ADFGLSKK | Activation Loop | | 6.3 | | −12.5 |
| MER, TYRO3 | UniRef100_Q06418, UniRef100_Q12866 | KIYSGDYYR | Activation Loop | 2.4 | −14.7 | 0.4 | 3.1 |
| MET | UniRef100_P08581 | DMYDKEYYSVHN K | Activation Loop | −12.9 | | −45.2 | |
| MLK1 | UniRef100_P80192 | DLKSSNILILQK | Lys2 | | 1 | | 9 |
| MLK3 | UniRef100_Q16584 | DLKSNNILLLQPIE SDDMEHK | Lys2 | −7.2 | 24.1 | 6.3 | 3.9 |
| MLK4 | UniRef100_Q5TCX8 | DLKSSNILLLEK | Lys2 | −3.8 | −22 | −11.8 | −18.5 |
| MLKL | UniRef100_Q8NB16 | APVAIKVFK | Lys1 | −5.6 | −4.7 | −4.6 | −3.9 |
| MPSK1 | UniRef100_O75716 | DLKPTNILLGDEG QPVLMDLGSMNQ ACIHVEGSR | Lys2 | −9.7 | 21.9 | 20.9 | 10.1 |
| MSK1 domain1 | UniRef100_O75582 | DIKLENILLDSNG HVVLTDFGLSK | Lys2 | −2.8 | −22.8 | −9 | −23.9 |
| MSK2 domain1 | UniRef100_O75676 | DLKLENVLLDSEG HIVLTDFGLSK | Lys2 | −2 | −27 | −17.3 | −18.7 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 µM no GF | I-9 1 µM GF | I-3 1 µM no GF | I-9 1 µM GF |
| MST1 | UniRef100_Q13043 | ETGQIVAIKQVPVESDLQEIIK | Lys1 | -4.5 | -28.8 | -20.9 | -11.3 |
| MST2 | UniRef100_Q13188 | ESGQVVAIKQVPVESDLQEIIK | Lys1 | -12.1 | -24.9 | -18 | -11.9 |
| MST3 | UniRef100_Q9Y6E0 | DIKAANVLLSEHGEVK | Lys2 | -2 | -1.9 | -3.8 | -1.4 |
| MST4 | UniRef100_Q9P289 | TQQVVAIKIIDLEEAEDEIEDIQQEITVLSQCDSSYVTK | Lys1 | -6.7 | -31.5 | -36.1 | -20 |
| MST4, YSK1 | UniRef100_O00506, UniRef100_Q9P289 | DIKAANVLLSEQGDVK | Lys2 | 18.1 | 9.7 | 15.5 | 15.2 |
| NDR1 | UniRef100_Q15208 | DIKPDNLLLDSK | Lys2 | 2.3 | -4.2 | -5.5 | 2.8 |
| NDR2 | UniRef100_Q9Y2H1 | DIKPDNLLLDAK | Lys2 | 11.6 | -5.6 | -9.6 | 2.9 |
| NEK1 | UniRef100_Q96PY6 | DIKSQNIFLTK | Lys2 | 7.4 | -3.7 | -7.6 | 4.6 |
| NEK2 | UniRef100_P51955 | DLKPANVFLDGK | Lys2 | 20.5 | -8.2 | 0.9 | 4.3 |
| NEK3 | UniRef100_P51956 | SKNIFLTQNGK | Activation Loop | | -21.2 | | -3.2 |
| NEK4 | UniRef100_P51957 | DLKTQNVFLTR | Lys2 | 10.1 | -13.1 | 7.3 | -1.7 |
| NEK6, NEK7 | UniRef100_Q8TDX7, UniRef100_Q9HC89 | DIKPANVFITATGVVK | Lys2 | 6.4 | -3.3 | -13.1 | -0.8 |
| NEK7 | UniRef100_Q8TDX7 | AACLLDGVPVALKK | Lys1 | 5.7 | 11.3 | -14.7 | 8 |
| NEK8 | UniRef100_Q86SG6 | DLKTQNILLDK | Lys2 | 5.1 | -14.1 | -14.5 | -5.8 |
| NEK9 | UniRef100_Q8TD19 | DIKTLNIFLTK | Lys2 | 15.4 | -21.3 | -9.9 | -12.6 |
| NLK | UniRef100_Q9UBE8 | DIKPGNLLVNSNCVLK | Lys2 | 66.2 | -1.2 | 85.9 | 51.8 |
| OSR1 | UniRef100_C9JIG9, UniRef100_O95747 | DVKAGNILLGEDGSVQIADFGVSAFLATGGDITR | Lys2 | 13.8 | 2.7 | 4 | 13.9 |
| p38a | UniRef100_Q16539 | DLKPSNLAVNEDCELK | Lys2 | 43.5 | -7.8 | 70 | 9.8 |
| p38a | UniRef100_Q16539 | QELNKTIWEVPER | Protein Kinase Domain | 32.6 | -2.9 | 67.9 | 8.7 |
| p38d, p38g | UniRef100_O15264, UniRef100_P53778 | DLKPGNLAVNEDCELK | Lys2 | 5.7 | -8.8 | -0.7 | -27.1 |
| p70S6K | UniRef100_P23443 | DLKPENIMLNHQGHVK | Lys2 | -77.2 | 15.9 | -51.5 | -8.6 |
| p70S6Kb | UniRef100_Q9UBS0 | DLKPENIMLSSQGHIK | Lys2 | -36.7 | 24.3 | 6.8 | 3.1 |
| PAN3 | UniRef100_Q58A45 | VMDPTKILITGK | Protein Kinase Domain | -17.5 | 23.2 | 2.5 | 4 |
| PCTAIRE1 | UniRef100_Q00536 | SKLTDNLVALKEIR | Lys1 | 10 | 4.1 | -14.7 | 6.5 |
| PCTAIRE2, PCTAIRE3 | UniRef100_Q00537, UniRef100_Q07002 | SKLTENLVALKEIR | Lys1 | -0.4 | -4.7 | -12 | -0.8 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 µM no GF | I-9 1 µM GF | I-3 1 µM no GF | I-9 1 µM GF |
| PDK1 | UniRef100_O15530 | EYAIKILEK | Lys1 | -8.4 | -6.4 | -3.5 | -6.6 |
| PEK | UniRef100_Q9NZJ5 | DLKPSNIFFTMDDVVK | Lys2 | -12.8 | 22.1 | 6.4 | 15.4 |
| PFTAIRE1 | UniRef100_O94921 | LVALKVIR | Lys1 | 0.9 | -3.9 | -6.6 | -3.1 |
| PHKg1 | UniRef100_Q16816 | DLKPENILLDDNMNIK | Protein Kinase Domain | 31.7 | -51 | -38.8 | -26.2 |
| PHKg2 | UniRef100_P15735 | ATGHEFAVKIMEVTAER | Lys1 | -31.2 | 12.5 | 22.3 | 5.3 |
| PI4K2B | UniRef100_Q8TCG2 | SEEPYGQLNPKWTK | ATP | | 2.6 | | 6.5 |
| PI4KA, PI4KAP2 | UniRef100_A4QPH2, UniRef100_P42356 | SGTPMQSAAKAPYLAK | ATP 3.6 | -3.7 | 20.3 | 12 | |
| PI4KB | UniRef100_Q9UBF8 | VPHTQAVVLNSKDK | ATP | 6.4 | -24.3 | -4.1 | -3.1 |
| PIK3C2B | UniRef100_O00750 | VIFKCGDDLRQDMLTLQMIR | ATP | -1.8 | 28.5 | 39.1 | 12.7 |
| PIK3C3 | UniRef100_Q8NEB9 | TEDGGKYPVIFKHGDDLR | ATP | 2.4 | -23.4 | -0.8 | -9.4 |
| PIK3CB | UniRef100_P42338 | VFGEDSVGVIFKNGDDLRQDMLTLQMLR | ATP | -9.1 | 33.6 | 39.9 | 18.5 |
| PIK3CD | UniRef100_O00329 | VNWLAHNVSKDNRQ | ATP | -3.4 | -19.7 | -17.2 | -9.7 |
| PIK3CG | UniRef100_P48736 | KKPLWLEFK | ATP | -9.6 | -15.1 | -3.4 | -9.6 |
| PIP4K2A | UniRef100_P48426 | AKELPTLKDNDFINEGQK | ATP | -4.9 | -10.5 | -15.2 | -8.3 |
| PIP4K2B | UniRef100_P78356 | AKDLPTFKDNDFLNEGQK | ATP | | 17.6 | | -19 |
| PIP4K2C | UniRef100_Q8TBX8 | TLVIKEVSSEDIADMHSNLSNYHQYIVK | ATP | -14.1 | 10 | 27 | -3.9 |
| PIP5K1A | UniRef100_Q99755 | EKPLPTFKDLDFLQDIPDGLFLDADMYNALCK | ATP | 26.2 | | 30.5 | |
| PIP5K3 | UniRef100_Q9Y2I7 | GGKSGAAFYATEDDRFILK | ATP | 6.5 | -6.7 | -4.6 | -4.6 |
| PITSLRE | UniRef100_P21127 | DLKTSNLLLSHAGILK | Lys2 | -14.1 | -10.8 | -8.6 | -0.6 |
| PKACa | UniRef100_P17612 | DLKPENLLIDQQGYIQVTDFGFAK | Lys2 | | -9.8 | | -8.4 |
| PKCa, PKCb | UniRef100_P05771, UniRef100_P17252 | DLKLDNVMLDSEGHIK | Lys2 | 2.4 | 16.9 | 3.3 | 25.3 |
| PKCe | UniRef100_Q02156 | DLKLDNILLDAEGHCK | Lys2 | | -38.2 | | -7 |
| PKCi | UniRef100_P41743 | IYAMKVVK | Lys1 | 16.5 | 18.6 | | |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 µM no GF | I-9 1 µM no GF | I-3 1 µM GF | I-9 1 µM GF |
| PKCt | UniRef100_Q04759 | GSFGKVFLAEFK | ATP Loop | -5.2 | | 23.5 | |
| PKD2 | UniRef100_Q9BZL6 | DVAVKVIDK | Lys1 | 5.5 | -11 | -1.4 | -4.2 |
| PKD3 | UniRef100_O94806 | DVAIKVIDK | Lys1 | | -15.2 | | -9.2 |
| PKN1 | UniRef100_Q16512 | VLLSEFRPSGELFAIKALK | Lys1 | -3.3 | -4.9 | -29.4 | -0.9 |
| PKN2 | UniRef100_Q16513 | DLKLDNLLLDTEGFVK | Lys2 | | -4.5 | | 13.6 |
| PKR | UniRef100_P19525 | DLKPSNIFLVDTK | Lys2 | -3.6 | -8 | -17.6 | -3.8 |
| PLK1 | UniRef100_P53350 | CFEISDADTKEVFAGKIVPK | Lys1 | 0.2 | 2.1 | -23 | 9.6 |
| PRP4 | UniRef100_Q13523 | CNILHADIKPDNILVNESK | Lys2 | 5.9 | -24.8 | -6.2 | -15.7 |
| PRPK | UniRef100_Q96S44 | FLSGLELVKQGAEAR | ATP Loop | 2.1 | -2 | 17.3 | -1.2 |
| PYK2 | UniRef100_Q14289 | YIEDEDYYKASVTR | Activation Loop | 1 | 5.1 | -12.1 | -0.9 |
| QSK | UniRef100_Q9Y2K2 | DLKAENLLLDANLNIK | Lys2 | | -1.8 | | 2.5 |
| RAF1 | UniRef100_P04049 | DMKSNNIFLHEGLTVK | Lys2 | -18.8 | 9.9 | 9.9 | -9.2 |
| RIPK3 | UniRef100_Q9Y572 | DLKPSNVLLDPELHVK | Lys2 | 13.4 | -15 | 22 | -27 |
| ROCK1 | UniRef100_Q13464 | KLQLELNQER | Protein Kinase Domain | 2.6 | -7.3 | -16.9 | -2.1 |
| ROCK1, ROCK2 | UniRef100_O75116, UniRef100_Q13464 | DVKPDNMLLDK | Lys2 | -22.2 | 24.4 | 12.5 | 1.7 |
| RSK1 domain1 | UniRef100_Q15418 | DLKPENILLDEEGHIKLTDFGLSKEAIDHEK | Lys2 | 9 | -2 | -16.9 | -5.1 |
| RSK1 domain1, RSK2 domain1, RSK3 domain1 | UniRef100_P51812, UniRef100_Q15418, UniRef100_Q15349 | DLKPENILLDEEGHIK | Lys2 | -14.8 | -12 | -7.3 | -6.1 |
| RSK1 domain2 | UniRef100_Q15418 | DLKPSNILYVDESGNPECLR | Lys2 | -1.9 | -9.7 | -20.8 | -4.1 |
| RSK2 domain1 | UniRef100_P51812 | DLKPENILLDEEGHIKLTDFGLSKESIDHEK | Lys2 | -2 | -5.6 | -15.5 | -8.4 |
| RSK2 domain2 | UniRef100_P51812 | DLKPSNILYVDESGNPESIR | Lys2 | -10.2 | -9.7 | -16.5 | 1.6 |
| RSK3 domain1 | UniRef100_Q15349 | DLKPENILLDEEGHIKITDFGLSK | Lys2 | 7.6 | -1.4 | -19 | -4.1 |
| RSK4 domain1 | UniRef100_Q9UK32 | DLKPENILLDEIGHIK | Lys2 | | 9.1 | | 15.8 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 µM no GF | I-9 1 µM GF | I-3 1 µM no GF | I-9 1 µM GF |
| RSKL1 | UniRef100_Q96S38 | VLGVIDKVLLVMDTR | ATP | −17 | 13.5 | −25.8 | 1.8 |
| SGK3 | UniRef100_Q96BR1 | FYAVKVLQK | Lys1 | −0.4 | 1.1 | −18.5 | −1.1 |
| SLK | UniRef100_Q9H2G2 | DLKAGNILFTLDGDIK | Lys2 | 13 | −6 | 1.6 | 4.3 |
| SMG1 | UniRef100_Q96Q15 | DTVTIHSVGGTITILPTKTKPK | ATP | 0.6 | −11.6 | −36.7 | −1 |
| SNRK | UniRef100_Q9NRH2 | DLKPENVVFEEK | Lys2 | 46.4 | 28.6 | 40.2 | 30.1 |
| SRC | UniRef100_P12931 | VAIKTLKPGTMSPEAFLQEAQVMKK | Lys1 | 91.7 | 78.6 | 96.7 | 86.1 |
| SRPK1 | UniRef100_Q96SB4 | IIHTDIKPENILLSVNEQYIR | Lys2 | −7.8 | −4 | −16.8 | −0.4 |
| SRPK1, SRPK2 | UniRef100_P78362, UniRef100_Q96SB4 | FVAMKVVK | Lys1 | −3 | 10 | 22.3 | 2.5 |
| STK33 | UniRef100_Q9BYT3 | DLKLENIMVK | Lys2 | −6.1 | 20.2 | 11.8 | 16.1 |
| STLK5 | UniRef100_Q7RTN6 | YSVKVLPWLSPEVLQQNLQGYDAK | Activation Loop | 10.4 | −12.9 | −17.7 | −9.4 |
| STLK6 | UniRef100_Q9COK7 | HTPTGTLVTIKITNLENCNEER | Lys1 | | 7.2 | | 4.8 |
| SYK | UniRef100_P43405 | ISDFGLSKALR | Activation Loop | −1.2 | −6.5 | −1.1 | −6.1 |
| TAK1 | UniRef100_O43318 | DLKPPNLLLVAGGTVLK | Lys2 | 2.3 | −1.4 | −2.5 | 1 |
| TA01, TA03 | UniRef100_Q7L7X3, UniRef100_Q9H2K8 | DIKAGNILLTEPGQVK | Lys2 | 7.8 | 5.1 | 14.3 | 9.3 |
| TA02 | UniRef100_Q9UL54 | DVKAGNILLSEPGLVK | Lys2 | 5 | 4.3 | 8 | 11.5 |
| TBK1 | UniRef100_Q9UHD2 | TGDLFAIKVFNNISFLRPVDVQMR | Lys1 | −25.1 | 23 | −1.6 | 10.8 |
| TEC | UniRef100_P42680 | YVLDDQYTSSSGAKFPVK | Activation Loop | >91 | 97.4 | >91 | 40.8 |
| TLK1 | UniRef100_Q9UKI8 | YLNEIKPPIIHYDLKPGNILLVDGTACGEIK | Lys2 | −0.7 | −7.9 | −6.9 | −2.3 |
| TLK2 | UniRef100_Q86UE8 | YLNEIKPPIIHYDLKPGNILLVNGTACGEIK | Lys2 | −3 | −13.3 | 4.7 | −1.9 |
| TYK2 domain2 | UniRef100_P29597 | IGDFGLAKAVPEGHEYYR | Activation Loop | −10.1 | −17.7 | −5.5 | −16.8 |
| ULK1 | UniRef100_O75385 | DLKPQNILLSNPAGR | Lys2 | 9.9 | −5.7 | −8.2 | −1.7 |
| ULK3 | UniRef100_D3DW67 | NISHLDLKPQNILLSSLEKPHLK | Lys2 | 8.2 | −16.4 | −47.2 | −9.6 |
| VRK2 | UniRef100_Q86Y07 | MLDVLEYIHENEYVHGDIKAANLLLGYK | Lys2 | −13.9 | 6.2 | 5.7 | −1.6 |
| Wee1 | UniRef100_P30291 | YIHSMSLVHMDIKPSNIFISR | Lys2 | −32.7 | 14.3 | −6.5 | 8.6 |

TABLE 2-continued

Exemplary KINATIV assay results of compounds I-3 and I-9.

| Kinase | Reference | Sequence | Labeling Site | % change of MS signal compared to control sample | | | |
|---|---|---|---|---|---|---|---|
| | | | | I-3 1 μM no GF | I-9 1 μM GF | I-3 1 μM no GF | I-9 1 μM GF |
| Wnk1, Wn1a | UniRef100_Q9Y3S1, UniRef100_D3DUP1 | GSFKTVYK | ATP Loop | 13.1 | −6.3 | 6.8 | 7.6 |
| Wnk1, Wn1a, Wnk3 | UniRef100_Q9Y3S1, UniRef100_D3DUP1, UniRef100_Q9BYP7 | DLKCDNIFITGPTGSVK | Lys2 | 14.9 | −10.8 | −1.2 | 4.4 |
| YANK3 | UniRef100_Q86UX6 | DVKPDNILLDER | Lys2 | | −8.6 | | −13.2 |
| YSK1 | UniRef100_O00506 | EVVAIKIIDLEEAEDEIEDIQQEITVLSQCDSPYITR | Lys1 | | −11.5 | | −20.8 |
| ZAK | UniRef100_Q9NYL2 | WISQDKEVAVKK | Lys1 | 1.6 | −9.3 | 21.2 | 12.1 |
| ZC1/HGK | UniRef100_O95819 | TGQLAAIKVMDVTEDEEEEIKLEINMLKK | Lys1 | −14.8 | 20.9 | −16.8 | 15.3 |
| ZC1/HGK, ZC2/TNIK, ZC3/MINK | UniRef100_O95819, UniRef100_Q9UKE5, UniRef100_Q8N4C8 | DIKGQNVLLTENAEVK | Lys2 | 2.7 | −2 | −0.1 | 1.8 |
| ZC2/TNIK | UniRef100_Q9UKE5 | TGQLAAIKVMDVTGDEEEEIKQEINMLKK | Lys1 | −15.6 | 23.4 | 32.9 | 11.4 |

Labeling Site Key:
Lys1: Conserved Lysine 1;
Lys2: Conserved Lysine 2;
ATP Loop: ATP binding loop;
Activation Loop: Activation loop;
ATP: ATP site in non-canonical kinase (e.g. lipid kinase);
Protein Kinase Domain: Other lysine within kinase domain, possibly not in ATP binding site; and
Other: Labeling of residue outside of the protein kinase domain, possibly not in ATP binding site.

Example 24. KINATIV assay of compounds I-4, I-7, I-8, and II-1

BCWM.1 cells were treated with compound I-4, I-7, I-8, or II-1 (1 μM) for 90 minutes. The cells were harvested and lysed. The lysates were directly labeled with an ATP-biotin probe. Bound kinases were identified and quantitated by ACTIVX as described in Patricelli et al., *Biochemistry*, 2007, 46(2): 350-358. The compounds were tested in duplicates against duplicate or quadruplicate control samples. Exemplary results are shown in Table 3, where the % changes of MS signals of compounds I-4, I-7, I-8, or II-1, compared to the control samples, are reported. The results shown in Table 3 were statistically significant (Student T-test score <0.04). A compound inhibited the kinase activity when a % change of the MS signal shown in Table 3 is positive (e.g., greater than 0%) or increased the kinase activity when a % change of the MS signal shown in Table 3 is negative (e.g., lower than 0%).

TABLE 3

Exemplary KINATIV assay results of compounds I-4, I-7, I-8, and II-1.

| Kinase | % change of MS signal compared to control sample | | | |
|---|---|---|---|---|
| | I-4 (1 μM) | I-7 (1 μM) | I-8 (1 μM) | II-1 (1 μM) |
| ABL, ARG | 91.7 | >97 | >97 | 39.5 |
| ABL, ARG | >90 | >90 | >90 | 76.1 |
| ACK | 27.0 | 80.7 | 69.9 | 51.7 |
| ACK | 22.8 | 88.5 | 82.4 | 50.8 |
| AKT1 | −11.0 | −16.4 | −19.5 | −17.8 |
| AMPKa1 | 10.1 | 2.7 | −0.6 | 5.1 |
| AMPKa1, AMPKa2 | −11.0 | −20.7 | −29.2 | −19.4 |
| AMPKa1, AMPKa2 | −40.3 | −22.3 | −13.2 | −27.3 |
| ATR | −66.1 | −48.0 | −24.9 | −55.3 |
| AurA | 3.7 | −15.7 | −15.2 | −10.8 |
| AurA | 1.7 | 7.2 | −0.1 | 3.6 |
| AurA, AurB, AurC | 2.3 | 0.4 | −2.9 | −3.6 |
| AurB | −10.1 | −6.1 | −14.3 | −7.2 |
| BARK1 | −8.1 | −29.7 | −19.6 | −23.3 |
| BLK | >95 | >95 | >95 | >95 |
| BRAF | 17.8 | 21.7 | 11.1 | 6.9 |
| BTK | 97.0 | 98.9 | 98.0 | 97.1 |
| BTK | >90 | >90 | >90 | >90 |

TABLE 3-continued

Exemplary KINATIV assay results of compounds I-4, I-7, I-8, and II-1.

| Kinase | % change of MS signal compared to control sample | | | |
|---|---|---|---|---|
| | I-4 (1 µM) | I-7 (1 µM) | I-8 (1 µM) | II-1 (1 µM) |
| CaMK1d | −12.5 | −19.1 | −14.1 | −7.9 |
| CaMK1d | −4.0 | −16.0 | −8.7 | −2.8 |
| CaMK2a, CaMK2b, CaMK2d, CaMK2g | 10.0 | 7.4 | 10.4 | 2.5 |
| CaMK2d | −8.5 | −22.5 | −22.3 | −14.8 |
| CaMK2g | −19.8 | −12.8 | −9.4 | −17.5 |
| CaMK4 | −7.1 | −24.9 | −26.3 | −10.3 |
| CaMKK2 | −1.5 | 28.6 | 17.3 | 16.1 |
| CaMKK2 | −10.2 | −29.6 | −27.8 | −18.7 |
| CASK | 23.2 | 37.7 | 43.0 | 29.4 |
| CDC2 | −24.9 | −0.9 | 14.5 | −5.2 |
| CDC2 | 5.1 | −16.2 | −10.9 | 2.7 |
| CDK11, CDK8 | −36.1 | −3.5 | 19.6 | −9.2 |
| CDK2 | 18.8 | 15.3 | 21.5 | 19.5 |
| CDK2 | 3.5 | −2.1 | −4.9 | −1.1 |
| CDK4 | 6.8 | 16.7 | 6.1 | 2.2 |
| CDK5 | −7.1 | −27.5 | −31.8 | −11.2 |
| CDK5 | −7.2 | −14.0 | −3.8 | −8.0 |
| CDK6 | 7.8 | 4.1 | 4.5 | 6.0 |
| CDK7 | 21.6 | 0.7 | −8.2 | 8.6 |
| CDK7 | 16.8 | 22.2 | 20.6 | 22.6 |
| CDK9 | −41.9 | −37.0 | −5.2 | −57.0 |
| CHK1 | −8.6 | 13.5 | 15.3 | 9.0 |
| CHK1 | 24.1 | 27.2 | 24.7 | 29.6 |
| CHK2 | −7.9 | −18.6 | −14.3 | −8.3 |
| CHK2 | 1.0 | −5.6 | −10.9 | 10.3 |
| CK1a | −41.3 | −0.7 | 14.9 | −14.4 |
| CK1g2 | −4.5 | −3.7 | −6.1 | −1.1 |
| CK2a1 | 24.6 | 14.3 | 13.9 | 24.7 |
| CK2a2 | −3.6 | −6.4 | 27.5 | 13.8 |
| CLK3 | −1.3 | −15.7 | −14.9 | −22.6 |
| CSK | 35.7 | 76.5 | 88.1 | 26.2 |
| CSK | 35.7 | 75.7 | 86.2 | 32.5 |
| DNAPK | −80.8 | −155.4 | −153.0 | −117.2 |
| DNAPK | −12.9 | −17.6 | −26.7 | −17.7 |
| eEF2K | 0.3 | 4.9 | −1.5 | −3.8 |
| EphB1 | >97 | >97 | >97 | 91.0 |
| EphB2 | >90 | >90 | >90 | >90 |
| Erk1 | −10.9 | −23.1 | −19.7 | −17.6 |
| Erk2 | −3.2 | −4.7 | −0.1 | −5.8 |
| Erk5 | −9.0 | −13.8 | −11.4 | −14.2 |
| FER | −13.4 | −5.8 | −7.7 | −10.0 |
| FER | 1.8 | −5.3 | −4.8 | 0.1 |
| FES | −15.6 | −20.9 | −13.3 | −15.0 |
| FGR | 87.0 | 94.7 | 86.0 | 87.8 |
| FRAP | 4.9 | −3.5 | −5.2 | 8.6 |
| FRK | 87.5 | 93.3 | 95.3 | 84.0 |
| FYN, SRC, YES | 97.4 | 98.4 | 97.9 | 88.1 |
| GCK | −13.9 | −12.2 | 2.0 | −10.9 |
| GCK | 11.6 | −4.1 | 2.4 | −22.5 |
| GCN2 | −11.0 | −13.3 | −20.3 | −6.2 |
| GCN2 | −5.7 | −6.3 | −13.6 | −4.1 |
| GSK3A | −10.5 | −11.3 | −14.2 | −11.8 |
| GSK3B | 0.7 | −1.9 | −10.7 | −5.1 |
| HPK1 | 0.4 | 23.4 | 32.8 | 23.0 |
| HPK1 | 26.6 | 19.8 | 24.6 | 12.1 |
| IKKa | 6.4 | −3.5 | −4.2 | −2.1 |
| IKKb | 3.1 | 10.9 | 23.2 | 15.1 |
| IKKb | 4.4 | −29.2 | −24.5 | −3.2 |
| IKKe | 2.2 | 0.4 | −5.9 | −1.0 |
| IKKe, TBK1 | −38.7 | −10.7 | 5.5 | −27.2 |
| ILK | 6.7 | 17.1 | 19.4 | 13.8 |
| ILK | −19.1 | 28.2 | 36.6 | −0.3 |
| IRAK1 | 20.3 | 19.0 | 13.6 | 26.3 |
| IRAK4 | 17.8 | 7.6 | 11.9 | 15.9 |
| IRAK4 | 25.9 | 25.6 | 26.7 | 18.5 |
| IRE1 | −44.3 | −15.7 | −1.5 | −29.5 |
| ITPK1 | 12.8 | −17.5 | −16.4 | 14.0 |
| JAK1 | −5.7 | 7.5 | −1.9 | 5.4 |
| JAK1 domain2 | −17.6 | −17.9 | −22.7 | −19.8 |
| JAK1 domain2 | −1.2 | −6.4 | −11.2 | −2.3 |
| JAK3 domain2 | −30.8 | −66.2 | −109.0 | −83.2 |
| JAK3 domain2 | −19.2 | −32.6 | −49.6 | −36.2 |
| JNK1, JNK2, JNK3 | 6.3 | −4.8 | −9.5 | −23.5 |
| KHS1 | −2.1 | −5.9 | −8.4 | −0.6 |
| KSR1, KSR2 | −8.9 | −10.1 | −8.8 | −8.7 |
| LATS2 | −9.2 | −6.6 | 10.6 | −2.9 |
| LCK | 96.1 | 96.5 | 94.8 | 92.4 |
| LKB1 | −4.5 | 1.2 | −1.8 | −1.2 |
| LOK | −4.1 | −15.0 | −14.7 | −5.5 |
| LOK | −27.4 | 2.9 | 19.2 | −15.4 |
| LRRK2 | −5.7 | −9.6 | −12.2 | −20.9 |
| LYN | >97 | >97 | >97 | 88.1 |
| LYN | >90 | >90 | >90 | >90 |
| MAP2K1 | −31.6 | −3.7 | 1.0 | −23.4 |
| MAP2K1, MAP2K2 | 9.9 | 7.4 | 9.8 | 20.5 |
| MAP2K1, MAP2K2 | −4.8 | −4.1 | −2.3 | −2.2 |
| MAP2K3 | −12.3 | −2.9 | 5.7 | −19.5 |
| MAP2K3 | −18.8 | −14.1 | −23.1 | −15.9 |
| MAP2K4 | −48.8 | −25.3 | −8.5 | −28.3 |
| MAP2K4 | −6.9 | −14.5 | −6.1 | 1.2 |
| MAP2K5 | 33.0 | 37.6 | 19.2 | 14.8 |
| MAP2K5 | −13.3 | 45.7 | 30.9 | −10.9 |
| MAP2K6 | −18.0 | 5.9 | 3.8 | −8.3 |
| MAP2K6 | −10.7 | 2.5 | −8.3 | −12.6 |
| MAP2K7 | −10.1 | 11.2 | −7.5 | −0.6 |
| MAP3K1 | 18.4 | 7.9 | 15.5 | −1.2 |
| MAP3K15, MAP3K5, MAP3K6 | 2.8 | 4.0 | 2.2 | 7.5 |
| MAP3K2 | 12.1 | 4.9 | 3.5 | 21.3 |
| MAP3K2, MAP3K3 | 24.8 | 15.6 | 19.4 | 17.1 |
| MAP3K3 | −0.7 | 42.8 | 7.9 | 13.7 |
| MAP3K4 | −20.5 | −24.2 | 12.8 | −23.9 |
| MAP3K5 | −10.7 | −9.3 | −0.7 | −22.9 |
| MAP3K6 | 10.9 | −21.3 | −8.1 | 18.9 |
| MAPKAPK3 | 7.0 | 0.9 | 0.5 | 6.2 |
| MARK1, MARK2 | 17.1 | 7.9 | 14.6 | 20.9 |
| MARK2 | 3.6 | 7.7 | 12.1 | 15.4 |
| MARK2, MARK3 | −31.5 | −11.0 | 7.5 | −10.1 |
| MARK3 | 13.5 | 12.7 | 7.8 | 18.4 |
| MARK3, MARK4 | 19.1 | 20.7 | 5.8 | 17.4 |
| MARK4 | −0.5 | 4.9 | −0.4 | 12.8 |
| MARK4 | 12.4 | 14.1 | 1.6 | 9.7 |
| MAST1, MAST2 | −62.1 | −35.0 | −32.5 | −81.3 |
| MAST3 | 2.0 | −1.6 | −8.3 | 3.8 |
| MASTL | −2.9 | −10.9 | −16.9 | −16.7 |
| MASTL | −0.3 | −13.8 | −9.5 | −8.2 |
| MELK | −11.7 | −11.0 | −10.0 | 4.2 |
| MLK3 | −27.2 | −4.6 | 11.7 | −18.0 |
| MLKL | −9.4 | −6.3 | −17.5 | −0.8 |
| MPSK1 | −17.4 | −15.5 | −10.0 | −4.0 |
| MPSK1 | −79.7 | −39.7 | −25.7 | −39.6 |
| MSK1 domain1 | −15.8 | −40.5 | −45.5 | −35.0 |
| MSK1, MSK2 domain1 | −28.9 | −40.4 | −29.7 | −37.4 |
| MSK2 domain1 | −9.6 | −45.3 | −47.7 | −33.9 |
| MST1 | 7.0 | 3.0 | 2.4 | 13.2 |
| MST1, MST2 | 3.8 | 9.5 | 8.7 | 3.1 |
| MST2 | 12.3 | 6.5 | 4.3 | 14.7 |
| MST3 | −17.6 | 5.0 | −1.5 | 5.9 |
| MST3 | 5.2 | −5.6 | −7.7 | 2.0 |
| MST4 | −13.2 | 11.6 | −0.8 | 21.1 |
| MST4, YSK1 | 20.5 | 12.7 | 19.3 | 9.2 |
| MYO3A, MYO3B | 15.9 | 17.2 | 23.1 | 12.9 |
| NDR1 | −38.8 | −18.1 | −0.8 | −21.2 |
| NDR1 | −4.7 | 4.5 | 2.2 | 3.9 |
| NDR2 | −42.0 | −20.0 | 1.9 | −11.0 |
| NDR2 | 7.2 | 7.4 | 9.1 | 18.7 |
| NEK1 | 7.3 | 11.4 | 12.8 | 14.9 |
| NEK2 | 22.3 | 8.5 | −3.0 | −6.0 |
| NEK3 | 3.5 | 15.6 | 3.2 | 8.1 |
| NEK4 | 12.3 | 7.9 | 15.2 | 18.5 |
| NEK6, NEK7 | 3.7 | −8.4 | −11.1 | −0.2 |
| NEK7 | −7.7 | 10.0 | −1.0 | −8.5 |
| NEK8 | 14.6 | 12.2 | 13.1 | 6.5 |
| NEK9 | −0.1 | 2.5 | −1.3 | −1.0 |

TABLE 3-continued

Exemplary KINATIV assay results of compounds I-4, I-7, I-8, and II-1.

| Kinase | % change of MS signal compared to control sample | | | |
|---|---|---|---|---|
| | I-4 (1 μM) | I-7 (1 μM) | I-8 (1 μM) | II-1 (1 μM) |
| NEK9 | 4.4 | 1.1 | −0.3 | −0.1 |
| NLK | 6.7 | 4.2 | 6.1 | 3.7 |
| OSR1 | 26.7 | 22.0 | 27.9 | 16.4 |
| p38a | 47.9 | 69.8 | 79.0 | 36.4 |
| p38a | 6.2 | 51.2 | 30.5 | −8.7 |
| p38b | −29.6 | −1.5 | 12.0 | −19.0 |
| p38d, p38g | −2.7 | 1.7 | 3.3 | −6.6 |
| p70S6K | −102.3 | −70.1 | −36.8 | −65.4 |
| p70S6Kb | −72.4 | −42.7 | −22.7 | −57.1 |
| PAN3 | −29.0 | −0.2 | 18.3 | −7.0 |
| PCTAIRE1 | 19.0 | 38.2 | 32.9 | 38.4 |
| PCTAIRE1, PCTAIRE3 | 12.7 | 14.9 | 19.8 | 11.4 |
| PCTAIRE2 | 13.4 | 9.9 | 8.5 | 7.7 |
| PCTAIRE2, PCTAIRE3 | 27.9 | 27.0 | 28.8 | 31.8 |
| PEK | −44.9 | 2.6 | 3.3 | −31.0 |
| PFTAIRE1 | 15.3 | 19.1 | 22.1 | 24.3 |
| PFTAIRE1 | 6.3 | 4.8 | 7.3 | 6.0 |
| PHKg2 | −15.6 | 0.6 | 6.4 | −9.1 |
| PI4KA, PI4KAP2 | −37.7 | −17.4 | −9.9 | −45.7 |
| PI4KB | 20.0 | 36.0 | 44.2 | 7.2 |
| PI4KB | 16.7 | 35.3 | 41.9 | 13.7 |
| PIK3C2B | −5.8 | 39.9 | 12.5 | −5.8 |
| PIK3C3 | −14.1 | −7.4 | −2.6 | −4.7 |
| PIK3C3 | −5.5 | 10.9 | 8.6 | −11.6 |
| PIK3CB | −61.3 | −42.6 | −10.1 | −64.9 |
| PIK3CD | −14.5 | −19.1 | −16.2 | −9.5 |
| PIK3CG | −46.3 | −51.9 | −55.4 | −45.9 |
| PIP4K2A | −8.9 | −36.0 | −37.8 | −20.5 |
| PIP4K2A | −21.4 | −7.4 | 9.0 | 1.3 |
| PIP4K2C | 71.0 | 70.9 | 97.6 | −17.6 |
| PIP4K2C | 43.0 | 60.1 | 85.7 | −32.0 |
| PIP5K3 | 14.5 | 4.3 | 4.2 | 16.3 |
| PITSLRE | −13.6 | −9.3 | −16.1 | −16.1 |
| PKD1, PKD2 | −4.7 | −8.3 | −15.3 | −19.8 |
| PKD2 | 12.9 | 10.0 | 8.7 | 12.7 |
| PKN1 | 17.4 | 4.2 | 13.7 | 20.9 |
| PKR | −0.1 | −2.8 | −8.0 | −3.2 |
| PKR | 16.9 | 21.9 | 21.3 | 22.3 |
| PLK1 | 1.9 | 2.7 | −7.8 | 0.5 |
| PLK1 | 17.4 | 16.1 | 12.8 | −0.2 |
| PRP4 | 6.9 | −4.1 | −10.7 | 6.9 |
| PRPK | −13.6 | −3.8 | 3.7 | −5.2 |
| PYK2 | 6.7 | 16.6 | 20.3 | 12.5 |
| PYK2 | 27.3 | 28.4 | 25.5 | 36.6 |
| ROCK1 | 6.7 | 6.6 | 4.4 | 12.8 |
| RSK1 domain1 | −62.2 | −97.5 | −108.2 | −76.3 |
| RSK1 domain1 | −53.4 | −75.8 | −91.8 | −76.3 |
| RSK1 domain2 | 12.5 | 4.9 | 0.5 | 14.0 |
| RSK1, RSK2, RSK3 domain1 | −44.0 | −58.3 | −55.6 | −52.0 |
| RSK2 domain1 | −90.2 | −128.5 | −163.6 | −132.7 |
| RSK2 domain1 | −72.7 | −102.7 | −122.4 | −100.2 |
| RSK2 domain2 | 13.8 | −0.3 | −6.8 | 9.7 |
| RSK3 | 16.8 | 12.6 | 2.9 | 22.3 |
| RSK3 domain1 | −26.9 | −48.6 | −62.5 | −58.4 |
| RSK4 domain1 | 3.5 | −13.5 | −8.2 | −22.4 |
| RSKL1 | 10.7 | 29.7 | 35.0 | 13.7 |
| SGK3 | 4.4 | 10.0 | 6.5 | 8.1 |
| SGK3 | 8.2 | −17.5 | −5.4 | −3.8 |
| SLK | −2.4 | −21.1 | −13.7 | 0.0 |
| SLK | 20.5 | 15.2 | 16.2 | −3.6 |
| SMG1 | −2.4 | −9.9 | −8.5 | 3.1 |
| SMG1 | 13.1 | 21.5 | 23.1 | 27.8 |
| SNRK | 35.3 | 40.7 | 45.1 | 47.8 |
| SNRK | 61.9 | 58.7 | 59.1 | 59.8 |
| SRC | >90 | >90 | >90 | >90 |
| SRPK1 | −2.1 | 1.2 | −19.5 | −4.7 |
| SRPK1, SRPK2 | −14.7 | 17.3 | 33.2 | 0.0 |
| STK33 | −23.0 | 21.1 | 29.8 | 11.0 |
| STLK5 | 2.0 | 3.3 | 1.1 | 2.6 |
| STLK5 | −4.4 | −13.9 | −4.0 | 3.8 |
| STLK6 | 7.4 | −16.3 | −12.9 | −0.8 |
| SYK | −2.2 | −16.5 | −12.5 | −3.2 |
| SYK | 12.5 | 5.7 | 12.4 | 16.1 |
| TAK1 | 27.8 | 14.5 | 9.7 | 25.6 |
| TAO1, TAO3 | 7.6 | −1.8 | −8.7 | −17.2 |
| TAO2 | −7.0 | −18.0 | −4.9 | −17.9 |
| TBK1 | −34.8 | −39.7 | −2.9 | −30.2 |
| TEC | 68.7 | 85.1 | 79.5 | 91.5 |
| TEC | 73.7 | 58.6 | 71.1 | 80.8 |
| TLK1 | 2.2 | 1.8 | −12.5 | 7.1 |
| TLK1 | 8.2 | 5.5 | 5.7 | 5.7 |
| TLK2 | 8.7 | 7.3 | 9.4 | 7.3 |
| TYK2 domain2 | −3.8 | −46.4 | −44.6 | −19.0 |
| ULK1 | 16.2 | 19.3 | 16.1 | 19.7 |
| ULK3 | 22.5 | 15.5 | 23.7 | 22.4 |
| ULK3 | 21.9 | 18.4 | 11.3 | 22.8 |
| VRK2 | −30.6 | −2.3 | 3.6 | 5.2 |
| Wnk1, Wnk2 | 7.8 | −8.6 | −16.4 | −3.8 |
| Wnk1, Wnk2, Wnk3 | 17.5 | 10.4 | 1.7 | 2.4 |
| Wnk1, Wnk2, Wnk4 | −0.5 | −6.6 | −16.3 | −8.1 |
| YSK1 | −58.5 | −19.9 | −29.2 | −27.4 |
| ZC1/HGK, ZC2/TNIK, ZC3/MINK | 3.3 | 6.2 | 13.6 | 4.2 |
| ZC2/TNIK | 48.8 | −1.5 | 19.0 | −10.0 |

Example 25. Ambit KINOMESCAN assay of compounds I-2 and I-3

Each of compounds I-2 (1 μM) and I-3 (1 μM) was subject to an Ambit KINOMESCAN (DISCOVERRX) assay according to the protocols described in Fabian et al. (*Nat. Biotechnol.* 2005, 23(3): 329-336) and/or Davis et al. (*Nat. Biotechnol.* 2011, 29(11): 1046-1051) to determine the inhibition against a broad panel of kinases. Exemplary results are shown in Tables 4 and 5.

TABLE 4

Exemplary KINOMESCAN assay results of compound I-3.

| Kinase | ENTREZ gene symbol | % change compared to control |
|---|---|---|
| ABL1(H396P)-phosphorylated | ABL1 | 0 |
| ABL1-phosphorylated | ABL1 | 0 |
| BLK | BLK | 0 |
| EPHA4 | EPHA4 | 0 |
| EPHB2 | EPHB2 | 0 |
| EPHB3 | EPHB3 | 0 |
| EPHB4 | EPHB4 | 0 |
| FGR | FGR | 0 |
| JAK3(JH1domain-catalytic) | JAK3 | 0 |
| KIT | KIT | 0 |
| KIT(L576P) | KIT | 0 |
| KIT(V559D) | KIT | 0 |
| PDGFRB | PDGFRB | 0 |
| SRC | SRC | 0 |
| YES | YES1 | 0 |
| ABL1(H396P)-nonphosphorylated | ABL1 | 0.05 |
| BTK | BTK | 0.05 |
| ABL1(Y253F)-phosphorylated | ABL1 | 0.1 |
| ABL1-nonphosphorylated | ABL1 | 0.1 |
| FRK | FRK | 0.1 |
| LYN | LYN | 0.1 |
| ABL1(Q252H)-nonphosphorylated | ABL1 | 0.15 |
| DDR1 | DDR1 | 0.15 |
| EPHB1 | EPHB1 | 0.2 |
| ERBB4 | ERBB4 | 0.2 |
| p38-alpha | MAPK14 | 0.2 |
| ABL2 | ABL2 | 0.25 |
| ABL1(Q252H)-phosphorylated | ABL1 | 0.3 |

TABLE 4-continued

Exemplary KINOMESCAN assay results of compound I-3.

| Kinase | ENTREZ gene symbol | % change compared to control |
|---|---|---|
| SIK | SIK1 | 0.4 |
| EPHA8 | EPHA8 | 0.45 |
| MEK5 | MAP2K5 | 0.45 |
| ABL1(E255K)-phosphorylated | ABL1 | 0.5 |
| ABL1(F317L)-nonphosphorylated | ABL1 | 0.5 |
| FYN | FYN | 0.5 |
| LCK | LCK | 0.55 |
| EPHA2 | EPHA2 | 0.6 |
| HCK | HCK | 0.6 |
| ABL1(M351T)-phosphorylated | ABL1 | 0.7 |
| TXK | TXK | 0.7 |
| EGFR(L858R) | EGFR | 0.75 |
| EGFR(L861Q) | EGFR | 0.8 |
| ERBB2 | ERBB2 | 0.8 |
| ERBB3 | ERBB3 | 0.8 |
| EPHA5 | EPHA5 | 0.85 |
| ABL1(F317I)-nonphosphorylated | ABL1 | 1.2 |
| EGFR(L747-E749del, A750P) | EGFR | 1.4 |
| CSK | CSK | 1.6 |
| EPHA1 | EPHA1 | 1.6 |
| ABL1(F317L)-phosphorylated | ABL1 | 2 |
| BRAF(V600E) | BRAF | 2.1 |
| EGFR | EGFR | 2.6 |
| KIT-autoinhibited | KIT | 2.6 |
| EGFR(E746-A750del) | EGFR | 2.9 |
| CSF1R-autoinhibited | CSF1R | 3.2 |
| CSF1R | CSF1R | 3.3 |
| TEC | TEC | 3.3 |
| EGFR(L747-S752del, P753S) | EGFR | 3.6 |
| EGFR(L747-T751del, Sins) | EGFR | 4.2 |
| EGFR(S752-I759del) | EGFR | 4.6 |
| EPHB6 | EPHB6 | 4.6 |
| BMX | BMX | 4.9 |
| ABL1(F317I)-phosphorylated | ABL1 | 5.2 |
| PDGFRA | PDGFRA | 6.5 |
| BRAF | BRAF | 6.8 |
| EGFR(G719S) | EGFR | 7.6 |
| PFCDPK1 (*P. falciparum*) | CDPK1 | 8.1 |
| DDR2 | DDR2 | 8.4 |
| BRK | PTK6 | 9.3 |
| NLK | NLK | 9.4 |
| KIT(A829P) | KIT | 10 |
| GAK | GAK | 11 |
| SRMS | SRMS | 12 |
| EGFR(G719C) | EGFR | 14 |
| KIT(D816V) | KIT | 14 |
| KIT(D816H) | KIT | 23 |
| KIT(V559D, V654A) | KIT | 25 |
| LIMK1 | LIMK1 | 25 |
| STK36 | STK36 | 25 |
| RAF1 | RAF1 | 26 |
| TYK2(JH2domain-pseudokinase) | TYK2 | 26 |
| RIPK2 | RIPK2 | 31 |
| PIK4CB | PI4KB | 36 |
| TYRO3 | TYRO3 | 41 |
| EGFR(L858R, T790M) | EGFR | 42 |
| TNK2 | TNK2 | 43 |
| TNNI3K | TNNI3K | 44 |
| BMPR1B | BMPR1B | 45 |
| PIK3C2B | PIK3C2B | 47 |
| PKMYT1 | PKMYT1 | 47 |
| ADCK3 | CABC1 | 49 |
| EPHA3 | EPHA3 | 49 |
| NEK11 | NEK11 | 49 |
| QSK | KIAA0999 | 50 |
| PAK3 | PAK3 | 51 |
| RPS6KA5(Kin. Dom. 2-C-terminal) | RPS6KA5 | 52 |
| EGFR(T790M) | EGFR | 56 |
| MARK3 | MARK3 | 57 |
| NDR2 | STK38L | 58 |
| SBK1 | SBK1 | 58 |
| HPK1 | MAP4K1 | 61 |
| SGK | SGK1 | 61 |
| ERK4 | MAPK4 | 62 |
| CAMK1 | CAMK1 | 63 |
| p38-beta | MAPK11 | 63 |
| TRPM6 | TRPM6 | 63 |
| NEK6 | NEK6 | 64 |
| SRPK2 | SRPK2 | 64 |
| LIMK2 | LIMK2 | 65 |
| PIP5K1C | PIP5K1C | 65 |
| DMPK2 | CDC42BPG | 66 |
| MINK | MINK1 | 66 |
| TAOK2 | TAOK2 | 67 |
| BUB1 | BUB1 | 68 |
| PRKR | EIF2AK2 | 69 |
| ABL1(T315I)-phosphorylated | ABL1 | 70 |
| CSNK2A2 | CSNK2A2 | 70 |
| VRK2 | VRK2 | 70 |
| AURKC | AURKC | 71 |
| STK39 | STK39 | 71 |
| PIM2 | PIM2 | 72 |
| DYRK1B | DYRK1B | 74 |
| DYRK2 | DYRK2 | 74 |
| NDR1 | STK38 | 74 |
| CDK9 | CDK9 | 75 |
| ROCK2 | ROCK2 | 75 |
| ACVRL1 | ACVRL1 | 76 |
| ALK(L1196M) | ALK | 76 |
| AXL | AXL | 76 |
| ERN1 | ERN1 | 76 |
| PLK2 | PLK2 | 76 |
| SGK2 | SGK2 | 76 |
| RIOK2 | RIOK2 | 77 |
| AMPK-alpha2 | PRKAA2 | 78 |
| CDC2L1 | CDK11B | 78 |
| CDKL2 | CDKL2 | 78 |
| TTK | TTK | 78 |
| AURKA | AURKA | 80 |
| DAPK2 | DAPK2 | 80 |
| MAP3K1 | MAP3K1 | 80 |
| MARK2 | MARK2 | 80 |
| MARK4 | MARK4 | 80 |
| AKT3 | AKT3 | 81 |
| CAMK2B | CAMK2B | 81 |
| CDKL3 | CDKL3 | 81 |
| CTK | MATK | 81 |
| JNK1 | MAPK8 | 81 |
| PCTK2 | CDK17 | 81 |
| PKN1 | PKN1 | 81 |
| PRKD3 | PRKD3 | 81 |
| SYK | SYK | 81 |
| ACVR2A | ACVR2A | 82 |
| JAK2(JH1domain-catalytic) | JAK2 | 82 |
| MELK | MELK | 82 |
| PLK4 | PLK4 | 82 |
| RIOK1 | RIOK1 | 82 |
| ALK | ALK | 83 |
| CAMK2A | CAMK2A | 83 |
| CDK11 | CDK19 | 83 |
| HUNK | HUNK | 83 |
| PLK1 | PLK1 | 83 |
| ALK(C1156Y) | ALK | 84 |
| CAMK4 | CAMK4 | 84 |
| CHEK1 | CHEK1 | 84 |
| DAPK3 | DAPK3 | 84 |
| DCAMKL1 | DCLK1 | 84 |
| FLT3 | FLT3 | 84 |
| NIK | MAP3K14 | 84 |
| NIM1 | MGC42105 | 84 |
| PAK6 | PAK6 | 84 |
| YANK1 | STK32A | 84 |
| CLK4 | CLK4 | 85 |
| MKK7 | MAP2K7 | 85 |
| MLK3 | MAP3K11 | 85 |
| NEK1 | NEK1 | 85 |
| PIK3CD | PIK3CD | 85 |
| PKAC-alpha | PRKACA | 85 |

TABLE 4-continued

Exemplary KINOMESCAN assay results of compound I-3.

| Kinase | ENTREZ gene symbol | % change compared to control |
|---|---|---|
| FLT1 | FLT1 | 86 |
| IKK-beta | IKBKB | 86 |
| MYO3B | MYO3B | 86 |
| RET | RET | 86 |
| RIPK5 | DSTYK | 86 |
| ULK1 | ULK1 | 86 |
| ICK | ICK | 87 |
| NEK5 | NEK5 | 87 |
| PDPK1 | PDPK1 | 87 |
| YSK1 | STK25 | 87 |
| CIT | CIT | 88 |
| FGFR2 | FGFR2 | 88 |
| HASPIN | GSG2 | 88 |
| LZK | MAP3K13 | 88 |
| MRCKA | CDC42BPA | 88 |
| PRKCH | PRKCH | 88 |
| RPS6KA5(Kin. Dom. 1-N-terminal) | RPS6KA5 | 88 |
| TESK1 | TESK1 | 88 |
| ERK3 | MAPK6 | 89 |
| MEK6 | MAP2K6 | 89 |
| PIK3CA(I800L) | PIK3CA | 89 |
| PIM3 | PIM3 | 89 |
| ROCK1 | ROCK1 | 89 |
| RSK3(Kin. Dom. 1-N-terminal) | RPS6KA2 | 89 |
| STK16 | STK16 | 89 |
| BIKE | BMP2K | 90 |
| CAMK1D | CAMK1D | 90 |
| ERK5 | MAPK7 | 90 |
| JNK2 | MAPK9 | 90 |
| NEK10 | NEK10 | 90 |
| PRKCI | PRKCI | 90 |
| RIOK3 | RIOK3 | 90 |
| ROS1 | ROS1 | 90 |
| TAK1 | MAP3K7 | 90 |
| ASK1 | MAP3K5 | 91 |
| JNK3 | MAPK10 | 91 |
| MAP4K2 | MAP4K2 | 91 |
| PIP5K1A | PIP5K1A | 91 |
| PKNB(M. tuberculosis) | pknB | 91 |
| PRKG2 | PRKG2 | 91 |
| RSK1(Kin. Dom. 1-N-terminal) | RPS6KA1 | 91 |
| TAOK3 | TAOK3 | 91 |
| TYK2(JH1domain-catalytic) | TYK2 | 91 |
| ULK2 | ULK2 | 91 |
| YANK3 | STK32C | 91 |
| ADCK4 | ADCK4 | 92 |
| BMPR1A | BMPR1A | 92 |
| CAMK2D | CAMK2D | 92 |
| DCAMKL3 | DCLK3 | 92 |
| LATS2 | LATS2 | 92 |
| MET(Y1235D) | MET | 92 |
| MLK1 | MAP3K9 | 92 |
| PCTK3 | CDK18 | 92 |
| SNRK | SNRK | 92 |
| TRKB | NTRK2 | 92 |
| CDC2L2 | CDC2L2 | 93 |
| CDKL1 | CDKL1 | 93 |
| CSNK1G2 | CSNK1G2 | 93 |
| DCAMKL2 | DCLK2 | 93 |
| FES | FES | 93 |
| FGFR1 | FGFR1 | 93 |
| INSR | INSR | 93 |
| IRAK1 | IRAK1 | 93 |
| IRAK3 | IRAK3 | 93 |
| LATS1 | LATS1 | 93 |
| MARK1 | MARK1 | 93 |
| MAST1 | MAST1 | 93 |
| MYLK | MYLK | 93 |
| PAK2 | PAK2 | 93 |
| TNIK | TNIK | 93 |
| CDK7 | CDK7 | 94 |
| MAP3K3 | MAP3K3 | 94 |
| MET | MET | 94 |
| MST2 | STK3 | 94 |
| PHKG2 | PHKG2 | 94 |
| PRKD1 | PRKD1 | 94 |
| SLK | SLK | 94 |
| TBK1 | TBK1 | 94 |
| TLK2 | TLK2 | 94 |
| ZAK | ZAK | 94 |
| ACVR2B | ACVR2B | 95 |
| AKT1 | AKT1 | 95 |
| BRSK2 | BRSK2 | 95 |
| CDK4-cyclinD3 | CDK4 | 95 |
| CLK3 | CLK3 | 95 |
| CSNK1A1L | CSNK1A1L | 95 |
| CSNK1G3 | CSNK1G3 | 95 |
| ERK1 | MAPK3 | 95 |
| HIPK1 | HIPK1 | 95 |
| MAP3K4 | MAP3K4 | 95 |
| MLK2 | MAP3K10 | 95 |
| NEK3 | NEK3 | 95 |
| PAK1 | PAK1 | 95 |
| PFTAIRE2 | CDK15 | 95 |
| PIM1 | PIM1 | 95 |
| PRKCD | PRKCD | 95 |
| SgK110 | SgK110 | 95 |
| WNK1 | WNK1 | 95 |
| CLK2 | CLK2 | 96 |
| CSNK1E | CSNK1E | 96 |
| GRK7 | GRK7 | 96 |
| IRAK4 | IRAK4 | 96 |
| MAP4K4 | MAP4K4 | 96 |
| MAP4K5 | MAP4K5 | 96 |
| MYO3A | MYO3A | 96 |
| NEK2 | NEK2 | 96 |
| PIK3CA(H1047Y) | PIK3CA | 96 |
| SRPK1 | SRPK1 | 96 |
| STK33 | STK33 | 96 |
| TRKC | NTRK3 | 96 |
| YANK2 | STK32B | 96 |
| CAMK1G | CAMK1G | 97 |
| CAMK2G | CAMK2G | 97 |
| CAMKK1 | CAMKK1 | 97 |
| CHEK2 | CHEK2 | 97 |
| EIF2AK1 | EIF2AK1 | 97 |
| GRK1 | GRK1 | 97 |
| GSK3A | GSK3A | 97 |
| HIPK4 | HIPK4 | 97 |
| LOK | STK10 | 97 |
| MST1 | STK4 | 97 |
| PAK7 | PAK7 | 97 |
| PIK3C2G | PIK3C2G | 97 |
| PLK3 | PLK3 | 97 |
| RSK2(Kin. Dom. 1-N-terminal) | RPS6KA3 | 97 |
| RSK3(Kin. Dom. 2-C-terminal) | RPS6KA2 | 97 |
| RSK4(Kin. Dom. 2-C-terminal) | RPS6KA6 | 97 |
| S6K1 | RPS6KB1 | 97 |
| SRPK3 | SRPK3 | 97 |
| TGFBR1 | TGFBR1 | 97 |
| WEE2 | WEE2 | 97 |
| AMPK-alpha1 | PRKAA1 | 98 |
| ASK2 | MAP3K6 | 98 |
| CASK | CASK | 98 |
| CDK8 | CDK8 | 98 |
| CSNK2A1 | CSNK2A1 | 98 |
| DMPK | DMPK | 98 |
| FLT3(ITD) | FLT3 | 98 |
| ITK | ITK | 98 |
| MAP3K2 | MAP3K2 | 98 |
| MKNK2 | MKNK2 | 98 |
| NEK7 | NEK7 | 98 |
| OSR1 | OXSR1 | 98 |
| PRKCQ | PRKCQ | 98 |
| SIK2 | SIK2 | 98 |
| TAOK1 | TAOK1 | 98 |
| ULK3 | ULK3 | 98 |
| CDK4-cyclinD1 | CDK4 | 99 |

TABLE 4-continued

Exemplary KINOMESCAN assay results of compound I-3.

| Kinase | ENTREZ gene symbol | % change compared to control |
|---|---|---|
| CSNK1D | CSNK1D | 99 |
| ERK8 | MAPK15 | 99 |
| FER | FER | 99 |
| FGFR3(G697C) | FGFR3 | 99 |
| LRRK2(G2019S) | LRRK2 | 99 |
| PFTK1 | CDK14 | 99 |
| PHKG1 | PHKG1 | 99 |
| PIK3CA(C420R) | PIK3CA | 99 |
| RET(M918T) | RET | 99 |
| TRKA | NTRK1 | 99 |
| AAK1 | AAK1 | 100 |
| ABL1(T315I)-nonphosphorylated | ABL1 | 100 |
| ACVR1 | ACVR1 | 100 |
| ACVR1B | ACVR1B | 100 |
| AKT2 | AKT2 | 100 |
| ANKK1 | ANKK1 | 100 |
| ARK5 | NUAK1 | 100 |
| AURKB | AURKB | 100 |
| BMPR2 | BMPR2 | 100 |
| BRSK1 | BRSK1 | 100 |
| CAMKK2 | CAMKK2 | 100 |
| CDC2L5 | CDK13 | 100 |
| CDK2 | CDK2 | 100 |
| CDK3 | CDK3 | 100 |
| CDK5 | CDK5 | 100 |
| CDKL5 | CDKL5 | 100 |
| CLK1 | CLK1 | 100 |
| CSNK1A1 | CSNK1A1 | 100 |
| CSNK1G1 | CSNK1G1 | 100 |
| DAPK1 | DAPK1 | 100 |
| DLK | MAP3K12 | 100 |
| DRAK1 | STK17A | 100 |
| DRAK2 | STK17B | 100 |
| DYRK1A | DYRK1A | 100 |
| EPHA6 | EPHA6 | 100 |
| EPHA7 | EPHA7 | 100 |
| ERK2 | MAPK1 | 100 |
| FAK | PTK2 | 100 |
| FGFR3 | FGFR3 | 100 |
| FGFR4 | FGFR4 | 100 |
| FLT3(D835H) | FLT3 | 100 |
| FLT3(D835Y) | FLT3 | 100 |
| FLT3(K663Q) | FLT3 | 100 |
| FLT3(N841I) | FLT3 | 100 |
| FLT3(R834Q) | FLT3 | 100 |
| FLT3-autoinhibited | FLT3 | 100 |
| FLT4 | FLT4 | 100 |
| GCN2(Kin. Dom. 2, S808G) | EIF2AK4 | 100 |
| GRK4 | GRK4 | 100 |
| GSK3B | GSK3B | 100 |
| HIPK2 | HIPK2 | 100 |
| HIPK3 | HIPK3 | 100 |
| IGF1R | IGF1R | 100 |
| IKK-alpha | CHUK | 100 |
| IKK-epsilon | IKBKE | 100 |
| INSRR | INSRR | 100 |
| JAK1(JH1domain-catalytic) | JAK1 | 100 |
| JAK1(JH2domain-pseudokinase) | JAK1 | 100 |
| KIT(V559D, T670I) | KIT | 100 |
| LKB1 | STK11 | 100 |
| LRRK2 | LRRK2 | 100 |
| LTK | LTK | 100 |
| MAK | MAK | 100 |
| MAP3K15 | MAP3K15 | 100 |
| MAP4K3 | MAP4K3 | 100 |
| MAPKAPK2 | MAPKAPK2 | 100 |
| MAPKAPK5 | MAPKAPK5 | 100 |
| MEK1 | MAP2K1 | 100 |
| MEK2 | MAP2K2 | 100 |
| MEK3 | MAP2K3 | 100 |
| MEK4 | MAP2K4 | 100 |
| MERTK | MERTK | 100 |
| MET(M1250T) | MET | 100 |
| MKNK1 | MKNK1 | 100 |

TABLE 4-continued

Exemplary KINOMESCAN assay results of compound I-3.

| Kinase | ENTREZ gene symbol | % change compared to control |
|---|---|---|
| MLCK | MYLK3 | 100 |
| MRCKB | CDC42BPB | 100 |
| MST1R | MST1R | 100 |
| MST3 | STK24 | 100 |
| MST4 | MST4 | 100 |
| MTOR | MTOR | 100 |
| MUSK | MUSK | 100 |
| MYLK2 | MYLK2 | 100 |
| MYLK4 | MYLK4 | 100 |
| NEK4 | NEK4 | 100 |
| NEK9 | NEK9 | 100 |
| p38-delta | MAPK13 | 100 |
| p38-gamma | MAPK12 | 100 |
| PAK4 | PAK4 | 100 |
| PCTK1 | CDK16 | 100 |
| PFPK5(P. falciparum) | MAL13P1.279 | 100 |
| PIK3CA | PIK3CA | 100 |
| PIK3CA(E542K) | PIK3CA | 100 |
| PIK3CA(E545A) | PIK3CA | 100 |
| PIK3CA(E545K) | PIK3CA | 100 |
| PIK3CA(H1047L) | PIK3CA | 100 |
| PIK3CA(M10431) | PIK3CA | 100 |
| PIK3CA(Q546K) | PIK3CA | 100 |
| PIK3CB | PIK3CB | 100 |
| PIK3CG | PIK3CG | 100 |
| PIP5K2B | PIP4K2B | 100 |
| PIP5K2C | PIP4K2C | 100 |
| PKAC-beta | PRKACB | 100 |
| PKN2 | PKN2 | 100 |
| PRKCE | PRKCE | 100 |
| PRKD2 | PRKD2 | 100 |
| PRKG1 | PRKG1 | 100 |
| PRKX | PRKX | 100 |
| PRP4 | PRPF4B | 100 |
| PYK2 | PTK2B | 100 |
| RET(V804L) | RET | 100 |
| RET(V804M) | RET | 100 |
| RIPK1 | RIPK1 | 100 |
| RIPK4 | RIPK4 | 100 |
| RPS6KA4(Kin. Dom. 1-N-terminal) | RPS6KA4 | 100 |
| RPS6KA4(Kin. Dom. 2-C-terminal) | RPS6KA4 | 100 |
| RSK1(Kin. Dom. 2-C-terminal) | RPS6KA1 | 100 |
| RSK2(Kin. Dom. 2-C-terminal) | RPS6KA3 | 100 |
| RSK4(Kin. Dom. 1-N-terminal) | RPS6KA6 | 100 |
| SGK3 | SGK3 | 100 |
| SNARK | NUAK2 | 100 |
| STK35 | STK35 | 100 |
| TGFBR2 | TGFBR2 | 100 |
| TIE1 | TIE1 | 100 |
| TIE2 | TEK | 100 |
| TLK1 | TLK1 | 100 |
| TNK1 | TNK1 | 100 |
| TSSK1B | TSSK1B | 100 |
| VEGFR2 | KDR | 100 |
| WEE1 | WEE1 | 100 |
| WNK3 | WNK3 | 100 |
| YSK4 | YSK4 | 100 |
| ZAP70 | ZAP70 | 100 |

TABLE 5

Exemplary KINOMESCAN assay results of compound I-2.

| Kinase | % change compared to control |
|---|---|
| ABL1(F317L)-nonphosphorylated | 0 |
| ABL1(H396P)-nonphosphorylated | 0 |
| ABL1(H396P)-phosphorylated | 0 |
| ABL1-phosphorylated | 0 |

TABLE 5-continued

Exemplary KINOMESCAN assay results of compound I-2.

| Kinase | % change compared to control |
|---|---|
| BLK | 0 |
| BTK | 0 |
| EPHA4 | 0 |
| EPHB2 | 0 |
| EPHB3 | 0 |
| EPHB4 | 0 |
| JAK3(JH1domain-catalytic) | 0 |
| KIT | 0 |
| KIT(L576P) | 0 |
| KIT(V559D) | 0 |
| LYN | 0 |
| PDGFRB | 0 |
| SRC | 0 |
| YES | 0 |
| ABL1-nonphosphorylated | 0.05 |
| ABL1(Y253F)-phosphorylated | 0.1 |
| ERBB3 | 0.1 |
| FGR | 0.1 |
| FRK | 0.1 |
| p38-alpha | 0.1 |
| ABL1(F317I)-nonphosphorylated | 0.15 |
| DDR1 | 0.2 |
| EPHA2 | 0.2 |
| ABL1(Q252H)-phosphorylated | 0.25 |
| MEK5 | 0.25 |
| ABL1(Q252H)-nonphosphorylated | 0.3 |
| ABL2 | 0.3 |
| FYN | 0.3 |
| EPHB1 | 0.35 |
| ABL1(E255K)-phosphorylated | 0.45 |
| ABL1(F317L)-phosphorylated | 0.5 |
| EPHA1 | 0.5 |
| ABL1(M351T)-phosphorylated | 0.6 |
| ERBB4 | 0.6 |
| TXK | 0.6 |
| LCK | 0.65 |
| EPHA8 | 0.75 |
| SIK | 0.8 |
| HCK | 0.9 |
| EPHA5 | 0.95 |
| EGFR(L861Q) | 1.3 |
| CSF1R-autoinhibited | 1.4 |
| BRAF(V600E) | 1.6 |
| BRK | 1.6 |
| CSK | 1.6 |
| KIT(D816V) | 1.7 |
| KIT-autoinhibited | 1.8 |
| EGFR(L747-T751del, Sins) | 2 |
| EGFR(L858R) | 2 |
| EGFR(L747-E749del, A750P) | 2.2 |
| CSF1R | 2.6 |
| STK36 | 3.5 |
| BMX | 3.6 |
| EGFR(L747-S752del, P753S) | 3.6 |
| TEC | 3.6 |
| EGFR(E746-A750del) | 3.7 |
| BRAF | 4.4 |
| PDGFRA | 4.5 |
| ABL1(F317I)-phosphorylated | 5.4 |
| EGFR | 5.6 |
| KIT(A829P) | 5.8 |
| KIT(V559D, V654A) | 7.2 |
| ERBB2 | 7.5 |
| SRMS | 7.6 |
| EPHB6 | 7.7 |
| DDR2 | 8.6 |
| ADCK3 | 9.2 |
| BMPR1B | 10 |
| GAK | 11 |
| NLK | 11 |
| KIT(D816H) | 14 |
| RIPK2 | 14 |
| TNNI3K | 16 |
| EGFR(G719S) | 17 |
| EGFR(S752-I759del) | 17 |
| EGFR(G719C) | 23 |
| PFCDPK1 (*P. falciparum*) | 24 |
| RAF1 | 26 |
| TYK2(JH2domain-pseudokinase) | 28 |
| TNK2 | 31 |
| QSK | 36 |
| TYRO3 | 41 |
| EPHA3 | 47 |
| EGFR(L858R, T790M) | 48 |
| EGFR(T790M) | 48 |
| TGFBR1 | 50 |
| DMPK2 | 51 |
| HPK1 | 51 |
| LIMK2 | 51 |
| LIMK1 | 52 |
| ACVRL1 | 54 |
| SBK1 | 54 |
| SGK | 56 |
| CSNK2A2 | 57 |
| PKMYT1 | 59 |
| SgK110 | 59 |
| TESK1 | 60 |
| TRPM6 | 61 |
| p38-beta | 62 |
| NDR1 | 63 |
| JAK2(JH1domain-catalytic) | 65 |
| MRCKA | 65 |
| TAOK2 | 65 |
| CTK | 67 |
| INSR | 67 |
| MEK1 | 67 |
| ACVR1B | 68 |
| ABL1(T315I)-phosphorylated | 69 |
| MST2 | 69 |
| MAP3K1 | 70 |
| MINK | 71 |
| ALK(L1196M) | 72 |
| PFTK1 | 72 |
| SGK2 | 72 |
| AURKA | 73 |
| CDK3 | 73 |
| FGFR2 | 73 |
| PKNB(*M. tuberculosis*) | 73 |
| PLK4 | 73 |
| RSK1(Kin. Dom. 1-N-terminal) | 73 |
| TSSK1B | 73 |
| ACVR1 | 74 |
| IKK-beta | 75 |
| PAK3 | 75 |
| ACVR2A | 76 |
| IRAK4 | 76 |
| PIK3CA(I800L) | 76 |
| ACVR2B | 78 |
| MEK2 | 78 |
| MAP3K3 | 79 |
| PIK3CD | 79 |
| ULK1 | 79 |
| OSR1 | 81 |
| PRKD3 | 81 |
| TAOK3 | 81 |
| MAP4K5 | 82 |
| MEK6 | 82 |
| ERN1 | 83 |
| MAP3K4 | 83 |
| NEK11 | 83 |
| PIK3CA(Q546K) | 83 |
| YANK3 | 83 |
| CAMK2B | 84 |
| CSNK1E | 84 |
| IRAK1 | 84 |
| MELK | 84 |
| PIK3CA(H1047L) | 84 |
| PIM2 | 84 |

TABLE 5-continued

Exemplary KINOMESCAN assay results of compound I-2.

| Kinase | % change compared to control |
|---|---|
| PKN2 | 84 |
| BUB1 | 85 |
| GCN2(Kin. Dom. 2, S808G) | 85 |
| MYLK | 85 |
| PKAC-alpha | 85 |
| YSK1 | 85 |
| CAMK2A | 86 |
| DAPK2 | 86 |
| ICK | 86 |
| PIK3C2B | 86 |
| STK33 | 86 |
| SYK | 86 |
| DCAMKL1 | 87 |
| MAP4K2 | 87 |
| ZAK | 87 |
| AKT2 | 88 |
| CDC2L1 | 88 |
| CDKL2 | 88 |
| CHEK1 | 88 |
| DYRK2 | 88 |
| MKK7 | 88 |
| NEK1 | 88 |
| ROCK1 | 88 |
| CAMK1G | 89 |
| DAPK3 | 89 |
| MLK1 | 89 |
| MRCKB | 89 |
| PRKR | 89 |
| TBK1 | 89 |
| TYK2(JH1domain-catalytic) | 89 |
| ULK2 | 89 |
| AKT3 | 90 |
| AURKC | 90 |
| CDK9 | 90 |
| CSNK2A1 | 90 |
| ERK4 | 90 |
| MERTK | 90 |
| RIOK1 | 90 |
| CAMK1 | 91 |
| CAMK2D | 91 |
| CAMK2G | 91 |
| ERK5 | 91 |
| FGFR1 | 91 |
| MARK4 | 91 |
| NIK | 91 |
| SRPK1 | 91 |
| AMPK-alpha2 | 92 |
| ASK2 | 92 |
| CDC2L2 | 92 |
| CLK1 | 92 |
| FLT3(ITD) | 92 |
| MAP3K15 | 92 |
| PAK2 | 92 |
| PIK3C2G | 92 |
| PIK3CA(E542K) | 92 |
| PIP5K1A | 92 |
| PKAC-beta | 92 |
| PLK1 | 92 |
| PLK2 | 92 |
| RET(M918T) | 92 |
| RIOK2 | 92 |
| SIK2 | 92 |
| SRPK2 | 92 |
| STK39 | 92 |
| CDK8 | 93 |
| FLT1 | 93 |
| HIPK1 | 93 |
| IKK-alpha | 93 |
| IRAK3 | 93 |
| MYO3A | 93 |
| MYO3B | 93 |
| NEK10 | 93 |
| NIM1 | 93 |
| PAK6 | 93 |
| PRKD1 | 93 |
| RSK3(Kin. Dom. 1-N-terminal) | 93 |
| TAOK1 | 93 |
| WEE1 | 93 |
| ALK(C1156Y) | 94 |
| ANKK1 | 94 |
| CDK4-cyclinD3 | 94 |
| CDK7 | 94 |
| CLK4 | 94 |
| DYRK1B | 94 |
| GRK1 | 94 |
| JNK1 | 94 |
| LRRK2 | 94 |
| MARK3 | 94 |
| NEK3 | 94 |
| PIK3CA(E545K) | 94 |
| PRKCI | 94 |
| PRKCQ | 94 |
| RPS6KA5(Kin. Dom. 2-C-terminal) | 94 |
| TGFBR2 | 94 |
| TRKB | 94 |
| VRK2 | 94 |
| ABL1(T315I)-nonphosphorylated | 95 |
| ADCK4 | 95 |
| AKT1 | 95 |
| FLT4 | 95 |
| HIPK3 | 95 |
| MET(Y1235D) | 95 |
| PRP4 | 95 |
| RIPK4 | 95 |
| ROCK2 | 95 |
| RSK2(Kin. Dom. 1-N-terminal) | 95 |
| TAK1 | 95 |
| ASK1 | 96 |
| AURKB | 96 |
| AXL | 96 |
| CAMK4 | 96 |
| CDK4-cyclinD1 | 96 |
| CSNK1G3 | 96 |
| FLT3(K663Q) | 96 |
| INSRR | 96 |
| LOK | 96 |
| MAP3K2 | 96 |
| MAP4K4 | 96 |
| NDR2 | 96 |
| NEK5 | 96 |
| PAK7 | 96 |
| PHKG2 | 96 |
| PIK3CA(M1043I) | 96 |
| PRKCD | 96 |
| RPS6KA4(Kin. Dom. 2-C-terminal) | 96 |
| SLK | 96 |
| AAK1 | 97 |
| ALK | 97 |
| CAMKK2 | 97 |
| CHEK2 | 97 |
| CSNK1G2 | 97 |
| DCAMKL3 | 97 |
| ERK1 | 97 |
| ERK8 | 97 |
| FLT3(D835Y) | 97 |
| GRK7 | 97 |
| HIPK2 | 97 |
| JNK3 | 97 |
| LZK | 97 |
| MARK1 | 97 |
| MET | 97 |
| PCTK1 | 97 |
| PIM1 | 97 |
| PIM3 | 97 |
| PRKCH | 97 |
| ROS1 | 97 |
| TLK2 | 97 |
| TNIK | 97 |

TABLE 5-continued

Exemplary KINOMESCAN assay results of compound I-2.

| Kinase | % change compared to control |
|---|---|
| ULK3 | 97 |
| CDK11 | 98 |
| CDKL3 | 98 |
| DCAMKL2 | 98 |
| DLK | 98 |
| DMPK | 98 |
| FES | 98 |
| MAST1 | 98 |
| MUSK | 98 |
| MYLK4 | 98 |
| PDPK1 | 98 |
| PIP5K2B | 98 |
| RET(V804L) | 98 |
| RIOK3 | 98 |
| RPS6KA5(Kin. Dom. 1-N-terminal) | 98 |
| TRKA | 98 |
| ARK5 | 99 |
| FGFR3 | 99 |
| MEK3 | 99 |
| MST1R | 99 |
| PCTK3 | 99 |
| PIP5K1C | 99 |
| PLK3 | 99 |
| PRKG2 | 99 |
| STK16 | 99 |
| STK35 | 99 |
| TRKC | 99 |
| ZAP70 | 99 |
| AMPK-alpha1 | 100 |
| BIKE | 100 |
| BMPR1A | 100 |
| BMPR2 | 100 |
| BRSK1 | 100 |
| BRSK2 | 100 |
| CAMK1D | 100 |
| CAMKK1 | 100 |
| CASK | 100 |
| CDC2L5 | 100 |
| CDK2 | 100 |
| CDK5 | 100 |
| CDKL1 | 100 |
| CDKL5 | 100 |
| CIT | 100 |
| CLK2 | 100 |
| CLK3 | 100 |
| CSNK1A1 | 100 |
| CSNK1A1L | 100 |
| CSNK1D | 100 |
| CSNK1G1 | 100 |
| DAPK1 | 100 |
| DRAK1 | 100 |
| DRAK2 | 100 |
| DYRK1A | 100 |
| EIF2AK1 | 100 |
| EPHA6 | 100 |
| EPHA7 | 100 |
| ERK2 | 100 |
| ERK3 | 100 |
| FAK | 100 |
| FER | 100 |
| FGFR3(G697C) | 100 |
| FGFR4 | 100 |
| FLT3 | 100 |
| FLT3(D835H) | 100 |
| FLT3(N841I) | 100 |
| FLT3(R834Q) | 100 |
| FLT3-autoinhibited | 100 |
| GRK4 | 100 |
| GSK3A | 100 |
| GSK3B | 100 |
| HASPIN | 100 |
| HIPK4 | 100 |
| HUNK | 100 |
| IGF1R | 100 |
| IKK-epsilon | 100 |
| ITK | 100 |
| JAK1(JH1domain-catalytic) | 100 |
| JAK1(JH2domain-pseudokinase) | 100 |
| JNK2 | 100 |
| KIT(V559D, T670I) | 100 |
| LATS1 | 100 |
| LATS2 | 100 |
| LKB1 | 100 |
| LRRK2(G2019S) | 100 |
| LTK | 100 |
| MAK | 100 |
| MAP4K3 | 100 |
| MAPKAPK2 | 100 |
| MAPKAPK5 | 100 |
| MARK2 | 100 |
| MEK4 | 100 |
| MET(M1250T) | 100 |
| MKNK1 | 100 |
| MKNK2 | 100 |
| MLCK | 100 |
| MLK2 | 100 |
| MLK3 | 100 |
| MST1 | 100 |
| MST3 | 100 |
| MST4 | 100 |
| MTOR | 100 |
| MYLK2 | 100 |
| NEK2 | 100 |
| NEK4 | 100 |
| NEK6 | 100 |
| NEK7 | 100 |
| NEK9 | 100 |
| p38-delta | 100 |
| p38-gamma | 100 |
| PAK1 | 100 |
| PAK4 | 100 |
| PCTK2 | 100 |
| PFPK5(*P. falciparum*) | 100 |
| PFTAIRE2 | 100 |
| PHKG1 | 100 |
| PIK3CA | 100 |
| PIK3CA(C420R) | 100 |
| PIK3CA(E545A) | 100 |
| PIK3CA(H1047Y) | 100 |
| PIK3CB | 100 |
| PIK3CG | 100 |
| PIK4CB | 100 |
| PIP5K2C | 100 |
| PKN1 | 100 |
| PRKCE | 100 |
| PRKD2 | 100 |
| PRKG1 | 100 |
| PRKX | 100 |
| PYK2 | 100 |
| RET | 100 |
| RET(V804M) | 100 |
| RIPK1 | 100 |
| RIPK5 | 100 |
| RPS6KA4(Kin. Dom. 1-N-terminal) | 100 |
| RSK1(Kin. Dom. 2-C-terminal) | 100 |
| RSK2(Kin. Dom. 2-C-terminal) | 100 |
| RSK3(Kin. Dom. 2-C-terminal) | 100 |
| RSK4(Kin. Dom. 1-N-terminal) | 100 |
| RSK4(Kin. Dom. 2-C-terminal) | 100 |
| S6K1 | 100 |
| SGK3 | 100 |
| SNARK | 100 |
| SNRK | 100 |
| SRPK3 | 100 |
| TIE1 | 100 |
| TIE2 | 100 |
| TLK1 | 100 |
| TNK1 | 100 |

TABLE 5-continued

Exemplary KINOMESCAN assay results of compound I-2.

| Kinase | % change compared to control |
|---|---|
| TTK | 100 |
| VEGFR2 | 100 |
| WEE2 | 100 |
| WNK1 | 100 |
| WNK3 | 100 |
| YANK1 | 100 |
| YANK2 | 100 |
| YSK4 | 100 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

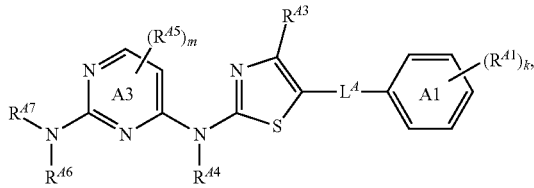

or a pharmaceutically acceptable salt thereof, wherein:
each instance of $R^{41}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

k is 0, 1, 2, 3, 4, or 5;

$L^A$ is —C(=O)—$NR^{42}$— or —$NR^{42}$—C(=O)—, wherein $R^{42}$ is hydrogen, substituted or unsubstituted $C_{1-6}$ alkyl, or a nitrogen protecting group;

$R^{43}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

$R^{44}$ is hydrogen, substituted or unsubstituted $C_{1-6}$ alkyl, or a nitrogen protecting group;

each instance of $R^{45}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

m is 0, 1, or 2;

$R^{46}$ is hydrogen, substituted or unsubstituted $C_{1-6}$ alkyl, or a nitrogen protecting group; and $R^{47}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, —C(=O)R$^a$, —C(=O)OR$^a$, —C(=O)N(R$^a$)$_2$, or a nitrogen protecting group;

wherein:

each substituent at a carbon atom is independently halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, heterocyclyl, $C_{6-14}$ aryl, or heteroaryl, wherein each one of the alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each substituent on a nitrogen atom is independently hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, heterocyclyl, $C_{6-14}$ aryl, or heteroaryl, wherein each one of the alkyl, alkenyl, alkynyl, carbocyclyl, heterocyclyl, aryl, and heteroaryl is independently substituted with 0, 1, 2, 3, 4, or 5 R$^{dd}$ groups;

each instance of the acyl is independently —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$;

each instance of R$^{aa}$ is independently $C_{1-10}$ alkyl, $C_{1-10}$ perhaloalkyl, $C_{2-10}$ alkenyl, $C_{2-10}$ alkynyl, $C_{3-10}$ carbocyclyl, heterocyclyl, $C_{6-14}$ aryl, or heteroaryl, or two R$^{aa}$ groups are joined to form heterocyclyl or heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is independently hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$R$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$), $C_{1-10}$ alkyl, $C_{1-10}$ perhaloalkyl, $C_{2-10}$ alkenyl, $C_{2-10}$ alkynyl, $C_{3-10}$ carbocyclyl, heterocyclyl, $C_{6-14}$ aryl, or heteroaryl, or two R$^{bb}$ groups are joined to form heterocyclyl or heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is independently hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, heterocyclyl, $C_{6-14}$ aryl, or heteroaryl, or two R$^{cc}$ groups are joined to form heterocyclyl or heteroaryl, wherein each one of the alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is independently halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —C(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, heterocyclyl, $C_{6-10}$ aryl, or heteroaryl, wherein each one of the alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents are joined to form =O or =S;

each instance of R$^{ee}$ is independently $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, heterocyclyl, or heteroaryl, wherein each one of the alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is independently hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, heterocyclyl, $C_{6-10}$ aryl, or heteroaryl, or two R$^{ff}$ groups are joined to form heterocyclyl or heteroaryl, wherein each one of the alkyl, alkenyl, alkynyl, carbocyclyl, heterocyclyl, aryl, and heteroaryl is independently substituted with 0, 1, 2, 3, 4, or 5 R$^{gg}$ groups;

each instance of $R^{gg}$ is independently halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, -NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, heterocyclyl, or heteroaryl; or two geminal $R^{gg}$ substituents are joined to form =O or =S;

X$^-$ is a counterion;

each instance of the heteroaryl and heteroaryl ring independently is 5- to 10-membered, and monocyclic or bicyclic, and has ring carbon atoms and 1 to 4 ring heteroatoms;

each instance of the heterocyclyl and heterocyclic ring independently is 3- to 10-membered; saturated or partially unsaturated; non-aromatic; and monocyclic, fused bicyclic, bridged bicyclic, or spiro bicyclic; and has ring carbon atoms and 1 to 4 ring heteroatoms;

each instance of the ring heteroatoms is independently nitrogen, oxygen, or sulfur; and each instance of the nitrogen protecting group is independently formamide, acetamide, chloroacetamide, trichloroacetamide, trifluoroacetamide, phenylacetamide, 3-phenylpropanamide, picolinamide, 3-pyridylcarboxamide, N-benzoylphenylalanyl, benzamide, p-phenylbenzamide, o-nitophenylacetamide, o-nitrophenoxyacetamide, acetoacetamide, (N'-dithiobenzyloxyacylamino)acetamide, 3-(p -hydroxyphenyl)propanamide, 3-(o-nitrophenyl)propanamide, 2-methyl-2-(o -nitrophenoxy)propanamide, 2-methyl-2-(o-phenylazophenoxy) propanamide, 4-chlorobutanamide, 3-methyl-3-nitrobutanamide, o-nitrocinnamide, N-acetylmethionine, o -nitrobenzamide, o-(benzoyloxymethyl)benzamide, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl[9-(10,10-dioxo-10,10,10,10-tetrahydrothioxanthyl)] methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- or 4'-pyridyl)ethyl carbamate (Pyoc), 2-(N,N-dicyclohexylcarboxamido) ethyl carbamate, t -butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p -(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, p -toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4', 8'-dimethoxynaphthylmethyl)benzenesulfonamide (DNMBS), benzylsulfonamide, trifluoromethylsulfonamide, phenacylsulfonamide, phenothiazinyl-(10)-acyl, N'-p-toluenesulfonylaminoacyl, N'-phenylaminothioacyl, N-benzoylphenylalanyl, N-acetylmethionine, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salt, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane, N-diphenylborinic acid, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidate, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, or 3-nitropyridinesulfenamide (Npys).

2. The compound of claim 1, wherein the compound is of the formula:

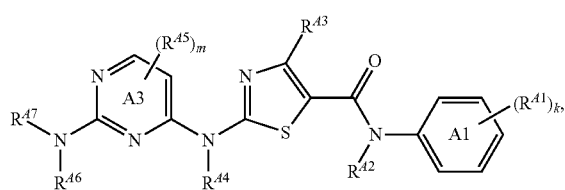

or a pharmaceutically acceptable salt thereof.

3. The compound of claim 1, or a pharmaceutically acceptable salt thereof, wherein

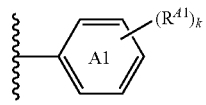

is

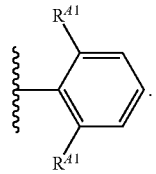

4. The compound of claim 1, or a pharmaceutically acceptable salt thereof, wherein

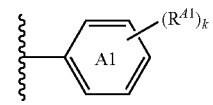

is

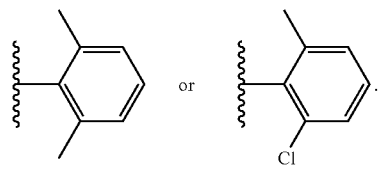

5. The compound of claim 1, or a pharmaceutically acceptable salt thereof, wherein k is 2.

6. The compound of claim 1, or a pharmaceutically acceptable salt thereof, wherein $L^A$ is —C(=O)—NH— or —NH—C(=O)—.

7. The compound of claim 1, or a pharmaceutically acceptable salt thereof, wherein $R^{A3}$ is hydrogen.

8. The compound of claim 1, or a pharmaceutically acceptable salt thereof, wherein $R^{A4}$ is hydrogen.

9. The compound of claim 1, or a pharmaceutically acceptable salt thereof, wherein

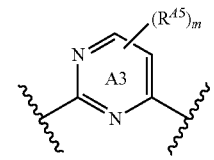

is

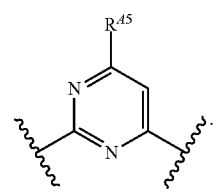

10. The compound of claim 1, or a pharmaceutically acceptable salt thereof, wherein at least one instance of $R^{A5}$ is substituted or unsubstituted alkyl, and m is 1 or 2.

11. The compound of claim 1, or a pharmaceutically acceptable salt thereof, wherein m is 0.

12. The compound of claim 1, or a pharmaceutically acceptable salt thereof, wherein $R^{A6}$ is hydrogen.

13. The compound of claim 1, or a pharmaceutically acceptable salt thereof, wherein $R^{A7}$ is substituted or unsubstituted alkyl.

14. The compound of claim 1, or a pharmaceutically acceptable salt thereof, wherein $R^{A7}$ is substituted or unsubstituted, 3- to 9-membered, monocyclic heterocyclyl comprising zero, one, or two double bonds in the heterocyclic ring system, wherein one, two, or three atoms of the heterocyclic ring system are independently nitrogen, oxygen, or sulfur.

15. The compound of claim 1, or a pharmaceutically acceptable salt thereof, wherein $R^{A7}$ is of the formula:

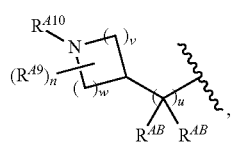

wherein:
each instance of $R^{A8}$ is independently hydrogen, halogen, or substituted or unsubstituted $C_{1-6}$ alkyl;
u is 0, 1, 2, 3, or 4;
v is 1, 2, 3, or 4;
w is 1, 2, or 3;
each instance of $R^{A9}$ is independently halogen, or substituted or unsubstituted $C_{1-6}$ alkyl;
n is an integer between 0 and 13, inclusive; and
$R^{A10}$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted carbocyclyl, —C(=O)R$^a$, —C(=O)OR$^a$, —C(=O)N(R$^a$)$_2$, a nitrogen protecting group, or of any one of Formulae (ii-1) to (ii-42):

(ii-1)
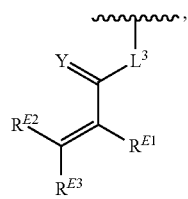

(ii-2)
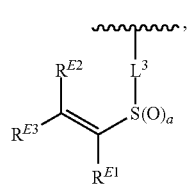

(ii-3)
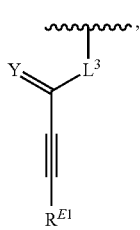

(ii-4)
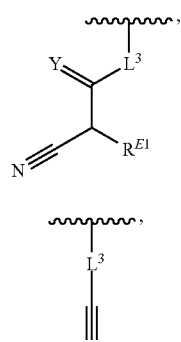

(ii-5)

(ii-6)
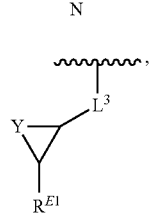

(ii-7)
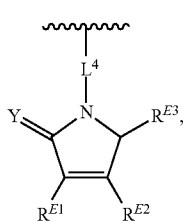

(ii-8)
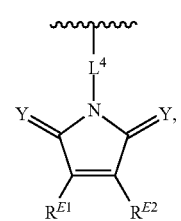

(ii-9)
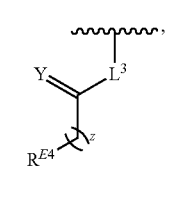

(ii-10)
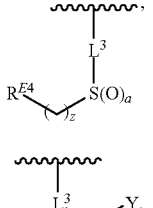

(ii-11)
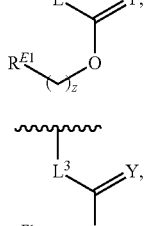

(ii-12)
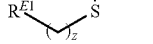

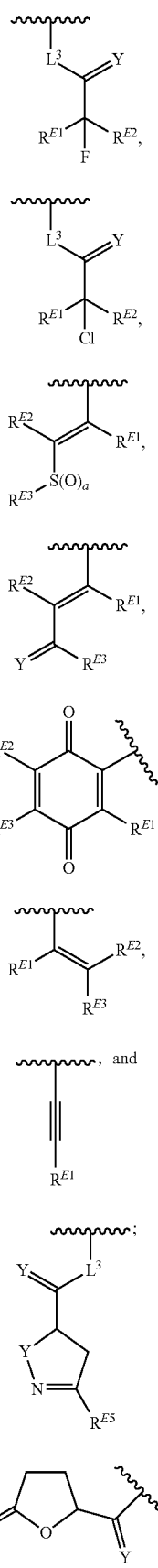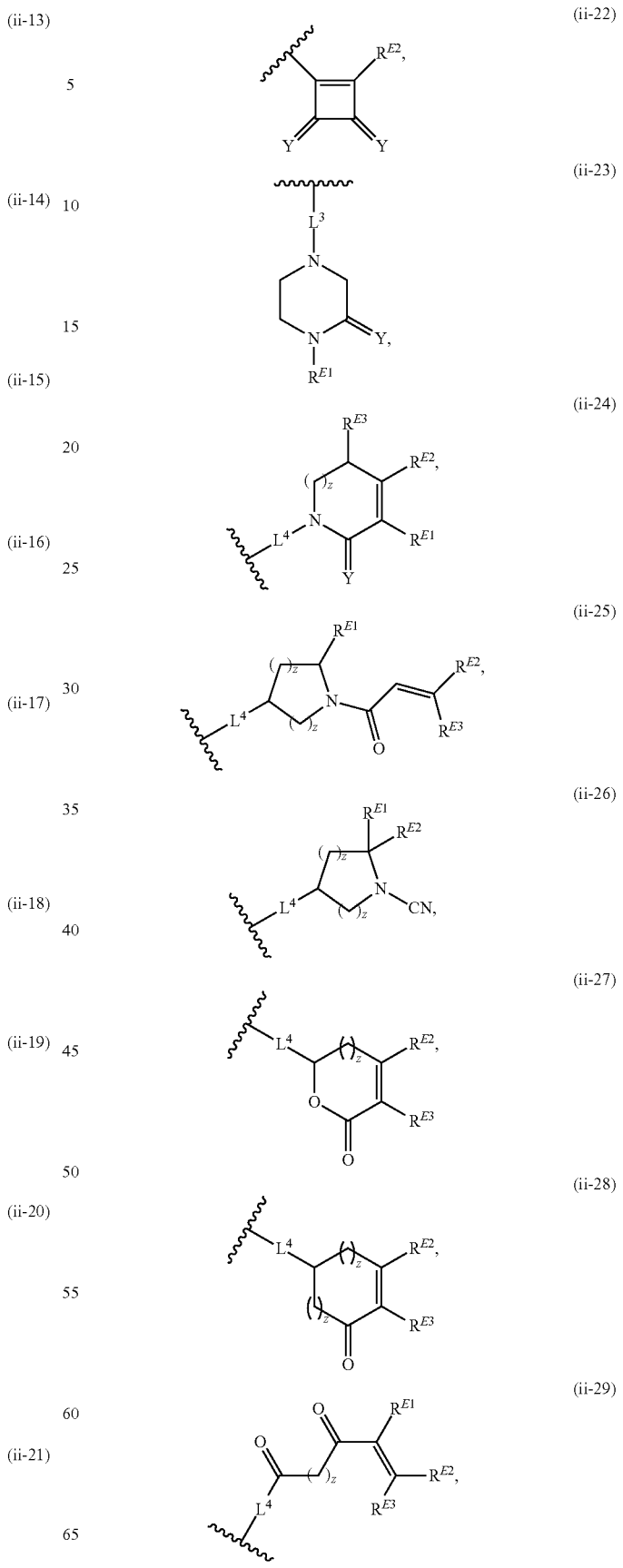

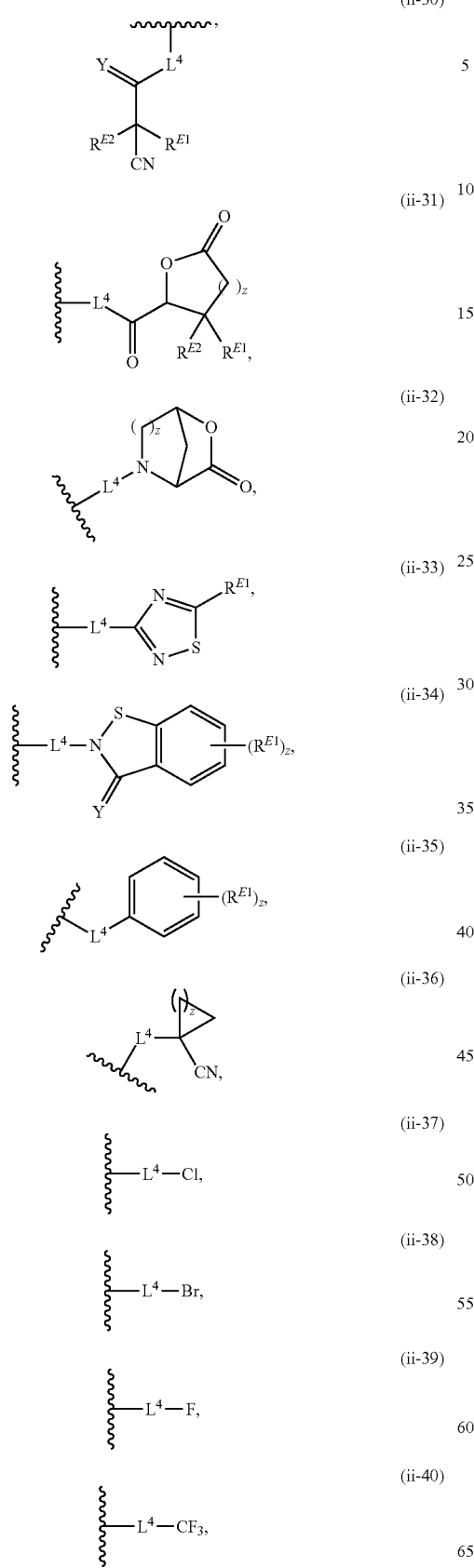

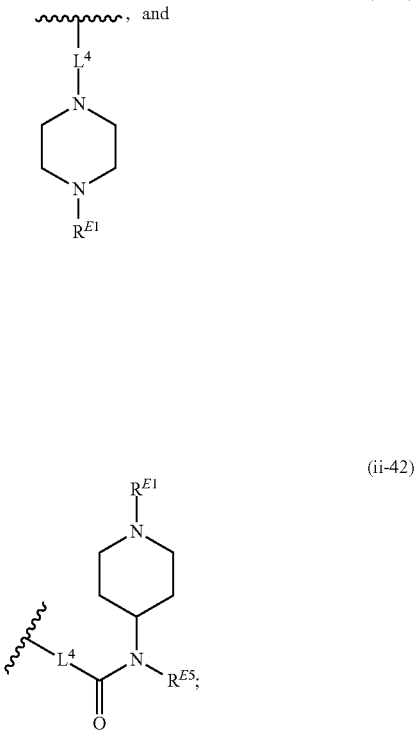

wherein:

$L^3$ is a bond or an optionally substituted $C_{1-4}$ hydrocarbon chain, optionally wherein one or more carbon units of the hydrocarbon chain are independently replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans—CR$^{L3b}$=CR$^{L3b}$—, cis—CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of RL3b is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

$L^4$ is a bond or an optionally substituted $C_{1-4}$ hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or NR$^{E6}$, wherein $R^{E6}$ is hydrogen, substituted or unsubstituted C$_{1-6}$ alkyl, or a nitrogen protecting group;

a is 1 or 2; and each instance of z is independently 0, 1, 2, 3, 4, 5, or 6.

16. The compound of claim 15, or a pharmaceutically acceptable salt thereof, wherein $R^{47}$ is of the formula:

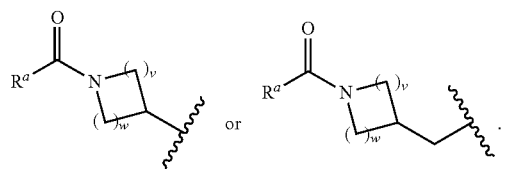

17. The compound of claim 1, wherein the compound is of the formula:

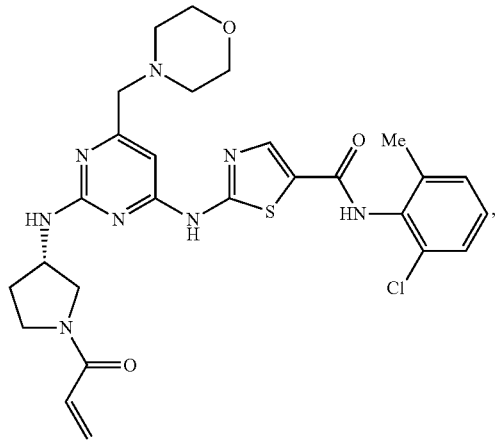

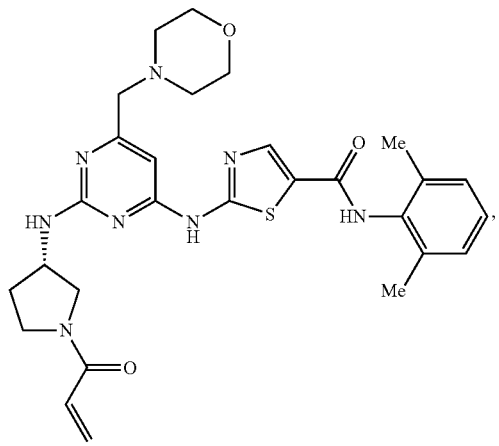

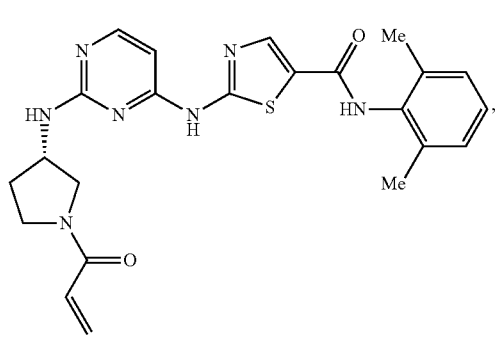

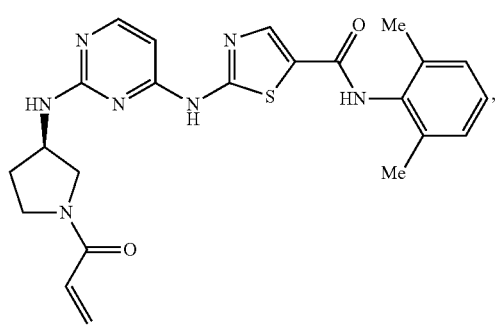

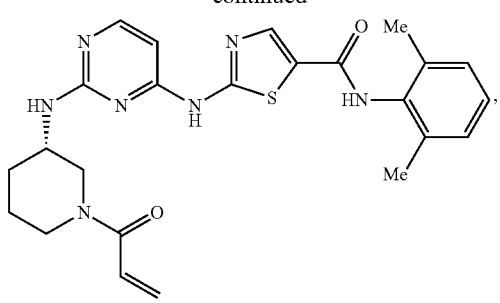

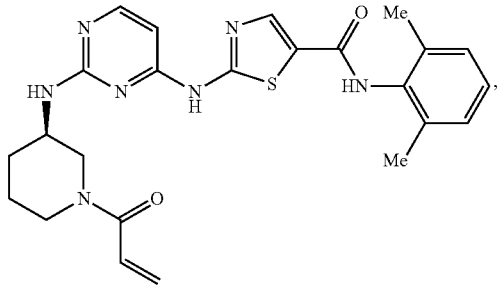

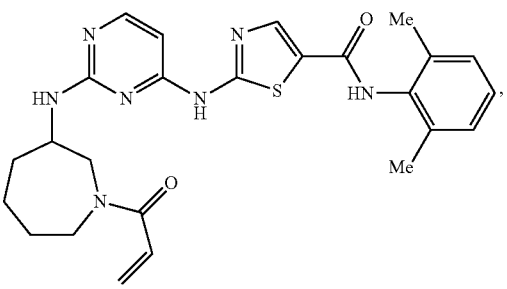

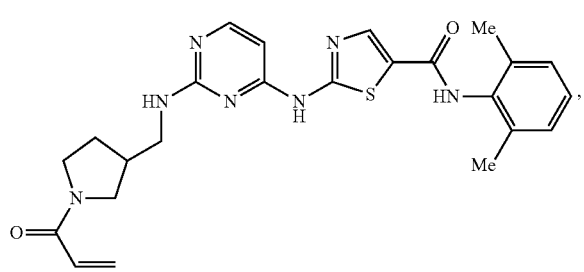

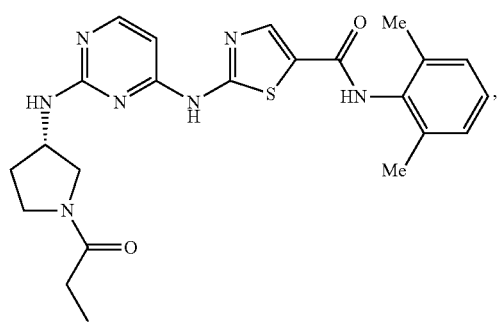

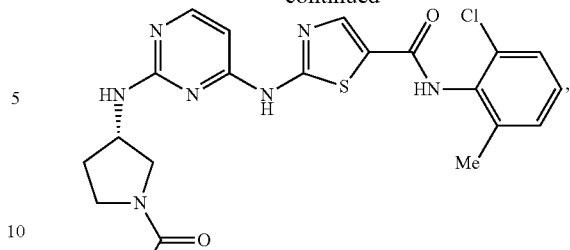

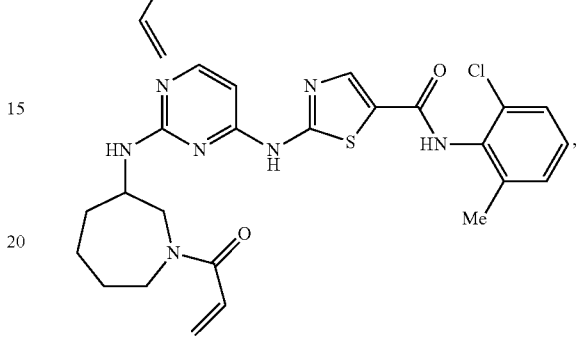

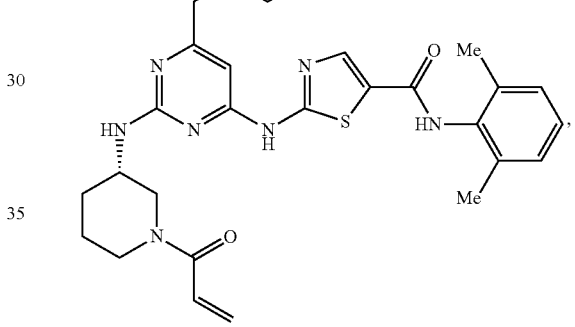

or a pharmaceutically acceptable salt thereof.

18. A pharmaceutical composition comprising a compound of claim 1, or a pharmaceutically acceptable salt thereof, and optionally a pharmaceutically acceptable excipient.

19. A method of treating a proliferative disease in a subject in need thereof, the method comprising administering to the subject an effective amount of a compound of claim 1, or a pharmaceutically acceptable salt thereof, wherein the proliferative disease is a hematological malignancy.

20. A method of inducing apoptosis in a cell, the method comprising contacting the cell with an effective amount of a compound of claim 1, or a pharmaceutically acceptable salt thereof, wherein the cell is a malignant blood cell.

21. The compound of claim 1, wherein the compound is of the formula:

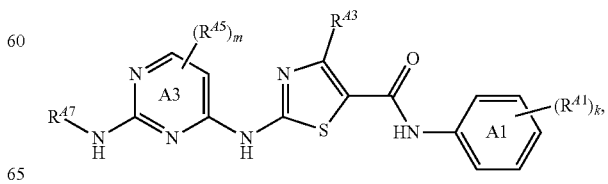

or a pharmaceutically acceptable salt thereof.

22. The compound of claim 1, wherein the compound is of the formula:

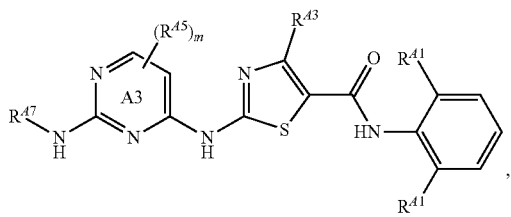

or a pharmaceutically acceptable salt thereof.

23. The compound of claim 1, wherein the compound is of the formula:

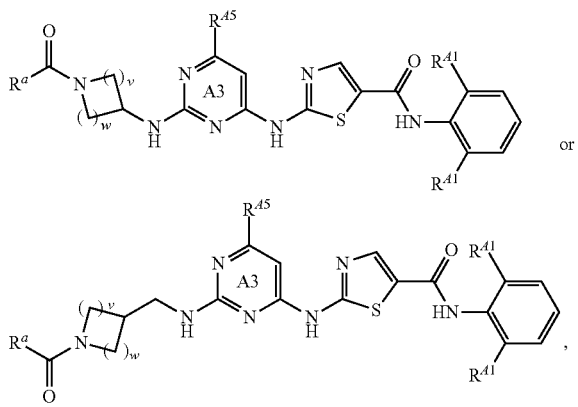

or a pharmaceutically acceptable salt thereof.

24. The compound of claim 1, or a pharmaceutically acceptable salt thereof, wherein at least one instance of $R^{A1}$ is halogen or substituted or unsubstituted $C_{1-6}$ alkyl.

25. The compound of claim 15, or a pharmaceutically acceptable salt thereof, wherein $R^{A10}$ is of the formula:

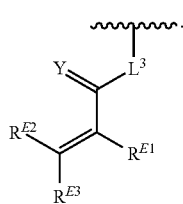

(ii-1)

26. The compound of claim 1, or a pharmaceutically acceptable salt thereof, wherein $R^{A7}$ is of the formula:

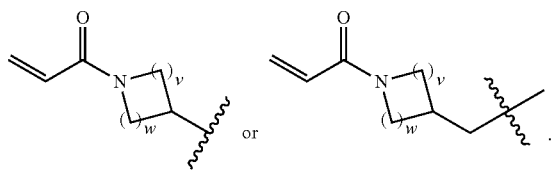

27. The compound of claim 1, wherein the compound is of the formula:

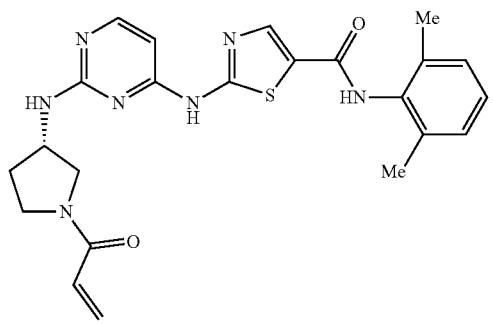

or a pharmaceutically acceptable salt thereof.

28. The method of claim 19, wherein the hematological malignancy is myelodysplasia.

29. The method of claim 19, wherein the hematological malignancy is leukemia.

30. The method of claim 19, wherein the hematological malignancy is lymphoma.

31. The method of claim 19, wherein the hematological malignancy is non-Hodgkin's lymphoma.

32. The method of claim 19, wherein the hematological malignancy is Hodgkin's lymphoma.

33. The method of claim 19, wherein the hematological malignancy is Waldenström's macroglobulinemia.

34. The method of claim 19, wherein the hematological malignancy is activated B-cell diffuse large B-cell lymphoma, central nervous system lymphoma, lymphoma of an immune privileged site, testicular lymphoma, or marginal zone lymphoma.

35. The method of claim 19, wherein the compound is of the formula:

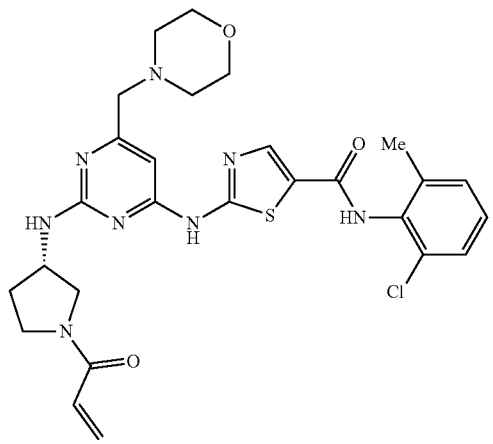

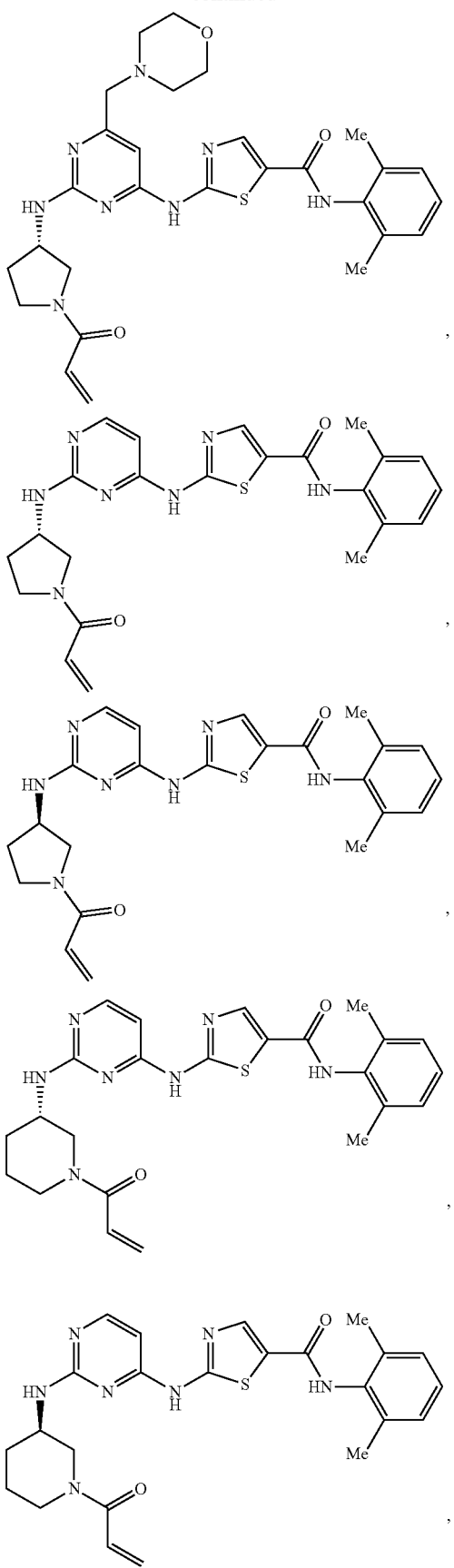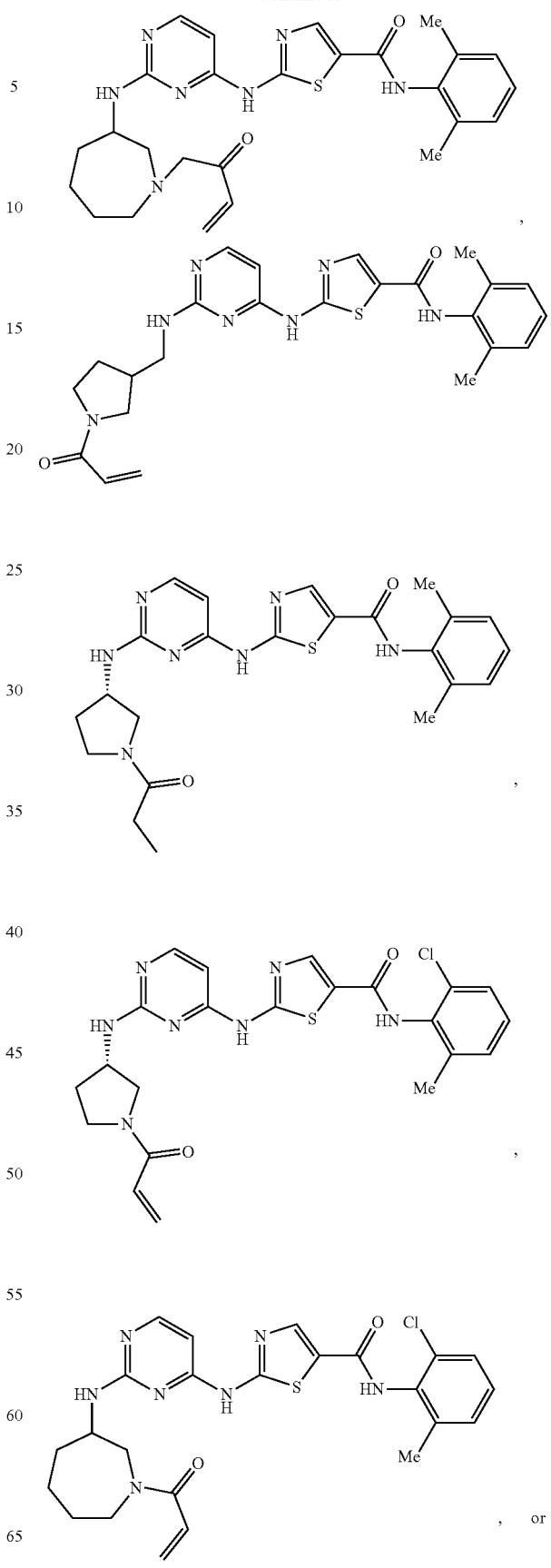

-continued
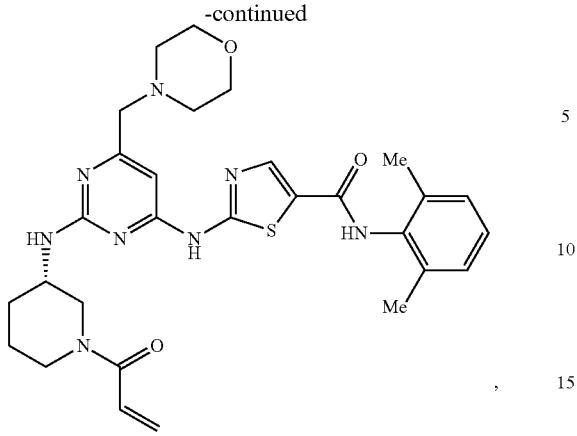
or a pharmaceutically acceptable salt thereof.
* * * * *

UNITED STATES PATENT AND TRADEMARK OFFICE
CERTIFICATE OF CORRECTION

PATENT NO. : 10,112,957 B2
APPLICATION NO. : 15/518541
DATED : October 30, 2018
INVENTOR(S) : Nathanael S. Gray et al.

Page 1 of 1

It is certified that error appears in the above-identified patent and that said Letters Patent is hereby corrected as shown below:

In the Claims

In Claim 19, at Column 306, Line 49, the text: "ora" should be replaced with the phrase: --or a--.

In Claim 20, at Column 306, Line 54, the text: "ora" should be replaced with the phrase: --or a--.

Signed and Sealed this
Eighteenth Day of February, 2020

Andrei Iancu
*Director of the United States Patent and Trademark Office*